US007479480B2

(12) United States Patent
Brewer, Jr.

(10) Patent No.: US 7,479,480 B2
(45) Date of Patent: *Jan. 20, 2009

(54) PEPTIDES THAT PROMOTE LIPID EFFLUX

(75) Inventor: H. Bryan Brewer, Jr., Potomac, MD (US)

(73) Assignee: Lipid Sciences, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/121,317

(22) Filed: May 15, 2008

(65) Prior Publication Data

US 2008/0255051 A1 Oct. 16, 2008

Related U.S. Application Data

(63) Continuation of application No. 12/021,629, filed on Jan. 29, 2008, which is a continuation-in-part of application No. 11/764,619, filed on Jun. 18, 2007.

(60) Provisional application No. 60/814,466, filed on Jun. 16, 2006, provisional application No. 60/847,586, filed on Sep. 26, 2006, provisional application No. 60/858,073, filed on Nov. 10, 2006.

(51) Int. Cl.
*C07K 14/00* (2006.01)

(52) U.S. Cl. .......................................... 514/2; 530/300

(58) Field of Classification Search ....................... None
See application file for complete search history.

(56) References Cited

U.S. PATENT DOCUMENTS 6,258,596 B1 * 7/2001 Benoit et al.
7,083,958 B2 * 8/2006 Sligar et al.

FOREIGN PATENT DOCUMENTS

| | | | |
|---|---|---|---|
| WO | WO 99/16459 | * | 4/1999 |
| WO | WO 02/062999 | * | 8/2002 |
| WO | WO 2005/058938 | * | 6/2005 |
| WO | WO 2006/044596 | * | 4/2006 |
| WO | WO 2007/002069 | * | 1/2007 |
| WO | WO 2007/149355 | * | 12/2007 |

OTHER PUBLICATIONS

Tang et al. 2006, published on-line Oct. 6, 2005; Janus kinase 2 modulates the lipid-removing but not protein-stabilizing interactions of amphipathic helices with ABCA1. Journal of Lipid Research 47: 107-114.*

Thuahnai et al. 2003; A quantitative analysis of apolipoprotein binding to SR-BI: multiple sites for lipid-free and lipid-associated apolipoproteins. Journal of Lipid Research 44: 1132-1142.*

Remaley et al. 2003; Synthetic amphipathic helical peptides promote lipid efflux from cells by an ABCA1-dependent and an ABCA1-independent pathway. Journal of Lipid Research. 44: 828-836.*

U.S. Appl. No. 12/021,629, filed Jan. 29, 2008, Brewer.*

U.S. Appl. No. 11/764,619, filed Jun. 18, 2007, Brewer.*

* cited by examiner

*Primary Examiner*—Karen Cochrane Carlson
(74) *Attorney, Agent, or Firm*—Kilpatrick Stockton LLP

(57) ABSTRACT

Disclosed herein are peptides with domains that promote lipid efflux from cells and optionally possess at least one anti-inflammatory domain or a domain that stimulates LCAT activity. Provided herein are methods of using the peptides to treat or inhibit diseases including dyslipidemic disorders, stroke and myocardial infarction. Also provided are methods of detecting plaque in vessels using the labeled peptides of the present invention.

6 Claims, 3 Drawing Sheets

Amino Acid Sequence of ApoA-I (SEQ ID NO: 1)

Asp Glu Pro Pro Gln Ser Pro Trp Asp Arg Val Lys Asp Leu Ala Thr Val Tyr Val Asp Val Leu Lys Asp Ser Gly Arg Asp Tyr Val
1 10 20 30

Ser Gln Phe Glu Gly Ser Ala Leu Gly Lys Gln Leu Asn Leu Lys Leu Leu Asp Asn Trp Asp Ser Val Thr Ser Thr Phe Ser Lys Leu
31 40 50 60

Arg Glu Gln Leu Gly Pro Val Thr Gln Glu Phe Trp Asp Asn Leu Glu Lys Glu Thr Glu Gly Leu Arg Gln Glu Met Ser Lys Asp Leu
61 70 80 90

Glu Glu Val Lys Ala Lys Val Gln Pro Tyr Leu Asp Asp Phe Gln Lys Lys Trp Gln Glu Glu Met Glu Leu Tyr Arg Gln Lys Val Glu
91 100 110 120

Pro Leu Arg Ala Glu Leu Gln Glu Gly Ala Arg Gln Lys Leu His Glu Leu Gln Glu Lys Leu Ser Pro Leu Gly Glu Glu Met Arg Asp
121 130 140 150

Arg Ala Arg Ala His Val Asp Ala Leu Arg Thr His Leu Ala Pro Tyr Ser Asp Glu Leu Arg Gln Arg Leu Ala Ala Arg Leu Glu Ala
151 160 170 180

Leu Lys Glu Asn Gly Gly Ala Arg Leu Ala Glu Tyr His Ala Lys Ala Thr Glu His Leu Ser Thr Leu Ser Glu Lys Ala Lys Pro Ala
181 190 200 210

Leu Glu Asp Leu Arg Gln Gly Leu Leu Pro Val Leu Glu Ser Phe Lys Val Ser Phe Leu Ser Ala Leu Glu Glu Tyr Thr Lys Lys Leu
211 220 230 240

Asn Thr Gln
241 243

FIG. 1

SEQUENCE LISTING

<160> NUMBER OF SEQ ID NOS: 610

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
1 5 10 15

Val Tyr Val Asp Val Leu Lys Asp Ser Gly Arg Asp Tyr Val Ser Gln
20 25 30

Phe Glu Gly Ser Ala Leu Gly Lys Gln Leu Asn Leu Lys Leu Leu Asp
35 40 45

Asn Trp Asp Ser Val Thr Ser Thr Phe Ser Lys Leu Arg Glu Gln Leu
50 55 60

Gly Pro Val Thr Gln Glu Phe Trp Asp Asn Leu Glu Lys Glu Thr Glu
65 70 75 80

Gly Leu Arg Gln Glu Met Ser Lys Asp Leu Glu Glu Val Lys Ala Lys
85 90 95

Val Gln Pro Tyr Leu Asp Asp Phe Gln Lys Lys Trp Gln Glu Glu Met
100 105 110

Glu Leu Tyr Arg Gln Lys Val Glu Pro Leu Arg Ala Glu Leu Gln Glu
115 120 125

Gly Ala Arg Gln Lys Leu His Glu Leu Gln Glu Lys Leu Ser Pro Leu
130 135 140

Gly Glu Glu Met Arg Asp Arg Ala Arg Ala His Val Asp Ala Leu Arg
145 150 155 160

Thr His Leu Ala Pro Tyr Ser Asp Glu Leu Arg Gln Arg Leu Ala Ala
165 170 175

Arg Leu Glu Ala Leu Lys Glu Asn Gly Gly Ala Arg Leu Ala Glu Tyr
180 185 190

His Ala Lys Ala Thr Glu His Leu Ser Thr Leu Ser Glu Lys Ala Lys
195 200 205

Pro Ala Leu Glu Asp Leu Arg Gln Gly Leu Leu Pro Val Leu Glu Ser
210 215 220

Phe Lys Val Ser Phe Leu Ser Ala Leu Glu Glu Tyr Thr Lys Lys Leu
225 230 235 240

Asn Thr Gln

-continued

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Leu Glu Ser Ala Lys Val Ser Ala Leu Ser Ala Leu Glu Glu Ala Thr
1 5 10 15

Lys Lys

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Lys Lys Thr Ala Glu Glu Leu Ala Ser Leu Ala Ser Val Lys Ala Ser
1 5 10 15

Glu Leu

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 4

Lys Leu Ser Pro Leu
1 5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

Leu Ser Pro Leu
1

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Ser Pro Leu
1

<210> SEQ ID NO 7
<211> LENGTH: 4
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 7

Lys Leu Ser Pro
1


<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Pro
1


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Pro Ser Leu Lys
1               5


<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Pro Ser Leu
1


<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Pro Ser
1


<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Ser Leu Lys
1
```

-continued

```
<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Ser Leu
1


<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Glu Ser Phe Lys Val Ser Phe Leu Ser Ala Leu Glu Glu Tyr Thr
1               5                   10                  15

Lys Lys


<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Thr Tyr Glu Glu Leu Ala Ser Leu Phe Ser Val Lys Phe Ser
1               5                   10                  15

Glu Leu


<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Asn Thr Gln
1


<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Thr Gln
1


<210> SEQ ID NO 18
<211> LENGTH: 3
<212> TYPE: PRT
<213> ORGANISM: Artificial Sequence
```

-continued

<220> FEATURE:
<223> OTHER INFORMATION: Description of Artificial Sequence: Synthetic
peptide

<400> SEQUENCE: 18

Leu Asn Thr
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Gln Thr Asn Leu
1

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Thr Asn Leu
1

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Gln Thr Asn
1

<210> SEQ ID NO 22
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 23
<211> LENGTH: 41
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 23

Leu Glu Ser Ala Lys Val Ser Ala Leu Ser Ala Leu Glu Glu Ala Thr
1 5 10 15

Lys Lys Leu Ser Pro Leu Leu Leu Glu Ser Phe Lys Val Ser Phe Leu
20 25 30

Ser Ala Leu Glu Glu Tyr Thr Lys Lys
35 40

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Leu Glu Ser Ala Lys Val Ser Ala Leu Ser Ala Leu Glu Glu Ala Thr
1 5 10 15

Lys Lys Ser Pro Leu Leu Leu Glu Ser Phe Lys Val Ser Phe Leu Ser
20 25 30

Ala Leu Glu Glu Tyr Thr Lys Lys
35 40

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Leu Glu Ser Ala Lys Val Ser Ala Leu Ser Ala Leu Glu Glu Ala Thr
1 5 10 15

Lys Lys Pro Leu Leu Leu Glu Ser Phe Lys Val Ser Phe Leu Ser Ala
20 25 30

Leu Glu Glu Tyr Thr Lys Lys
35

<210> SEQ ID NO 26
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 27
<211> LENGTH: 40
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 27

Leu Glu Ser Ala Lys Val Ser Ala Leu Ser Ala Leu Glu Glu Ala Thr
1 5 10 15

Lys Lys Leu Ser Pro Leu Leu Glu Ser Phe Lys Val Ser Phe Leu Ser
20 25 30

Ala Leu Glu Glu Tyr Thr Lys Lys
35 40

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Leu Glu Ser Ala Lys Val Ser Ala Leu Ser Ala Leu Glu Glu Ala Thr
1 5 10 15

Lys Lys Ser Pro Leu Leu Glu Ser Phe Lys Val Ser Phe Leu Ser Ala
20 25 30

Leu Glu Glu Tyr Thr Lys Lys
35

<210> SEQ ID NO 29
<211> LENGTH: 42
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Leu Glu Ser Ala Lys Val Ser Ala Leu Ser Ala Leu Glu Glu Ala Thr
1 5 10 15

Lys Lys Leu Pro Ser Leu Lys Leu Leu Glu Ser Phe Lys Val Ser Phe
20 25 30

Leu Ser Ala Leu Glu Glu Tyr Thr Lys Lys
35 40

<210> SEQ ID NO 30
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Leu Glu Ser Ala Lys Val Ser Ala Leu Ser Ala Leu Glu Glu Ala Thr
1 5 10 15

Lys Lys Leu Pro Ser Leu Leu Leu Glu Ser Phe Lys Val Ser Phe Leu
20 25 30

Ser Ala Leu Glu Glu Tyr Thr Lys Lys
35 40

<210> SEQ ID NO 31
<211> LENGTH: 40
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 31

Leu Glu Ser Ala Lys Val Ser Ala Leu Ser Ala Leu Glu Glu Ala Thr
1 5 10 15

Lys Lys Leu Pro Ser Leu Leu Glu Ser Phe Lys Val Ser Phe Leu Ser
20 25 30

Ala Leu Glu Glu Tyr Thr Lys Lys
35 40

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Leu Glu Ser Ala Lys Val Ser Ala Leu Ser Ala Leu Glu Glu Ala Thr
1 5 10 15

Lys Lys Leu Pro Leu Leu Glu Ser Phe Lys Val Ser Phe Leu Ser Ala
20 25 30

Leu Glu Glu Tyr Thr Lys Lys
35

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Leu Glu Ser Ala Lys Val Ser Ala Leu Ser Ala Leu Glu Glu Ala Thr
1 5 10 15

Lys Lys Pro Ser Leu Lys Leu Leu Glu Ser Phe Lys Val Ser Phe Leu
20 25 30

Ser Ala Leu Glu Glu Tyr Thr Lys Lys
35 40

<210> SEQ ID NO 34
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Leu Glu Ser Ala Lys Val Ser Ala Leu Ser Ala Leu Glu Glu Ala Thr
1 5 10 15

Lys Lys Pro Ser Leu Leu Leu Glu Ser Phe Lys Val Ser Phe Leu Ser
20 25 30

Ala Leu Glu Glu Tyr Thr Lys Lys
35 40

<210> SEQ ID NO 35
<211> LENGTH: 39

-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Leu Glu Ser Ala Lys Val Ser Ala Leu Ser Ala Leu Glu Glu Ala Thr
1               5                   10                  15

Lys Lys Pro Ser Leu Leu Glu Ser Phe Lys Val Ser Phe Leu Ser Ala
            20                  25                  30

Leu Glu Glu Tyr Thr Lys Lys
        35
```

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Leu Glu Ser Ala Lys Val Ser Ala Leu Ser Ala Leu Glu Glu Ala Thr
1               5                   10                  15

Lys Lys Pro Leu Leu Glu Ser Phe Lys Val Ser Phe Leu Ser Ala Leu
            20                  25                  30

Glu Glu Tyr Thr Lys Lys
        35
```

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Leu Leu Glu Ser Phe Lys Val Ser Phe Leu Ser Ala Leu Glu Glu Tyr
1               5                   10                  15

Thr Lys Lys Lys Leu Ser Pro Leu Leu Glu Ser Ala Lys Val Ser Ala
            20                  25                  30

Leu Ser Ala Leu Glu Glu Ala Thr Lys Lys
        35                  40
```

<210> SEQ ID NO 38
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Leu Leu Glu Ser Phe Lys Val Ser Phe Leu Ser Ala Leu Glu Glu Tyr
1               5                   10                  15

Thr Lys Lys Leu Ser Pro Leu Leu Glu Ser Ala Lys Val Ser Ala Leu
            20                  25                  30

Ser Ala Leu Glu Glu Ala Thr Lys Lys
        35                  40
```

<210> SEQ ID NO 39

-continued

<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

```
Leu Leu Glu Ser Phe Lys Val Ser Phe Leu Ser Ala Leu Glu Glu Tyr
1               5                   10                  15

Thr Lys Lys Ser Pro Leu Leu Glu Ser Ala Lys Val Ser Ala Leu Ser
            20                  25                  30

Ala Leu Glu Glu Ala Thr Lys Lys
        35                  40
```

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

```
Leu Leu Glu Ser Phe Lys Val Ser Phe Leu Ser Ala Leu Glu Glu Tyr
1               5                   10                  15

Thr Lys Lys Pro Leu Leu Glu Ser Ala Lys Val Ser Ala Leu Ser Ala
            20                  25                  30

Leu Glu Glu Ala Thr Lys Lys
        35
```

<210> SEQ ID NO 41
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

```
Leu Leu Glu Ser Phe Lys Val Ser Phe Leu Ser Ala Leu Glu Glu Tyr
1               5                   10                  15

Thr Lys Lys Lys Leu Ser Pro Leu Glu Ser Ala Lys Val Ser Ala Leu
            20                  25                  30

Ser Ala Leu Glu Glu Ala Thr Lys Lys
        35                  40
```

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

```
Leu Leu Glu Ser Phe Lys Val Ser Phe Leu Ser Ala Leu Glu Glu Tyr
1               5                   10                  15

Thr Lys Lys Leu Ser Pro Leu Glu Ser Ala Lys Val Ser Ala Leu Ser
            20                  25                  30

Ala Leu Glu Glu Ala Thr Lys Lys
        35                  40
```

-continued

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Leu Leu Glu Ser Phe Lys Val Ser Phe Leu Ser Ala Leu Glu Glu Tyr
1               5                   10                  15

Thr Lys Lys Ser Pro Leu Glu Ser Ala Lys Val Ser Ala Leu Ser Ala
            20                  25                  30

Leu Glu Glu Ala Thr Lys Lys
        35
```

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Leu Leu Glu Ser Phe Lys Val Ser Phe Leu Ser Ala Leu Glu Glu Tyr
1               5                   10                  15

Thr Lys Lys Leu Pro Ser Leu Lys Leu Glu Ser Ala Lys Val Ser Ala
            20                  25                  30

Leu Ser Ala Leu Glu Glu Ala Thr Lys Lys
        35                  40
```

<210> SEQ ID NO 45
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

```
Leu Leu Glu Ser Phe Lys Val Ser Phe Leu Ser Ala Leu Glu Glu Tyr
1               5                   10                  15

Thr Lys Lys Leu Pro Ser Leu Leu Glu Ser Ala Lys Val Ser Ala Leu
            20                  25                  30

Ser Ala Leu Glu Glu Ala Thr Lys Lys
        35                  40
```

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

```
Leu Leu Glu Ser Phe Lys Val Ser Phe Leu Ser Ala Leu Glu Glu Tyr
1               5                   10                  15

Thr Lys Lys Leu Pro Ser Leu Glu Ser Ala Lys Val Ser Ala Leu Ser
            20                  25                  30

Ala Leu Glu Glu Ala Thr Lys Lys
        35                  40
```

-continued

<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Leu Leu Glu Ser Phe Lys Val Ser Phe Leu Ser Ala Leu Glu Glu Tyr
1 5 10 15

Thr Lys Lys Leu Pro Leu Glu Ser Ala Lys Val Ser Ala Leu Ser Ala
20 25 30

Leu Glu Glu Ala Thr Lys Lys
35

<210> SEQ ID NO 48
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Leu Leu Glu Ser Phe Lys Val Ser Phe Leu Ser Ala Leu Glu Glu Tyr
1 5 10 15

Thr Lys Lys Pro Ser Leu Lys Leu Glu Ser Ala Lys Val Ser Ala Leu
20 25 30

Ser Ala Leu Glu Glu Ala Thr Lys Lys
35 40

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Leu Leu Glu Ser Phe Lys Val Ser Phe Leu Ser Ala Leu Glu Glu Tyr
1 5 10 15

Thr Lys Lys Pro Ser Leu Leu Glu Ser Ala Lys Val Ser Ala Leu Ser
20 25 30

Ala Leu Glu Glu Ala Thr Lys Lys
35 40

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Leu Leu Glu Ser Phe Lys Val Ser Phe Leu Ser Ala Leu Glu Glu Tyr
1 5 10 15

Thr Lys Lys Pro Ser Leu Glu Ser Ala Lys Val Ser Ala Leu Ser Ala
20 25 30

Leu Glu Glu Ala Thr Lys Lys
35

-continued

<210> SEQ ID NO 51
<211> LENGTH: 38
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

```
Leu Leu Glu Ser Phe Lys Val Ser Phe Leu Ser Ala Leu Glu Glu Tyr
1               5                   10                  15

Thr Lys Lys Pro Leu Glu Ser Ala Lys Val Ser Ala Leu Ser Ala Leu
            20                  25                  30

Glu Glu Ala Thr Lys Lys
        35
```

<210> SEQ ID NO 52
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

```
Lys Lys Thr Ala Glu Glu Leu Ala Ser Leu Ala Ser Val Lys Ala Ser
1               5                   10                  15

Glu Leu Lys Leu Ser Pro Leu Lys Lys Thr Tyr Glu Glu Leu Ala Ser
            20                  25                  30

Leu Phe Ser Val Lys Phe Ser Glu Leu
        35                  40
```

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

```
Lys Lys Thr Ala Glu Glu Leu Ala Ser Leu Ala Ser Val Lys Ala Ser
1               5                   10                  15

Glu Leu Leu Ser Pro Leu Lys Lys Thr Tyr Glu Glu Leu Ala Ser Leu
            20                  25                  30

Phe Ser Val Lys Phe Ser Glu Leu
        35                  40
```

<210> SEQ ID NO 54
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

```
Lys Lys Thr Ala Glu Glu Leu Ala Ser Leu Ala Ser Val Lys Ala Ser
1               5                   10                  15

Glu Leu Ser Pro Leu Lys Lys Thr Tyr Glu Glu Leu Ala Ser Leu Phe
            20                  25                  30
```

```
Ser Val Lys Phe Ser Glu Leu
        35


<210> SEQ ID NO 55
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Lys Thr Ala Glu Glu Leu Ala Ser Leu Ala Ser Val Lys Ala Ser
1               5                   10                  15

Glu Leu Pro Leu Lys Lys Thr Tyr Glu Glu Leu Ala Ser Leu Phe Ser
            20                  25                  30

Val Lys Phe Ser Glu Leu
        35


<210> SEQ ID NO 56
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Lys Thr Ala Glu Glu Leu Ala Ser Leu Ala Ser Val Lys Ala Ser
1               5                   10                  15

Glu Leu Lys Leu Ser Pro Lys Lys Thr Tyr Glu Glu Leu Ala Ser Leu
            20                  25                  30

Phe Ser Val Lys Phe Ser Glu Leu
        35                  40


<210> SEQ ID NO 57
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Lys Thr Ala Glu Glu Leu Ala Ser Leu Ala Ser Val Lys Ala Ser
1               5                   10                  15

Glu Leu Leu Ser Pro Lys Lys Thr Tyr Glu Glu Leu Ala Ser Leu Phe
            20                  25                  30

Ser Val Lys Phe Ser Glu Leu
        35


<210> SEQ ID NO 58
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Lys Thr Ala Glu Glu Leu Ala Ser Leu Ala Ser Val Lys Ala Ser
1               5                   10                  15

Glu Leu Ser Pro Lys Lys Thr Tyr Glu Glu Leu Ala Ser Leu Phe Ser
```

-continued

```
            20                  25                  30

Val Lys Phe Ser Glu Leu
        35


<210> SEQ ID NO 59
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Lys Thr Ala Glu Glu Leu Ala Ser Leu Ala Ser Val Lys Ala Ser
1               5                   10                  15

Glu Leu Leu Pro Ser Leu Lys Lys Lys Thr Tyr Glu Glu Leu Ala Ser
            20                  25                  30

Leu Phe Ser Val Lys Phe Ser Glu Leu
        35                  40


<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Lys Thr Ala Glu Glu Leu Ala Ser Leu Ala Ser Val Lys Ala Ser
1               5                   10                  15

Glu Leu Leu Pro Ser Leu Lys Lys Thr Tyr Glu Glu Leu Ala Ser Leu
            20                  25                  30

Phe Ser Val Lys Phe Ser Glu Leu
        35                  40


<210> SEQ ID NO 61
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Lys Thr Ala Glu Glu Leu Ala Ser Leu Ala Ser Val Lys Ala Ser
1               5                   10                  15

Glu Leu Leu Pro Ser Lys Lys Thr Tyr Glu Glu Leu Ala Ser Leu Phe
            20                  25                  30

Ser Val Lys Phe Ser Glu Leu
        35


<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Lys Thr Ala Glu Glu Leu Ala Ser Leu Ala Ser Val Lys Ala Ser
1               5                   10                  15
```

-continued

```
Glu Leu Leu Pro Lys Lys Thr Tyr Glu Glu Leu Ala Ser Leu Phe Ser
            20                  25                  30

Val Lys Phe Ser Glu Leu
        35
```

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

```
Lys Lys Thr Ala Glu Glu Leu Ala Ser Leu Ala Ser Val Lys Ala Ser
1               5                   10                  15

Glu Leu Pro Ser Leu Lys Lys Lys Thr Tyr Glu Glu Leu Ala Ser Leu
            20                  25                  30

Phe Ser Val Lys Phe Ser Glu Leu
        35                  40
```

<210> SEQ ID NO 64
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

```
Lys Lys Thr Ala Glu Glu Leu Ala Ser Leu Ala Ser Val Lys Ala Ser
1               5                   10                  15

Glu Leu Pro Ser Leu Lys Lys Thr Tyr Glu Glu Leu Ala Ser Leu Phe
            20                  25                  30

Ser Val Lys Phe Ser Glu Leu
        35
```

<210> SEQ ID NO 65
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

```
Lys Lys Thr Ala Glu Glu Leu Ala Ser Leu Ala Ser Val Lys Ala Ser
1               5                   10                  15

Glu Leu Pro Ser Lys Lys Thr Tyr Glu Glu Leu Ala Ser Leu Phe Ser
            20                  25                  30

Val Lys Phe Ser Glu Leu
        35
```

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

```
Lys Lys Thr Ala Glu Glu Leu Ala Ser Leu Ala Ser Val Lys Ala Ser
1               5                   10                  15
```

-continued

Glu Leu Pro Lys Lys Thr Tyr Glu Glu Leu Ala Ser Leu Phe Ser Val
            20                  25                  30

Lys Phe Ser Glu Leu
        35

<210> SEQ ID NO 67
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Lys Thr Tyr Glu Glu Leu Ala Ser Leu Phe Ser Val Lys Phe Ser
1               5                   10                  15

Glu Leu Lys Leu Ser Pro Leu Lys Lys Thr Ala Glu Glu Leu Ala Ser
            20                  25                  30

Leu Ala Ser Val Lys Ala Ser Glu Leu
        35                  40

<210> SEQ ID NO 68
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Lys Thr Tyr Glu Glu Leu Ala Ser Leu Phe Ser Val Lys Phe Ser
1               5                   10                  15

Glu Leu Leu Ser Pro Leu Lys Lys Thr Ala Glu Glu Leu Ala Ser Leu
            20                  25                  30

Ala Ser Val Lys Ala Ser Glu Leu
        35                  40

<210> SEQ ID NO 69
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Lys Thr Tyr Glu Glu Leu Ala Ser Leu Phe Ser Val Lys Phe Ser
1               5                   10                  15

Glu Leu Ser Pro Leu Lys Lys Thr Ala Glu Glu Leu Ala Ser Leu Ala
            20                  25                  30

Ser Val Lys Ala Ser Glu Leu
        35

<210> SEQ ID NO 70
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Lys Thr Tyr Glu Glu Leu Ala Ser Leu Phe Ser Val Lys Phe Ser

-continued

```
1               5                   10                  15

Glu Leu Pro Leu Lys Lys Thr Ala Glu Glu Leu Ala Ser Leu Ala Ser
            20                  25                  30

Val Lys Ala Ser Glu Leu
        35
```

<210> SEQ ID NO 71
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

```
Lys Lys Thr Tyr Glu Glu Leu Ala Ser Leu Phe Ser Val Lys Phe Ser
1               5                   10                  15

Glu Leu Lys Leu Ser Pro Lys Lys Thr Ala Glu Glu Leu Ala Ser Leu
            20                  25                  30

Ala Ser Val Lys Ala Ser Glu Leu
        35                  40
```

<210> SEQ ID NO 72
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

```
Lys Lys Thr Tyr Glu Glu Leu Ala Ser Leu Phe Ser Val Lys Phe Ser
1               5                   10                  15

Glu Leu Leu Ser Pro Lys Lys Thr Ala Glu Glu Leu Ala Ser Leu Ala
            20                  25                  30

Ser Val Lys Ala Ser Glu Leu
        35
```

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Lys Lys Thr Tyr Glu Glu Leu Ala Ser Leu Phe Ser Val Lys Phe Ser
1               5                   10                  15

Glu Leu Ser Pro Lys Lys Thr Ala Glu Glu Leu Ala Ser Leu Ala Ser
            20                  25                  30

Val Lys Ala Ser Glu Leu
        35
```

<210> SEQ ID NO 74
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

-continued

```
Lys Lys Thr Tyr Glu Glu Leu Ala Ser Leu Phe Ser Val Lys Phe Ser
1               5                   10                  15

Glu Leu Leu Pro Ser Leu Lys Lys Lys Thr Ala Glu Glu Leu Ala Ser
            20                  25                  30

Leu Ala Ser Val Lys Ala Ser Glu Leu
        35                  40


<210> SEQ ID NO 75
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Lys Thr Tyr Glu Glu Leu Ala Ser Leu Phe Ser Val Lys Phe Ser
1               5                   10                  15

Glu Leu Leu Pro Ser Leu Lys Lys Thr Ala Glu Glu Leu Ala Ser Leu
            20                  25                  30

Ala Ser Val Lys Ala Ser Glu Leu
        35                  40


<210> SEQ ID NO 76
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Lys Thr Tyr Glu Glu Leu Ala Ser Leu Phe Ser Val Lys Phe Ser
1               5                   10                  15

Glu Leu Leu Pro Ser Lys Lys Thr Ala Glu Glu Leu Ala Ser Leu Ala
            20                  25                  30

Ser Val Lys Ala Ser Glu Leu
        35


<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Lys Thr Tyr Glu Glu Leu Ala Ser Leu Phe Ser Val Lys Phe Ser
1               5                   10                  15

Glu Leu Leu Pro Lys Lys Thr Ala Glu Glu Leu Ala Ser Leu Ala Ser
            20                  25                  30

Val Lys Ala Ser Glu Leu
        35


<210> SEQ ID NO 78
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Lys Lys Thr Tyr Glu Glu Leu Ala Ser Leu Phe Ser Val Lys Phe Ser
1               5                   10                  15

Glu Leu Pro Ser Leu Lys Lys Lys Thr Ala Glu Glu Leu Ala Ser Leu
            20                  25                  30

Ala Ser Val Lys Ala Ser Glu Leu
        35                  40


<210> SEQ ID NO 79
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Lys Thr Tyr Glu Glu Leu Ala Ser Leu Phe Ser Val Lys Phe Ser
1               5                   10                  15

Glu Leu Pro Ser Leu Lys Lys Thr Ala Glu Glu Leu Ala Ser Leu Ala
            20                  25                  30

Ser Val Lys Ala Ser Glu Leu
        35


<210> SEQ ID NO 80
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Lys Lys Thr Tyr Glu Glu Leu Ala Ser Leu Phe Ser Val Lys Phe Ser
1               5                   10                  15

Glu Leu Pro Ser Lys Lys Thr Ala Glu Glu Leu Ala Ser Leu Ala Ser
            20                  25                  30

Val Lys Ala Ser Glu Leu
        35


<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Lys Thr Tyr Glu Glu Leu Ala Ser Leu Phe Ser Val Lys Phe Ser
1               5                   10                  15

Glu Leu Pro Lys Lys Thr Ala Glu Glu Leu Ala Ser Leu Ala Ser Val
            20                  25                  30

Lys Ala Ser Glu Leu
        35


<210> SEQ ID NO 82
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 82

Lys Lys Thr Ala Glu Glu Leu Ala Ser Leu Ala Ser Val Lys Ala Ser
1 5 10 15

Glu Leu Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Lys Lys Thr Ala Glu Glu Leu Ala Ser Leu Ala Ser Val Lys Ala Ser
1 5 10 15

Glu Leu Leu Ser Pro Leu
20

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Lys Lys Thr Ala Glu Glu Leu Ala Ser Leu Ala Ser Val Lys Ala Ser
1 5 10 15

Glu Leu Ser Pro Leu Leu Glu Ser Phe Lys Val Ser Phe Leu Ser Ala
20 25 30

Leu Glu Glu Tyr Thr Lys Lys
35

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Lys Lys Thr Ala Glu Glu Leu Ala Ser Leu Ala Ser Val Lys Ala Ser
1 5 10 15

Glu Leu Pro Leu
20

<210> SEQ ID NO 86
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Lys Lys Thr Ala Glu Glu Leu Ala Ser Leu Ala Ser Val Lys Ala Ser
1 5 10 15

-continued

Glu Leu Lys Leu Ser Pro Leu Glu Ser Phe Lys Val Ser Phe Leu Ser
20 25 30

Ala Leu Glu Glu Tyr Thr Lys Lys
35 40

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Lys Lys Thr Ala Glu Glu Leu Ala Ser Leu Ala Ser Val Lys Ala Ser
1 5 10 15

Glu Leu Leu Ser Pro Leu Glu Ser Phe Lys Val Ser Phe Leu Ser Ala
20 25 30

Leu Glu Glu Tyr Thr Lys Lys
35

<210> SEQ ID NO 88
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Lys Lys Thr Ala Glu Glu Leu Ala Ser Leu Ala Ser Val Lys Ala Ser
1 5 10 15

Glu Leu Ser Pro Leu Glu Ser Phe Lys Val Ser Phe Leu Ser Ala Leu
20 25 30

Glu Glu Tyr Thr Lys Lys
35

<210> SEQ ID NO 89
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Lys Lys Thr Ala Glu Glu Leu Ala Ser Leu Ala Ser Val Lys Ala Ser
1 5 10 15

Glu Leu Leu Pro Ser Leu Lys Leu Glu Ser Phe Lys Val Ser Phe Leu
20 25 30

Ser Ala Leu Glu Glu Tyr Thr Lys Lys
35 40

<210> SEQ ID NO 90
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Lys Lys Thr Ala Glu Glu Leu Ala Ser Leu Ala Ser Val Lys Ala Ser
1 5 10 15

-continued

```
Glu Leu Leu Pro Ser Leu Leu Glu Ser Phe Lys Val Ser Phe Leu Ser
            20                  25                  30

Ala Leu Glu Glu Tyr Thr Lys Lys
        35                  40


<210> SEQ ID NO 91
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Lys Thr Ala Glu Glu Leu Ala Ser Leu Ala Ser Val Lys Ala Ser
1               5                   10                  15

Glu Leu Leu Pro Ser Leu Glu Ser Phe Lys Val Ser Phe Leu Ser Ala
            20                  25                  30

Leu Glu Glu Tyr Thr Lys Lys
        35


<210> SEQ ID NO 92
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Lys Thr Ala Glu Glu Leu Ala Ser Leu Ala Ser Val Lys Ala Ser
1               5                   10                  15

Glu Leu Leu Pro Leu Glu Ser Phe Lys Val Ser Phe Leu Ser Ala Leu
            20                  25                  30

Glu Glu Tyr Thr Lys Lys
        35


<210> SEQ ID NO 93
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Lys Thr Ala Glu Glu Leu Ala Ser Leu Ala Ser Val Lys Ala Ser
1               5                   10                  15

Glu Leu Pro Ser Leu Lys Leu Glu Ser Phe Lys Val Ser Phe Leu Ser
            20                  25                  30

Ala Leu Glu Glu Tyr Thr Lys Lys
        35                  40


<210> SEQ ID NO 94
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Lys Lys Thr Ala Glu Glu Leu Ala Ser Leu Ala Ser Val Lys Ala Ser
```

-continued 1 5 10 15

Glu Leu Pro Ser Leu Leu Glu Ser Phe Lys Val Ser Phe Leu Ser Ala
20 25 30

Leu Glu Glu Tyr Thr Lys Lys
35

<210> SEQ ID NO 95
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Lys Lys Thr Ala Glu Glu Leu Ala Ser Leu Ala Ser Val Lys Ala Ser
1 5 10 15

Glu Leu Pro Ser Leu Glu Ser Phe Lys Val Ser Phe Leu Ser Ala Leu
20 25 30

Glu Glu Tyr Thr Lys Lys
35

<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Lys Lys Thr Ala Glu Glu Leu Ala Ser Leu Ala Ser Val Lys Ala Ser
1 5 10 15

Glu Leu Pro Leu Glu Ser Phe Lys Val Ser Phe Leu Ser Ala Leu Glu
20 25 30

Glu Tyr Thr Lys Lys
35

<210> SEQ ID NO 97
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Leu Glu Ser Ala Lys Val Ser Ala Leu Ser Ala Leu Glu Glu Ala Thr
1 5 10 15

Lys Lys Lys Leu Ser Pro Leu Lys Lys Thr Tyr Glu Glu Leu Ala Ser
20 25 30

Leu Phe Ser Val Lys Phe Ser Glu Leu
35 40

<210> SEQ ID NO 98
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

-continued

```
Leu Glu Ser Ala Lys Val Ser Ala Leu Ser Ala Leu Glu Glu Ala Thr
1               5                   10                  15

Lys Lys Leu Ser Pro Leu Lys Lys Thr Tyr Glu Glu Leu Ala Ser Leu
            20                  25                  30

Phe Ser Val Lys Phe Ser Glu Leu
        35                  40


<210> SEQ ID NO 99
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Glu Ser Ala Lys Val Ser Ala Leu Ser Ala Leu Glu Glu Ala Thr
1               5                   10                  15

Lys Lys Ser Pro Leu Lys Lys Thr Tyr Glu Glu Leu Ala Ser Leu Phe
            20                  25                  30

Ser Val Lys Phe Ser Glu Leu
        35


<210> SEQ ID NO 100
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Glu Ser Ala Lys Val Ser Ala Leu Ser Ala Leu Glu Glu Ala Thr
1               5                   10                  15

Lys Lys Pro Leu Lys Lys Thr Tyr Glu Glu Leu Ala Ser Leu Phe Ser
            20                  25                  30

Val Lys Phe Ser Glu Leu
        35


<210> SEQ ID NO 101
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Glu Ser Ala Lys Val Ser Ala Leu Ser Ala Leu Glu Glu Ala Thr
1               5                   10                  15

Lys Lys Lys Leu Ser Pro Lys Lys Thr Tyr Glu Glu Leu Ala Ser Leu
            20                  25                  30

Phe Ser Val Lys Phe Ser Glu Leu
        35                  40


<210> SEQ ID NO 102
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

-continued

```
Leu Glu Ser Ala Lys Val Ser Ala Leu Ser Ala Leu Glu Glu Ala Thr
1               5                   10                  15

Lys Lys Leu Ser Pro Lys Lys Thr Tyr Glu Glu Leu Ala Ser Leu Phe
            20                  25                  30

Ser Val Lys Phe Ser Glu Leu
        35


<210> SEQ ID NO 103
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Glu Ser Ala Lys Val Ser Ala Leu Ser Ala Leu Glu Glu Ala Thr
1               5                   10                  15

Lys Lys Ser Pro Lys Lys Thr Tyr Glu Glu Leu Ala Ser Leu Phe Ser
            20                  25                  30

Val Lys Phe Ser Glu Leu
        35


<210> SEQ ID NO 104
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Glu Ser Ala Lys Val Ser Ala Leu Ser Ala Leu Glu Glu Ala Thr
1               5                   10                  15

Lys Lys Leu Pro Ser Leu Lys Lys Lys Thr Tyr Glu Glu Leu Ala Ser
            20                  25                  30

Leu Phe Ser Val Lys Phe Ser Glu Leu
        35                  40


<210> SEQ ID NO 105
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Glu Ser Ala Lys Val Ser Ala Leu Ser Ala Leu Glu Glu Ala Thr
1               5                   10                  15

Lys Lys Leu Pro Ser Leu Lys Lys Thr Tyr Glu Glu Leu Ala Ser Leu
            20                  25                  30

Phe Ser Val Lys Phe Ser Glu Leu
        35                  40


<210> SEQ ID NO 106
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 106

Leu Glu Ser Ala Lys Val Ser Ala Leu Ser Ala Leu Glu Glu Ala Thr
1 5 10 15

Lys Lys Leu Pro Ser Lys Lys Thr Tyr Glu Glu Leu Ala Ser Leu Phe
20 25 30

Ser Val Lys Phe Ser Glu Leu
35

<210> SEQ ID NO 107
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Leu Glu Ser Ala Lys Val Ser Ala Leu Ser Ala Leu Glu Glu Ala Thr
1 5 10 15

Lys Lys Leu Pro Lys Lys Thr Tyr Glu Glu Leu Ala Ser Leu Phe Ser
20 25 30

Val Lys Phe Ser Glu Leu
35

<210> SEQ ID NO 108
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Leu Glu Ser Ala Lys Val Ser Ala Leu Ser Ala Leu Glu Glu Ala Thr
1 5 10 15

Lys Lys Pro Ser Leu Lys Lys Lys Thr Tyr Glu Glu Leu Ala Ser Leu
20 25 30

Phe Ser Val Lys Phe Ser Glu Leu
35 40

<210> SEQ ID NO 109
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Leu Glu Ser Ala Lys Val Ser Ala Leu Ser Ala Leu Glu Glu Ala Thr
1 5 10 15

Lys Lys Pro Ser Leu Lys Lys Thr Tyr Glu Glu Leu Ala Ser Leu Phe
20 25 30

Ser Val Lys Phe Ser Glu Leu
35

<210> SEQ ID NO 110
<211> LENGTH: 38
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 110

Leu Glu Ser Ala Lys Val Ser Ala Leu Ser Ala Leu Glu Glu Ala Thr
1 5 10 15

Lys Lys Pro Ser Lys Lys Thr Tyr Glu Glu Leu Ala Ser Leu Phe Ser
20 25 30

Val Lys Phe Ser Glu Leu
35

<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Leu Glu Ser Ala Lys Val Ser Ala Leu Ser Ala Leu Glu Glu Ala Thr
1 5 10 15

Lys Lys Pro Lys Lys Thr Tyr Glu Glu Leu Ala Ser Leu Phe Ser Val
20 25 30

Lys Phe Ser Glu Leu
35

<210> SEQ ID NO 112
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Leu Glu Ser Phe Lys Val Ser Phe Leu Ser Ala Leu Glu Glu Tyr Thr
1 5 10 15

Lys Lys Lys Leu Ser Pro Leu Lys Lys Thr Ala Glu Glu Leu Ala Ser
20 25 30

Leu Ala Ser Val Lys Ala Ser Glu Leu
35 40

<210> SEQ ID NO 113
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Leu Glu Ser Phe Lys Val Ser Phe Leu Ser Ala Leu Glu Glu Tyr Thr
1 5 10 15

Lys Lys Leu Ser Pro Leu Lys Lys Thr Ala Glu Glu Leu Ala Ser Leu
20 25 30

Ala Ser Val Lys Ala Ser Glu Leu
35 40

<210> SEQ ID NO 114
<211> LENGTH: 39
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 114

```
Leu Glu Ser Phe Lys Val Ser Phe Leu Ser Ala Leu Glu Glu Tyr Thr
1               5                   10                  15

Lys Lys Ser Pro Leu Lys Lys Thr Ala Glu Glu Leu Ala Ser Leu Ala
            20                  25                  30

Ser Val Lys Ala Ser Glu Leu
        35
```

<210> SEQ ID NO 115
<211> LENGTH: 38
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

```
Leu Glu Ser Phe Lys Val Ser Phe Leu Ser Ala Leu Glu Glu Tyr Thr
1               5                   10                  15

Lys Lys Pro Leu Lys Lys Thr Ala Glu Glu Leu Ala Ser Leu Ala Ser
            20                  25                  30

Val Lys Ala Ser Glu Leu
        35
```

<210> SEQ ID NO 116
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

```
Leu Glu Ser Phe Lys Val Ser Phe Leu Ser Ala Leu Glu Glu Tyr Thr
1               5                   10                  15

Lys Lys Lys Leu Ser Pro Lys Lys Thr Ala Glu Glu Leu Ala Ser Leu
            20                  25                  30

Ala Ser Val Lys Ala Ser Glu Leu
        35                  40
```

<210> SEQ ID NO 117
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

```
Leu Glu Ser Phe Lys Val Ser Phe Leu Ser Ala Leu Glu Glu Tyr Thr
1               5                   10                  15

Lys Lys Leu Ser Pro Lys Lys Thr Ala Glu Glu Leu Ala Ser Leu Ala
            20                  25                  30

Ser Val Lys Ala Ser Glu Leu
        35
```

<210> SEQ ID NO 118
<211> LENGTH: 38
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 118

Leu Glu Ser Phe Lys Val Ser Phe Leu Ser Ala Leu Glu Glu Tyr Thr
1 5 10 15

Lys Lys Ser Pro Lys Lys Thr Ala Glu Glu Leu Ala Ser Leu Ala Ser
20 25 30

Val Lys Ala Ser Glu Leu
35

<210> SEQ ID NO 119
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Leu Glu Ser Phe Lys Val Ser Phe Leu Ser Ala Leu Glu Glu Tyr Thr
1 5 10 15

Lys Lys Leu Pro Ser Leu Lys Lys Lys Thr Ala Glu Glu Leu Ala Ser
20 25 30

Leu Ala Ser Val Lys Ala Ser Glu Leu
35 40

<210> SEQ ID NO 120
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Leu Glu Ser Phe Lys Val Ser Phe Leu Ser Ala Leu Glu Glu Tyr Thr
1 5 10 15

Lys Lys Leu Pro Ser Leu Lys Lys Thr Ala Glu Glu Leu Ala Ser Leu
20 25 30

Ala Ser Val Lys Ala Ser Glu Leu
35 40

<210> SEQ ID NO 121
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Leu Glu Ser Phe Lys Val Ser Phe Leu Ser Ala Leu Glu Glu Tyr Thr
1 5 10 15

Lys Lys Leu Pro Ser Lys Lys Thr Ala Glu Glu Leu Ala Ser Leu Ala
20 25 30

Ser Val Lys Ala Ser Glu Leu
35

<210> SEQ ID NO 122
<211> LENGTH: 38

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Leu Glu Ser Phe Lys Val Ser Phe Leu Ser Ala Leu Glu Glu Tyr Thr
1 5 10 15

Lys Lys Leu Pro Lys Lys Thr Ala Glu Glu Leu Ala Ser Leu Ala Ser
20 25 30

Val Lys Ala Ser Glu Leu
35

<210> SEQ ID NO 123
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Leu Glu Ser Phe Lys Val Ser Phe Leu Ser Ala Leu Glu Glu Tyr Thr
1 5 10 15

Lys Lys Pro Ser Leu Lys Lys Lys Thr Ala Glu Glu Leu Ala Ser Leu
20 25 30

Ala Ser Val Lys Ala Ser Glu Leu
35 40

<210> SEQ ID NO 124
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Leu Glu Ser Phe Lys Val Ser Phe Leu Ser Ala Leu Glu Glu Tyr Thr
1 5 10 15

Lys Lys Pro Ser Leu Lys Lys Thr Ala Glu Glu Leu Ala Ser Leu Ala
20 25 30

Ser Val Lys Ala Ser Glu Leu
35

<210> SEQ ID NO 125
<211> LENGTH: 38
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Leu Glu Ser Phe Lys Val Ser Phe Leu Ser Ala Leu Glu Glu Tyr Thr
1 5 10 15

Lys Lys Pro Ser Lys Lys Thr Ala Glu Glu Leu Ala Ser Leu Ala Ser
20 25 30

Val Lys Ala Ser Glu Leu
35

<210> SEQ ID NO 126

-continued

```
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Glu Ser Phe Lys Val Ser Phe Leu Ser Ala Leu Glu Glu Tyr Thr
1               5                   10                  15

Lys Lys Pro Lys Lys Thr Ala Glu Glu Leu Ala Ser Leu Ala Ser Val
            20                  25                  30

Lys Ala Ser Glu Leu
        35


<210> SEQ ID NO 127
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Lys Lys Thr Tyr Glu Glu Leu Ala Ser Leu Phe Ser Val Lys Phe Ser
1               5                   10                  15

Glu Leu Lys Leu Ser Pro Leu Leu Glu Ser Ala Lys Val Ser Ala Leu
            20                  25                  30

Ser Ala Leu Glu Glu Ala Thr Lys Lys
        35                  40


<210> SEQ ID NO 128
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Lys Thr Tyr Glu Glu Leu Ala Ser Leu Phe Ser Val Lys Phe Ser
1               5                   10                  15

Glu Leu Leu Ser Pro Leu
            20


<210> SEQ ID NO 129
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Lys Lys Thr Tyr Glu Glu Leu Ala Ser Leu Phe Ser Val Lys Phe Ser
1               5                   10                  15

Glu Leu Ser Pro Leu Leu Glu Ser Ala Lys Val Ser Ala Leu Ser Ala
            20                  25                  30

Leu Glu Glu Ala Thr Lys Lys
        35


<210> SEQ ID NO 130
<211> LENGTH: 38
<212> TYPE: PRT
```

-continued

<213> ORGANISM: Artificial Sequence
<220> FEATURE:
<223> OTHER INFORMATION: Description of Artificial Sequence: Synthetic peptide

<400> SEQUENCE: 130

```
Lys Lys Thr Tyr Glu Glu Leu Ala Ser Leu Phe Ser Val Lys Phe Ser
1               5                   10                  15

Glu Leu Pro Leu Leu Glu Ser Ala Lys Val Ser Ala Leu Ser Ala Leu
            20                  25                  30

Glu Glu Ala Thr Lys Lys
        35
```

<210> SEQ ID NO 131
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

```
Lys Lys Thr Tyr Glu Glu Leu Ala Ser Leu Phe Ser Val Lys Phe Ser
1               5                   10                  15

Glu Leu Lys Leu Ser Pro Leu Glu Ser Ala Lys Val Ser Ala Leu Ser
            20                  25                  30

Ala Leu Glu Glu Ala Thr Lys Lys
        35                  40
```

<210> SEQ ID NO 132
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

```
Lys Lys Thr Tyr Glu Glu Leu Ala Ser Leu Phe Ser Val Lys Phe Ser
1               5                   10                  15

Glu Leu Leu Ser Pro Leu Glu Ser Ala Lys Val Ser Ala Leu Ser Ala
            20                  25                  30

Leu Glu Glu Ala Thr Lys Lys
        35
```

<210> SEQ ID NO 133
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

```
Lys Lys Thr Tyr Glu Glu Leu Ala Ser Leu Phe Ser Val Lys Phe Ser
1               5                   10                  15

Glu Leu Ser Pro Leu Glu Ser Ala Lys Val Ser Ala Leu Ser Ala Leu
            20                  25                  30

Glu Glu Ala Thr Lys Lys
        35
```

<210> SEQ ID NO 134
<211> LENGTH: 41

-continued

<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

```
Lys Lys Thr Tyr Glu Glu Leu Ala Ser Leu Phe Ser Val Lys Phe Ser
1               5                   10                  15

Glu Leu Leu Pro Ser Leu Lys Leu Glu Ser Ala Lys Val Ser Ala Leu
            20                  25                  30

Ser Ala Leu Glu Glu Ala Thr Lys Lys
        35                  40
```

<210> SEQ ID NO 135
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

```
Lys Lys Thr Tyr Glu Glu Leu Ala Ser Leu Phe Ser Val Lys Phe Ser
1               5                   10                  15

Glu Leu Leu Pro Ser Leu Leu Glu Ser Ala Lys Val Ser Ala Leu Ser
            20                  25                  30

Ala Leu Glu Glu Ala Thr Lys Lys
        35                  40
```

<210> SEQ ID NO 136
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

```
Lys Lys Thr Tyr Glu Glu Leu Ala Ser Leu Phe Ser Val Lys Phe Ser
1               5                   10                  15

Glu Leu Leu Pro Ser Leu Glu Ser Ala Lys Val Ser Ala Leu Ser Ala
            20                  25                  30

Leu Glu Glu Ala Thr Lys Lys
        35
```

<210> SEQ ID NO 137
<211> LENGTH: 38
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

```
Lys Lys Thr Tyr Glu Glu Leu Ala Ser Leu Phe Ser Val Lys Phe Ser
1               5                   10                  15

Glu Leu Leu Pro Leu Glu Ser Ala Lys Val Ser Ala Leu Ser Ala Leu
            20                  25                  30

Glu Glu Ala Thr Lys Lys
        35
```

<210> SEQ ID NO 138

-continued

```
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Lys Thr Tyr Glu Glu Leu Ala Ser Leu Phe Ser Val Lys Phe Ser
1               5                   10                  15

Glu Leu Pro Ser Leu Lys Leu Glu Ser Ala Lys Val Ser Ala Leu Ser
            20                  25                  30

Ala Leu Glu Glu Ala Thr Lys Lys
        35                  40


<210> SEQ ID NO 139
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Lys Thr Tyr Glu Glu Leu Ala Ser Leu Phe Ser Val Lys Phe Ser
1               5                   10                  15

Glu Leu Pro Ser Leu Leu Glu Ser Ala Lys Val Ser Ala Leu Ser Ala
            20                  25                  30

Leu Glu Glu Ala Thr Lys Lys
        35


<210> SEQ ID NO 140
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Lys Lys Thr Tyr Glu Glu Leu Ala Ser Leu Phe Ser Val Lys Phe Ser
1               5                   10                  15

Glu Leu Pro Ser Leu Glu Ser Ala Lys Val Ser Ala Leu Ser Ala Leu
            20                  25                  30

Glu Glu Ala Thr Lys Lys
        35


<210> SEQ ID NO 141
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Lys Lys Thr Tyr Glu Glu Leu Ala Ser Leu Phe Ser Val Lys Phe Ser
1               5                   10                  15

Glu Leu Pro Leu Glu Ser Ala Lys Val Ser Ala Leu Ser Ala Leu Glu
            20                  25                  30

Glu Ala Thr Lys Lys
        35
```

-continued

<210> SEQ ID NO 142
<211> LENGTH: 48
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 143
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

```
Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

<210> SEQ ID NO 144
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

```
Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 145
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr Gln
        35                  40                  45
```

<210> SEQ ID NO 146
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Ser Pro Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

<210> SEQ ID NO 147
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Ser Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 148
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Pro Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 149
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Leu Pro Ser Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 150
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

```
Pro Ser Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

<210> SEQ ID NO 151
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

```
Leu Pro Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

<210> SEQ ID NO 152
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Asn Thr Gln
        35                  40                  45
```

<210> SEQ ID NO 153
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Thr Gln
```

-continued 35 40 45

<210> SEQ ID NO 154
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Gln
35 40 45

<210> SEQ ID NO 155
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys
35 40

<210> SEQ ID NO 156
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Leu Asn Thr
35 40 45

<210> SEQ ID NO 157
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

-continued

```
Ser Phe Leu Ser Ala Leu Glu Glu Tyr Thr Lys Lys Leu Asn
        35                  40                  45


<210> SEQ ID NO 158
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu
        35                  40                  45


<210> SEQ ID NO 159
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Gln Thr Asn Leu
        35                  40                  45


<210> SEQ ID NO 160
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Thr Asn Leu
        35                  40                  45


<210> SEQ ID NO 161
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30
```

-continued

```
Ser Phe Leu Ser Ala Leu Glu Glu Tyr Thr Lys Lys Asn Leu
        35                  40                  45


<210> SEQ ID NO 162
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Gln Thr Asn
        35                  40                  45


<210> SEQ ID NO 163
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Gln Thr
        35                  40                  45


<210> SEQ ID NO 164
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr
        35                  40                  45


<210> SEQ ID NO 165
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
```

-continued

```
            20                  25                  30

Phe Leu Ser Ala Leu Glu Glu Tyr Thr Lys Lys Leu Asn
        35                  40                  45


<210> SEQ ID NO 166
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu
        35                  40


<210> SEQ ID NO 167
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys
        35                  40


<210> SEQ ID NO 168
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 169
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Leu Glu Ser Ala Lys Val Ser Ala Leu Ser Ala Leu Glu Glu Ala
1               5                   10                  15
```

-continued

```
Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 170
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 171
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu
        35                  40


<210> SEQ ID NO 172
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys
        35                  40


<210> SEQ ID NO 173
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Glu Ser Ala Lys Val Ser Ala Leu Ser Ala Leu Glu Glu Ala Thr
1               5                   10                  15
```

-continued

```
Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 174
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn
        35                  40


<210> SEQ ID NO 175
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu
        35                  40


<210> SEQ ID NO 176
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 177
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Pro Leu Leu Glu Ser Ala Lys Val Ser Ala Leu Ser Ala Leu Glu
```

-continued

```
1               5                   10                  15

Glu Ala Thr Lys Lys Ser Pro Leu Leu Leu Glu Ser Phe Lys Val Ser
            20                  25                  30

Phe Leu Ser Ala Leu Glu Glu Tyr Thr Lys Lys Leu Asn Thr Gln
        35                  40                  45


<210> SEQ ID NO 178
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Pro Leu Leu Glu Ser Ala Lys Val Ser Ala Leu Ser Ala Leu Glu
1               5                   10                  15

Glu Ala Thr Lys Lys Pro Leu Leu Leu Glu Ser Phe Lys Val Ser Phe
            20                  25                  30

Leu Ser Ala Leu Glu Glu Tyr Thr Lys Lys
        35                  40


<210> SEQ ID NO 179
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 180
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr Gln
        35                  40                  45


<210> SEQ ID NO 181
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181
```

-continued

```
Ser Pro Leu Leu Glu Ser Ala Lys Val Ser Ala Leu Ser Ala Leu Glu
1               5                   10                  15

Glu Ala Thr Lys Lys Ser Pro Leu Leu Glu Ser Phe Lys Val Ser Phe
            20                  25                  30

Leu Ser Ala Leu Glu Glu Tyr Thr Lys Lys
        35                  40


<210> SEQ ID NO 182
<211> LENGTH: 49
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Pro Leu Leu Glu Ser Ala Lys Val Ser Ala Leu Ser Ala Leu Glu
1               5                   10                  15

Glu Ala Thr Lys Lys Leu Pro Ser Leu Lys Leu Leu Glu Ser Phe Lys
            20                  25                  30

Val Ser Phe Leu Ser Ala Leu Glu Glu Tyr Thr Lys Lys Leu Asn Thr
        35                  40                  45

Gln


<210> SEQ ID NO 183
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Pro Leu Leu Glu Ser Ala Lys Val Ser Ala Leu Ser Ala Leu Glu
1               5                   10                  15

Glu Ala Thr Lys Lys Leu Pro Ser Leu Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 184
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Pro Leu Leu Glu Ser Ala Lys Val Ser Ala Leu Ser Ala Leu Glu
1               5                   10                  15

Glu Ala Thr Lys Lys Leu Pro Ser Leu Leu Glu Ser Phe Lys Val Ser
            20                  25                  30

Phe Leu Ser Ala Leu Glu Glu Tyr Thr Lys Lys Leu Asn Thr Gln
        35                  40                  45


<210> SEQ ID NO 185
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 185

Ser Pro Leu Leu Glu Ser Ala Lys Val Ser Ala Leu Ser Ala Leu Glu
1 5 10 15

Glu Ala Thr Lys Lys Leu Pro Leu Leu Glu Ser Phe Lys Val Ser Phe
20 25 30

Leu Ser Ala Leu Glu Glu Tyr Thr Lys Lys
35 40

<210> SEQ ID NO 186
<211> LENGTH: 48
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Ser Pro Leu Leu Glu Ser Ala Lys Val Ser Ala Leu Ser Ala Leu Glu
1 5 10 15

Glu Ala Thr Lys Lys Pro Ser Leu Lys Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 187
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Ser Pro Leu Leu Glu Ser Ala Lys Val Ser Ala Leu Ser Ala Leu Glu
1 5 10 15

Glu Ala Thr Lys Lys Pro Ser Leu Leu Leu Glu Ser Phe Lys Val Ser
20 25 30

Phe Leu Ser Ala Leu Glu Glu Tyr Thr Lys Lys Leu Asn Thr Gln
35 40 45

<210> SEQ ID NO 188
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Ser Pro Leu Leu Glu Ser Ala Lys Val Ser Ala Leu Ser Ala Leu Glu
1 5 10 15

Glu Ala Thr Lys Lys Pro Ser Leu Leu Glu Ser Phe Lys Val Ser Phe
20 25 30

Leu Ser Ala Leu Glu Glu Tyr Thr Lys Lys Leu Asn Thr Gln
35 40 45

<210> SEQ ID NO 189
<211> LENGTH: 45
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 189

Ser Pro Leu Leu Glu Ser Ala Lys Val Ser Ala Leu Ser Ala Leu Glu
1 5 10 15

Glu Ala Thr Lys Lys Pro Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 190
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Pro Leu Leu Glu Ser Ala Lys Val Ser Ala Leu Ser Ala Leu Glu Glu
1 5 10 15

Ala Thr Lys Lys Lys Leu Ser Pro Leu Leu Glu Ser Phe Lys Val Ser
20 25 30

Phe Leu Ser Ala Leu Glu Glu Tyr Thr Lys Lys Leu Asn Thr Gln
35 40 45

<210> SEQ ID NO 191
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Leu Leu Glu Ser Ala Lys Val Ser Ala Leu Ser Ala Leu Glu Glu Ala
1 5 10 15

Thr Lys Lys Lys Leu Ser Pro Leu Leu Glu Ser Phe Lys Val Ser Phe
20 25 30

Leu Ser Ala Leu Glu Glu Tyr Thr Lys Lys Leu Asn Thr Gln
35 40 45

<210> SEQ ID NO 192
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 193
<211> LENGTH: 47
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 193

Pro Leu Leu Glu Ser Ala Lys Val Ser Ala Leu Ser Ala Leu Glu Glu
1               5                   10                  15

Ala Thr Lys Lys Leu Ser Pro Leu Leu Leu Glu Ser Phe Lys Val Ser
            20                  25                  30

Phe Leu Ser Ala Leu Glu Glu Tyr Thr Lys Lys Leu Asn Thr Gln
        35                  40                  45


<210> SEQ ID NO 194
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Leu Glu Ser Ala Lys Val Ser Ala Leu Ser Ala Leu Glu Glu Ala
1               5                   10                  15

Thr Lys Lys Leu Ser Pro Leu Leu Leu Glu Ser Phe Lys Val Ser Phe
            20                  25                  30

Leu Ser Ala Leu Glu Glu Tyr Thr Lys Lys Leu Asn Thr Gln
        35                  40                  45


<210> SEQ ID NO 195
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Leu Glu Ser Ala Lys Val Ser Ala Leu Ser Ala Leu Glu Glu Ala Thr
1               5                   10                  15

Lys Lys Leu Ser Pro Leu Leu Leu Glu Ser Phe Lys Val Ser Phe Leu
            20                  25                  30

Ser Ala Leu Glu Glu Tyr Thr Lys Lys Leu Asn Thr Gln
        35                  40                  45


<210> SEQ ID NO 196
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Pro Leu Leu Glu Ser Ala Lys Val Ser Ala Leu Ser Ala Leu Glu Glu
1               5                   10                  15

Ala Thr Lys Lys Ser Pro Leu Leu Leu Glu Ser Phe Lys Val Ser Phe
            20                  25                  30

Leu Ser Ala Leu Glu Glu Tyr Thr Lys Lys Leu Asn Thr Gln
        35                  40                  45


<210> SEQ ID NO 197
<211> LENGTH: 45
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Leu Leu Glu Ser Ala Lys Val Ser Ala Leu Ser Ala Leu Glu Glu Ala
1               5                   10                  15

Thr Lys Lys Ser Pro Leu Leu Leu Glu Ser Phe Lys Val Ser Phe Leu
            20                  25                  30

Ser Ala Leu Glu Glu Tyr Thr Lys Lys Leu Asn Thr Gln
        35                  40                  45


<210> SEQ ID NO 198
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Glu Ser Ala Lys Val Ser Ala Leu Ser Ala Leu Glu Glu Ala Thr
1               5                   10                  15

Lys Lys Ser Pro Leu Leu Leu Glu Ser Phe Lys Val Ser Phe Leu Ser
            20                  25                  30

Ala Leu Glu Glu Tyr Thr Lys Lys Leu Asn Thr Gln
        35                  40


<210> SEQ ID NO 199
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Pro Leu Leu Glu Ser Ala Lys Val Ser Ala Leu Ser Ala Leu Glu Glu
1               5                   10                  15

Ala Thr Lys Lys Pro Leu Leu Leu Glu Ser Phe Lys Val Ser Phe Leu
            20                  25                  30

Ser Ala Leu Glu Glu Tyr Thr Lys Lys Leu Asn Thr Gln
        35                  40                  45


<210> SEQ ID NO 200
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Leu Glu Ser Ala Lys Val Ser Ala Leu Ser Ala Leu Glu Glu Ala
1               5                   10                  15

Thr Lys Lys Pro Leu Leu Leu Glu Ser Phe Lys Val Ser Phe Leu Ser
            20                  25                  30

Ala Leu Glu Glu Tyr Thr Lys Lys Leu Asn Thr Gln
        35                  40


<210> SEQ ID NO 201
```

-continued

<211> LENGTH: 43
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Leu Glu Ser Ala Lys Val Ser Ala Leu Ser Ala Leu Glu Glu Ala Thr
1 5 10 15

Lys Lys Pro Leu Leu Leu Glu Ser Phe Lys Val Ser Phe Leu Ser Ala
20 25 30

Leu Glu Glu Tyr Thr Lys Lys Leu Asn Thr Gln
35 40

<210> SEQ ID NO 202
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Pro Leu Leu Glu Ser Ala Lys Val Ser Ala Leu Ser Ala Leu Glu Glu
1 5 10 15

Ala Thr Lys Lys Lys Leu Ser Pro Leu Leu Glu Ser Phe Lys Val Ser
20 25 30

Phe Leu Ser Ala Leu Glu Glu Tyr Thr Lys Lys Leu Asn Thr Gln
35 40 45

<210> SEQ ID NO 203
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Leu Leu Glu Ser Ala Lys Val Ser Ala Leu Ser Ala Leu Glu Glu Ala
1 5 10 15

Thr Lys Lys Lys Leu Ser Pro Leu Leu Glu Ser Phe Lys Val Ser Phe
20 25 30

Leu Ser Ala Leu Glu Glu Tyr Thr Lys Lys Leu Asn Thr Gln
35 40 45

<210> SEQ ID NO 204
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys Leu Asn Thr Gln
35 40 45

-continued

<210> SEQ ID NO 205
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

```
Pro Leu Leu Glu Ser Ala Lys Val Ser Ala Leu Ser Ala Leu Glu Glu
1               5                   10                  15

Ala Thr Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 206
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

```
Leu Leu Glu Ser Ala Lys Val Ser Ala Leu Ser Ala Leu Glu Glu Ala
1               5                   10                  15

Thr Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr Gln
        35                  40                  45
```

<210> SEQ ID NO 207
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

```
Leu Glu Ser Ala Lys Val Ser Ala Leu Ser Ala Leu Glu Glu Ala Thr
1               5                   10                  15

Lys Lys Leu Ser Pro Leu Leu Glu Ser Phe Lys Val Ser Phe Leu Ser
            20                  25                  30

Ala Leu Glu Glu Tyr Thr Lys Lys Leu Asn Thr Gln
        35                  40
```

<210> SEQ ID NO 208
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

```
Pro Leu Leu Glu Ser Ala Lys Val Ser Ala Leu Ser Ala Leu Glu Glu
1               5                   10                  15

Ala Thr Lys Lys Ser Pro Leu Leu Glu Ser Phe Lys Val Ser Phe Leu
            20                  25                  30

Ser Ala Leu Glu Glu Tyr Thr Lys Lys Leu Asn Thr Gln
        35                  40                  45
```

-continued

<210> SEQ ID NO 209
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 209

```
Leu Leu Glu Ser Ala Lys Val Ser Ala Leu Ser Ala Leu Glu Glu Ala
1               5                   10                  15

Thr Lys Lys Ser Pro Leu Leu Glu Ser Phe Lys Val Ser Phe Leu Ser
            20                  25                  30

Ala Leu Glu Glu Tyr Thr Lys Lys Leu Asn Thr Gln
        35                  40
```

<210> SEQ ID NO 210
<211> LENGTH: 43
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 210

```
Leu Glu Ser Ala Lys Val Ser Ala Leu Ser Ala Leu Glu Glu Ala Thr
1               5                   10                  15

Lys Lys Ser Pro Leu Leu Glu Ser Phe Lys Val Ser Phe Leu Ser Ala
            20                  25                  30

Leu Glu Glu Tyr Thr Lys Lys Leu Asn Thr Gln
        35                  40
```

<210> SEQ ID NO 211
<211> LENGTH: 48
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 211

```
Pro Leu Leu Glu Ser Ala Lys Val Ser Ala Leu Ser Ala Leu Glu Glu
1               5                   10                  15

Ala Thr Lys Lys Leu Pro Ser Leu Lys Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 212
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

```
Leu Leu Glu Ser Ala Lys Val Ser Ala Leu Ser Ala Leu Glu Glu Ala
1               5                   10                  15

Thr Lys Lys Leu Pro Ser Leu Lys Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

-continued

<210> SEQ ID NO 213
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

```
Leu Glu Ser Ala Lys Val Ser Ala Leu Ser Ala Leu Glu Glu Ala Thr
1               5                   10                  15

Lys Lys Leu Pro Ser Leu Lys Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 214
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

```
Pro Leu Leu Glu Ser Ala Lys Val Ser Ala Leu Ser Ala Leu Glu Glu
1               5                   10                  15

Ala Thr Lys Lys Leu Pro Ser Leu Leu Leu Glu Ser Phe Lys Val Ser
            20                  25                  30

Phe Leu Ser Ala Leu Glu Glu Tyr Thr Lys Lys Leu Asn Thr Gln
        35                  40                  45
```

<210> SEQ ID NO 215
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

```
Leu Leu Glu Ser Ala Lys Val Ser Ala Leu Ser Ala Leu Glu Glu Ala
1               5                   10                  15

Thr Lys Lys Leu Pro Ser Leu Leu Leu Glu Ser Phe Lys Val Ser Phe
            20                  25                  30

Leu Ser Ala Leu Glu Glu Tyr Thr Lys Lys Leu Asn Thr Gln
        35                  40                  45
```

<210> SEQ ID NO 216
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

```
Leu Glu Ser Ala Lys Val Ser Ala Leu Ser Ala Leu Glu Glu Ala Thr
1               5                   10                  15

Lys Lys Leu Pro Ser Leu Leu Leu Glu Ser Phe Lys Val Ser Phe Leu
            20                  25                  30

Ser Ala Leu Glu Glu Tyr Thr Lys Lys Leu Asn Thr Gln
```

-continued 35 40 45

<210> SEQ ID NO 217
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Pro Leu Leu Glu Ser Ala Lys Val Ser Ala Leu Ser Ala Leu Glu Glu
1 5 10 15

Ala Thr Lys Lys Leu Pro Ser Leu Leu Glu Ser Phe Lys Val Ser Phe
20 25 30

Leu Ser Ala Leu Glu Glu Tyr Thr Lys Lys Leu Asn Thr Gln
35 40 45

<210> SEQ ID NO 218
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Leu Leu Glu Ser Ala Lys Val Ser Ala Leu Ser Ala Leu Glu Glu Ala
1 5 10 15

Thr Lys Lys Leu Pro Ser Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 219
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Leu Glu Ser Ala Lys Val Ser Ala Leu Ser Ala Leu Glu Glu Ala Thr
1 5 10 15

Lys Lys Leu Pro Ser Leu Leu Glu Ser Phe Lys Val Ser Phe Leu Ser
20 25 30

Ala Leu Glu Glu Tyr Thr Lys Lys Leu Asn Thr Gln
35 40

<210> SEQ ID NO 220
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Pro Leu Leu Glu Ser Ala Lys Val Ser Ala Leu Ser Ala Leu Glu Glu
1 5 10 15

Ala Thr Lys Lys Leu Pro Leu Leu Glu Ser Phe Lys Val Ser Phe Leu
20 25 30

-continued

```
Ser Ala Leu Glu Glu Tyr Thr Lys Lys Leu Asn Thr Gln
        35                  40                  45


<210> SEQ ID NO 221
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Leu Leu Glu Ser Ala Lys Val Ser Ala Leu Ser Ala Leu Glu Glu Ala
1               5                   10                  15

Thr Lys Lys Leu Pro Leu Leu Glu Ser Phe Lys Val Ser Phe Leu Ser
            20                  25                  30

Ala Leu Glu Glu Tyr Thr Lys Lys Leu Asn Thr Gln
        35                  40


<210> SEQ ID NO 222
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Leu Glu Ser Ala Lys Val Ser Ala Leu Ser Ala Leu Glu Glu Ala Thr
1               5                   10                  15

Lys Lys Leu Pro Leu Leu Glu Ser Phe Lys Val Ser Phe Leu Ser Ala
            20                  25                  30

Leu Glu Glu Tyr Thr Lys Lys Leu Asn Thr Gln
        35                  40


<210> SEQ ID NO 223
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Pro Leu Leu Glu Ser Ala Lys Val Ser Ala Leu Ser Ala Leu Glu Glu
1               5                   10                  15

Ala Thr Lys Lys Pro Ser Leu Lys Leu Leu Glu Ser Phe Lys Val Ser
            20                  25                  30

Phe Leu Ser Ala Leu Glu Glu Tyr Thr Lys Lys Leu Asn Thr Gln
        35                  40                  45


<210> SEQ ID NO 224
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Leu Leu Glu Ser Ala Lys Val Ser Ala Leu Ser Ala Leu Glu Glu Ala
1               5                   10                  15

Thr Lys Lys Pro Ser Leu Lys Leu Leu Glu Ser Phe Lys Val Ser Phe
            20                  25                  30
```

Leu Ser Ala Leu Glu Glu Tyr Thr Lys Lys Leu Asn Thr Gln
35 40 45

<210> SEQ ID NO 225
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Leu Glu Ser Ala Lys Val Ser Ala Leu Ser Ala Leu Glu Glu Ala Thr
1 5 10 15

Lys Lys Pro Ser Leu Lys Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 226
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Pro Leu Leu Glu Ser Ala Lys Val Ser Ala Leu Ser Ala Leu Glu Glu
1 5 10 15

Ala Thr Lys Lys Pro Ser Leu Leu Leu Glu Ser Phe Lys Val Ser Phe
20 25 30

Leu Ser Ala Leu Glu Glu Tyr Thr Lys Lys Leu Asn Thr Gln
35 40 45

<210> SEQ ID NO 227
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Leu Leu Glu Ser Ala Lys Val Ser Ala Leu Ser Ala Leu Glu Glu Ala
1 5 10 15

Thr Lys Lys Pro Ser Leu Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 228
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Leu Glu Ser Ala Lys Val Ser Ala Leu Ser Ala Leu Glu Glu Ala Thr
1 5 10 15

Lys Lys Pro Ser Leu Leu Leu Glu Ser Phe Lys Val Ser Phe Leu Ser

-continued

```
            20                  25                  30

Ala Leu Glu Glu Tyr Thr Lys Lys Leu Asn Thr Gln
        35                  40


<210> SEQ ID NO 229
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Pro Leu Leu Glu Ser Ala Lys Val Ser Ala Leu Ser Ala Leu Glu Glu
1               5                   10                  15

Ala Thr Lys Lys Pro Ser Leu Leu Glu Ser Phe Lys Val Ser Phe Leu
            20                  25                  30

Ser Ala Leu Glu Glu Tyr Thr Lys Lys Leu Asn Thr Gln
        35                  40                  45


<210> SEQ ID NO 230
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Leu Leu Glu Ser Ala Lys Val Ser Ala Leu Ser Ala Leu Glu Glu Ala
1               5                   10                  15

Thr Lys Lys Pro Ser Leu Leu Glu Ser Phe Lys Val Ser Phe Leu Ser
            20                  25                  30

Ala Leu Glu Glu Tyr Thr Lys Lys Leu Asn Thr Gln
        35                  40


<210> SEQ ID NO 231
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Leu Glu Ser Ala Lys Val Ser Ala Leu Ser Ala Leu Glu Glu Ala Thr
1               5                   10                  15

Lys Lys Pro Ser Leu Leu Glu Ser Phe Lys Val Ser Phe Leu Ser Ala
            20                  25                  30

Leu Glu Glu Tyr Thr Lys Lys Leu Asn Thr Gln
        35                  40


<210> SEQ ID NO 232
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Pro Leu Leu Glu Ser Ala Lys Val Ser Ala Leu Ser Ala Leu Glu Glu
1               5                   10                  15
```

-continued

```
Ala Thr Lys Lys Pro Leu Leu Glu Ser Phe Lys Val Ser Phe Leu Ser
            20                  25                  30

Ala Leu Glu Glu Tyr Thr Lys Lys Leu Asn Thr Gln
        35                  40


<210> SEQ ID NO 233
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Leu Leu Glu Ser Ala Lys Val Ser Ala Leu Ser Ala Leu Glu Glu Ala
1               5                   10                  15

Thr Lys Lys Pro Leu Leu Glu Ser Phe Lys Val Ser Phe Leu Ser Ala
            20                  25                  30

Leu Glu Glu Tyr Thr Lys Lys Leu Asn Thr Gln
        35                  40


<210> SEQ ID NO 234
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Leu Glu Ser Ala Lys Val Ser Ala Leu Ser Ala Leu Glu Glu Ala Thr
1               5                   10                  15

Lys Lys Pro Leu Leu Glu Ser Phe Lys Val Ser Phe Leu Ser Ala Leu
            20                  25                  30

Glu Glu Tyr Thr Lys Lys Leu Asn Thr Gln
        35                  40


<210> SEQ ID NO 235
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr
        35                  40                  45


<210> SEQ ID NO 236
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Pro Leu Leu Glu Ser Ala Lys Val Ser Ala Leu Ser Ala Leu Glu
1               5                   10                  15
```

-continued

```
Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn
        35                  40                  45


<210> SEQ ID NO 237
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu
        35                  40                  45


<210> SEQ ID NO 238
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys
        35                  40


<210> SEQ ID NO 239
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Leu Glu Ser Phe Lys Val
            20                  25                  30

Ser Phe Leu Ser Ala Leu Glu Glu Tyr Thr Lys Lys Leu Asn Thr
        35                  40                  45


<210> SEQ ID NO 240
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ser Pro Leu Leu Glu Ser Ala Lys Val Ser Ala Leu Ser Ala Leu Glu
```

-continued

```
1               5                   10                  15

Glu Ala Thr Lys Lys Leu Ser Pro Leu Leu Leu Glu Ser Phe Lys Val
            20                  25                  30

Ser Phe Leu Ser Ala Leu Glu Glu Tyr Thr Lys Lys Leu Asn
        35                  40                  45


<210> SEQ ID NO 241
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Leu Glu Ser Phe Lys Val
            20                  25                  30

Ser Phe Leu Ser Ala Leu Glu Glu Tyr Thr Lys Lys Leu
        35                  40                  45


<210> SEQ ID NO 242
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Leu Glu Ser Phe Lys Val
            20                  25                  30

Ser Phe Leu Ser Ala Leu Glu Glu Tyr Thr Lys Lys
        35                  40


<210> SEQ ID NO 243
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ser Pro Leu Leu Glu Ser Ala Lys Val Ser Ala Leu Ser Ala Leu Glu
1               5                   10                  15

Glu Ala Thr Lys Lys Ser Pro Leu Leu Leu Glu Ser Phe Lys Val Ser
            20                  25                  30

Phe Leu Ser Ala Leu Glu Glu Tyr Thr Lys Lys Leu Asn Thr
        35                  40                  45


<210> SEQ ID NO 244
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244
```

-continued

```
Ser Pro Leu Leu Glu Ser Ala Lys Val Ser Ala Leu Ser Ala Leu Glu
1               5                   10                  15

Glu Ala Thr Lys Lys Ser Pro Leu Leu Leu Glu Ser Phe Lys Val Ser
            20                  25                  30

Phe Leu Ser Ala Leu Glu Glu Tyr Thr Lys Lys Leu Asn
        35                  40                  45


<210> SEQ ID NO 245
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Pro Leu Leu Glu Ser Ala Lys Val Ser Ala Leu Ser Ala Leu Glu
1               5                   10                  15

Glu Ala Thr Lys Lys Ser Pro Leu Leu Leu Glu Ser Phe Lys Val Ser
            20                  25                  30

Phe Leu Ser Ala Leu Glu Glu Tyr Thr Lys Lys Leu
        35                  40


<210> SEQ ID NO 246
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Pro Leu Leu Glu Ser Ala Lys Val Ser Ala Leu Ser Ala Leu Glu
1               5                   10                  15

Glu Ala Thr Lys Lys Ser Pro Leu Leu Leu Glu Ser Phe Lys Val Ser
            20                  25                  30

Phe Leu Ser Ala Leu Glu Glu Tyr Thr Lys Lys
        35                  40


<210> SEQ ID NO 247
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ser Pro Leu Leu Glu Ser Ala Lys Val Ser Ala Leu Ser Ala Leu Glu
1               5                   10                  15

Glu Ala Thr Lys Lys Pro Leu Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 248
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248
```

-continued

```
Ser Pro Leu Leu Glu Ser Ala Lys Val Ser Ala Leu Ser Ala Leu Glu
1               5                   10                  15

Glu Ala Thr Lys Lys Pro Leu Leu Leu Glu Ser Phe Lys Val Ser Phe
            20                  25                  30

Leu Ser Ala Leu Glu Glu Tyr Thr Lys Lys Leu Asn
        35                  40
```

<210> SEQ ID NO 249
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

```
Ser Pro Leu Leu Glu Ser Ala Lys Val Ser Ala Leu Ser Ala Leu Glu
1               5                   10                  15

Glu Ala Thr Lys Lys Pro Leu Leu Leu Glu Ser Phe Lys Val Ser Phe
            20                  25                  30

Leu Ser Ala Leu Glu Glu Tyr Thr Lys Lys Leu
        35                  40
```

<210> SEQ ID NO 250
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

```
Ser Pro Leu Leu Glu Ser Ala Lys Val Ser Ala Leu Ser Ala Leu Glu
1               5                   10                  15

Glu Ala Thr Lys Lys Pro Leu Leu Leu Glu Ser Phe Lys Val Ser Phe
            20                  25                  30

Leu Ser Ala Leu Glu Glu Tyr Thr Lys Lys
        35                  40
```

<210> SEQ ID NO 251
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr
        35                  40                  45
```

<210> SEQ ID NO 252
<211> LENGTH: 46
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 252

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn
        35                  40                  45

<210> SEQ ID NO 253
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu
        35                  40                  45

<210> SEQ ID NO 254
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys
        35                  40

<210> SEQ ID NO 255
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr
        35                  40                  45

<210> SEQ ID NO 256
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 256

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Glu Ser Phe Lys Val Ser
            20                  25                  30

Phe Leu Ser Ala Leu Glu Glu Tyr Thr Lys Lys Leu Asn
        35                  40                  45


<210> SEQ ID NO 257
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Glu Ser Phe Lys Val Ser
            20                  25                  30

Phe Leu Ser Ala Leu Glu Glu Tyr Thr Lys Lys Leu
        35                  40


<210> SEQ ID NO 258
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ser Pro Leu Leu Glu Ser Ala Lys Val Ser Ala Leu Ser Ala Leu Glu
1               5                   10                  15

Glu Ala Thr Lys Lys Leu Ser Pro Leu Leu Glu Ser Phe Lys Val Ser
            20                  25                  30

Phe Leu Ser Ala Leu Glu Glu Tyr Thr Lys Lys
        35                  40


<210> SEQ ID NO 259
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ser Pro Leu Leu Glu Ser Ala Lys Val Ser Ala Leu Ser Ala Leu Glu
1               5                   10                  15

Glu Ala Thr Lys Lys Ser Pro Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 260
<211> LENGTH: 44
<212> TYPE: PRT
<213> ORGANISM: Artificial Sequence
```

-continued

<220> FEATURE:
<223> OTHER INFORMATION: Description of Artificial Sequence: Synthetic
peptide

<400> SEQUENCE: 260

Ser Pro Leu Leu Glu Ser Ala Lys Val Ser Ala Leu Ser Ala Leu Glu
1 5 10 15

Glu Ala Thr Lys Lys Ser Pro Leu Leu Glu Ser Phe Lys Val Ser Phe
20 25 30

Leu Ser Ala Leu Glu Glu Tyr Thr Lys Lys Leu Asn
35 40

<210> SEQ ID NO 261
<211> LENGTH: 43
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

Ser Pro Leu Leu Glu Ser Ala Lys Val Ser Ala Leu Ser Ala Leu Glu
1 5 10 15

Glu Ala Thr Lys Lys Ser Pro Leu Leu Glu Ser Phe Lys Val Ser Phe
20 25 30

Leu Ser Ala Leu Glu Glu Tyr Thr Lys Lys Leu
35 40

<210> SEQ ID NO 262
<211> LENGTH: 42
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Ser Pro Leu Leu Glu Ser Ala Lys Val Ser Ala Leu Ser Ala Leu Glu
1 5 10 15

Glu Ala Thr Lys Lys Ser Pro Leu Leu Glu Ser Phe Lys Val Ser Phe
20 25 30

Leu Ser Ala Leu Glu Glu Tyr Thr Lys Lys
35 40

<210> SEQ ID NO 263
<211> LENGTH: 48
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Ser Pro Leu Leu Glu Ser Ala Lys Val Ser Ala Leu Ser Ala Leu Glu
1 5 10 15

Glu Ala Thr Lys Lys Leu Pro Ser Leu Lys Leu Leu Glu Ser Phe Lys
20 25 30

Val Ser Phe Leu Ser Ala Leu Glu Glu Tyr Thr Lys Lys Leu Asn Thr
35 40 45

<210> SEQ ID NO 264
<211> LENGTH: 47
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 264

Ser Pro Leu Leu Glu Ser Ala Lys Val Ser Ala Leu Ser Ala Leu Glu
1 5 10 15

Glu Ala Thr Lys Lys Leu Pro Ser Leu Lys Leu Leu Glu Ser Phe Lys
20 25 30

Val Ser Phe Leu Ser Ala Leu Glu Glu Tyr Thr Lys Lys Leu Asn
35 40 45

<210> SEQ ID NO 265
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 265

Ser Pro Leu Leu Glu Ser Ala Lys Val Ser Ala Leu Ser Ala Leu Glu
1 5 10 15

Glu Ala Thr Lys Lys Leu Pro Ser Leu Lys Leu Leu Glu Ser Phe Lys
20 25 30

Val Ser Phe Leu Ser Ala Leu Glu Glu Tyr Thr Lys Lys Leu
35 40 45

<210> SEQ ID NO 266
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 266

Ser Pro Leu Leu Glu Ser Ala Lys Val Ser Ala Leu Ser Ala Leu Glu
1 5 10 15

Glu Ala Thr Lys Lys Leu Pro Ser Leu Lys Leu Leu Glu Ser Phe Lys
20 25 30

Val Ser Phe Leu Ser Ala Leu Glu Glu Tyr Thr Lys Lys
35 40 45

<210> SEQ ID NO 267
<211> LENGTH: 47
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 267

Ser Pro Leu Leu Glu Ser Ala Lys Val Ser Ala Leu Ser Ala Leu Glu
1 5 10 15

Glu Ala Thr Lys Lys Leu Pro Ser Leu Leu Leu Glu Ser Phe Lys Val
20 25 30

Ser Phe Leu Ser Ala Leu Glu Glu Tyr Thr Lys Lys Leu Asn Thr
35 40 45

<210> SEQ ID NO 268
<211> LENGTH: 46

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 268

Ser Pro Leu Leu Glu Ser Ala Lys Val Ser Ala Leu Ser Ala Leu Glu
1 5 10 15

Glu Ala Thr Lys Lys Leu Pro Ser Leu Leu Leu Glu Ser Phe Lys Val
20 25 30

Ser Phe Leu Ser Ala Leu Glu Glu Tyr Thr Lys Lys Leu Asn
35 40 45

<210> SEQ ID NO 269
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 269

Ser Pro Leu Leu Glu Ser Ala Lys Val Ser Ala Leu Ser Ala Leu Glu
1 5 10 15

Glu Ala Thr Lys Lys Leu Pro Ser Leu Leu Leu Glu Ser Phe Lys Val
20 25 30

Ser Phe Leu Ser Ala Leu Glu Glu Tyr Thr Lys Lys Leu
35 40 45

<210> SEQ ID NO 270
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 270

Ser Pro Leu Leu Glu Ser Ala Lys Val Ser Ala Leu Ser Ala Leu Glu
1 5 10 15

Glu Ala Thr Lys Lys Leu Pro Ser Leu Leu Leu Glu Ser Phe Lys Val
20 25 30

Ser Phe Leu Ser Ala Leu Glu Glu Tyr Thr Lys Lys
35 40

<210> SEQ ID NO 271
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 271

Ser Pro Leu Leu Glu Ser Ala Lys Val Ser Ala Leu Ser Ala Leu Glu
1 5 10 15

Glu Ala Thr Lys Lys Leu Pro Ser Leu Leu Glu Ser Phe Lys Val Ser
20 25 30

Phe Leu Ser Ala Leu Glu Glu Tyr Thr Lys Lys Leu Asn Thr
35 40 45

<210> SEQ ID NO 272

-continued

<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Ser Pro Leu Leu Glu Ser Ala Lys Val Ser Ala Leu Ser Ala Leu Glu
1 5 10 15

Glu Ala Thr Lys Lys Leu Pro Ser Leu Leu Glu Ser Phe Lys Val Ser
20 25 30

Phe Leu Ser Ala Leu Glu Glu Tyr Thr Lys Lys Leu Asn
35 40 45

<210> SEQ ID NO 273
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Ser Pro Leu Leu Glu Ser Ala Lys Val Ser Ala Leu Ser Ala Leu Glu
1 5 10 15

Glu Ala Thr Lys Lys Leu Pro Ser Leu Leu Glu Ser Phe Lys Val Ser
20 25 30

Phe Leu Ser Ala Leu Glu Glu Tyr Thr Lys Lys Leu
35 40

<210> SEQ ID NO 274
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Ser Pro Leu Leu Glu Ser Ala Lys Val Ser Ala Leu Ser Ala Leu Glu
1 5 10 15

Glu Ala Thr Lys Lys Leu Pro Ser Leu Leu Glu Ser Phe Lys Val Ser
20 25 30

Phe Leu Ser Ala Leu Glu Glu Tyr Thr Lys Lys
35 40

<210> SEQ ID NO 275
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Ser Pro Leu Leu Glu Ser Ala Lys Val Ser Ala Leu Ser Ala Leu Glu
1 5 10 15

Glu Ala Thr Lys Lys Leu Pro Leu Leu Glu Ser Phe Lys Val Ser Phe
20 25 30

Leu Ser Ala Leu Glu Glu Tyr Thr Lys Lys Leu Asn Thr
35 40 45

-continued

<210> SEQ ID NO 276
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

```
Ser Pro Leu Leu Glu Ser Ala Lys Val Ser Ala Leu Ser Ala Leu Glu
1               5                   10                  15

Glu Ala Thr Lys Lys Leu Pro Leu Leu Glu Ser Phe Lys Val Ser Phe
            20                  25                  30

Leu Ser Ala Leu Glu Glu Tyr Thr Lys Lys Leu Asn
        35                  40
```

<210> SEQ ID NO 277
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

```
Ser Pro Leu Leu Glu Ser Ala Lys Val Ser Ala Leu Ser Ala Leu Glu
1               5                   10                  15

Glu Ala Thr Lys Lys Leu Pro Leu Leu Glu Ser Phe Lys Val Ser Phe
            20                  25                  30

Leu Ser Ala Leu Glu Glu Tyr Thr Lys Lys Leu
        35                  40
```

<210> SEQ ID NO 278
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

```
Ser Pro Leu Leu Glu Ser Ala Lys Val Ser Ala Leu Ser Ala Leu Glu
1               5                   10                  15

Glu Ala Thr Lys Lys Leu Pro Leu Leu Glu Ser Phe Lys Val Ser Phe
            20                  25                  30

Leu Ser Ala Leu Glu Glu Tyr Thr Lys Lys
        35                  40
```

<210> SEQ ID NO 279
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

```
Ser Pro Leu Leu Glu Ser Ala Lys Val Ser Ala Leu Ser Ala Leu Glu
1               5                   10                  15

Glu Ala Thr Lys Lys Pro Ser Leu Lys Leu Leu Glu Ser Phe Lys Val
            20                  25                  30

Ser Phe Leu Ser Ala Leu Glu Glu Tyr Thr Lys Lys Leu Asn Thr
        35                  40                  45
```

-continued

<210> SEQ ID NO 280
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

Ser Pro Leu Leu Glu Ser Ala Lys Val Ser Ala Leu Ser Ala Leu Glu
1 5 10 15

Glu Ala Thr Lys Lys Pro Ser Leu Lys Leu Leu Glu Ser Phe Lys Val
20 25 30

Ser Phe Leu Ser Ala Leu Glu Glu Tyr Thr Lys Lys Leu Asn
35 40 45

<210> SEQ ID NO 281
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 281

Ser Pro Leu Leu Glu Ser Ala Lys Val Ser Ala Leu Ser Ala Leu Glu
1 5 10 15

Glu Ala Thr Lys Lys Pro Ser Leu Lys Leu Leu Glu Ser Phe Lys Val
20 25 30

Ser Phe Leu Ser Ala Leu Glu Glu Tyr Thr Lys Lys Leu
35 40 45

<210> SEQ ID NO 282
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 282

Ser Pro Leu Leu Glu Ser Ala Lys Val Ser Ala Leu Ser Ala Leu Glu
1 5 10 15

Glu Ala Thr Lys Lys Pro Ser Leu Lys Leu Leu Glu Ser Phe Lys Val
20 25 30

Ser Phe Leu Ser Ala Leu Glu Glu Tyr Thr Lys Lys
35 40

<210> SEQ ID NO 283
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Ser Pro Leu Leu Glu Ser Ala Lys Val Ser Ala Leu Ser Ala Leu Glu
1 5 10 15

Glu Ala Thr Lys Lys Pro Ser Leu Leu Leu Glu Ser Phe Lys Val Ser
20 25 30

Phe Leu Ser Ala Leu Glu Glu Tyr Thr Lys Lys Leu Asn Thr
35 40 45

-continued

<210> SEQ ID NO 284
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

```
Ser Pro Leu Leu Glu Ser Ala Lys Val Ser Ala Leu Ser Ala Leu Glu
1               5                   10                  15

Glu Ala Thr Lys Lys Pro Ser Leu Leu Leu Glu Ser Phe Lys Val Ser
            20                  25                  30

Phe Leu Ser Ala Leu Glu Glu Tyr Thr Lys Lys Leu Asn
        35                  40                  45
```

<210> SEQ ID NO 285
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

```
Ser Pro Leu Leu Glu Ser Ala Lys Val Ser Ala Leu Ser Ala Leu Glu
1               5                   10                  15

Glu Ala Thr Lys Lys Pro Ser Leu Leu Leu Glu Ser Phe Lys Val Ser
            20                  25                  30

Phe Leu Ser Ala Leu Glu Glu Tyr Thr Lys Lys Leu
        35                  40
```

<210> SEQ ID NO 286
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 286

```
Ser Pro Leu Leu Glu Ser Ala Lys Val Ser Ala Leu Ser Ala Leu Glu
1               5                   10                  15

Glu Ala Thr Lys Lys Pro Ser Leu Leu Leu Glu Ser Phe Lys Val Ser
            20                  25                  30

Phe Leu Ser Ala Leu Glu Glu Tyr Thr Lys Lys
        35                  40
```

<210> SEQ ID NO 287
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 287

```
Ser Pro Leu Leu Glu Ser Ala Lys Val Ser Ala Leu Ser Ala Leu Glu
1               5                   10                  15

Glu Ala Thr Lys Lys Pro Ser Leu Leu Glu Ser Phe Lys Val Ser Phe
            20                  25                  30
```

-continued

```
Leu Ser Ala Leu Glu Glu Tyr Thr Lys Lys Leu Asn Thr
        35                  40                  45


<210> SEQ ID NO 288
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Pro Leu Leu Glu Ser Ala Lys Val Ser Ala Leu Ser Ala Leu Glu
1               5                   10                  15

Glu Ala Thr Lys Lys Pro Ser Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 289
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ser Pro Leu Leu Glu Ser Ala Lys Val Ser Ala Leu Ser Ala Leu Glu
1               5                   10                  15

Glu Ala Thr Lys Lys Pro Ser Leu Leu Glu Ser Phe Lys Val Ser Phe
            20                  25                  30

Leu Ser Ala Leu Glu Glu Tyr Thr Lys Lys Leu
        35                  40


<210> SEQ ID NO 290
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ser Pro Leu Leu Glu Ser Ala Lys Val Ser Ala Leu Ser Ala Leu Glu
1               5                   10                  15

Glu Ala Thr Lys Lys Pro Ser Leu Leu Glu Ser Phe Lys Val Ser Phe
            20                  25                  30

Leu Ser Ala Leu Glu Glu Tyr Thr Lys Lys
        35                  40


<210> SEQ ID NO 291
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ser Pro Leu Leu Glu Ser Ala Lys Val Ser Ala Leu Ser Ala Leu Glu
1               5                   10                  15

Glu Ala Thr Lys Lys Pro Leu Leu Glu Ser Phe Lys Val Ser Phe Leu
```

-continued

```
            20                  25                  30

Ser Ala Leu Glu Glu Tyr Thr Lys Lys Leu Asn Thr
        35                  40


<210> SEQ ID NO 292
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ser Pro Leu Leu Glu Ser Ala Lys Val Ser Ala Leu Ser Ala Leu Glu
1               5                   10                  15

Glu Ala Thr Lys Lys Pro Leu Leu Glu Ser Phe Lys Val Ser Phe Leu
            20                  25                  30

Ser Ala Leu Glu Glu Tyr Thr Lys Lys Leu Asn
        35                  40


<210> SEQ ID NO 293
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ser Pro Leu Leu Glu Ser Ala Lys Val Ser Ala Leu Ser Ala Leu Glu
1               5                   10                  15

Glu Ala Thr Lys Lys Pro Leu Leu Glu Ser Phe Lys Val Ser Phe Leu
            20                  25                  30

Ser Ala Leu Glu Glu Tyr Thr Lys Lys Leu
        35                  40


<210> SEQ ID NO 294
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ser Pro Leu Leu Glu Ser Ala Lys Val Ser Ala Leu Ser Ala Leu Glu
1               5                   10                  15

Glu Ala Thr Lys Lys Pro Leu Leu Glu Ser Phe Lys Val Ser Phe Leu
            20                  25                  30

Ser Ala Leu Glu Glu Tyr Thr Lys Lys
        35                  40


<210> SEQ ID NO 295
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Pro Leu Leu Glu Ser Ala Lys Val Ser Ala Leu Ser Ala Leu Glu Glu
1               5                   10                  15
```

-continued

```
Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr
        35                  40                  45


<210> SEQ ID NO 296
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 297
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 298
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn
        35                  40                  45


<210> SEQ ID NO 299
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Leu Leu Glu Ser Ala Lys Val Ser Ala Leu Ser Ala Leu Glu Glu Ala
1               5                   10                  15
```

-continued

```
Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 300
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn
        35                  40


<210> SEQ ID NO 301
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu
        35                  40


<210> SEQ ID NO 302
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu
        35                  40


<210> SEQ ID NO 303
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Leu Glu Ser Ala Lys Val Ser Ala Leu Ser Ala Leu Glu Glu Ala Thr
```

-continued

```
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu
        35                  40


<210> SEQ ID NO 304
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys
        35                  40


<210> SEQ ID NO 305
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys
        35                  40


<210> SEQ ID NO 306
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 307
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307
```

-continued

```
Pro Leu Leu Glu Ser Ala Lys Val Ser Ala Leu Ser Ala Leu Glu Glu
1               5                   10                  15

Ala Thr Lys Lys Leu Ser Pro Leu Leu Leu Glu Ser Phe Lys Val Ser
            20                  25                  30

Phe Leu Ser Ala Leu Glu Glu Tyr Thr Lys Lys Leu Asn Thr
        35                  40                  45
```

<210> SEQ ID NO 308
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

```
Leu Leu Glu Ser Ala Lys Val Ser Ala Leu Ser Ala Leu Glu Glu Ala
1               5                   10                  15

Thr Lys Lys Leu Ser Pro Leu Leu Leu Glu Ser Phe Lys Val Ser Phe
            20                  25                  30

Leu Ser Ala Leu Glu Glu Tyr Thr Lys Lys Leu Asn Thr
        35                  40                  45
```

<210> SEQ ID NO 309
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

```
Leu Glu Ser Ala Lys Val Ser Ala Leu Ser Ala Leu Glu Glu Ala Thr
1               5                   10                  15

Lys Lys Leu Ser Pro Leu Leu Leu Glu Ser Phe Lys Val Ser Phe Leu
            20                  25                  30

Ser Ala Leu Glu Glu Tyr Thr Lys Lys Leu Asn Thr
        35                  40
```

<210> SEQ ID NO 310
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

```
Pro Leu Leu Glu Ser Ala Lys Val Ser Ala Leu Ser Ala Leu Glu Glu
1               5                   10                  15

Ala Thr Lys Lys Leu Ser Pro Leu Leu Leu Glu Ser Phe Lys Val Ser
            20                  25                  30

Phe Leu Ser Ala Leu Glu Glu Tyr Thr Lys Lys Leu Asn
        35                  40                  45
```

<210> SEQ ID NO 311
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

-continued

Leu Leu Glu Ser Ala Lys Val Ser Ala Leu Ser Ala Leu Glu Glu Ala
1 5 10 15

Thr Lys Lys Leu Ser Pro Leu Leu Leu Glu Ser Phe Lys Val Ser Phe
20 25 30

Leu Ser Ala Leu Glu Glu Tyr Thr Lys Lys Leu Asn
35 40

<210> SEQ ID NO 312
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 312

Leu Glu Ser Ala Lys Val Ser Ala Leu Ser Ala Leu Glu Glu Ala Thr
1 5 10 15

Lys Lys Leu Ser Pro Leu Leu Leu Glu Ser Phe Lys Val Ser Phe Leu
20 25 30

Ser Ala Leu Glu Glu Tyr Thr Lys Lys Leu Asn
35 40

<210> SEQ ID NO 313
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Pro Leu Leu Glu Ser Ala Lys Val Ser Ala Leu Ser Ala Leu Glu Glu
1 5 10 15

Ala Thr Lys Lys Leu Ser Pro Leu Leu Leu Glu Ser Phe Lys Val Ser
20 25 30

Phe Leu Ser Ala Leu Glu Glu Tyr Thr Lys Lys Leu
35 40

<210> SEQ ID NO 314
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Leu Leu Glu Ser Ala Lys Val Ser Ala Leu Ser Ala Leu Glu Glu Ala
1 5 10 15

Thr Lys Lys Leu Ser Pro Leu Leu Leu Glu Ser Phe Lys Val Ser Phe
20 25 30

Leu Ser Ala Leu Glu Glu Tyr Thr Lys Lys Leu
35 40

<210> SEQ ID NO 315
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Leu Glu Ser Ala Lys Val Ser Ala Leu Ser Ala Leu Glu Glu Ala Thr
1 5 10 15

Lys Lys Leu Ser Pro Leu Leu Leu Glu Ser Phe Lys Val Ser Phe Leu
20 25 30

Ser Ala Leu Glu Glu Tyr Thr Lys Lys Leu
35 40

<210> SEQ ID NO 316
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Pro Leu Leu Glu Ser Ala Lys Val Ser Ala Leu Ser Ala Leu Glu Glu
1 5 10 15

Ala Thr Lys Lys Leu Ser Pro Leu Leu Leu Glu Ser Phe Lys Val Ser
20 25 30

Phe Leu Ser Ala Leu Glu Glu Tyr Thr Lys Lys
35 40

<210> SEQ ID NO 317
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Leu Leu Glu Ser Ala Lys Val Ser Ala Leu Ser Ala Leu Glu Glu Ala
1 5 10 15

Thr Lys Lys Leu Ser Pro Leu Leu Leu Glu Ser Phe Lys Val Ser Phe
20 25 30

Leu Ser Ala Leu Glu Glu Tyr Thr Lys Lys
35 40

<210> SEQ ID NO 318
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Leu Glu Ser Ala Lys Val Ser Ala Leu Ser Ala Leu Glu Glu Ala Thr
1 5 10 15

Lys Lys Leu Ser Pro Leu Leu Leu Glu Ser Phe Lys Val Ser Phe Leu
20 25 30

Ser Ala Leu Glu Glu Tyr Thr Lys Lys
35 40

<210> SEQ ID NO 319
<211> LENGTH: 45
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 319

Pro Leu Leu Glu Ser Ala Lys Val Ser Ala Leu Ser Ala Leu Glu Glu
1 5 10 15

Ala Thr Lys Lys Ser Pro Leu Leu Leu Glu Ser Phe Lys Val Ser Phe
20 25 30

Leu Ser Ala Leu Glu Glu Tyr Thr Lys Lys Leu Asn Thr
35 40 45

<210> SEQ ID NO 320
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Leu Leu Glu Ser Ala Lys Val Ser Ala Leu Ser Ala Leu Glu Glu Ala
1 5 10 15

Thr Lys Lys Ser Pro Leu Leu Leu Glu Ser Phe Lys Val Ser Phe Leu
20 25 30

Ser Ala Leu Glu Glu Tyr Thr Lys Lys Leu Asn Thr
35 40

<210> SEQ ID NO 321
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Leu Glu Ser Ala Lys Val Ser Ala Leu Ser Ala Leu Glu Glu Ala Thr
1 5 10 15

Lys Lys Ser Pro Leu Leu Leu Glu Ser Phe Lys Val Ser Phe Leu Ser
20 25 30

Ala Leu Glu Glu Tyr Thr Lys Lys Leu Asn Thr
35 40

<210> SEQ ID NO 322
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Pro Leu Leu Glu Ser Ala Lys Val Ser Ala Leu Ser Ala Leu Glu Glu
1 5 10 15

Ala Thr Lys Lys Ser Pro Leu Leu Leu Glu Ser Phe Lys Val Ser Phe
20 25 30

Leu Ser Ala Leu Glu Glu Tyr Thr Lys Lys Leu Asn
35 40

<210> SEQ ID NO 323
<211> LENGTH: 43
<212> TYPE: PRT
<213> ORGANISM: Artificial Sequence -continued
<220> FEATURE:
<223> OTHER INFORMATION: Description of Artificial Sequence: Synthetic
      peptide

<400> SEQUENCE: 323

```
Leu Leu Glu Ser Ala Lys Val Ser Ala Leu Ser Ala Leu Glu Glu Ala
1               5                   10                  15

Thr Lys Lys Ser Pro Leu Leu Leu Glu Ser Phe Lys Val Ser Phe Leu
            20                  25                  30

Ser Ala Leu Glu Glu Tyr Thr Lys Lys Leu Asn
        35                  40
```

<210> SEQ ID NO 324
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

```
Leu Glu Ser Ala Lys Val Ser Ala Leu Ser Ala Leu Glu Glu Ala Thr
1               5                   10                  15

Lys Lys Ser Pro Leu Leu Leu Glu Ser Phe Lys Val Ser Phe Leu Ser
            20                  25                  30

Ala Leu Glu Glu Tyr Thr Lys Lys Leu Asn
        35                  40
```

<210> SEQ ID NO 325
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

```
Pro Leu Leu Glu Ser Ala Lys Val Ser Ala Leu Ser Ala Leu Glu Glu
1               5                   10                  15

Ala Thr Lys Lys Ser Pro Leu Leu Leu Glu Ser Phe Lys Val Ser Phe
            20                  25                  30

Leu Ser Ala Leu Glu Glu Tyr Thr Lys Lys Leu
        35                  40
```

<210> SEQ ID NO 326
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

```
Leu Leu Glu Ser Ala Lys Val Ser Ala Leu Ser Ala Leu Glu Glu Ala
1               5                   10                  15

Thr Lys Lys Ser Pro Leu Leu Leu Glu Ser Phe Lys Val Ser Phe Leu
            20                  25                  30

Ser Ala Leu Glu Glu Tyr Thr Lys Lys Leu
        35                  40
```

<210> SEQ ID NO 327
<211> LENGTH: 41
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 327

Leu Glu Ser Ala Lys Val Ser Ala Leu Ser Ala Leu Glu Glu Ala Thr
1 5 10 15

Lys Lys Ser Pro Leu Leu Leu Glu Ser Phe Lys Val Ser Phe Leu Ser
20 25 30

Ala Leu Glu Glu Tyr Thr Lys Lys Leu
35 40

<210> SEQ ID NO 328
<211> LENGTH: 42
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Pro Leu Leu Glu Ser Ala Lys Val Ser Ala Leu Ser Ala Leu Glu Glu
1 5 10 15

Ala Thr Lys Lys Ser Pro Leu Leu Leu Glu Ser Phe Lys Val Ser Phe
20 25 30

Leu Ser Ala Leu Glu Glu Tyr Thr Lys Lys
35 40

<210> SEQ ID NO 329
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 329

Leu Leu Glu Ser Ala Lys Val Ser Ala Leu Ser Ala Leu Glu Glu Ala
1 5 10 15

Thr Lys Lys Ser Pro Leu Leu Leu Glu Ser Phe Lys Val Ser Phe Leu
20 25 30

Ser Ala Leu Glu Glu Tyr Thr Lys Lys
35 40

<210> SEQ ID NO 330
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Leu Glu Ser Ala Lys Val Ser Ala Leu Ser Ala Leu Glu Glu Ala Thr
1 5 10 15

Lys Lys Ser Pro Leu Leu Leu Glu Ser Phe Lys Val Ser Phe Leu Ser
20 25 30

Ala Leu Glu Glu Tyr Thr Lys Lys
35 40

<210> SEQ ID NO 331
<211> LENGTH: 44

-continued

<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Pro Leu Leu Glu Ser Ala Lys Val Ser Ala Leu Ser Ala Leu Glu Glu
1 5 10 15

Ala Thr Lys Lys Pro Leu Leu Leu Glu Ser Phe Lys Val Ser Phe Leu
20 25 30

Ser Ala Leu Glu Glu Tyr Thr Lys Lys Leu Asn Thr
35 40

<210> SEQ ID NO 332
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Leu Leu Glu Ser Ala Lys Val Ser Ala Leu Ser Ala Leu Glu Glu Ala
1 5 10 15

Thr Lys Lys Pro Leu Leu Leu Glu Ser Phe Lys Val Ser Phe Leu Ser
20 25 30

Ala Leu Glu Glu Tyr Thr Lys Lys Leu Asn Thr
35 40

<210> SEQ ID NO 333
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

Leu Glu Ser Ala Lys Val Ser Ala Leu Ser Ala Leu Glu Glu Ala Thr
1 5 10 15

Lys Lys Pro Leu Leu Leu Glu Ser Phe Lys Val Ser Phe Leu Ser Ala
20 25 30

Leu Glu Glu Tyr Thr Lys Lys Leu Asn Thr
35 40

<210> SEQ ID NO 334
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Pro Leu Leu Glu Ser Ala Lys Val Ser Ala Leu Ser Ala Leu Glu Glu
1 5 10 15

Ala Thr Lys Lys Pro Leu Leu Leu Glu Ser Phe Lys Val Ser Phe Leu
20 25 30

Ser Ala Leu Glu Glu Tyr Thr Lys Lys Leu Asn
35 40

<210> SEQ ID NO 335

<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

```
Leu Leu Glu Ser Ala Lys Val Ser Ala Leu Ser Ala Leu Glu Glu Ala
1               5                   10                  15

Thr Lys Lys Pro Leu Leu Leu Glu Ser Phe Lys Val Ser Phe Leu Ser
            20                  25                  30

Ala Leu Glu Glu Tyr Thr Lys Lys Leu Asn
        35                  40
```

<210> SEQ ID NO 336
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

```
Leu Glu Ser Ala Lys Val Ser Ala Leu Ser Ala Leu Glu Glu Ala Thr
1               5                   10                  15

Lys Lys Pro Leu Leu Leu Glu Ser Phe Lys Val Ser Phe Leu Ser Ala
            20                  25                  30

Leu Glu Glu Tyr Thr Lys Lys Leu Asn
        35                  40
```

<210> SEQ ID NO 337
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

```
Pro Leu Leu Glu Ser Ala Lys Val Ser Ala Leu Ser Ala Leu Glu Glu
1               5                   10                  15

Ala Thr Lys Lys Pro Leu Leu Leu Glu Ser Phe Lys Val Ser Phe Leu
            20                  25                  30

Ser Ala Leu Glu Glu Tyr Thr Lys Lys Leu
        35                  40
```

<210> SEQ ID NO 338
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

```
Leu Leu Glu Ser Ala Lys Val Ser Ala Leu Ser Ala Leu Glu Glu Ala
1               5                   10                  15

Thr Lys Lys Pro Leu Leu Leu Glu Ser Phe Lys Val Ser Phe Leu Ser
            20                  25                  30

Ala Leu Glu Glu Tyr Thr Lys Lys Leu
        35                  40
```

-continued

<210> SEQ ID NO 339
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

```
Leu Glu Ser Ala Lys Val Ser Ala Leu Ser Ala Leu Glu Glu Ala Thr
1               5                   10                  15

Lys Lys Pro Leu Leu Leu Glu Ser Phe Lys Val Ser Phe Leu Ser Ala
            20                  25                  30

Leu Glu Glu Tyr Thr Lys Lys Leu
        35                  40
```

<210> SEQ ID NO 340
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

```
Pro Leu Leu Glu Ser Ala Lys Val Ser Ala Leu Ser Ala Leu Glu Glu
1               5                   10                  15

Ala Thr Lys Lys Pro Leu Leu Leu Glu Ser Phe Lys Val Ser Phe Leu
            20                  25                  30

Ser Ala Leu Glu Glu Tyr Thr Lys Lys
        35                  40
```

<210> SEQ ID NO 341
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 341

```
Leu Leu Glu Ser Ala Lys Val Ser Ala Leu Ser Ala Leu Glu Glu Ala
1               5                   10                  15

Thr Lys Lys Pro Leu Leu Leu Glu Ser Phe Lys Val Ser Phe Leu Ser
            20                  25                  30

Ala Leu Glu Glu Tyr Thr Lys Lys
        35                  40
```

<210> SEQ ID NO 342
<211> LENGTH: 39
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

```
Leu Glu Ser Ala Lys Val Ser Ala Leu Ser Ala Leu Glu Glu Ala Thr
1               5                   10                  15

Lys Lys Pro Leu Leu Leu Glu Ser Phe Lys Val Ser Phe Leu Ser Ala
            20                  25                  30

Leu Glu Glu Tyr Thr Lys Lys
        35
```

-continued

<210> SEQ ID NO 343
<211> LENGTH: 46
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

```
Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn Thr
        35                  40                  45
```

<210> SEQ ID NO 344
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

```
Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr
        35                  40                  45
```

<210> SEQ ID NO 345
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr
        35                  40
```

<210> SEQ ID NO 346
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

```
Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu Asn
        35                  40                  45
```

-continued

<210> SEQ ID NO 347
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

```
Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu Asn
        35                  40
```

<210> SEQ ID NO 348
<211> LENGTH: 43
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys Leu Asn
        35                  40
```

<210> SEQ ID NO 349
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

```
Pro Leu Leu Glu Ser Ala Lys Val Ser Ala Leu Ser Ala Leu Glu Glu
1               5                   10                  15

Ala Thr Lys Lys Lys Leu Ser Pro Leu Leu Glu Ser Phe Lys Val Ser
            20                  25                  30

Phe Leu Ser Ala Leu Glu Glu Tyr Thr Lys Lys Leu
        35                  40
```

<210> SEQ ID NO 350
<211> LENGTH: 43
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

```
Leu Leu Glu Ser Ala Lys Val Ser Ala Leu Ser Ala Leu Glu Glu Ala
1               5                   10                  15

Thr Lys Lys Lys Leu Ser Pro Leu Leu Glu Ser Phe Lys Val Ser Phe
            20                  25                  30

Leu Ser Ala Leu Glu Glu Tyr Thr Lys Lys Leu
```

-continued 35 40

<210> SEQ ID NO 351
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys Leu
35 40

<210> SEQ ID NO 352
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Pro Leu Leu Glu Ser Ala Lys Val Ser Ala Leu Ser Ala Leu Glu Glu
1 5 10 15

Ala Thr Lys Lys Lys Leu Ser Pro Leu Leu Glu Ser Phe Lys Val Ser
20 25 30

Phe Leu Ser Ala Leu Glu Glu Tyr Thr Lys Lys
35 40

<210> SEQ ID NO 353
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Leu Leu Glu Ser Ala Lys Val Ser Ala Leu Ser Ala Leu Glu Glu Ala
1 5 10 15

Thr Lys Lys Lys Leu Ser Pro Leu Leu Glu Ser Phe Lys Val Ser Phe
20 25 30

Leu Ser Ala Leu Glu Glu Tyr Thr Lys Lys
35 40

<210> SEQ ID NO 354
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

```
Ser Ala Leu Glu Glu Tyr Thr Lys Lys
        35                  40


<210> SEQ ID NO 355
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Pro Leu Leu Glu Ser Ala Lys Val Ser Ala Leu Ser Ala Leu Glu Glu
1               5                   10                  15

Ala Thr Lys Lys Leu Ser Pro Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 356
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Leu Leu Glu Ser Ala Lys Val Ser Ala Leu Ser Ala Leu Glu Glu Ala
1               5                   10                  15

Thr Lys Lys Leu Ser Pro Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 357
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Leu Glu Ser Ala Lys Val Ser Ala Leu Ser Ala Leu Glu Glu Ala Thr
1               5                   10                  15

Lys Lys Leu Ser Pro Leu Leu Glu Ser Phe Lys Val Ser Phe Leu Ser
            20                  25                  30

Ala Leu Glu Glu Tyr Thr Lys Lys Leu Asn Thr
        35                  40


<210> SEQ ID NO 358
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Pro Leu Leu Glu Ser Ala Lys Val Ser Ala Leu Ser Ala Leu Glu Glu
1               5                   10                  15

Ala Thr Lys Lys Leu Ser Pro Leu Leu Glu Ser Phe Lys Val Ser Phe
            20                  25                  30
```

Leu Ser Ala Leu Glu Glu Tyr Thr Lys Lys Leu Asn
35 40

<210> SEQ ID NO 359
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Leu Leu Glu Ser Ala Lys Val Ser Ala Leu Ser Ala Leu Glu Glu Ala
1 5 10 15

Thr Lys Lys Leu Ser Pro Leu Leu Glu Ser Phe Lys Val Ser Phe Leu
20 25 30

Ser Ala Leu Glu Glu Tyr Thr Lys Lys Leu Asn
35 40

<210> SEQ ID NO 360
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Leu Glu Ser Ala Lys Val Ser Ala Leu Ser Ala Leu Glu Glu Ala Thr
1 5 10 15

Lys Lys Leu Ser Pro Leu Leu Glu Ser Phe Lys Val Ser Phe Leu Ser
20 25 30

Ala Leu Glu Glu Tyr Thr Lys Lys Leu Asn
35 40

<210> SEQ ID NO 361
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Pro Leu Leu Glu Ser Ala Lys Val Ser Ala Leu Ser Ala Leu Glu Glu
1 5 10 15

Ala Thr Lys Lys Leu Ser Pro Leu Leu Glu Ser Phe Lys Val Ser Phe
20 25 30

Leu Ser Ala Leu Glu Glu Tyr Thr Lys Lys Leu
35 40

<210> SEQ ID NO 362
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Leu Leu Glu Ser Ala Lys Val Ser Ala Leu Ser Ala Leu Glu Glu Ala
1 5 10 15

Thr Lys Lys Leu Ser Pro Leu Leu Glu Ser Phe Lys Val Ser Phe Leu

-continued

```
            20                  25                  30

Ser Ala Leu Glu Glu Tyr Thr Lys Lys Leu
        35                  40


<210> SEQ ID NO 363
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Leu Glu Ser Ala Lys Val Ser Ala Leu Ser Ala Leu Glu Glu Ala Thr
1               5                   10                  15

Lys Lys Leu Ser Pro Leu Leu Glu Ser Phe Lys Val Ser Phe Leu Ser
            20                  25                  30

Ala Leu Glu Glu Tyr Thr Lys Lys Leu
        35                  40


<210> SEQ ID NO 364
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Pro Leu Leu Glu Ser Ala Lys Val Ser Ala Leu Ser Ala Leu Glu Glu
1               5                   10                  15

Ala Thr Lys Lys Leu Ser Pro Leu Leu Glu Ser Phe Lys Val Ser Phe
            20                  25                  30

Leu Ser Ala Leu Glu Glu Tyr Thr Lys Lys
        35                  40


<210> SEQ ID NO 365
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Leu Leu Glu Ser Ala Lys Val Ser Ala Leu Ser Ala Leu Glu Glu Ala
1               5                   10                  15

Thr Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 366
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Leu Glu Ser Ala Lys Val Ser Ala Leu Ser Ala Leu Glu Glu Ala Thr
1               5                   10                  15
```

-continued

```
Lys Lys Leu Ser Pro Leu Leu Glu Ser Phe Lys Val Ser Phe Leu Ser
            20                  25                  30

Ala Leu Glu Glu Tyr Thr Lys Lys
        35                  40


<210> SEQ ID NO 367
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Pro Leu Leu Glu Ser Ala Lys Val Ser Ala Leu Ser Ala Leu Glu Glu
1               5                   10                  15

Ala Thr Lys Lys Ser Pro Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 368
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Leu Leu Glu Ser Ala Lys Val Ser Ala Leu Ser Ala Leu Glu Glu Ala
1               5                   10                  15

Thr Lys Lys Ser Pro Leu Leu Glu Ser Phe Lys Val Ser Phe Leu Ser
            20                  25                  30

Ala Leu Glu Glu Tyr Thr Lys Lys Leu Asn Thr
        35                  40


<210> SEQ ID NO 369
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Leu Glu Ser Ala Lys Val Ser Ala Leu Ser Ala Leu Glu Glu Ala Thr
1               5                   10                  15

Lys Lys Ser Pro Leu Leu Glu Ser Phe Lys Val Ser Phe Leu Ser Ala
            20                  25                  30

Leu Glu Glu Tyr Thr Lys Lys Leu Asn Thr
        35                  40


<210> SEQ ID NO 370
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Pro Leu Leu Glu Ser Ala Lys Val Ser Ala Leu Ser Ala Leu Glu Glu
1               5                   10                  15
```

Ala Thr Lys Lys Ser Pro Leu Leu Glu Ser Phe Lys Val Ser Phe Leu
20 25 30

Ser Ala Leu Glu Glu Tyr Thr Lys Lys Leu Asn
35 40

<210> SEQ ID NO 371
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 371

Leu Leu Glu Ser Ala Lys Val Ser Ala Leu Ser Ala Leu Glu Glu Ala
1 5 10 15

Thr Lys Lys Ser Pro Leu Leu Glu Ser Phe Lys Val Ser Phe Leu Ser
20 25 30

Ala Leu Glu Glu Tyr Thr Lys Lys Leu Asn
35 40

<210> SEQ ID NO 372
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 372

Leu Glu Ser Ala Lys Val Ser Ala Leu Ser Ala Leu Glu Glu Ala Thr
1 5 10 15

Lys Lys Ser Pro Leu Leu Glu Ser Phe Lys Val Ser Phe Leu Ser Ala
20 25 30

Leu Glu Glu Tyr Thr Lys Lys Leu Asn
35 40

<210> SEQ ID NO 373
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 373

Pro Leu Leu Glu Ser Ala Lys Val Ser Ala Leu Ser Ala Leu Glu Glu
1 5 10 15

Ala Thr Lys Lys Ser Pro Leu Leu Glu Ser Phe Lys Val Ser Phe Leu
20 25 30

Ser Ala Leu Glu Glu Tyr Thr Lys Lys Leu
35 40

<210> SEQ ID NO 374
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

Leu Leu Glu Ser Ala Lys Val Ser Ala Leu Ser Ala Leu Glu Glu Ala

-continued

```
1               5                   10                  15

Thr Lys Lys Ser Pro Leu Leu Glu Ser Phe Lys Val Ser Phe Leu Ser
            20                  25                  30

Ala Leu Glu Glu Tyr Thr Lys Lys Leu
        35                  40


<210> SEQ ID NO 375
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Leu Glu Ser Ala Lys Val Ser Ala Leu Ser Ala Leu Glu Glu Ala Thr
1               5                   10                  15

Lys Lys Ser Pro Leu Leu Glu Ser Phe Lys Val Ser Phe Leu Ser Ala
            20                  25                  30

Leu Glu Glu Tyr Thr Lys Lys Leu
        35                  40


<210> SEQ ID NO 376
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Pro Leu Leu Glu Ser Ala Lys Val Ser Ala Leu Ser Ala Leu Glu Glu
1               5                   10                  15

Ala Thr Lys Lys Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 377
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Leu Leu Glu Ser Ala Lys Val Ser Ala Leu Ser Ala Leu Glu Glu Ala
1               5                   10                  15

Thr Lys Lys Ser Pro Leu Leu Glu Ser Phe Lys Val Ser Phe Leu Ser
            20                  25                  30

Ala Leu Glu Glu Tyr Thr Lys Lys
        35                  40


<210> SEQ ID NO 378
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378
```

-continued

```
Leu Glu Ser Ala Lys Val Ser Ala Leu Ser Ala Leu Glu Glu Ala Thr
1               5                   10                  15

Lys Lys Ser Pro Leu Leu Glu Ser Phe Lys Val Ser Phe Leu Ser Ala
            20                  25                  30

Leu Glu Glu Tyr Thr Lys Lys
        35
```

<210> SEQ ID NO 379
<211> LENGTH: 47
<212> TYPE: PRT
<213> ORGANISM: Artificial Sequence
<220> FEATURE:
<223> OTHER INFORMATION: Description of Artificial Sequence: Synthetic peptide

<400> SEQUENCE: 379

```
Pro Leu Leu Glu Ser Ala Lys Val Ser Ala Leu Ser Ala Leu Glu Glu
1               5                   10                  15

Ala Thr Lys Lys Leu Pro Ser Leu Lys Leu Leu Glu Ser Phe Lys Val
            20                  25                  30

Ser Phe Leu Ser Ala Leu Glu Glu Tyr Thr Lys Lys Leu Asn Thr
        35                  40                  45
```

<210> SEQ ID NO 380
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 380

```
Leu Leu Glu Ser Ala Lys Val Ser Ala Leu Ser Ala Leu Glu Glu Ala
1               5                   10                  15

Thr Lys Lys Leu Pro Ser Leu Lys Leu Leu Glu Ser Phe Lys Val Ser
            20                  25                  30

Phe Leu Ser Ala Leu Glu Glu Tyr Thr Lys Lys Leu Asn Thr
        35                  40                  45
```

<210> SEQ ID NO 381
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 381

```
Leu Glu Ser Ala Lys Val Ser Ala Leu Ser Ala Leu Glu Glu Ala Thr
1               5                   10                  15

Lys Lys Leu Pro Ser Leu Lys Leu Leu Glu Ser Phe Lys Val Ser Phe
            20                  25                  30

Leu Ser Ala Leu Glu Glu Tyr Thr Lys Lys Leu Asn Thr
        35                  40                  45
```

<210> SEQ ID NO 382
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 382

-continued

Pro Leu Leu Glu Ser Ala Lys Val Ser Ala Leu Ser Ala Leu Glu Glu
1 5 10 15

Ala Thr Lys Lys Leu Pro Ser Leu Lys Leu Leu Glu Ser Phe Lys Val
20 25 30

Ser Phe Leu Ser Ala Leu Glu Glu Tyr Thr Lys Lys Leu Asn
35 40 45

<210> SEQ ID NO 383
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 383

Leu Leu Glu Ser Ala Lys Val Ser Ala Leu Ser Ala Leu Glu Glu Ala
1 5 10 15

Thr Lys Lys Leu Pro Ser Leu Lys Leu Leu Glu Ser Phe Lys Val Ser
20 25 30

Phe Leu Ser Ala Leu Glu Glu Tyr Thr Lys Lys Leu Asn
35 40 45

<210> SEQ ID NO 384
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Leu Glu Ser Ala Lys Val Ser Ala Leu Ser Ala Leu Glu Glu Ala Thr
1 5 10 15

Lys Lys Leu Pro Ser Leu Lys Leu Leu Glu Ser Phe Lys Val Ser Phe
20 25 30

Leu Ser Ala Leu Glu Glu Tyr Thr Lys Lys Leu Asn
35 40

<210> SEQ ID NO 385
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Pro Leu Leu Glu Ser Ala Lys Val Ser Ala Leu Ser Ala Leu Glu Glu
1 5 10 15

Ala Thr Lys Lys Leu Pro Ser Leu Lys Leu Leu Glu Ser Phe Lys Val
20 25 30

Ser Phe Leu Ser Ala Leu Glu Glu Tyr Thr Lys Lys Leu
35 40 45

<210> SEQ ID NO 386
<211> LENGTH: 44
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 386

```
Leu Leu Glu Ser Ala Lys Val Ser Ala Leu Ser Ala Leu Glu Glu Ala
1               5                   10                  15

Thr Lys Lys Leu Pro Ser Leu Lys Leu Leu Glu Ser Phe Lys Val Ser
            20                  25                  30

Phe Leu Ser Ala Leu Glu Glu Tyr Thr Lys Lys Leu
        35                  40
```

<210> SEQ ID NO 387
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

```
Leu Glu Ser Ala Lys Val Ser Ala Leu Ser Ala Leu Glu Glu Ala Thr
1               5                   10                  15

Lys Lys Leu Pro Ser Leu Lys Leu Leu Glu Ser Phe Lys Val Ser Phe
            20                  25                  30

Leu Ser Ala Leu Glu Glu Tyr Thr Lys Lys Leu
        35                  40
```

<210> SEQ ID NO 388
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

```
Pro Leu Leu Glu Ser Ala Lys Val Ser Ala Leu Ser Ala Leu Glu Glu
1               5                   10                  15

Ala Thr Lys Lys Leu Pro Ser Leu Lys Leu Leu Glu Ser Phe Lys Val
            20                  25                  30

Ser Phe Leu Ser Ala Leu Glu Glu Tyr Thr Lys Lys
        35                  40
```

<210> SEQ ID NO 389
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

```
Leu Leu Glu Ser Ala Lys Val Ser Ala Leu Ser Ala Leu Glu Glu Ala
1               5                   10                  15

Thr Lys Lys Leu Pro Ser Leu Lys Leu Leu Glu Ser Phe Lys Val Ser
            20                  25                  30

Phe Leu Ser Ala Leu Glu Glu Tyr Thr Lys Lys
        35                  40
```

<210> SEQ ID NO 390
<211> LENGTH: 42
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 390

Leu Glu Ser Ala Lys Val Ser Ala Leu Ser Ala Leu Glu Glu Ala Thr
1 5 10 15

Lys Lys Leu Pro Ser Leu Lys Leu Leu Glu Ser Phe Lys Val Ser Phe
20 25 30

Leu Ser Ala Leu Glu Glu Tyr Thr Lys Lys
35 40

<210> SEQ ID NO 391
<211> LENGTH: 46
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Pro Leu Leu Glu Ser Ala Lys Val Ser Ala Leu Ser Ala Leu Glu Glu
1 5 10 15

Ala Thr Lys Lys Leu Pro Ser Leu Leu Leu Glu Ser Phe Lys Val Ser
20 25 30

Phe Leu Ser Ala Leu Glu Glu Tyr Thr Lys Lys Leu Asn Thr
35 40 45

<210> SEQ ID NO 392
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Leu Leu Glu Ser Ala Lys Val Ser Ala Leu Ser Ala Leu Glu Glu Ala
1 5 10 15

Thr Lys Lys Leu Pro Ser Leu Leu Leu Glu Ser Phe Lys Val Ser Phe
20 25 30

Leu Ser Ala Leu Glu Glu Tyr Thr Lys Lys Leu Asn Thr
35 40 45

<210> SEQ ID NO 393
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

Leu Glu Ser Ala Lys Val Ser Ala Leu Ser Ala Leu Glu Glu Ala Thr
1 5 10 15

Lys Lys Leu Pro Ser Leu Leu Leu Glu Ser Phe Lys Val Ser Phe Leu
20 25 30

Ser Ala Leu Glu Glu Tyr Thr Lys Lys Leu Asn Thr
35 40

<210> SEQ ID NO 394
<211> LENGTH: 45
<212> TYPE: PRT
<213> ORGANISM: Artificial Sequence -continued
<220> FEATURE:
<223> OTHER INFORMATION: Description of Artificial Sequence: Synthetic
      peptide

<400> SEQUENCE: 394

```
Pro Leu Leu Glu Ser Ala Lys Val Ser Ala Leu Ser Ala Leu Glu Glu
1               5                   10                  15

Ala Thr Lys Lys Leu Pro Ser Leu Leu Leu Glu Ser Phe Lys Val Ser
            20                  25                  30

Phe Leu Ser Ala Leu Glu Glu Tyr Thr Lys Lys Leu Asn
        35                  40                  45
```

<210> SEQ ID NO 395
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

```
Leu Leu Glu Ser Ala Lys Val Ser Ala Leu Ser Ala Leu Glu Glu Ala
1               5                   10                  15

Thr Lys Lys Leu Pro Ser Leu Leu Leu Glu Ser Phe Lys Val Ser Phe
            20                  25                  30

Leu Ser Ala Leu Glu Glu Tyr Thr Lys Lys Leu Asn
        35                  40
```

<210> SEQ ID NO 396
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

```
Leu Glu Ser Ala Lys Val Ser Ala Leu Ser Ala Leu Glu Glu Ala Thr
1               5                   10                  15

Lys Lys Leu Pro Ser Leu Leu Leu Glu Ser Phe Lys Val Ser Phe Leu
            20                  25                  30

Ser Ala Leu Glu Glu Tyr Thr Lys Lys Leu Asn
        35                  40
```

<210> SEQ ID NO 397
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

```
Pro Leu Leu Glu Ser Ala Lys Val Ser Ala Leu Ser Ala Leu Glu Glu
1               5                   10                  15

Ala Thr Lys Lys Leu Pro Ser Leu Leu Leu Glu Ser Phe Lys Val Ser
            20                  25                  30

Phe Leu Ser Ala Leu Glu Glu Tyr Thr Lys Lys Leu
        35                  40
```

<210> SEQ ID NO 398
<211> LENGTH: 43
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 398

Leu Leu Glu Ser Ala Lys Val Ser Ala Leu Ser Ala Leu Glu Glu Ala
1               5                   10                  15

Thr Lys Lys Leu Pro Ser Leu Leu Leu Glu Ser Phe Lys Val Ser Phe
            20                  25                  30

Leu Ser Ala Leu Glu Glu Tyr Thr Lys Lys Leu
        35                  40


<210> SEQ ID NO 399
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Leu Glu Ser Ala Lys Val Ser Ala Leu Ser Ala Leu Glu Glu Ala Thr
1               5                   10                  15

Lys Lys Leu Pro Ser Leu Leu Leu Glu Ser Phe Lys Val Ser Phe Leu
            20                  25                  30

Ser Ala Leu Glu Glu Tyr Thr Lys Lys Leu
        35                  40


<210> SEQ ID NO 400
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Pro Leu Leu Glu Ser Ala Lys Val Ser Ala Leu Ser Ala Leu Glu Glu
1               5                   10                  15

Ala Thr Lys Lys Leu Pro Ser Leu Leu Leu Glu Ser Phe Lys Val Ser
            20                  25                  30

Phe Leu Ser Ala Leu Glu Glu Tyr Thr Lys Lys
        35                  40


<210> SEQ ID NO 401
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Leu Leu Glu Ser Ala Lys Val Ser Ala Leu Ser Ala Leu Glu Glu Ala
1               5                   10                  15

Thr Lys Lys Leu Pro Ser Leu Leu Leu Glu Ser Phe Lys Val Ser Phe
            20                  25                  30

Leu Ser Ala Leu Glu Glu Tyr Thr Lys Lys
        35                  40


<210> SEQ ID NO 402
<211> LENGTH: 41
```

-continued

<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

```
Leu Glu Ser Ala Lys Val Ser Ala Leu Ser Ala Leu Glu Glu Ala Thr
1               5                   10                  15

Lys Lys Leu Pro Ser Leu Leu Leu Glu Ser Phe Lys Val Ser Phe Leu
            20                  25                  30

Ser Ala Leu Glu Glu Tyr Thr Lys Lys
        35                  40
```

<210> SEQ ID NO 403
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

```
Pro Leu Leu Glu Ser Ala Lys Val Ser Ala Leu Ser Ala Leu Glu Glu
1               5                   10                  15

Ala Thr Lys Lys Leu Pro Ser Leu Leu Glu Ser Phe Lys Val Ser Phe
            20                  25                  30

Leu Ser Ala Leu Glu Glu Tyr Thr Lys Lys Leu Asn Thr
        35                  40                  45
```

<210> SEQ ID NO 404
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

```
Leu Leu Glu Ser Ala Lys Val Ser Ala Leu Ser Ala Leu Glu Glu Ala
1               5                   10                  15

Thr Lys Lys Leu Pro Ser Leu Leu Glu Ser Phe Lys Val Ser Phe Leu
            20                  25                  30

Ser Ala Leu Glu Glu Tyr Thr Lys Lys Leu Asn Thr
        35                  40
```

<210> SEQ ID NO 405
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

```
Leu Glu Ser Ala Lys Val Ser Ala Leu Ser Ala Leu Glu Glu Ala Thr
1               5                   10                  15

Lys Lys Leu Pro Ser Leu Leu Glu Ser Phe Lys Val Ser Phe Leu Ser
            20                  25                  30

Ala Leu Glu Glu Tyr Thr Lys Lys Leu Asn Thr
        35                  40
```

<210> SEQ ID NO 406

<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

```
Pro Leu Leu Glu Ser Ala Lys Val Ser Ala Leu Ser Ala Leu Glu Glu
1               5                   10                  15

Ala Thr Lys Lys Leu Pro Ser Leu Leu Glu Ser Phe Lys Val Ser Phe
            20                  25                  30

Leu Ser Ala Leu Glu Glu Tyr Thr Lys Lys Leu Asn
        35                  40
```

<210> SEQ ID NO 407
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

```
Leu Leu Glu Ser Ala Lys Val Ser Ala Leu Ser Ala Leu Glu Glu Ala
1               5                   10                  15

Thr Lys Lys Leu Pro Ser Leu Leu Glu Ser Phe Lys Val Ser Phe Leu
            20                  25                  30

Ser Ala Leu Glu Glu Tyr Thr Lys Lys Leu Asn
        35                  40
```

<210> SEQ ID NO 408
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

```
Leu Glu Ser Ala Lys Val Ser Ala Leu Ser Ala Leu Glu Glu Ala Thr
1               5                   10                  15

Lys Lys Leu Pro Ser Leu Leu Glu Ser Phe Lys Val Ser Phe Leu Ser
            20                  25                  30

Ala Leu Glu Glu Tyr Thr Lys Lys Leu Asn
        35                  40
```

<210> SEQ ID NO 409
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

```
Pro Leu Leu Glu Ser Ala Lys Val Ser Ala Leu Ser Ala Leu Glu Glu
1               5                   10                  15

Ala Thr Lys Lys Leu Pro Ser Leu Leu Glu Ser Phe Lys Val Ser Phe
            20                  25                  30

Leu Ser Ala Leu Glu Glu Tyr Thr Lys Lys Leu
        35                  40
```

-continued

<210> SEQ ID NO 410
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 410

```
Leu Leu Glu Ser Ala Lys Val Ser Ala Leu Ser Ala Leu Glu Glu Ala
1               5                   10                  15

Thr Lys Lys Leu Pro Ser Leu Leu Glu Ser Phe Lys Val Ser Phe Leu
            20                  25                  30

Ser Ala Leu Glu Glu Tyr Thr Lys Lys Leu
        35                  40
```

<210> SEQ ID NO 411
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

```
Leu Glu Ser Ala Lys Val Ser Ala Leu Ser Ala Leu Glu Glu Ala Thr
1               5                   10                  15

Lys Lys Leu Pro Ser Leu Leu Glu Ser Phe Lys Val Ser Phe Leu Ser
            20                  25                  30

Ala Leu Glu Glu Tyr Thr Lys Lys Leu
        35                  40
```

<210> SEQ ID NO 412
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 412

```
Pro Leu Leu Glu Ser Ala Lys Val Ser Ala Leu Ser Ala Leu Glu Glu
1               5                   10                  15

Ala Thr Lys Lys Leu Pro Ser Leu Leu Glu Ser Phe Lys Val Ser Phe
            20                  25                  30

Leu Ser Ala Leu Glu Glu Tyr Thr Lys Lys
        35                  40
```

<210> SEQ ID NO 413
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

```
Leu Leu Glu Ser Ala Lys Val Ser Ala Leu Ser Ala Leu Glu Glu Ala
1               5                   10                  15

Thr Lys Lys Leu Pro Ser Leu Leu Glu Ser Phe Lys Val Ser Phe Leu
            20                  25                  30

Ser Ala Leu Glu Glu Tyr Thr Lys Lys
        35                  40
```

-continued

<210> SEQ ID NO 414
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 414

```
Leu Glu Ser Ala Lys Val Ser Ala Leu Ser Ala Leu Glu Glu Ala Thr
1               5                   10                  15

Lys Lys Leu Pro Ser Leu Leu Glu Ser Phe Lys Val Ser Phe Leu Ser
            20                  25                  30

Ala Leu Glu Glu Tyr Thr Lys Lys
        35                  40
```

<210> SEQ ID NO 415
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 415

```
Pro Leu Leu Glu Ser Ala Lys Val Ser Ala Leu Ser Ala Leu Glu Glu
1               5                   10                  15

Ala Thr Lys Lys Leu Pro Leu Leu Glu Ser Phe Lys Val Ser Phe Leu
            20                  25                  30

Ser Ala Leu Glu Glu Tyr Thr Lys Lys Leu Asn Thr
        35                  40
```

<210> SEQ ID NO 416
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

```
Leu Leu Glu Ser Ala Lys Val Ser Ala Leu Ser Ala Leu Glu Glu Ala
1               5                   10                  15

Thr Lys Lys Leu Pro Leu Leu Glu Ser Phe Lys Val Ser Phe Leu Ser
            20                  25                  30

Ala Leu Glu Glu Tyr Thr Lys Lys Leu Asn Thr
        35                  40
```

<210> SEQ ID NO 417
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

```
Leu Glu Ser Ala Lys Val Ser Ala Leu Ser Ala Leu Glu Glu Ala Thr
1               5                   10                  15

Lys Lys Leu Pro Leu Leu Glu Ser Phe Lys Val Ser Phe Leu Ser Ala
            20                  25                  30

Leu Glu Glu Tyr Thr Lys Lys Leu Asn Thr
        35                  40
```

-continued

<210> SEQ ID NO 418
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

```
Pro Leu Leu Glu Ser Ala Lys Val Ser Ala Leu Ser Ala Leu Glu Glu
1               5                   10                  15

Ala Thr Lys Lys Leu Pro Leu Leu Glu Ser Phe Lys Val Ser Phe Leu
            20                  25                  30

Ser Ala Leu Glu Glu Tyr Thr Lys Lys Leu Asn
        35                  40
```

<210> SEQ ID NO 419
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

```
Leu Leu Glu Ser Ala Lys Val Ser Ala Leu Ser Ala Leu Glu Glu Ala
1               5                   10                  15

Thr Lys Lys Leu Pro Leu Leu Glu Ser Phe Lys Val Ser Phe Leu Ser
            20                  25                  30

Ala Leu Glu Glu Tyr Thr Lys Lys Leu Asn
        35                  40
```

<210> SEQ ID NO 420
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

```
Leu Glu Ser Ala Lys Val Ser Ala Leu Ser Ala Leu Glu Glu Ala Thr
1               5                   10                  15

Lys Lys Leu Pro Leu Leu Glu Ser Phe Lys Val Ser Phe Leu Ser Ala
            20                  25                  30

Leu Glu Glu Tyr Thr Lys Lys Leu Asn
        35                  40
```

<210> SEQ ID NO 421
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

```
Pro Leu Leu Glu Ser Ala Lys Val Ser Ala Leu Ser Ala Leu Glu Glu
1               5                   10                  15

Ala Thr Lys Lys Leu Pro Leu Leu Glu Ser Phe Lys Val Ser Phe Leu
            20                  25                  30

Ser Ala Leu Glu Glu Tyr Thr Lys Lys Leu
```

-continued 35 40

<210> SEQ ID NO 422
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Leu Leu Glu Ser Ala Lys Val Ser Ala Leu Ser Ala Leu Glu Glu Ala
1 5 10 15

Thr Lys Lys Leu Pro Leu Leu Glu Ser Phe Lys Val Ser Phe Leu Ser
20 25 30

Ala Leu Glu Glu Tyr Thr Lys Lys Leu
35 40

<210> SEQ ID NO 423
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Leu Glu Ser Ala Lys Val Ser Ala Leu Ser Ala Leu Glu Glu Ala Thr
1 5 10 15

Lys Lys Leu Pro Leu Leu Glu Ser Phe Lys Val Ser Phe Leu Ser Ala
20 25 30

Leu Glu Glu Tyr Thr Lys Lys Leu
35 40

<210> SEQ ID NO 424
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Pro Leu Leu Glu Ser Ala Lys Val Ser Ala Leu Ser Ala Leu Glu Glu
1 5 10 15

Ala Thr Lys Lys Leu Pro Leu Leu Glu Ser Phe Lys Val Ser Phe Leu
20 25 30

Ser Ala Leu Glu Glu Tyr Thr Lys Lys
35 40

<210> SEQ ID NO 425
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Leu Leu Glu Ser Ala Lys Val Ser Ala Leu Ser Ala Leu Glu Glu Ala
1 5 10 15

Thr Lys Lys Leu Pro Leu Leu Glu Ser Phe Lys Val Ser Phe Leu Ser
20 25 30

-continued

```
Ala Leu Glu Glu Tyr Thr Lys Lys
        35                  40


<210> SEQ ID NO 426
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Leu Glu Ser Ala Lys Val Ser Ala Leu Ser Ala Leu Glu Glu Ala Thr
1               5                   10                  15

Lys Lys Leu Pro Leu Leu Glu Ser Phe Lys Val Ser Phe Leu Ser Ala
            20                  25                  30

Leu Glu Glu Tyr Thr Lys Lys
        35


<210> SEQ ID NO 427
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Pro Leu Leu Glu Ser Ala Lys Val Ser Ala Leu Ser Ala Leu Glu Glu
1               5                   10                  15

Ala Thr Lys Lys Pro Ser Leu Lys Leu Leu Glu Ser Phe Lys Val Ser
            20                  25                  30

Phe Leu Ser Ala Leu Glu Glu Tyr Thr Lys Lys Leu Asn Thr
        35                  40                  45


<210> SEQ ID NO 428
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Leu Leu Glu Ser Ala Lys Val Ser Ala Leu Ser Ala Leu Glu Glu Ala
1               5                   10                  15

Thr Lys Lys Pro Ser Leu Lys Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 429
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Leu Glu Ser Ala Lys Val Ser Ala Leu Ser Ala Leu Glu Glu Ala Thr
1               5                   10                  15

Lys Lys Pro Ser Leu Lys Leu Leu Glu Ser Phe Lys Val Ser Phe Leu
            20                  25                  30
```

-continued

```
Ser Ala Leu Glu Glu Tyr Thr Lys Lys Leu Asn Thr
        35                  40


<210> SEQ ID NO 430
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Pro Leu Leu Glu Ser Ala Lys Val Ser Ala Leu Ser Ala Leu Glu Glu
1               5                   10                  15

Ala Thr Lys Lys Pro Ser Leu Lys Leu Leu Glu Ser Phe Lys Val Ser
            20                  25                  30

Phe Leu Ser Ala Leu Glu Glu Tyr Thr Lys Lys Leu Asn
        35                  40                  45


<210> SEQ ID NO 431
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Leu Leu Glu Ser Ala Lys Val Ser Ala Leu Ser Ala Leu Glu Glu Ala
1               5                   10                  15

Thr Lys Lys Pro Ser Leu Lys Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 432
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Leu Glu Ser Ala Lys Val Ser Ala Leu Ser Ala Leu Glu Glu Ala Thr
1               5                   10                  15

Lys Lys Pro Ser Leu Lys Leu Leu Glu Ser Phe Lys Val Ser Phe Leu
            20                  25                  30

Ser Ala Leu Glu Glu Tyr Thr Lys Lys Leu Asn
        35                  40


<210> SEQ ID NO 433
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Pro Leu Leu Glu Ser Ala Lys Val Ser Ala Leu Ser Ala Leu Glu Glu
1               5                   10                  15

Ala Thr Lys Lys Pro Ser Leu Lys Leu Leu Glu Ser Phe Lys Val Ser
```

-continued

```
            20                  25                  30

Phe Leu Ser Ala Leu Glu Glu Tyr Thr Lys Lys Leu
        35                  40


<210> SEQ ID NO 434
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Leu Leu Glu Ser Ala Lys Val Ser Ala Leu Ser Ala Leu Glu Glu Ala
1               5                   10                  15

Thr Lys Lys Pro Ser Leu Lys Leu Leu Glu Ser Phe Lys Val Ser Phe
            20                  25                  30

Leu Ser Ala Leu Glu Glu Tyr Thr Lys Lys Leu
        35                  40


<210> SEQ ID NO 435
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Leu Glu Ser Ala Lys Val Ser Ala Leu Ser Ala Leu Glu Glu Ala Thr
1               5                   10                  15

Lys Lys Pro Ser Leu Lys Leu Leu Glu Ser Phe Lys Val Ser Phe Leu
            20                  25                  30

Ser Ala Leu Glu Glu Tyr Thr Lys Lys Leu
        35                  40


<210> SEQ ID NO 436
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Pro Leu Leu Glu Ser Ala Lys Val Ser Ala Leu Ser Ala Leu Glu Glu
1               5                   10                  15

Ala Thr Lys Lys Pro Ser Leu Lys Leu Leu Glu Ser Phe Lys Val Ser
            20                  25                  30

Phe Leu Ser Ala Leu Glu Glu Tyr Thr Lys Lys
        35                  40


<210> SEQ ID NO 437
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Leu Leu Glu Ser Ala Lys Val Ser Ala Leu Ser Ala Leu Glu Glu Ala
1               5                   10                  15
```

-continued

```
Thr Lys Lys Pro Ser Leu Lys Leu Leu Glu Ser Phe Lys Val Ser Phe
            20                  25                  30

Leu Ser Ala Leu Glu Glu Tyr Thr Lys Lys
        35                  40


<210> SEQ ID NO 438
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Leu Glu Ser Ala Lys Val Ser Ala Leu Ser Ala Leu Glu Glu Ala Thr
1               5                   10                  15

Lys Lys Pro Ser Leu Lys Leu Leu Glu Ser Phe Lys Val Ser Phe Leu
            20                  25                  30

Ser Ala Leu Glu Glu Tyr Thr Lys Lys
        35                  40


<210> SEQ ID NO 439
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Pro Leu Leu Glu Ser Ala Lys Val Ser Ala Leu Ser Ala Leu Glu Glu
1               5                   10                  15

Ala Thr Lys Lys Pro Ser Leu Leu Leu Glu Ser Phe Lys Val Ser Phe
            20                  25                  30

Leu Ser Ala Leu Glu Glu Tyr Thr Lys Lys Leu Asn Thr
        35                  40                  45


<210> SEQ ID NO 440
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Leu Leu Glu Ser Ala Lys Val Ser Ala Leu Ser Ala Leu Glu Glu Ala
1               5                   10                  15

Thr Lys Lys Pro Ser Leu Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 441
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Leu Glu Ser Ala Lys Val Ser Ala Leu Ser Ala Leu Glu Glu Ala Thr
1               5                   10                  15
```

-continued

```
Lys Lys Pro Ser Leu Leu Leu Glu Ser Phe Lys Val Ser Phe Leu Ser
            20                  25                  30

Ala Leu Glu Glu Tyr Thr Lys Lys Leu Asn Thr
        35                  40


<210> SEQ ID NO 442
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Pro Leu Leu Glu Ser Ala Lys Val Ser Ala Leu Ser Ala Leu Glu Glu
1               5                   10                  15

Ala Thr Lys Lys Pro Ser Leu Leu Leu Glu Ser Phe Lys Val Ser Phe
            20                  25                  30

Leu Ser Ala Leu Glu Glu Tyr Thr Lys Lys Leu Asn
        35                  40


<210> SEQ ID NO 443
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Leu Leu Glu Ser Ala Lys Val Ser Ala Leu Ser Ala Leu Glu Glu Ala
1               5                   10                  15

Thr Lys Lys Pro Ser Leu Leu Leu Glu Ser Phe Lys Val Ser Phe Leu
            20                  25                  30

Ser Ala Leu Glu Glu Tyr Thr Lys Lys Leu Asn
        35                  40


<210> SEQ ID NO 444
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Glu Ser Ala Lys Val Ser Ala Leu Ser Ala Leu Glu Glu Ala Thr
1               5                   10                  15

Lys Lys Pro Ser Leu Leu Leu Glu Ser Phe Lys Val Ser Phe Leu Ser
            20                  25                  30

Ala Leu Glu Glu Tyr Thr Lys Lys Leu Asn
        35                  40


<210> SEQ ID NO 445
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Pro Leu Leu Glu Ser Ala Lys Val Ser Ala Leu Ser Ala Leu Glu Glu
```

-continued

```
1               5                   10                  15

Ala Thr Lys Lys Pro Ser Leu Leu Leu Glu Ser Phe Lys Val Ser Phe
            20                  25                  30

Leu Ser Ala Leu Glu Glu Tyr Thr Lys Lys Leu
        35                  40
```

<210> SEQ ID NO 446
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

```
Leu Leu Glu Ser Ala Lys Val Ser Ala Leu Ser Ala Leu Glu Glu Ala
1               5                   10                  15

Thr Lys Lys Pro Ser Leu Leu Leu Glu Ser Phe Lys Val Ser Phe Leu
            20                  25                  30

Ser Ala Leu Glu Glu Tyr Thr Lys Lys Leu
        35                  40
```

<210> SEQ ID NO 447
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 447

```
Leu Glu Ser Ala Lys Val Ser Ala Leu Ser Ala Leu Glu Glu Ala Thr
1               5                   10                  15

Lys Lys Pro Ser Leu Leu Leu Glu Ser Phe Lys Val Ser Phe Leu Ser
            20                  25                  30

Ala Leu Glu Glu Tyr Thr Lys Lys Leu
        35                  40
```

<210> SEQ ID NO 448
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 448

```
Pro Leu Leu Glu Ser Ala Lys Val Ser Ala Leu Ser Ala Leu Glu Glu
1               5                   10                  15

Ala Thr Lys Lys Pro Ser Leu Leu Leu Glu Ser Phe Lys Val Ser Phe
            20                  25                  30

Leu Ser Ala Leu Glu Glu Tyr Thr Lys Lys
        35                  40
```

<210> SEQ ID NO 449
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 449

-continued

```
Leu Leu Glu Ser Ala Lys Val Ser Ala Leu Ser Ala Leu Glu Glu Ala
1               5                   10                  15

Thr Lys Lys Pro Ser Leu Leu Leu Glu Ser Phe Lys Val Ser Phe Leu
            20                  25                  30

Ser Ala Leu Glu Glu Tyr Thr Lys Lys
        35                  40


<210> SEQ ID NO 450
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Leu Glu Ser Ala Lys Val Ser Ala Leu Ser Ala Leu Glu Glu Ala Thr
1               5                   10                  15

Lys Lys Pro Ser Leu Leu Leu Glu Ser Phe Lys Val Ser Phe Leu Ser
            20                  25                  30

Ala Leu Glu Glu Tyr Thr Lys Lys
        35                  40


<210> SEQ ID NO 451
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Pro Leu Leu Glu Ser Ala Lys Val Ser Ala Leu Ser Ala Leu Glu Glu
1               5                   10                  15

Ala Thr Lys Lys Pro Ser Leu Leu Glu Ser Phe Lys Val Ser Phe Leu
            20                  25                  30

Ser Ala Leu Glu Glu Tyr Thr Lys Lys Leu Asn Thr
        35                  40


<210> SEQ ID NO 452
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Leu Leu Glu Ser Ala Lys Val Ser Ala Leu Ser Ala Leu Glu Glu Ala
1               5                   10                  15

Thr Lys Lys Pro Ser Leu Leu Glu Ser Phe Lys Val Ser Phe Leu Ser
            20                  25                  30

Ala Leu Glu Glu Tyr Thr Lys Lys Leu Asn Thr
        35                  40


<210> SEQ ID NO 453
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453
```

-continued

Leu Glu Ser Ala Lys Val Ser Ala Leu Ser Ala Leu Glu Glu Ala Thr
1 5 10 15

Lys Lys Pro Ser Leu Leu Glu Ser Phe Lys Val Ser Phe Leu Ser Ala
20 25 30

Leu Glu Glu Tyr Thr Lys Lys Leu Asn Thr
35 40

<210> SEQ ID NO 454
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 454

Pro Leu Leu Glu Ser Ala Lys Val Ser Ala Leu Ser Ala Leu Glu Glu
1 5 10 15

Ala Thr Lys Lys Pro Ser Leu Leu Glu Ser Phe Lys Val Ser Phe Leu
20 25 30

Ser Ala Leu Glu Glu Tyr Thr Lys Lys Leu Asn
35 40

<210> SEQ ID NO 455
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 455

Leu Leu Glu Ser Ala Lys Val Ser Ala Leu Ser Ala Leu Glu Glu Ala
1 5 10 15

Thr Lys Lys Pro Ser Leu Leu Glu Ser Phe Lys Val Ser Phe Leu Ser
20 25 30

Ala Leu Glu Glu Tyr Thr Lys Lys Leu Asn
35 40

<210> SEQ ID NO 456
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 456

Leu Glu Ser Ala Lys Val Ser Ala Leu Ser Ala Leu Glu Glu Ala Thr
1 5 10 15

Lys Lys Pro Ser Leu Leu Glu Ser Phe Lys Val Ser Phe Leu Ser Ala
20 25 30

Leu Glu Glu Tyr Thr Lys Lys Leu Asn
35 40

<210> SEQ ID NO 457
<211> LENGTH: 42
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 457

Pro Leu Leu Glu Ser Ala Lys Val Ser Ala Leu Ser Ala Leu Glu Glu
1 5 10 15

Ala Thr Lys Lys Pro Ser Leu Leu Glu Ser Phe Lys Val Ser Phe Leu
20 25 30

Ser Ala Leu Glu Glu Tyr Thr Lys Lys Leu
35 40

<210> SEQ ID NO 458
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 458

Leu Leu Glu Ser Ala Lys Val Ser Ala Leu Ser Ala Leu Glu Glu Ala
1 5 10 15

Thr Lys Lys Pro Ser Leu Leu Glu Ser Phe Lys Val Ser Phe Leu Ser
20 25 30

Ala Leu Glu Glu Tyr Thr Lys Lys Leu
35 40

<210> SEQ ID NO 459
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 459

Leu Glu Ser Ala Lys Val Ser Ala Leu Ser Ala Leu Glu Glu Ala Thr
1 5 10 15

Lys Lys Pro Ser Leu Leu Glu Ser Phe Lys Val Ser Phe Leu Ser Ala
20 25 30

Leu Glu Glu Tyr Thr Lys Lys Leu
35 40

<210> SEQ ID NO 460
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 460

Pro Leu Leu Glu Ser Ala Lys Val Ser Ala Leu Ser Ala Leu Glu Glu
1 5 10 15

Ala Thr Lys Lys Pro Ser Leu Leu Glu Ser Phe Lys Val Ser Phe Leu
20 25 30

Ser Ala Leu Glu Glu Tyr Thr Lys Lys
35 40

<210> SEQ ID NO 461
<211> LENGTH: 40
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 461

Leu Leu Glu Ser Ala Lys Val Ser Ala Leu Ser Ala Leu Glu Glu Ala
1 5 10 15

Thr Lys Lys Pro Ser Leu Leu Glu Ser Phe Lys Val Ser Phe Leu Ser
20 25 30

Ala Leu Glu Glu Tyr Thr Lys Lys
35 40

<210> SEQ ID NO 462
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 462

Leu Glu Ser Ala Lys Val Ser Ala Leu Ser Ala Leu Glu Glu Ala Thr
1 5 10 15

Lys Lys Pro Ser Leu Leu Glu Ser Phe Lys Val Ser Phe Leu Ser Ala
20 25 30

Leu Glu Glu Tyr Thr Lys Lys
35

<210> SEQ ID NO 463
<211> LENGTH: 43
<212> TYPE: PRT
<213> ORGANISM: Artificial Sequence
<220> FEATURE:
<223> OTHER INFORMATION: Description of Artificial Sequence: Synthetic peptide

<400> SEQUENCE: 463

Pro Leu Leu Glu Ser Ala Lys Val Ser Ala Leu Ser Ala Leu Glu Glu
1 5 10 15

Ala Thr Lys Lys Pro Leu Leu Glu Ser Phe Lys Val Ser Phe Leu Ser
20 25 30

Ala Leu Glu Glu Tyr Thr Lys Lys Leu Asn Thr
35 40

<210> SEQ ID NO 464
<211> LENGTH: 42
<212> TYPE: PRT
<213> ORGANISM: Artificial Sequence
<220> FEATURE:
<223> OTHER INFORMATION: Description of Artificial Sequence: Synthetic peptide

<400> SEQUENCE: 464

Leu Leu Glu Ser Ala Lys Val Ser Ala Leu Ser Ala Leu Glu Glu Ala
1 5 10 15

Thr Lys Lys Pro Leu Leu Glu Ser Phe Lys Val Ser Phe Leu Ser Ala
20 25 30

Leu Glu Glu Tyr Thr Lys Lys Leu Asn Thr
35 40

<210> SEQ ID NO 465
<211> LENGTH: 41
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 465

Leu Glu Ser Ala Lys Val Ser Ala Leu Ser Ala Leu Glu Glu Ala Thr
1               5                   10                  15

Lys Lys Pro Leu Leu Glu Ser Phe Lys Val Ser Phe Leu Ser Ala Leu
            20                  25                  30

Glu Glu Tyr Thr Lys Lys Leu Asn Thr
        35                  40


<210> SEQ ID NO 466
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Pro Leu Leu Glu Ser Ala Lys Val Ser Ala Leu Ser Ala Leu Glu Glu
1               5                   10                  15

Ala Thr Lys Lys Pro Leu Leu Glu Ser Phe Lys Val Ser Phe Leu Ser
            20                  25                  30

Ala Leu Glu Glu Tyr Thr Lys Lys Leu Asn
        35                  40


<210> SEQ ID NO 467
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Leu Leu Glu Ser Ala Lys Val Ser Ala Leu Ser Ala Leu Glu Glu Ala
1               5                   10                  15

Thr Lys Lys Pro Leu Leu Glu Ser Phe Lys Val Ser Phe Leu Ser Ala
            20                  25                  30

Leu Glu Glu Tyr Thr Lys Lys Leu Asn
        35                  40


<210> SEQ ID NO 468
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Leu Glu Ser Ala Lys Val Ser Ala Leu Ser Ala Leu Glu Glu Ala Thr
1               5                   10                  15

Lys Lys Pro Leu Leu Glu Ser Phe Lys Val Ser Phe Leu Ser Ala Leu
            20                  25                  30

Glu Glu Tyr Thr Lys Lys Leu Asn
        35                  40


<210> SEQ ID NO 469
<211> LENGTH: 41
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 469

Pro Leu Leu Glu Ser Ala Lys Val Ser Ala Leu Ser Ala Leu Glu Glu
1               5                   10                  15

Ala Thr Lys Lys Pro Leu Leu Glu Ser Phe Lys Val Ser Phe Leu Ser
            20                  25                  30

Ala Leu Glu Glu Tyr Thr Lys Lys Leu
        35                  40


<210> SEQ ID NO 470
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Leu Leu Glu Ser Ala Lys Val Ser Ala Leu Ser Ala Leu Glu Glu Ala
1               5                   10                  15

Thr Lys Lys Pro Leu Leu Glu Ser Phe Lys Val Ser Phe Leu Ser Ala
            20                  25                  30

Leu Glu Glu Tyr Thr Lys Lys Leu
        35                  40


<210> SEQ ID NO 471
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Leu Glu Ser Ala Lys Val Ser Ala Leu Ser Ala Leu Glu Glu Ala Thr
1               5                   10                  15

Lys Lys Pro Leu Leu Glu Ser Phe Lys Val Ser Phe Leu Ser Ala Leu
            20                  25                  30

Glu Glu Tyr Thr Lys Lys Leu
        35


<210> SEQ ID NO 472
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Pro Leu Leu Glu Ser Ala Lys Val Ser Ala Leu Ser Ala Leu Glu Glu
1               5                   10                  15

Ala Thr Lys Lys Pro Leu Leu Glu Ser Phe Lys Val Ser Phe Leu Ser
            20                  25                  30

Ala Leu Glu Glu Tyr Thr Lys Lys
        35                  40


<210> SEQ ID NO 473
<211> LENGTH: 39
```

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 473

Leu Leu Glu Ser Ala Lys Val Ser Ala Leu Ser Ala Leu Glu Glu Ala
1 5 10 15

Thr Lys Lys Pro Leu Leu Glu Ser Phe Lys Val Ser Phe Leu Ser Ala
20 25 30

Leu Glu Glu Tyr Thr Lys Lys
35

<210> SEQ ID NO 474
<211> LENGTH: 38
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 474

Leu Glu Ser Ala Lys Val Ser Ala Leu Ser Ala Leu Glu Glu Ala Thr
1 5 10 15

Lys Lys Pro Leu Leu Glu Ser Phe Lys Val Ser Phe Leu Ser Ala Leu
20 25 30

Glu Glu Tyr Thr Lys Lys
35

<210> SEQ ID NO 475
<211> LENGTH: 48
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 475

Ser Pro Leu Lys Lys Thr Ala Glu Glu Leu Ala Ser Leu Ala Ser Val
1 5 10 15

Lys Ala Ser Glu Leu Lys Leu Ser Pro Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 476
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 476

Lys Lys Thr Ala Glu Glu Leu Ala Ser Leu Ala Ser Val Lys Ala Ser
1 5 10 15

Glu Leu Lys Leu Ser Pro Leu Leu Glu Ser Phe Lys Val Ser Phe Leu
20 25 30

Ser Ala Leu Glu Glu Tyr Thr Lys Lys Leu Asn Thr Gln
35 40 45

<210> SEQ ID NO 477

-continued

<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 477

```
Ser Pro Leu Lys Lys Thr Ala Glu Glu Leu Ala Ser Leu Ala Ser Val
1               5                   10                  15

Lys Ala Ser Glu Leu Lys Leu Ser Pro Leu Leu Glu Ser Phe Lys Val
            20                  25                  30

Ser Phe Leu Ser Ala Leu Glu Glu Tyr Thr Lys Lys
        35                  40
```

<210> SEQ ID NO 478
<211> LENGTH: 48
<212> TYPE: PRT
<213> ORGANISM: Artificial Sequence
<220> FEATURE:
<223> OTHER INFORMATION: Description of Artificial Sequence: Synthetic peptide

<400> SEQUENCE: 478

```
Ser Pro Leu Lys Lys Thr Ala Glu Glu Leu Ala Ser Leu Ala Ser Val
1               5                   10                  15

Lys Ala Ser Glu Leu Lys Leu Ser Pro Leu Lys Lys Thr Tyr Glu Glu
            20                  25                  30

Leu Ala Ser Leu Phe Ser Val Lys Phe Ser Glu Leu Leu Asn Thr Gln
        35                  40                  45
```

<210> SEQ ID NO 479
<211> LENGTH: 45
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

```
Lys Lys Thr Ala Glu Glu Leu Ala Ser Leu Ala Ser Val Lys Ala Ser
1               5                   10                  15

Glu Leu Lys Leu Ser Pro Leu Lys Lys Thr Tyr Glu Glu Leu Ala Ser
            20                  25                  30

Leu Phe Ser Val Lys Phe Ser Glu Leu Leu Asn Thr Gln
        35                  40                  45
```

<210> SEQ ID NO 480
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

```
Ser Pro Leu Lys Lys Thr Ala Glu Glu Leu Ala Ser Leu Ala Ser Val
1               5                   10                  15

Lys Ala Ser Glu Leu Lys Leu Ser Pro Leu Lys Lys Thr Tyr Glu Glu
            20                  25                  30

Leu Ala Ser Leu Phe Ser Val Lys Phe Ser Glu Leu
        35                  40
```

-continued

<210> SEQ ID NO 481
<211> LENGTH: 48
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 481

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Lys Lys Thr Tyr Glu Glu
            20                  25                  30

Leu Ala Ser Leu Phe Ser Val Lys Phe Ser Glu Leu Leu Asn Thr Gln
        35                  40                  45
```

<210> SEQ ID NO 482
<211> LENGTH: 45
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 482

```
Leu Glu Ser Ala Lys Val Ser Ala Leu Ser Ala Leu Glu Glu Ala Thr
1               5                   10                  15

Lys Lys Lys Leu Ser Pro Leu Lys Lys Thr Tyr Glu Glu Leu Ala Ser
            20                  25                  30

Leu Phe Ser Val Lys Phe Ser Glu Leu Leu Asn Thr Gln
        35                  40                  45
```

<210> SEQ ID NO 483
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 483

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Lys Lys Thr Tyr Glu Glu
            20                  25                  30

Leu Ala Ser Leu Phe Ser Val Lys Phe Ser Glu Leu
        35                  40
```

<210> SEQ ID NO 484
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 484

```
Ser Pro Leu Leu Glu Ser Ala Lys Val Ser Ala Leu Ser Ala Leu Glu
1               5                   10                  15

Glu Ala Thr Lys Lys Pro Leu Glu Ser Phe Lys Val Ser Phe Leu Ser
            20                  25                  30

Ala Leu Glu Glu Tyr Thr Lys Lys Leu Asn Thr Gln
        35                  40
```

-continued

<210> SEQ ID NO 485
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 485

Leu Glu Ser Ala Lys Val Ser Ala Leu Ser Ala Leu Glu Glu Ala Thr
1 5 10 15

Lys Lys Pro Leu Glu Ser Phe Lys Val Ser Phe Leu Ser Ala Leu Glu
20 25 30

Glu Tyr Thr Lys Lys Leu Asn Thr Gln
35 40

<210> SEQ ID NO 486
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 486

Ser Pro Leu Leu Glu Ser Ala Lys Val Ser Ala Leu Ser Ala Leu Glu
1 5 10 15

Glu Ala Thr Lys Lys Pro Leu Glu Ser Phe Lys Val Ser Phe Leu Ser
20 25 30

Ala Leu Glu Glu Tyr Thr Lys Lys
35 40

<210> SEQ ID NO 487
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 487

Ser Pro Leu Lys Lys Thr Ala Glu Glu Leu Ala Ser Leu Ala Ser Val
1 5 10 15

Lys Ala Ser Glu Leu Pro Leu Glu Ser Phe Lys Val Ser Phe Leu Ser
20 25 30

Ala Leu Glu Glu Tyr Thr Lys Lys Leu Asn Thr Gln
35 40

<210> SEQ ID NO 488
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 488

Lys Lys Thr Ala Glu Glu Leu Ala Ser Leu Ala Ser Val Lys Ala Ser
1 5 10 15

Glu Leu Pro Leu Glu Ser Phe Lys Val Ser Phe Leu Ser Ala Leu Glu
20 25 30

Glu Tyr Thr Lys Lys Leu Asn Thr Gln
35 40

-continued

<210> SEQ ID NO 489
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 489

Ser Pro Leu Lys Lys Thr Ala Glu Glu Leu Ala Ser Leu Ala Ser Val
1 5 10 15

Lys Ala Ser Glu Leu Pro Leu Glu Ser Phe Lys Val Ser Phe Leu Ser
20 25 30

Ala Leu Glu Glu Tyr Thr Lys Lys
35 40

<210> SEQ ID NO 490
<211> LENGTH: 44
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 490

Ser Pro Leu Lys Lys Thr Ala Glu Glu Leu Ala Ser Leu Ala Ser Val
1 5 10 15

Lys Ala Ser Glu Leu Pro Lys Lys Thr Tyr Glu Glu Leu Ala Ser Leu
20 25 30

Phe Ser Val Lys Phe Ser Glu Leu Leu Asn Thr Gln
35 40

<210> SEQ ID NO 491
<211> LENGTH: 41
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 491

Lys Lys Thr Ala Glu Glu Leu Ala Ser Leu Ala Ser Val Lys Ala Ser
1 5 10 15

Glu Leu Pro Lys Lys Thr Tyr Glu Glu Leu Ala Ser Leu Phe Ser Val
20 25 30

Lys Phe Ser Glu Leu Leu Asn Thr Gln
35 40

<210> SEQ ID NO 492
<211> LENGTH: 40
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 492

Ser Pro Leu Lys Lys Thr Ala Glu Glu Leu Ala Ser Leu Ala Ser Val
1 5 10 15

Lys Ala Ser Glu Leu Pro Lys Lys Thr Tyr Glu Glu Leu Ala Ser Leu
20 25 30

Phe Ser Val Lys Phe Ser Glu Leu

-continued 35 40

<210> SEQ ID NO 493
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 493

Ser Pro Leu Leu Glu Ser Ala Lys Val Ser Ala Leu Ser Ala Leu Glu
1 5 10 15

Glu Ala Thr Lys Lys Pro Lys Lys Thr Tyr Glu Glu Leu Ala Ser Leu
20 25 30

Phe Ser Val Lys Phe Ser Glu Leu Leu Asn Thr Gln
35 40

<210> SEQ ID NO 494
<211> LENGTH: 41
<212> TYPE: PRT
<213> ORGANISM: Artificial Sequence
<220> FEATURE:
<223> OTHER INFORMATION: Description of Artificial Sequence: Synthetic peptide

<400> SEQUENCE: 494

Leu Glu Ser Ala Lys Val Ser Ala Leu Ser Ala Leu Glu Glu Ala Thr
1 5 10 15

Lys Lys Pro Lys Lys Thr Tyr Glu Glu Leu Ala Ser Leu Phe Ser Val
20 25 30

Lys Phe Ser Glu Leu Leu Asn Thr Gln
35 40

<210> SEQ ID NO 495
<211> LENGTH: 40
<212> TYPE: PRT
<213> ORGANISM: Artificial Sequence
<220> FEATURE:
<223> OTHER INFORMATION: Description of Artificial Sequence: Synthetic peptide

<400> SEQUENCE: 495

Ser Pro Leu Leu Glu Ser Ala Lys Val Ser Ala Leu Ser Ala Leu Glu
1 5 10 15

Glu Ala Thr Lys Lys Pro Lys Lys Thr Tyr Glu Glu Leu Ala Ser Leu
20 25 30

Phe Ser Val Lys Phe Ser Glu Leu
35 40

<210> SEQ ID NO 496
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 496

Leu Glu Ser Ala His Val Ser Ala Leu Ser Ala Leu Glu Glu Ala Thr
1 5 10 15

Lys Lys

-continued

```
<210> SEQ ID NO 497
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Leu Glu Ser Ala Lys Val Ser Ala Leu Ser Ala Leu Glu Glu Ala Thr
1               5                   10                  15

His Lys


<210> SEQ ID NO 498
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Leu Glu Ser Ala Lys Val Ser Ala Leu Ser Ala Leu Glu Glu Ala Thr
1               5                   10                  15

Lys His


<210> SEQ ID NO 499
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Leu Glu Ser Ala His Val Ser Ala Leu Ser Ala Leu Glu Glu Ala Thr
1               5                   10                  15

His Lys


<210> SEQ ID NO 500
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Leu Glu Ser Ala Lys Val Ser Ala Leu Ser Ala Leu Glu Glu Ala Thr
1               5                   10                  15

His His


<210> SEQ ID NO 501
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Leu Glu Ser Ala His Val Ser Ala Leu Ser Ala Leu Glu Glu Ala Thr
1               5                   10                  15

Lys His
```

-continued

<210> SEQ ID NO 502
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Leu Glu Ser Ala His Val Ser Ala Leu Ser Ala Leu Glu Glu Ala Thr
1               5                   10                  15

His His

<210> SEQ ID NO 503
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Leu Glu Ser Ala Arg Val Ser Ala Leu Ser Ala Leu Glu Glu Ala Thr
1               5                   10                  15

Lys Lys

<210> SEQ ID NO 504
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Leu Glu Ser Ala Lys Val Ser Ala Leu Ser Ala Leu Glu Glu Ala Thr
1               5                   10                  15

Arg Lys

<210> SEQ ID NO 505
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Leu Glu Ser Ala Lys Val Ser Ala Leu Ser Ala Leu Glu Glu Ala Thr
1               5                   10                  15

Lys Arg

<210> SEQ ID NO 506
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Leu Glu Ser Ala Arg Val Ser Ala Leu Ser Ala Leu Glu Glu Ala Thr
1               5                   10                  15

Arg Lys

-continued

<210> SEQ ID NO 507
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 507

Leu Glu Ser Ala Lys Val Ser Ala Leu Ser Ala Leu Glu Glu Ala Thr
1 5 10 15

Arg Arg

<210> SEQ ID NO 508
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 508

Leu Glu Ser Ala Arg Val Ser Ala Leu Ser Ala Leu Glu Glu Ala Thr
1 5 10 15

Lys Arg

<210> SEQ ID NO 509
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 509

Leu Glu Ser Ala Arg Val Ser Ala Leu Ser Ala Leu Glu Glu Ala Thr
1 5 10 15

Arg Arg

<210> SEQ ID NO 510
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 510

Leu Glu Ser Ala Arg Val Ser Ala Leu Ser Ala Leu Glu Glu Ala Thr
1 5 10 15

His His

<210> SEQ ID NO 511
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Leu Glu Ser Ala His Val Ser Ala Leu Ser Ala Leu Glu Glu Ala Thr
1 5 10 15

-continued

Arg His

<210> SEQ ID NO 512
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 512

Leu Glu Ser Ala His Val Ser Ala Leu Ser Ala Leu Glu Glu Ala Thr
1 5 10 15

His Arg

<210> SEQ ID NO 513
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 513

Leu Glu Ser Ala Arg Val Ser Ala Leu Ser Ala Leu Glu Glu Ala Thr
1 5 10 15

Arg His

<210> SEQ ID NO 514
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 514

Leu Glu Ser Ala Arg Val Ser Ala Leu Ser Ala Leu Glu Glu Ala Thr
1 5 10 15

His Arg

<210> SEQ ID NO 515
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 515

Leu Glu Ser Ala His Val Ser Ala Leu Ser Ala Leu Glu Glu Ala Thr
1 5 10 15

Arg Arg

<210> SEQ ID NO 516
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

Leu Glu Ser Ala Lys Val Ser Ala Leu Ser Ala Leu Glu Glu Ala Thr
1 5 10 15

-continued

Arg His

<210> SEQ ID NO 517
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 517

Leu Glu Ser Ala Lys Val Ser Ala Leu Ser Ala Leu Glu Glu Ala Thr
1 5 10 15

His Arg

<210> SEQ ID NO 518
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 518

Leu Glu Ser Ala Arg Val Ser Ala Leu Ser Ala Leu Glu Glu Ala Thr
1 5 10 15

Lys His

<210> SEQ ID NO 519
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 519

Leu Glu Ser Ala Arg Val Ser Ala Leu Ser Ala Leu Glu Glu Ala Thr
1 5 10 15

His Lys

<210> SEQ ID NO 520
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 520

Leu Glu Ser Ala His Val Ser Ala Leu Ser Ala Leu Glu Glu Ala Thr
1 5 10 15

Lys Arg

<210> SEQ ID NO 521
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 521

Leu Glu Ser Ala Lys Val Ser Ala Leu Ser Ala Leu Glu Glu Ala Thr

-continued

```
1               5                   10                  15

Arg Lys


<210> SEQ ID NO 522
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Leu Glu Ser Phe His Val Ser Phe Leu Ser Ala Leu Glu Glu Tyr Thr
1               5                   10                  15

Lys Lys


<210> SEQ ID NO 523
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Leu Glu Ser Phe Lys Val Ser Phe Leu Ser Ala Leu Glu Glu Tyr Thr
1               5                   10                  15

His Lys


<210> SEQ ID NO 524
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Leu Glu Ser Phe Lys Val Ser Phe Leu Ser Ala Leu Glu Glu Tyr Thr
1               5                   10                  15

Lys His


<210> SEQ ID NO 525
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Leu Glu Ser Phe His Val Ser Phe Leu Ser Ala Leu Glu Glu Tyr Thr
1               5                   10                  15

His Lys


<210> SEQ ID NO 526
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526
```

-continued

Leu Glu Ser Phe Lys Val Ser Phe Leu Ser Ala Leu Glu Glu Tyr Thr
1 5 10 15

His His

<210> SEQ ID NO 527
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 527

Leu Glu Ser Phe His Val Ser Phe Leu Ser Ala Leu Glu Glu Tyr Thr
1 5 10 15

Lys His

<210> SEQ ID NO 528
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Leu Glu Ser Phe His Val Ser Phe Leu Ser Ala Leu Glu Glu Tyr Thr
1 5 10 15

His His

<210> SEQ ID NO 529
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Leu Glu Ser Phe Arg Val Ser Phe Leu Ser Ala Leu Glu Glu Tyr Thr
1 5 10 15

Lys Lys

<210> SEQ ID NO 530
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Leu Glu Ser Phe Lys Val Ser Phe Leu Ser Ala Leu Glu Glu Tyr Thr
1 5 10 15

Arg Lys

<210> SEQ ID NO 531
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

-continued

```
Leu Glu Ser Phe Lys Val Ser Phe Leu Ser Ala Leu Glu Glu Tyr Thr
1               5                   10                  15

Lys Arg


<210> SEQ ID NO 532
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Leu Glu Ser Phe Arg Val Ser Phe Leu Ser Ala Leu Glu Glu Tyr Thr
1               5                   10                  15

Arg Lys


<210> SEQ ID NO 533
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Leu Glu Ser Phe Lys Val Ser Phe Leu Ser Ala Leu Glu Glu Tyr Thr
1               5                   10                  15

Arg Arg


<210> SEQ ID NO 534
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Leu Glu Ser Phe Arg Val Ser Phe Leu Ser Ala Leu Glu Glu Tyr Thr
1               5                   10                  15

Lys Arg


<210> SEQ ID NO 535
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Leu Glu Ser Phe Arg Val Ser Phe Leu Ser Ala Leu Glu Glu Tyr Thr
1               5                   10                  15

Arg Arg


<210> SEQ ID NO 536
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 536

```
Leu Glu Ser Phe Arg Val Ser Phe Leu Ser Ala Leu Glu Glu Tyr Thr
1               5                   10                  15

His His
```

<210> SEQ ID NO 537
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 537

```
Leu Glu Ser Phe His Val Ser Phe Leu Ser Ala Leu Glu Glu Tyr Thr
1               5                   10                  15

Arg His
```

<210> SEQ ID NO 538
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 538

```
Leu Glu Ser Phe His Val Ser Phe Leu Ser Ala Leu Glu Glu Tyr Thr
1               5                   10                  15

His Arg
```

<210> SEQ ID NO 539
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 539

```
Leu Glu Ser Phe Arg Val Ser Phe Leu Ser Ala Leu Glu Glu Tyr Thr
1               5                   10                  15

Arg His
```

<210> SEQ ID NO 540
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 540

```
Leu Glu Ser Phe Arg Val Ser Phe Leu Ser Ala Leu Glu Glu Tyr Thr
1               5                   10                  15

His Arg
```

<210> SEQ ID NO 541
<211> LENGTH: 18
<212> TYPE: PRT
<213> ORGANISM: Artificial Sequence
<220> FEATURE:
<223> OTHER INFORMATION: Description of Artificial Sequence: Synthetic peptide -continued

<400> SEQUENCE: 541

Leu Glu Ser Phe His Val Ser Phe Leu Ser Ala Leu Glu Glu Tyr Thr
1 5 10 15

Arg Arg

<210> SEQ ID NO 542
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 542

Leu Glu Ser Phe Lys Val Ser Phe Leu Ser Ala Leu Glu Glu Tyr Thr
1 5 10 15

Arg His

<210> SEQ ID NO 543
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 543

Leu Glu Ser Phe Lys Val Ser Phe Leu Ser Ala Leu Glu Glu Tyr Thr
1 5 10 15

His Arg

<210> SEQ ID NO 544
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 544

Leu Glu Ser Phe Arg Val Ser Phe Leu Ser Ala Leu Glu Glu Tyr Thr
1 5 10 15

Lys His

<210> SEQ ID NO 545
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 545

Leu Glu Ser Phe Arg Val Ser Phe Leu Ser Ala Leu Glu Glu Tyr Thr
1 5 10 15

His Lys

<210> SEQ ID NO 546
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 546

Leu Glu Ser Phe His Val Ser Phe Leu Ser Ala Leu Glu Glu Tyr Thr
1 5 10 15

Lys Arg

<210> SEQ ID NO 547
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 547

Leu Glu Ser Phe Lys Val Ser Phe Leu Ser Ala Leu Glu Glu Tyr Thr
1 5 10 15

Arg Lys

<210> SEQ ID NO 548
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 548

Leu Asp Ser Ala Lys Val Ser Ala Leu Ser Ala Leu Glu Glu Ala Thr
1 5 10 15

Lys Lys

<210> SEQ ID NO 549
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 549

Leu Glu Ser Ala Lys Val Ser Ala Leu Ser Ala Leu Asp Glu Ala Thr
1 5 10 15

Lys Lys

<210> SEQ ID NO 550
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 550

Leu Glu Ser Ala Lys Val Ser Ala Leu Ser Ala Leu Glu Asp Ala Thr
1 5 10 15

Lys Lys

<210> SEQ ID NO 551
<211> LENGTH: 18
<212> TYPE: PRT

-continued

<213> ORGANISM: Artificial Sequence
<220> FEATURE:
<223> OTHER INFORMATION: Description of Artificial Sequence: Synthetic
peptide

<400> SEQUENCE: 551

Leu Asp Ser Ala Lys Val Ser Ala Leu Ser Ala Leu Asp Glu Ala Thr
1 5 10 15

Lys Lys

<210> SEQ ID NO 552
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 552

Leu Asp Ser Ala Lys Val Ser Ala Leu Ser Ala Leu Glu Asp Ala Thr
1 5 10 15

Lys Lys

<210> SEQ ID NO 553
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 553

Leu Glu Ser Ala Lys Val Ser Ala Leu Ser Ala Leu Asp Asp Ala Thr
1 5 10 15

Lys Lys

<210> SEQ ID NO 554
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 554

Leu Asp Ser Ala Lys Val Ser Ala Leu Ser Ala Leu Asp Asp Ala Thr
1 5 10 15

Lys Lys

<210> SEQ ID NO 555
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 555

Leu Asp Ser Phe Lys Val Ser Phe Leu Ser Ala Leu Glu Glu Tyr Thr
1 5 10 15

Lys Lys

<210> SEQ ID NO 556
<211> LENGTH: 18

-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Leu Glu Ser Phe Lys Val Ser Phe Leu Ser Ala Leu Asp Glu Tyr Thr
1               5                   10                  15

Lys Lys

<210> SEQ ID NO 557
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Leu Glu Ser Phe Lys Val Ser Phe Leu Ser Ala Leu Glu Asp Tyr Thr
1               5                   10                  15

Lys Lys

<210> SEQ ID NO 558
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Leu Asp Ser Phe Lys Val Ser Phe Leu Ser Ala Leu Asp Glu Tyr Thr
1               5                   10                  15

Lys Lys

<210> SEQ ID NO 559
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Leu Asp Ser Phe Lys Val Ser Phe Leu Ser Ala Leu Glu Asp Tyr Thr
1               5                   10                  15

Lys Lys

<210> SEQ ID NO 560
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Leu Glu Ser Phe Lys Val Ser Phe Leu Ser Ala Leu Asp Asp Tyr Thr
1               5                   10                  15

Lys Lys

<210> SEQ ID NO 561

-continued

<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 561

Leu Asp Ser Phe Lys Val Ser Phe Leu Ser Ala Leu Asp Asp Tyr Thr
1 5 10 15

Lys Lys

<210> SEQ ID NO 562
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 562

Leu Glu Ser Phe Lys Val Ser Phe Leu Ser Ala Leu Glu Glu Phe Thr
1 5 10 15

Lys Lys

<210> SEQ ID NO 563
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 563

Leu Glu Ser Phe Lys Val Ser Tyr Leu Ser Ala Leu Glu Glu Phe Thr
1 5 10 15

Lys Lys

<210> SEQ ID NO 564
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 564

Leu Glu Ser Phe Lys Val Ser Tyr Leu Ser Ala Leu Glu Glu Tyr Thr
1 5 10 15

Lys Lys

<210> SEQ ID NO 565
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 565

Leu Glu Ser Tyr Lys Val Ser Phe Leu Ser Ala Leu Glu Glu Tyr Thr
1 5 10 15

Lys Lys

<210> SEQ ID NO 566
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 566

Leu Glu Ser Tyr Lys Val Ser Tyr Leu Ser Ala Leu Glu Glu Phe Thr
1 5 10 15

Lys Lys

<210> SEQ ID NO 567
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 567

Leu Glu Ser Tyr Lys Val Ser Tyr Leu Ser Ala Leu Glu Glu Tyr Thr
1 5 10 15

Lys Lys

<210> SEQ ID NO 568
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 568

Leu Glu Ser Tyr Lys Val Ser Phe Leu Ser Ala Leu Glu Glu Phe Thr
1 5 10 15

Lys Lys

<210> SEQ ID NO 569
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Leu

<400> SEQUENCE: 569

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 570
<211> LENGTH: 41
<212> TYPE: PRT
<213> ORGANISM: Artificial Sequence
<220> FEATURE:
<223> OTHER INFORMATION: Description of Artificial Sequence: Synthetic peptide -continued
<220> FEATURE:
<221> NAME/KEY: MOD_RES
<222> LOCATION: (41)
<223> OTHER INFORMATION: D-Lys

<400> SEQUENCE: 570

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 571
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (41)
<223> OTHER INFORMATION: D-Lys

<400> SEQUENCE: 571

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 572
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (2)
<223> OTHER INFORMATION: D-Glu
<220> FEATURE:
<221> NAME/KEY: MOD_RES
<222> LOCATION: (3)
<223> OTHER INFORMATION: D-Ser
<220> FEATURE:
<221> NAME/KEY: MOD_RES
<222> LOCATION: (4)
<223> OTHER INFORMATION: D-Ala
<220> FEATURE:
<221> NAME/KEY: MOD_RES
<222> LOCATION: (5)
<223> OTHER INFORMATION: D-Lys
<220> FEATURE:
<221> NAME/KEY: MOD_RES
<222> LOCATION: (6)
<223> OTHER INFORMATION: D-Val
<220> FEATURE:
<221> NAME/KEY: MOD_RES
<222> LOCATION: (7)

-continued

<223> OTHER INFORMATION: D-Ser
<220> FEATURE:
<221> NAME/KEY: MOD_RES
<222> LOCATION: (8)
<223> OTHER INFORMATION: D-Ala
<220> FEATURE:
<221> NAME/KEY: MOD_RES
<222> LOCATION: (9)
<223> OTHER INFORMATION: D-Leu
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Glu
<220> FEATURE:
<221> NAME/KEY: MOD_RES
<222> LOCATION: (14)
<223> OTHER INFORMATION: D-Glu
<220> FEATURE:
<221> NAME/KEY: MOD_RES
<222> LOCATION: (15)
<223> OTHER INFORMATION: D-Ala
<220> FEATURE:
<221> NAME/KEY: MOD_RES
<222> LOCATION: (16)
<223> OTHER INFORMATION: D-Thr
<220> FEATURE:
<221> NAME/KEY: MOD_RES
<222> LOCATION: (17)
<223> OTHER INFORMATION: D-Lys
<220> FEATURE:
<221> NAME/KEY: MOD_RES
<222> LOCATION: (18)
<223> OTHER INFORMATION: D-Lys
<220> FEATURE:
<221> NAME/KEY: MOD_RES
<222> LOCATION: (19)
<223> OTHER INFORMATION: D-Lys
<220> FEATURE:
<221> NAME/KEY: MOD_RES
<222> LOCATION: (20)
<223> OTHER INFORMATION: D-Leu
<220> FEATURE:
<221> NAME/KEY: MOD_RES
<222> LOCATION: (21)
<223> OTHER INFORMATION: D-Ser
<220> FEATURE:
<221> NAME/KEY: MOD_RES
<222> LOCATION: (22)
<223> OTHER INFORMATION: D-Pro
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Leu
<220> FEATURE:
<221> NAME/KEY: MOD_RES
<222> LOCATION: (25)
<223> OTHER INFORMATION: D-Glu
<220> FEATURE:
<221> NAME/KEY: MOD_RES
<222> LOCATION: (26)
<223> OTHER INFORMATION: D-Ser
<220> FEATURE:
<221> NAME/KEY: MOD_RES

-continued

<222> LOCATION: (27)
<223> OTHER INFORMATION: D-Phe
<220> FEATURE:
<221> NAME/KEY: MOD_RES
<222> LOCATION: (28)
<223> OTHER INFORMATION: D-Lys
<220> FEATURE:
<221> NAME/KEY: MOD_RES
<222> LOCATION: (29)
<223> OTHER INFORMATION: D-Val
<220> FEATURE:
<221> NAME/KEY: MOD_RES
<222> LOCATION: (30)
<223> OTHER INFORMATION: D-Ser
<220> FEATURE:
<221> NAME/KEY: MOD_RES
<222> LOCATION: (31)
<223> OTHER INFORMATION: D-Phe
<220> FEATURE:
<221> NAME/KEY: MOD_RES
<222> LOCATION: (32)
<223> OTHER INFORMATION: D-Leu
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Ala
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Glu
<220> FEATURE:
<221> NAME/KEY: MOD_RES
<222> LOCATION: (37)
<223> OTHER INFORMATION: D-Glu
<220> FEATURE:
<221> NAME/KEY: MOD_RES
<222> LOCATION: (38)
<223> OTHER INFORMATION: D-Tyr
<220> FEATURE:
<221> NAME/KEY: MOD_RES
<222> LOCATION: (39)
<223> OTHER INFORMATION: D-Thr
<220> FEATURE:
<221> NAME/KEY: MOD_RES
<222> LOCATION: (40)
<223> OTHER INFORMATION: D-Lys
<220> FEATURE:
<221> NAME/KEY: MOD_RES
<222> LOCATION: (41)
<223> OTHER INFORMATION: D-Lys

<400> SEQUENCE: 572

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 573
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:

-continued

<221> NAME/KEY: MOD_RES
<222> LOCATION: (1)
<223> OTHER INFORMATION: D-Ser

<400> SEQUENCE: 573

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 574
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (48)
<223> OTHER INFORMATION: D-Gln

<400> SEQUENCE: 574

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 575
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (48)
<223> OTHER INFORMATION: D-Gln

<400> SEQUENCE: 575

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 576
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Ser -continued
<220> FEATURE:
<221> NAME/KEY: MOD_RES
<222> LOCATION: (2)
<223> OTHER INFORMATION: D-Pro
<220> FEATURE:
<221> NAME/KEY: MOD_RES
<222> LOCATION: (3)
<223> OTHER INFORMATION: D-Leu
<220> FEATURE:
<221> NAME/KEY: MOD_RES
<222> LOCATION: (4)
<223> OTHER INFORMATION: D-Leu
<220> FEATURE:
<221> NAME/KEY: MOD_RES
<222> LOCATION: (5)
<223> OTHER INFORMATION: D-Glu
<220> FEATURE:
<221> NAME/KEY: MOD_RES
<222> LOCATION: (6)
<223> OTHER INFORMATION: D-Ser
<220> FEATURE:
<221> NAME/KEY: MOD_RES
<222> LOCATION: (7)
<223> OTHER INFORMATION: D-Ala
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (9)
<223> OTHER INFORMATION: D-Val
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Ser
<220> FEATURE:
<221> NAME/KEY: MOD_RES
<222> LOCATION: (14)
<223> OTHER INFORMATION: D-Ala
<220> FEATURE:
<221> NAME/KEY: MOD_RES
<222> LOCATION: (15)
<223> OTHER INFORMATION: D-Leu
<220> FEATURE:
<221> NAME/KEY: MOD_RES
<222> LOCATION: (16)
<223> OTHER INFORMATION: D-Glu
<220> FEATURE:
<221> NAME/KEY: MOD_RES
<222> LOCATION: (17)
<223> OTHER INFORMATION: D-Glu
<220> FEATURE:
<221> NAME/KEY: MOD_RES
<222> LOCATION: (18)
<223> OTHER INFORMATION: D-Ala
<220> FEATURE:
<221> NAME/KEY: MOD_RES
<222> LOCATION: (19)
<223> OTHER INFORMATION: D-Thr
<220> FEATURE:
<221> NAME/KEY: MOD_RES
<222> LOCATION: (20)
<223> OTHER INFORMATION: D-Lys
<220> FEATURE:
<221> NAME/KEY: MOD_RES
<222> LOCATION: (21)

-continued

<223> OTHER INFORMATION: D-Lys
<220> FEATURE:
<221> NAME/KEY: MOD_RES
<222> LOCATION: (22)
<223> OTHER INFORMATION: D-Lys
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Ser
<220> FEATURE:
<221> NAME/KEY: MOD_RES
<222> LOCATION: (25)
<223> OTHER INFORMATION: D-Pro
<220> FEATURE:
<221> NAME/KEY: MOD_RES
<222> LOCATION: (26)
<223> OTHER INFORMATION: D-Leu
<220> FEATURE:
<221> NAME/KEY: MOD_RES
<222> LOCATION: (27)
<223> OTHER INFORMATION: D-Leu
<220> FEATURE:
<221> NAME/KEY: MOD_RES
<222> LOCATION: (28)
<223> OTHER INFORMATION: D-Glu
<220> FEATURE:
<221> NAME/KEY: MOD_RES
<222> LOCATION: (29)
<223> OTHER INFORMATION: D-Ser
<220> FEATURE:
<221> NAME/KEY: MOD_RES
<222> LOCATION: (30)
<223> OTHER INFORMATION: D-Phe
<220> FEATURE:
<221> NAME/KEY: MOD_RES
<222> LOCATION: (31)
<223> OTHER INFORMATION: D-Lys
<220> FEATURE:
<221> NAME/KEY: MOD_RES
<222> LOCATION: (32)
<223> OTHER INFORMATION: D-Val
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Phe
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Ser
<220> FEATURE:
<221> NAME/KEY: MOD_RES
<222> LOCATION: (37)
<223> OTHER INFORMATION: D-Ala
<220> FEATURE:
<221> NAME/KEY: MOD_RES
<222> LOCATION: (38)
<223> OTHER INFORMATION: D-Leu
<220> FEATURE:
<221> NAME/KEY: MOD_RES
<222> LOCATION: (39)
<223> OTHER INFORMATION: D-Glu
<220> FEATURE:
<221> NAME/KEY: MOD_RES
<222> LOCATION: (40)
<223> OTHER INFORMATION: D-Glu
<220> FEATURE:
<221> NAME/KEY: MOD_RES

<222> LOCATION: (41)
<223> OTHER INFORMATION: D-Tyr
<220> FEATURE:
<221> NAME/KEY: MOD_RES
<222> LOCATION: (42)
<223> OTHER INFORMATION: D-Thr
<220> FEATURE:
<221> NAME/KEY: MOD_RES
<222> LOCATION: (43)
<223> OTHER INFORMATION: D-Lys
<220> FEATURE:
<221> NAME/KEY: MOD_RES
<222> LOCATION: (44)
<223> OTHER INFORMATION: D-Lys
<220> FEATURE:
<221> NAME/KEY: MOD_RES
<222> LOCATION: (45)
<223> OTHER INFORMATION: D-Leu
<220> FEATURE:
<221> NAME/KEY: MOD_RES
<222> LOCATION: (46)
<223> OTHER INFORMATION: D-Asn
<220> FEATURE:
<221> NAME/KEY: MOD_RES
<222> LOCATION: (47)
<223> OTHER INFORMATION: D-Thr
<220> FEATURE:
<221> NAME/KEY: MOD_RES
<222> LOCATION: (48)
<223> OTHER INFORMATION: D-Gln

<400> SEQUENCE: 576

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 577
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated

<400> SEQUENCE: 577

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 578
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Leu -continued

<400> SEQUENCE: 578

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 579
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (41)
<223> OTHER INFORMATION: D-Lys

<400> SEQUENCE: 579

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 580
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (41)
<223> OTHER INFORMATION: D-Lys

<400> SEQUENCE: 580

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 581
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES -continued
<222> LOCATION: (1)
<223> OTHER INFORMATION: D-Leu
<220> FEATURE:
<221> NAME/KEY: MOD_RES
<222> LOCATION: (2)
<223> OTHER INFORMATION: D-Glu
<220> FEATURE:
<221> NAME/KEY: MOD_RES
<222> LOCATION: (3)
<223> OTHER INFORMATION: D-Ser
<220> FEATURE:
<221> NAME/KEY: MOD_RES
<222> LOCATION: (4)
<223> OTHER INFORMATION: D-Ala
<220> FEATURE:
<221> NAME/KEY: MOD_RES
<222> LOCATION: (5)
<223> OTHER INFORMATION: D-Lys
<220> FEATURE:
<221> NAME/KEY: MOD_RES
<222> LOCATION: (6)
<223> OTHER INFORMATION: D-Val
<220> FEATURE:
<221> NAME/KEY: MOD_RES
<222> LOCATION: (7)
<223> OTHER INFORMATION: D-Ser
<220> FEATURE:
<221> NAME/KEY: MOD_RES
<222> LOCATION: (8)
<223> OTHER INFORMATION: D-Ala
<220> FEATURE:
<221> NAME/KEY: MOD_RES
<222> LOCATION: (9)
<223> OTHER INFORMATION: D-Leu
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Glu
<220> FEATURE:
<221> NAME/KEY: MOD_RES
<222> LOCATION: (14)
<223> OTHER INFORMATION: D-Glu
<220> FEATURE:
<221> NAME/KEY: MOD_RES
<222> LOCATION: (15)
<223> OTHER INFORMATION: D-Ala
<220> FEATURE:
<221> NAME/KEY: MOD_RES
<222> LOCATION: (16)
<223> OTHER INFORMATION: D-Thr
<220> FEATURE:
<221> NAME/KEY: MOD_RES
<222> LOCATION: (17)
<223> OTHER INFORMATION: D-Lys
<220> FEATURE:
<221> NAME/KEY: MOD_RES
<222> LOCATION: (18)
<223> OTHER INFORMATION: D-Lys
<220> FEATURE:
<221> NAME/KEY: MOD_RES
<222> LOCATION: (19)
<223> OTHER INFORMATION: D-Lys
<220> FEATURE:
<221> NAME/KEY: MOD_RES
<222> LOCATION: (20)
<223> OTHER INFORMATION: D-Leu
<220> FEATURE:

-continued

<221> NAME/KEY: MOD_RES
<222> LOCATION: (21)
<223> OTHER INFORMATION: D-Ser
<220> FEATURE:
<221> NAME/KEY: MOD_RES
<222> LOCATION: (22)
<223> OTHER INFORMATION: D-Pro
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Leu
<220> FEATURE:
<221> NAME/KEY: MOD_RES
<222> LOCATION: (25)
<223> OTHER INFORMATION: D-Glu
<220> FEATURE:
<221> NAME/KEY: MOD_RES
<222> LOCATION: (26)
<223> OTHER INFORMATION: D-Ser
<220> FEATURE:
<221> NAME/KEY: MOD_RES
<222> LOCATION: (27)
<223> OTHER INFORMATION: D-Phe
<220> FEATURE:
<221> NAME/KEY: MOD_RES
<222> LOCATION: (28)
<223> OTHER INFORMATION: D-Lys
<220> FEATURE:
<221> NAME/KEY: MOD_RES
<222> LOCATION: (29)
<223> OTHER INFORMATION: D-Val
<220> FEATURE:
<221> NAME/KEY: MOD_RES
<222> LOCATION: (30)
<223> OTHER INFORMATION: D-Ser
<220> FEATURE:
<221> NAME/KEY: MOD_RES
<222> LOCATION: (31)
<223> OTHER INFORMATION: D-Phe
<220> FEATURE:
<221> NAME/KEY: MOD_RES
<222> LOCATION: (32)
<223> OTHER INFORMATION: D-Leu
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Ala
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Glu
<220> FEATURE:
<221> NAME/KEY: MOD_RES
<222> LOCATION: (37)
<223> OTHER INFORMATION: D-Glu
<220> FEATURE:
<221> NAME/KEY: MOD_RES
<222> LOCATION: (38)
<223> OTHER INFORMATION: D-Tyr
<220> FEATURE:
<221> NAME/KEY: MOD_RES
<222> LOCATION: (39)
<223> OTHER INFORMATION: D-Thr
<220> FEATURE:
<221> NAME/KEY: MOD_RES
<222> LOCATION: (40)
<223> OTHER INFORMATION: D-Lys

```
<220> FEATURE:
<221> NAME/KEY: MOD_RES
<222> LOCATION: (41)
<223> OTHER INFORMATION: D-Lys

<400> SEQUENCE: 581

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 582
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 582

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 583
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser

<400> SEQUENCE: 583

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 584
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (48)
<223> OTHER INFORMATION: D-Gln
```

-continued

<400> SEQUENCE: 584

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 585
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (48)
<223> OTHER INFORMATION: D-Gln

<400> SEQUENCE: 585

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 586
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (2)
<223> OTHER INFORMATION: D-Pro
<220> FEATURE:
<221> NAME/KEY: MOD_RES
<222> LOCATION: (3)
<223> OTHER INFORMATION: D-Leu
<220> FEATURE:
<221> NAME/KEY: MOD_RES
<222> LOCATION: (4)
<223> OTHER INFORMATION: D-Leu
<220> FEATURE:
<221> NAME/KEY: MOD_RES
<222> LOCATION: (5)
<223> OTHER INFORMATION: D-Glu
<220> FEATURE:
<221> NAME/KEY: MOD_RES
<222> LOCATION: (6)
<223> OTHER INFORMATION: D-Ser
<220> FEATURE:
<221> NAME/KEY: MOD_RES
<222> LOCATION: (7)
<223> OTHER INFORMATION: D-Ala -continued
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (9)
<223> OTHER INFORMATION: D-Val
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Ser
<220> FEATURE:
<221> NAME/KEY: MOD_RES
<222> LOCATION: (14)
<223> OTHER INFORMATION: D-Ala
<220> FEATURE:
<221> NAME/KEY: MOD_RES
<222> LOCATION: (15)
<223> OTHER INFORMATION: D-Leu
<220> FEATURE:
<221> NAME/KEY: MOD_RES
<222> LOCATION: (16)
<223> OTHER INFORMATION: D-Glu
<220> FEATURE:
<221> NAME/KEY: MOD_RES
<222> LOCATION: (17)
<223> OTHER INFORMATION: D-Glu
<220> FEATURE:
<221> NAME/KEY: MOD_RES
<222> LOCATION: (18)
<223> OTHER INFORMATION: D-Ala
<220> FEATURE:
<221> NAME/KEY: MOD_RES
<222> LOCATION: (19)
<223> OTHER INFORMATION: D-Thr
<220> FEATURE:
<221> NAME/KEY: MOD_RES
<222> LOCATION: (20)
<223> OTHER INFORMATION: D-Lys
<220> FEATURE:
<221> NAME/KEY: MOD_RES
<222> LOCATION: (21)
<223> OTHER INFORMATION: D-Lys
<220> FEATURE:
<221> NAME/KEY: MOD_RES
<222> LOCATION: (22)
<223> OTHER INFORMATION: D-Lys
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Ser
<220> FEATURE:
<221> NAME/KEY: MOD_RES
<222> LOCATION: (25)
<223> OTHER INFORMATION: D-Pro
<220> FEATURE:
<221> NAME/KEY: MOD_RES
<222> LOCATION: (26)
<223> OTHER INFORMATION: D-Leu
<220> FEATURE:
<221> NAME/KEY: MOD_RES
<222> LOCATION: (27)

-continued

```
<223> OTHER INFORMATION: D-Leu
<220> FEATURE:
<221> NAME/KEY: MOD_RES
<222> LOCATION: (28)
<223> OTHER INFORMATION: D-Glu
<220> FEATURE:
<221> NAME/KEY: MOD_RES
<222> LOCATION: (29)
<223> OTHER INFORMATION: D-Ser
<220> FEATURE:
<221> NAME/KEY: MOD_RES
<222> LOCATION: (30)
<223> OTHER INFORMATION: D-Phe
<220> FEATURE:
<221> NAME/KEY: MOD_RES
<222> LOCATION: (31)
<223> OTHER INFORMATION: D-Lys
<220> FEATURE:
<221> NAME/KEY: MOD_RES
<222> LOCATION: (32)
<223> OTHER INFORMATION: D-Val
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Phe
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Ser
<220> FEATURE:
<221> NAME/KEY: MOD_RES
<222> LOCATION: (37)
<223> OTHER INFORMATION: D-Ala
<220> FEATURE:
<221> NAME/KEY: MOD_RES
<222> LOCATION: (38)
<223> OTHER INFORMATION: D-Leu
<220> FEATURE:
<221> NAME/KEY: MOD_RES
<222> LOCATION: (39)
<223> OTHER INFORMATION: D-Glu
<220> FEATURE:
<221> NAME/KEY: MOD_RES
<222> LOCATION: (40)
<223> OTHER INFORMATION: D-Glu
<220> FEATURE:
<221> NAME/KEY: MOD_RES
<222> LOCATION: (41)
<223> OTHER INFORMATION: D-Tyr
<220> FEATURE:
<221> NAME/KEY: MOD_RES
<222> LOCATION: (42)
<223> OTHER INFORMATION: D-Thr
<220> FEATURE:
<221> NAME/KEY: MOD_RES
<222> LOCATION: (43)
<223> OTHER INFORMATION: D-Lys
<220> FEATURE:
<221> NAME/KEY: MOD_RES
<222> LOCATION: (44)
<223> OTHER INFORMATION: D-Lys
<220> FEATURE:
<221> NAME/KEY: MOD_RES
<222> LOCATION: (45)
<223> OTHER INFORMATION: D-Leu
<220> FEATURE:
<221> NAME/KEY: MOD_RES
<222> LOCATION: (46)
<223> OTHER INFORMATION: D-Asn
<220> FEATURE:
<221> NAME/KEY: MOD_RES
```

-continued

<222> LOCATION: (47)
<223> OTHER INFORMATION: D-Thr
<220> FEATURE:
<221> NAME/KEY: MOD_RES
<222> LOCATION: (48)
<223> OTHER INFORMATION: D-Gln

<400> SEQUENCE: 586

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 587
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: C-term amidated

<400> SEQUENCE: 587

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 588
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Leu
<220> FEATURE:
<223> OTHER INFORMATION: C-term amidated

<400> SEQUENCE: 588

Leu Glu Ser Ala Lys Val Ser Ala Leu Ser Ala Leu Glu Glu Ala Thr
1 5 10 15

Lys Lys Lys Leu Ser Pro Leu Leu Glu Ser Phe Lys Val Ser Phe Leu
20 25 30

Ser Ala Leu Glu Glu Tyr Thr Lys Lys
35 40

<210> SEQ ID NO 589
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (41)
<223> OTHER INFORMATION: D-Lys
<220> FEATURE:

-continued

```
<223> OTHER INFORMATION: C-term amidated

<400> SEQUENCE: 589

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 590
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (41)
<223> OTHER INFORMATION: D-Lys
<220> FEATURE:
<223> OTHER INFORMATION: C-term amidated

<400> SEQUENCE: 590

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 591
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (2)
<223> OTHER INFORMATION: D-Glu
<220> FEATURE:
<221> NAME/KEY: MOD_RES
<222> LOCATION: (3)
<223> OTHER INFORMATION: D-Ser
<220> FEATURE:
<221> NAME/KEY: MOD_RES
<222> LOCATION: (4)
<223> OTHER INFORMATION: D-Ala
<220> FEATURE:
<221> NAME/KEY: MOD_RES
<222> LOCATION: (5)
<223> OTHER INFORMATION: D-Lys
<220> FEATURE:
<221> NAME/KEY: MOD_RES
<222> LOCATION: (6)
<223> OTHER INFORMATION: D-Val
<220> FEATURE:
<221> NAME/KEY: MOD_RES
<222> LOCATION: (7)
<223> OTHER INFORMATION: D-Ser
```

-continued

<220> FEATURE:
<221> NAME/KEY: MOD_RES
<222> LOCATION: (8)
<223> OTHER INFORMATION: D-Ala
<220> FEATURE:
<221> NAME/KEY: MOD_RES
<222> LOCATION: (9)
<223> OTHER INFORMATION: D-Leu
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Glu
<220> FEATURE:
<221> NAME/KEY: MOD_RES
<222> LOCATION: (14)
<223> OTHER INFORMATION: D-Glu
<220> FEATURE:
<221> NAME/KEY: MOD_RES
<222> LOCATION: (15)
<223> OTHER INFORMATION: D-Ala
<220> FEATURE:
<221> NAME/KEY: MOD_RES
<222> LOCATION: (16)
<223> OTHER INFORMATION: D-Thr
<220> FEATURE:
<221> NAME/KEY: MOD_RES
<222> LOCATION: (17)
<223> OTHER INFORMATION: D-Lys
<220> FEATURE:
<221> NAME/KEY: MOD_RES
<222> LOCATION: (18)
<223> OTHER INFORMATION: D-Lys
<220> FEATURE:
<221> NAME/KEY: MOD_RES
<222> LOCATION: (19)
<223> OTHER INFORMATION: D-Lys
<220> FEATURE:
<221> NAME/KEY: MOD_RES
<222> LOCATION: (20)
<223> OTHER INFORMATION: D-Leu
<220> FEATURE:
<221> NAME/KEY: MOD_RES
<222> LOCATION: (21)
<223> OTHER INFORMATION: D-Ser
<220> FEATURE:
<221> NAME/KEY: MOD_RES
<222> LOCATION: (22)
<223> OTHER INFORMATION: D-Pro
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Leu
<220> FEATURE:
<221> NAME/KEY: MOD_RES
<222> LOCATION: (25)
<223> OTHER INFORMATION: D-Glu
<220> FEATURE:
<221> NAME/KEY: MOD_RES
<222> LOCATION: (26)
<223> OTHER INFORMATION: D-Ser
<220> FEATURE:
<221> NAME/KEY: MOD_RES
<222> LOCATION: (27)

-continued

<223> OTHER INFORMATION: D-Phe
<220> FEATURE:
<221> NAME/KEY: MOD_RES
<222> LOCATION: (28)
<223> OTHER INFORMATION: D-Lys
<220> FEATURE:
<221> NAME/KEY: MOD_RES
<222> LOCATION: (29)
<223> OTHER INFORMATION: D-Val
<220> FEATURE:
<221> NAME/KEY: MOD_RES
<222> LOCATION: (30)
<223> OTHER INFORMATION: D-Ser
<220> FEATURE:
<221> NAME/KEY: MOD_RES
<222> LOCATION: (31)
<223> OTHER INFORMATION: D-Phe
<220> FEATURE:
<221> NAME/KEY: MOD_RES
<222> LOCATION: (32)
<223> OTHER INFORMATION: D-Leu
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Ala
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Glu
<220> FEATURE:
<221> NAME/KEY: MOD_RES
<222> LOCATION: (37)
<223> OTHER INFORMATION: D-Glu
<220> FEATURE:
<221> NAME/KEY: MOD_RES
<222> LOCATION: (38)
<223> OTHER INFORMATION: D-Tyr
<220> FEATURE:
<221> NAME/KEY: MOD_RES
<222> LOCATION: (39)
<223> OTHER INFORMATION: D-Thr
<220> FEATURE:
<221> NAME/KEY: MOD_RES
<222> LOCATION: (40)
<223> OTHER INFORMATION: D-Lys
<220> FEATURE:
<221> NAME/KEY: MOD_RES
<222> LOCATION: (41)
<223> OTHER INFORMATION: D-Lys
<220> FEATURE:
<223> OTHER INFORMATION: C-term amidated

<400> SEQUENCE: 591

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 592
<211> LENGTH: 48
<212> TYPE: PRT
<213> ORGANISM: Artificial Sequence
<220> FEATURE:
<223> OTHER INFORMATION: Description of Artificial Sequence: Synthetic
peptide <220> FEATURE:
<223> OTHER INFORMATION: C-term amidated

<400> SEQUENCE: 592

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 593
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Ser
<220> FEATURE:
<223> OTHER INFORMATION: C-term amidated

<400> SEQUENCE: 593

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 594
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (48)
<223> OTHER INFORMATION: D-Gln
<220> FEATURE:
<223> OTHER INFORMATION: C-term amidated

<400> SEQUENCE: 594

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 595
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)
<223> OTHER INFORMATION: D-Ser
<220> FEATURE:

-continued

<221> NAME/KEY: MOD_RES
<222> LOCATION: (48)
<223> OTHER INFORMATION: D-Gln
<220> FEATURE:
<223> OTHER INFORMATION: C-term amidated

<400> SEQUENCE: 595

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 596
<211> LENGTH: 48
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (2)
<223> OTHER INFORMATION: D-Pro
<220> FEATURE:
<221> NAME/KEY: MOD_RES
<222> LOCATION: (3)
<223> OTHER INFORMATION: D-Leu
<220> FEATURE:
<221> NAME/KEY: MOD_RES
<222> LOCATION: (4)
<223> OTHER INFORMATION: D-Leu
<220> FEATURE:
<221> NAME/KEY: MOD_RES
<222> LOCATION: (5)
<223> OTHER INFORMATION: D-Glu
<220> FEATURE:
<221> NAME/KEY: MOD_RES
<222> LOCATION: (6)
<223> OTHER INFORMATION: D-Ser
<220> FEATURE:
<221> NAME/KEY: MOD_RES
<222> LOCATION: (7)
<223> OTHER INFORMATION: D-Ala
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (9)
<223> OTHER INFORMATION: D-Val
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Ser
<220> FEATURE:
<221> NAME/KEY: MOD_RES -continued
<222> LOCATION: (14)
<223> OTHER INFORMATION: D-Ala
<220> FEATURE:
<221> NAME/KEY: MOD_RES
<222> LOCATION: (15)
<223> OTHER INFORMATION: D-Leu
<220> FEATURE:
<221> NAME/KEY: MOD_RES
<222> LOCATION: (16)
<223> OTHER INFORMATION: D-Glu
<220> FEATURE:
<221> NAME/KEY: MOD_RES
<222> LOCATION: (17)
<223> OTHER INFORMATION: D-Glu
<220> FEATURE:
<221> NAME/KEY: MOD_RES
<222> LOCATION: (18)
<223> OTHER INFORMATION: D-Ala
<220> FEATURE:
<221> NAME/KEY: MOD_RES
<222> LOCATION: (19)
<223> OTHER INFORMATION: D-Thr
<220> FEATURE:
<221> NAME/KEY: MOD_RES
<222> LOCATION: (20)
<223> OTHER INFORMATION: D-Lys
<220> FEATURE:
<221> NAME/KEY: MOD_RES
<222> LOCATION: (21)
<223> OTHER INFORMATION: D-Lys
<220> FEATURE:
<221> NAME/KEY: MOD_RES
<222> LOCATION: (22)
<223> OTHER INFORMATION: D-Lys
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Ser
<220> FEATURE:
<221> NAME/KEY: MOD_RES
<222> LOCATION: (25)
<223> OTHER INFORMATION: D-Pro
<220> FEATURE:
<221> NAME/KEY: MOD_RES
<222> LOCATION: (26)
<223> OTHER INFORMATION: D-Leu
<220> FEATURE:
<221> NAME/KEY: MOD_RES
<222> LOCATION: (27)
<223> OTHER INFORMATION: D-Leu
<220> FEATURE:
<221> NAME/KEY: MOD_RES
<222> LOCATION: (28)
<223> OTHER INFORMATION: D-Glu
<220> FEATURE:
<221> NAME/KEY: MOD_RES
<222> LOCATION: (29)
<223> OTHER INFORMATION: D-Ser
<220> FEATURE:
<221> NAME/KEY: MOD_RES
<222> LOCATION: (30)
<223> OTHER INFORMATION: D-Phe
<220> FEATURE:
<221> NAME/KEY: MOD_RES
<222> LOCATION: (31)
<223> OTHER INFORMATION: D-Lys
<220> FEATURE:
<221> NAME/KEY: MOD_RES
<222> LOCATION: (32)
<223> OTHER INFORMATION: D-Val
<220> FEATURE:
<221> NAME/KEY: MOD_RES
<222> LOCATION: (33)
<223> OTHER INFORMATION: D-Ser
<220> FEATURE:

-continued

<221> NAME/KEY: MOD_RES
<222> LOCATION: (34)
<223> OTHER INFORMATION: D-Phe
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Ser
<220> FEATURE:
<221> NAME/KEY: MOD_RES
<222> LOCATION: (37)
<223> OTHER INFORMATION: D-Ala
<220> FEATURE:
<221> NAME/KEY: MOD_RES
<222> LOCATION: (38)
<223> OTHER INFORMATION: D-Leu
<220> FEATURE:
<221> NAME/KEY: MOD_RES
<222> LOCATION: (39)
<223> OTHER INFORMATION: D-Glu
<220> FEATURE:
<221> NAME/KEY: MOD_RES
<222> LOCATION: (40)
<223> OTHER INFORMATION: D-Glu
<220> FEATURE:
<221> NAME/KEY: MOD_RES
<222> LOCATION: (41)
<223> OTHER INFORMATION: D-Tyr
<220> FEATURE:
<221> NAME/KEY: MOD_RES
<222> LOCATION: (42)
<223> OTHER INFORMATION: D-Thr
<220> FEATURE:
<221> NAME/KEY: MOD_RES
<222> LOCATION: (43)
<223> OTHER INFORMATION: D-Lys
<220> FEATURE:
<221> NAME/KEY: MOD_RES
<222> LOCATION: (44)
<223> OTHER INFORMATION: D-Lys
<220> FEATURE:
<221> NAME/KEY: MOD_RES
<222> LOCATION: (45)
<223> OTHER INFORMATION: D-Leu
<220> FEATURE:
<221> NAME/KEY: MOD_RES
<222> LOCATION: (46)
<223> OTHER INFORMATION: D-Asn
<220> FEATURE:
<221> NAME/KEY: MOD_RES
<222> LOCATION: (47)
<223> OTHER INFORMATION: D-Thr
<220> FEATURE:
<221> NAME/KEY: MOD_RES
<222> LOCATION: (48)
<223> OTHER INFORMATION: D-Gln
<220> FEATURE:
<223> OTHER INFORMATION: C-term amidated

<400> SEQUENCE: 596

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 597
<211> LENGTH: 41
<212> TYPE: PRT
<213> ORGANISM: Artificial Sequence
<220> FEATURE:

<223> OTHER INFORMATION: Description of Artificial Sequence: Synthetic peptide
<220> FEATURE:
<223> OTHER INFORMATION: N-term acetylated
<220> FEATURE:
<223> OTHER INFORMATION: C-term amidated

<400> SEQUENCE: 597

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 598
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Leu
<220> FEATURE:
<223> OTHER INFORMATION: C-term amidated

<400> SEQUENCE: 598

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 599
<211> LENGTH: 41
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (41)
<223> OTHER INFORMATION: D-Lys
<220> FEATURE:
<223> OTHER INFORMATION: C-term amidated

<400> SEQUENCE: 599

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 600
<211> LENGTH: 41
<212> TYPE: PRT
<213> ORGANISM: Artificial Sequence -continued
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (41)
<223> OTHER INFORMATION: D-Lys
<220> FEATURE:
<223> OTHER INFORMATION: C-term amidated

<400> SEQUENCE: 600

```
Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40
```

<210> SEQ ID NO 601
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Leu
<220> FEATURE:
<221> NAME/KEY: MOD_RES
<222> LOCATION: (2)
<223> OTHER INFORMATION: D-Glu
<220> FEATURE:
<221> NAME/KEY: MOD_RES
<222> LOCATION: (3)
<223> OTHER INFORMATION: D-Ser
<220> FEATURE:
<221> NAME/KEY: MOD_RES
<222> LOCATION: (4)
<223> OTHER INFORMATION: D-Ala
<220> FEATURE:
<221> NAME/KEY: MOD_RES
<222> LOCATION: (5)
<223> OTHER INFORMATION: D-Lys
<220> FEATURE:
<221> NAME/KEY: MOD_RES
<222> LOCATION: (6)
<223> OTHER INFORMATION: D-Val
<220> FEATURE:
<221> NAME/KEY: MOD_RES
<222> LOCATION: (7)
<223> OTHER INFORMATION: D-Ser
<220> FEATURE:
<221> NAME/KEY: MOD_RES
<222> LOCATION: (8)
<223> OTHER INFORMATION: D-Ala
<220> FEATURE:
<221> NAME/KEY: MOD_RES
<222> LOCATION: (9)
<223> OTHER INFORMATION: D-Leu
<220> FEATURE:
<221> NAME/KEY: MOD_RES
<222> LOCATION: (10)
<223> OTHER INFORMATION: D-Ser
<220> FEATURE:
<221> NAME/KEY: MOD_RES -continued
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Glu
<220> FEATURE:
<221> NAME/KEY: MOD_RES
<222> LOCATION: (14)
<223> OTHER INFORMATION: D-Glu
<220> FEATURE:
<221> NAME/KEY: MOD_RES
<222> LOCATION: (15)
<223> OTHER INFORMATION: D-Ala
<220> FEATURE:
<221> NAME/KEY: MOD_RES
<222> LOCATION: (16)
<223> OTHER INFORMATION: D-Thr
<220> FEATURE:
<221> NAME/KEY: MOD_RES
<222> LOCATION: (17)
<223> OTHER INFORMATION: D-Lys
<220> FEATURE:
<221> NAME/KEY: MOD_RES
<222> LOCATION: (18)
<223> OTHER INFORMATION: D-Lys
<220> FEATURE:
<221> NAME/KEY: MOD_RES
<222> LOCATION: (19)
<223> OTHER INFORMATION: D-Lys
<220> FEATURE:
<221> NAME/KEY: MOD_RES
<222> LOCATION: (20)
<223> OTHER INFORMATION: D-Leu
<220> FEATURE:
<221> NAME/KEY: MOD_RES
<222> LOCATION: (21)
<223> OTHER INFORMATION: D-Ser
<220> FEATURE:
<221> NAME/KEY: MOD_RES
<222> LOCATION: (22)
<223> OTHER INFORMATION: D-Pro
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Leu
<220> FEATURE:
<221> NAME/KEY: MOD_RES
<222> LOCATION: (25)
<223> OTHER INFORMATION: D-Glu
<220> FEATURE:
<221> NAME/KEY: MOD_RES
<222> LOCATION: (26)
<223> OTHER INFORMATION: D-Ser
<220> FEATURE:
<221> NAME/KEY: MOD_RES
<222> LOCATION: (27)
<223> OTHER INFORMATION: D-Phe
<220> FEATURE:
<221> NAME/KEY: MOD_RES
<222> LOCATION: (28)
<223> OTHER INFORMATION: D-Lys
<220> FEATURE:
<221> NAME/KEY: MOD_RES
<222> LOCATION: (29)
<223> OTHER INFORMATION: D-Val
<220> FEATURE:
<221> NAME/KEY: MOD_RES
<222> LOCATION: (30)
<223> OTHER INFORMATION: D-Ser
<220> FEATURE:

-continued

```
<221> NAME/KEY: MOD_RES
<222> LOCATION: (31)
<223> OTHER INFORMATION: D-Phe
<220> FEATURE:
<221> NAME/KEY: MOD_RES
<222> LOCATION: (32)
<223> OTHER INFORMATION: D-Leu
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Ala
<220> FEATURE:
<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Glu
<220> FEATURE:
<221> NAME/KEY: MOD_RES
<222> LOCATION: (37)
<223> OTHER INFORMATION: D-Glu
<220> FEATURE:
<221> NAME/KEY: MOD_RES
<222> LOCATION: (38)
<223> OTHER INFORMATION: D-Tyr
<220> FEATURE:
<221> NAME/KEY: MOD_RES
<222> LOCATION: (39)
<223> OTHER INFORMATION: D-Thr
<220> FEATURE:
<221> NAME/KEY: MOD_RES
<222> LOCATION: (40)
<223> OTHER INFORMATION: D-Lys
<220> FEATURE:
<221> NAME/KEY: MOD_RES
<222> LOCATION: (41)
<223> OTHER INFORMATION: D-Lys
<220> FEATURE:
<223> OTHER INFORMATION: C-term amidated

<400> SEQUENCE: 601

Leu Glu Ser Ala Lys Val Ser Ala Leu Ser Ala Leu Glu Glu Ala Thr
1               5                   10                  15

Lys Lys Lys Leu Ser Pro Leu Leu Glu Ser Phe Lys Val Ser Phe Leu
            20                  25                  30

Ser Ala Leu Glu Glu Tyr Thr Lys Lys
        35                  40


<210> SEQ ID NO 602
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 602

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
```

-continued

```
        35                  40                  45


<210> SEQ ID NO 603
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser
<220> FEATURE:
<223> OTHER INFORMATION: C-term amidated

<400> SEQUENCE: 603

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 604
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (48)
<223> OTHER INFORMATION: D-Gln
<220> FEATURE:
<223> OTHER INFORMATION: C-term amidated

<400> SEQUENCE: 604

Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45


<210> SEQ ID NO 605
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (48)
<223> OTHER INFORMATION: D-Gln
<220> FEATURE:
<223> OTHER INFORMATION: C-term amidated
```

-continued

<400> SEQUENCE: 605

Ser Pro Leu Leu Glu Ser Ala Lys Val Ser Ala Leu Ser Ala Leu Glu
1 5 10 15

Glu Ala Thr Lys Lys Lys Leu Ser Pro Leu Leu Glu Ser Phe Lys Val
20 25 30

Ser Phe Leu Ser Ala Leu Glu Glu Tyr Thr Lys Lys Leu Asn Thr Gln
35 40 45

<210> SEQ ID NO 606
<211> LENGTH: 48
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term acetylated
<220> FEATURE:
<221> NAME/KEY: MOD_RES
<222> LOCATION: (1)
<223> OTHER INFORMATION: D-Ser
<220> FEATURE:
<221> NAME/KEY: MOD_RES
<222> LOCATION: (2)
<223> OTHER INFORMATION: D-Pro
<220> FEATURE:
<221> NAME/KEY: MOD_RES
<222> LOCATION: (3)
<223> OTHER INFORMATION: D-Leu
<220> FEATURE:
<221> NAME/KEY: MOD_RES
<222> LOCATION: (4)
<223> OTHER INFORMATION: D-Leu
<220> FEATURE:
<221> NAME/KEY: MOD_RES
<222> LOCATION: (5)
<223> OTHER INFORMATION: D-Glu
<220> FEATURE:
<221> NAME/KEY: MOD_RES
<222> LOCATION: (6)
<223> OTHER INFORMATION: D-Ser
<220> FEATURE:
<221> NAME/KEY: MOD_RES
<222> LOCATION: (7)
<223> OTHER INFORMATION: D-Ala
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (9)
<223> OTHER INFORMATION: D-Val
<220> FEATURE:
<221> NAME/KEY: MOD_RES
<222> LOCATION: (10)
<223> OTHER INFORMATION: D-Ser
<220> FEATURE:
<221> NAME/KEY: MOD_RES
<222> LOCATION: (11)
<223> OTHER INFORMATION: D-Ala
<220> FEATURE:
<221> NAME/KEY: MOD_RES
<222> LOCATION: (12)
<223> OTHER INFORMATION: D-Leu
<220> FEATURE:
<221> NAME/KEY: MOD_RES
<222> LOCATION: (13)
<223> OTHER INFORMATION: D-Ser
<220> FEATURE:
<221> NAME/KEY: MOD_RES
<222> LOCATION: (14)
<223> OTHER INFORMATION: D-Ala
<220> FEATURE:
<221> NAME/KEY: MOD_RES -continued
<222> LOCATION: (15)
<223> OTHER INFORMATION: D-Leu
<220> FEATURE:
<221> NAME/KEY: MOD_RES
<222> LOCATION: (16)
<223> OTHER INFORMATION: D-Glu
<220> FEATURE:
<221> NAME/KEY: MOD_RES
<222> LOCATION: (17)
<223> OTHER INFORMATION: D-Glu
<220> FEATURE:
<221> NAME/KEY: MOD_RES
<222> LOCATION: (18)
<223> OTHER INFORMATION: D-Ala
<220> FEATURE:
<221> NAME/KEY: MOD_RES
<222> LOCATION: (19)
<223> OTHER INFORMATION: D-Thr
<220> FEATURE:
<221> NAME/KEY: MOD_RES
<222> LOCATION: (20)
<223> OTHER INFORMATION: D-Lys
<220> FEATURE:
<221> NAME/KEY: MOD_RES
<222> LOCATION: (21)
<223> OTHER INFORMATION: D-Lys
<220> FEATURE:
<221> NAME/KEY: MOD_RES
<222> LOCATION: (22)
<223> OTHER INFORMATION: D-Lys
<220> FEATURE:
<221> NAME/KEY: MOD_RES
<222> LOCATION: (23)
<223> OTHER INFORMATION: D-Leu
<220> FEATURE:
<221> NAME/KEY: MOD_RES
<222> LOCATION: (24)
<223> OTHER INFORMATION: D-Ser
<220> FEATURE:
<221> NAME/KEY: MOD_RES
<222> LOCATION: (25)
<223> OTHER INFORMATION: D-Pro
<220> FEATURE:
<221> NAME/KEY: MOD_RES
<222> LOCATION: (26)
<223> OTHER INFORMATION: D-Leu
<220> FEATURE:
<221> NAME/KEY: MOD_RES
<222> LOCATION: (27)
<223> OTHER INFORMATION: D-Leu
<220> FEATURE:
<221> NAME/KEY: MOD_RES
<222> LOCATION: (28)
<223> OTHER INFORMATION: D-Glu
<220> FEATURE:
<221> NAME/KEY: MOD_RES
<222> LOCATION: (29)
<223> OTHER INFORMATION: D-Ser
<220> FEATURE:
<221> NAME/KEY: MOD_RES
<222> LOCATION: (30)
<223> OTHER INFORMATION: D-Phe
<220> FEATURE:
<221> NAME/KEY: MOD_RES
<222> LOCATION: (31)
<223> OTHER INFORMATION: D-Lys
<220> FEATURE:
<221> NAME/KEY: MOD_RES
<222> LOCATION: (32)
<223> OTHER INFORMATION: D-Val
<220> FEATURE:
<221> NAME/KEY: MOD_RES
<222> LOCATION: (33)
<223> OTHER INFORMATION: D-Ser
<220> FEATURE:
<221> NAME/KEY: MOD_RES
<222> LOCATION: (34)
<223> OTHER INFORMATION: D-Phe
<220> FEATURE:

-continued

<221> NAME/KEY: MOD_RES
<222> LOCATION: (35)
<223> OTHER INFORMATION: D-Leu
<220> FEATURE:
<221> NAME/KEY: MOD_RES
<222> LOCATION: (36)
<223> OTHER INFORMATION: D-Ser
<220> FEATURE:
<221> NAME/KEY: MOD_RES
<222> LOCATION: (37)
<223> OTHER INFORMATION: D-Ala
<220> FEATURE:
<221> NAME/KEY: MOD_RES
<222> LOCATION: (38)
<223> OTHER INFORMATION: D-Leu
<220> FEATURE:
<221> NAME/KEY: MOD_RES
<222> LOCATION: (39)
<223> OTHER INFORMATION: D-Glu
<220> FEATURE:
<221> NAME/KEY: MOD_RES
<222> LOCATION: (40)
<223> OTHER INFORMATION: D-Glu
<220> FEATURE:
<221> NAME/KEY: MOD_RES
<222> LOCATION: (41)
<223> OTHER INFORMATION: D-Tyr
<220> FEATURE:
<221> NAME/KEY: MOD_RES
<222> LOCATION: (42)
<223> OTHER INFORMATION: D-Thr
<220> FEATURE:
<221> NAME/KEY: MOD_RES
<222> LOCATION: (43)
<223> OTHER INFORMATION: D-Lys
<220> FEATURE:
<221> NAME/KEY: MOD_RES
<222> LOCATION: (44)
<223> OTHER INFORMATION: D-Lys
<220> FEATURE:
<221> NAME/KEY: MOD_RES
<222> LOCATION: (45)
<223> OTHER INFORMATION: D-Leu
<220> FEATURE:
<221> NAME/KEY: MOD_RES
<222> LOCATION: (46)
<223> OTHER INFORMATION: D-Asn
<220> FEATURE:
<221> NAME/KEY: MOD_RES
<222> LOCATION: (47)
<223> OTHER INFORMATION: D-Thr
<220> FEATURE:
<221> NAME/KEY: MOD_RES
<222> LOCATION: (48)
<223> OTHER INFORMATION: D-Gln
<220> FEATURE:
<223> OTHER INFORMATION: C-term amidated

<400> SEQUENCE: 606

```
Ser Pro Leu Leu Glu Ser Ala Lys Val Ser Ala Leu Ser Ala Leu Glu
1               5                   10                  15

Glu Ala Thr Lys Lys Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

<210> SEQ ID NO 607
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 607

-continued

```
tctcctcttc ttgagtctgc taaggtttct gctctttctg ctcttgaaga agctactaaa     60

aaaaaacttt ctcctcttct tgaaagtttt aaagtttctt ttctttctgc tcttgaagaa    120

tatactaaaa aattaaatac tcaa                                            144


<210> SEQ ID NO 608
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
        35


<210> SEQ ID NO 609
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: D-Met

<400> SEQUENCE: 609

Trp Lys Tyr Met Val Met
1               5


<210> SEQ ID NO 610
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Ser Pro Leu Ser Asp Glu Leu Arg Gln Arg Leu Ala Ala Arg Leu Glu
1               5                   10                  15

Ala Leu Lys Glu Asn Lys Leu Ser Pro Leu Leu Glu Ser Phe Lys Val
            20                  25                  30

Ser Phe Leu Ser Ala Leu Glu Glu Tyr Thr Lys Lys Leu Asn Thr Gln
        35                  40                  45
```

PEPTIDES THAT PROMOTE LIPID EFFLUX

PRIOR RELATED APPLICATIONS

This application is a continuation of and claims benefit of priority from U.S. Ser. No. 12/021,629 (filed Jan. 29, 2008), which is a continuation-in-part of and claims benefit of priority from U.S. Ser. No. 11/764,619 (filed Jun. 18, 2007), which claims benefit of priority from U.S. Provisional Patent Application Nos. 60/814,466 (filed Jun. 16, 2006), 60/847,586 (filed Sep. 26, 2006), and 60/858,073 (filed Nov. 10, 2006). Each of the preceding applications is herein incorporated by reference in its entirety.

FIELD OF THE INVENTION

This present invention relates to peptides or peptide analogs that contain functional domains and promote lipid efflux. These peptides or peptide analogs optionally contain one or more anti-inflammatory domain and one or more domains that affects lecithin cholesterol acyltransferase (LCAT) activity. The disclosure further relates to methods for administering these peptides in the treatment and prevention of dyslipidemic and vascular disorders. The disclosure further relates to methods for using these peptides in assays and in methods of imaging sites of association of these peptides with receptors and with sites of lipid deposition.

BACKGROUND OF THE INVENTION

Clearance of excess cholesterol from cells by high density lipoproteins (HDL) is facilitated by the interaction of HDL apolipoprotein with cell-surface binding sites or receptors. Research has demonstrated an inverse correlation between the occurrence of atherosclerosis events and levels of HDL and its most abundant protein constituent, apolipoprotein A-I (ApoA-I) (Panagotopulos et al., *J. Biol. Chem.* 277:39477-39484, 2002). ApoA-I has been shown to promote lipid efflux from ABCA1-transfected cells (Wang et al., *J. Biol. Chem.* 275:33053-33058, 2000; Hamon et al., *Nat. Cell Biol.* 2:399-406, 2000; and Remaley et al., *Biochem. Biophys. Res. Commun.* 280:818-823, 2001). However, the nature of the interaction between ApoA-I and ABCA1 is not fully understood.

There exists a need for non-cytotoxic, synthetic peptide mimetics of apolipoproteins that promote specific lipid efflux from cells, perhaps by an ABCA1-dependent pathway, for use in the treatment and prevention of cardiovascular diseases, such as atherosclerosis.

Inflammation is believed to contribute to a variety of disease processes, including vascular disease. Inflammation is believed to contribute to the process of atherosclerosis, and physicians often prescribe anti-inflammatory medicine, such as aspirin, to patients with atherosclerosis, in conjunction with statins, in an attempt to decrease the ongoing inflammatory process that contributes to atherosclerosis and vascular disease. What is needed are compounds that decrease inflammation.

LCAT is the major enzyme involved in the esterification of free cholesterol present in circulating plasma lipoproteins, and a major determinant of plasma HDL concentrations. What is needed are compounds that increase LCAT activity.

What is needed are new compositions that promote lipid efflux. What is also needed are new compositions with functional domains that promote lipid efflux and have anti-inflammatory properties and/or activity to modulate LCAT activity, or a combination of domains that have anti-inflammatory properties and the activity to modulate LCAT activity.

SUMMARY OF THE INVENTION

The present invention solves the problems described above by providing novel peptide compositions with functional domains. In several embodiments, these novel peptide compositions promote lipid efflux. In several embodiments, these novel peptide compositions promote lipid efflux and have anti-inflammatory properties. In several embodiments, these novel peptide compositions promote lipid efflux and have one or more anti-inflammatory domains. In several embodiments, these novel peptide compositions promote lipid efflux and have one or more domains that affect LCAT activity. In several embodiments, these novel peptide compositions promote lipid efflux and have one or more anti-inflammatory domains and one or more domains that affect LCAT activity.

These novel peptide compositions may be labeled and used in a variety of applications including the visualization of plaque in vessels. These novel peptide compositions also display low toxicity.

The peptides of the present invention may be combined with pharmaceutically acceptable carriers and administered to a human or an animal as a composition. Administration may be through any means described herein and includes but is not limited to parenteral and oral administration and also administration on a coated device such as a stent or catheter.

Also described herein is a method of treating dyslipidemic and vascular disorders in an animal or a human, including administering to the animal or the human a therapeutically effective amount of the peptides or peptide analogs thereof presented herein. Dyslipidemic and vascular disorders amenable to treatment with the peptides disclosed herein include, but are not limited to, hyperlipidemia, hyperlipoproteinemia, hypercholesterolemia, hypertriglyceridemia, HDL deficiency, apoA-I deficiency, coronary artery disease, atherosclerosis, myocardial infarction, stroke and inflammation secondary to stroke, ischemia, ischemic stroke, thrombotic stroke, peripheral vascular disease including peripheral arterial disease, restenosis, thrombosis, acute coronary syndrome, and reperfusion myocardial injury.

The peptides of the present invention may be labeled with labels known to one of ordinary skill in the art and used for numerous applications, including but not limited to use in imaging applications to visualize atherosclerotic plaque. Labels include but are not limited to colorimetric labels, radiodense labels and radioisotopic labels. Other uses include but are not limited to use in assays, such as ELISAs, Western blots, radioimmunoassays and radioreceptor assays.

The peptides of the present invention may be used to generate antisera using techniques known to one of ordinary skill in the art.

The amino acid sequences disclosed herein are shown using standard three letter codes for amino acids, as defined in 37 C.F.R. 1.822 and as commonly known to one of ordinary skill in the art. When the three letter designation for an amino acid is shown in three upper case letters, for example SER for serine, the SER is a D amino acid.

The generic formulae described herein refer to the helical region 8 (Helix 8) of ApoA-I and a modified version of Helix 8 that contains three amino acid substitutions. Helix 8 of ApoA-I contains eighteen amino acids and consists of amino acid residues 222-239 of ApoA-I. FIG. 1 shows the numbered amino acid sequence of ApoA-I (SEQ ID NO: 1).

In one embodiment, the peptides of the present invention are described by the following generic formula I:

$$(A\text{-}B\text{-}C)_n \qquad \text{I.}$$

wherein A comprises a modified form of Helix 8 of ApoA-I (also referred to herein as Helix 8'), C comprises Helix 8 of ApoA-I, B comprises a linking group between A and C, and n is an integer from 1 to 10.

In one embodiment, A (Helix 8') is SEQ ID NO: 2 Leu Glu Ser Ala Lys Val Ser Ala Leu Ser Ala Leu Glu Glu Ala Thr Lys Lys, or a substitution thereof. These amino acids may also appear in reverse orientation such that Lys is at the N-terminus and Leu is at the C-terminus as in SEQ ID NO: 3 Lys Lys Thr Ala Glu Glu Leu Ala Ser Leu Ala Ser Val Lys Ala Ser Glu Leu.

The modification of Helix 8 to yield Helix 8' involves substitutions at positions 4 (Phe to Ala), 8 (Phe to Ala) and 15 (Tyr to Ala). It is to be understood that the present invention encompasses other amino acid substitutions at these locations. At positions 4 and 8, Phe may be substituted with Val, Leu, Gly, Thr, Ser or gamma aminobutyric acid (GABA: GABA is also designated as 4Abu herein). At position 15, Tyr may be substituted with Val, Leu, Gly, Thr, Ser or GABA. While not wanting to be bound by the following statement, it is believed that A, the modified form of helix 8 of ApoA-I, has a lower lipid affinity than C, the unmodified form of helix 8 of ApoA-I.

In one embodiment, B is Pro; SEQ ID NO: 4 Lys Leu Ser Pro Leu; SEQ ID NO: 5 Leu Ser Pro Leu; SEQ ID NO: 6 Ser Pro Leu; Pro Leu; SEQ ID NO: 7 Lys Leu Ser Pro; SEQ ID NO: 8 Leu Ser Pro; Ser Pro; or a substitution thereof. These amino acids may appear in reverse orientation, for example, as in SEQ ID NO: 9 Leu Pro Ser Leu Lys; SEQ ID NO: 10 Leu Pro Ser Leu; SEQ ID NO: 11 Leu Pro Ser; Leu Pro; SEQ ID NO: 12 Pro Ser Leu Lys; SEQ ID NO: 13 Pro Ser Leu; Pro Ser; or a substitution thereof.

In one embodiment, C is helix 8 of ApoA-I and is SEQ ID NO: 14 Leu Glu Ser Phe Lys Val Ser Phe Leu Ser Ala Leu Glu Glu Tyr Thr Lys Lys, or a substitution thereof. These amino acids may also appear in reverse orientation such that Lys is at the N-terminus and Leu is at the C-terminus as SEQ ID NO: 15 Lys Lys Thr Tyr Glu Glu Leu Ala Ser Leu Phe Ser Val Lys Phe Ser Glu Leu.

It is to be understood that A and C may be switched in location as in C-B-A.

In a further embodiment, peptides of the present invention are described by the following subgeneric formula II, in which one or more additional elements indicated as variables G and H, are added to formula I to make subgeneric formula II.

$$G\text{-}(A\text{-}B\text{-}C)_n\text{-}H \qquad \text{II.}$$

$(A\text{-}B\text{-}C)_n$ are as described in formula I above,

G is absent or present and is a peptide as defined in the present specification. In one embodiment, G is SEQ ID NO: 6 Ser Pro Leu; Pro Leu; Leu; Ser Pro; Ser; Pro; or a substitution thereof. These amino acids can also appear in reverse orientation: SEQ ID NO: 11 Leu Pro Ser; Pro Ser; Leu Pro; or a substitution thereof. It is to be understood that one or more of the amino acids in the G peptide may be D amino acids.

H is absent or present and is a peptide as defined in the present specification. In one embodiment, H is SEQ ID NO: 16 Leu Asn Thr Gln; SEQ ID NO: 17 Asn Thr Gln; Thr Gln; Gln; SEQ ID NO: 18 Leu Asn Thr; Leu Asn; Leu; or a substitution thereof. These amino acids can also appear in reverse orientation: SEQ ID NO: 19 Gln Thr Asn Leu; SEQ ID NO: 20 Thr Asn Leu; Asn Leu; SEQ ID NO: 21 Gln Thr Asn; Gln Thr; or a substitution thereof. It is to be understood that one or more of the amino acids in the H peptide may be D amino acids.

The present invention also includes compositions comprising combinations of individual peptides of the present invention in an acceptable carrier. It is to be understood that a mixture of peptides may include different amounts of the individual peptides. For example, in one embodiment, each peptide component of the combination may be present in a different relative percentage than each other peptide component due to differences in relative efficacy to promote lipid efflux or to provide one or more types of anti-inflammatory activity.

It is to be understood that the letters in the generic formulae I and II or in components thereof are defined by the text that follows each letter and do not designate an individual amino acid.

It is to be understood that in some embodiments, one or more of the amino acids of the peptides of the present invention are D amino acids. In one embodiment, the N-terminal amino acid, the C-terminal amino acid or both are D amino acids. The presence of these D amino acids can help protect against peptide degradation. In another embodiment, all the amino acids of the peptides of the present invention are D amino acids. This embodiment is useful for protection against degradation following oral administration of a pharmaceutical composition comprising the peptides of the present invention.

The N and/or C-terminal amino acids may also be modified by amidation, acetylation or other modifications known to one of ordinary skill in the art. The peptides of the present invention may optionally be acetylated at the N-terminus or the C-terminus using techniques known to one of ordinary skill in the art. The peptides of the present invention may optionally be amidated at the N-terminus or the C-terminus using techniques known to one of ordinary skill in the art. In one embodiment, the peptides of the present invention are acetylated at the N-terminus, amidated at the C-terminus, or both acetylated at the N-terminus and amidated at the C-terminus. In some embodiments, the peptides of the present invention may have both an acetylated N-terminus and a carboxy terminal amide. In the present application, when a peptide is acetylated on an N or C terminus, the letters Ac are indicated. In the present application, when a peptide is amidated on an N or C terminus, the designation $NH_2$ is employed.

The present invention also includes compositions comprising one or more individual peptides of the present invention in an acceptable carrier. These peptides are as defined above and may be labeled or unlabelled. It is to be understood that a mixture of peptides, may include different amounts of the individual peptides. For example, in one embodiment, each peptide component of the combination may be present in a different relative percentage than each other peptide component due to differences in relative efficacy to promote lipid efflux or to provide one or more types of anti-inflammatory activity.

Accordingly, it is an object of the present invention to provide novel peptides.

Accordingly, it is an object of the present invention to provide novel peptides that facilitate lipid efflux.

Yet another object of the present invention is to provide novel peptides that facilitate lipid efflux and possess anti-inflammatory biological activity.

Still another object of the present invention is to provide novel peptides that facilitate lipid efflux and stimulate LCAT activity.

Yet another object of the present invention is to provide novel peptides that facilitate lipid efflux, possess anti-inflammatory biological activity, and stimulate LCAT activity.

It is another object of the present invention to provide new methods for visualizing plaque using labeled peptides of the present invention.

It is yet another object of the present invention to provide new methods for the treatment of atherosclerosis, cardiovascular disease and cerebrovascular disease in an animal or a human by administering pharmaceutical compositions comprising one or more peptides of the present invention with a pharmaceutically acceptable carrier, or on a medical device.

These and other objects, features and advantages of the present invention will become apparent after a review of the following detailed description of the disclosed embodiments and claims.

BRIEF DESCRIPTION OF THE DRAWINGS

FIG. 1 shows the amino acid sequence of ApoA-I (SEQ ID NO: 1).

DETAILED DESCRIPTION OF THE INVENTION

Figure 2:
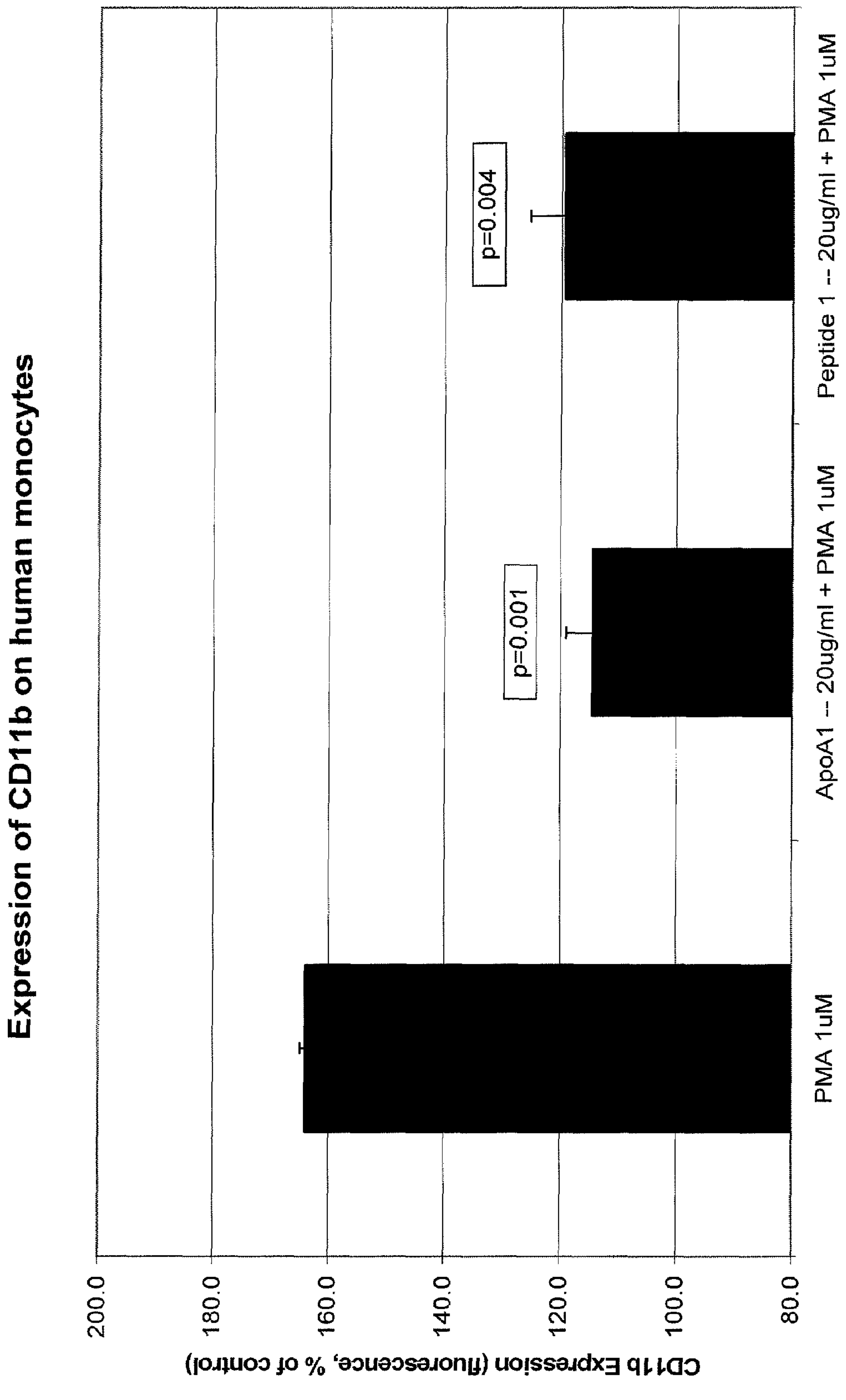
FIG. 2 is a schematic illustration of the statistically significant, anti-inflammatory effects of ApoA-I (SEQ ID NO: 1) and Peptide 1 (SEQ ID NO: 602), (each at 20 ug/ml) to decrease PMA (1 uM) induced expression of CD11b in human monocytes.

The present invention provides novel peptides. The present invention solves the problems described above by providing novel peptide compositions with functional domains. In some embodiments, these novel peptide compositions promote lipid efflux. In some embodiments, these novel peptide compositions promote lipid efflux and have anti-inflammatory properties. In other embodiments, these novel peptide compositions promote lipid efflux and have one or more anti-inflammatory domains. In yet other embodiments, these novel peptide compositions promote lipid efflux and have one or more domains that affect activity of lecithin-cholesterol acetyltransferase (LCAT), an enzyme that converts free cholesterol to cholesterol ester on high-density lipoprotein (HDL). In several embodiments, these novel peptide compositions promote lipid efflux and have one or more anti-inflammatory domains and one or more domain that affects LCAT activity.

Any of the peptides of the present invention may optionally be acetylated at the N-terminus or the C-terminus using techniques known to one of ordinary skill in the art. The peptides of the present invention may optionally be amidated at the N-terminus or the C-terminus using techniques known to one of ordinary skill in the art. In one embodiment, the peptides of the present invention are acetylated at the N-terminus, amidated at the C-terminus, or both acetylated at the N-terminus and amidated at the C-terminus. In some embodiments, the peptides of the present invention may have both an acetylated N-terminus and a carboxy terminal amide. In the present application, when a peptide is acetylated on an N or C terminus, the letters Ac are indicated. In the present application, when a peptide is amidated on an N or C terminus, the designation $NH_2$ is employed.

One or more of these peptides may be combined with an acceptable carrier and administered as compositions to individuals in order to provide lipid efflux and anti-inflammatory activities. These compositions may be administered to treat dyslipidemic and vascular disorders or to delay or prevent the onset or progression of dyslipidemic and vascular disorders. In one embodiment, these compositions may be administered to treat atherosclerosis or to delay or prevent its onset or progression. These novel peptide compositions may be labeled and used in a variety of applications including the visualization of plaque in vessels. These novel peptide compositions also display low toxicity.

I. Abbreviations

ABCA1: ATP-binding cassette transporter Al
apoA-I: apolipoprotein A-I
DMPC: dimyristoyl phosphatidyl choline
HDL: high-density lipoprotein
HPLC: high-pressure liquid chromatography
LDL: low-density lipoprotein
RBC: red blood cell

II. Terms

Unless otherwise noted, technical terms are used according to conventional usage. Definitions of common terms in molecular biology may be found in Benjamin Lewin, *Genes VII,* published by Oxford University Press, 2000 (ISBN 019879276X); Kendrew et al. (eds.), *The Encyclopedia of Molecular Biology,* published by Blackwell Publishers, 1994 (ISBN 0632021829); and Robert A. Meyers (ed.), *Molecular Biology and Biotechnology: a Comprehensive Desk Reference,* published by Wiley, John & Sons, Inc., 1995 (ISBN 0471186341); and other similar references.

As used herein, the singular terms “a,” “an,” and “the” include plural referents unless context clearly indicates otherwise. Similarly, the word “or” is intended to include “and” unless the context clearly indicates otherwise. Also, as used herein, the term “comprises ” means “includes.” Hence “comprising A or B” means including A, B, or A and B.

In order to facilitate review of the various embodiments of this disclosure, the following explanations of specific terms are provided:

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology,* 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term “subject” includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes.

Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, e.g., Harlow and Lane, *Using Antibodies: A Laboratory Manual,* CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual,* CSHL, New York, 1999.

Domain: A domain of a protein is a part of a protein that shares common structural, physiochemical and functional features; for example hydrophobic, polar, globular, helical domains or properties, for example a DNA binding domain, an ATP binding domain, an anti-inflammatory domain, an LCAT activating domain and the like. Some peptides of the present invention possess a domain or domains that have more than one functional feature, for example both lipid efflux activity and anti-inflammatory activity.

Dyslipidemic disorder: A disorder associated with any altered amount of any or all of the lipids or lipoproteins in the blood. Dyslipidemic disorders include, for example, hyperlipidemia, hyperlipoproteinemia, hypercholesterolemia, hypertriglyceridemia, HDL deficiency, apoA-I deficiency, and cardiovascular disease (e.g., coronary artery disease, atherosclerosis and restenosis).

Efflux: The process of flowing out. As applied to the results described herein, lipid efflux refers to a process whereby lipid, such as cholesterol and phospholipid, is complexed with an acceptor, such as an apolipoprotein or apolipoprotein peptide mimetic, or a peptide of the present invention and removed from vesicles or cells. "ABCA1-dependent lipid efflux" (or lipid efflux by an "ABCA1-dependent pathway") refers to a process whereby apolipoproteins, synthetic peptide mimetics of apolipoproteins, or a peptide of the present invention, bind to a cell and efflux lipid from the cell by a process that is facilitated by the ABCA1 transporter.

Helix: The molecular conformation of a spiral nature, generated by regularly repeating rotations around the backbone bonds of a macromolecule. Helix 8 of ApoA-I contains eighteen amino acids and consists of amino acid residues 222-239 of ApoA-I FIG. 1 shows the amino acid sequence of ApoA-I (SEQ ID NO: 36 1).

Hydrophobic: A hydrophobic (or lipophilic) group is electrically neutral and nonpolar, and thus prefers other neutral and nonpolar solvents or molecular environments. Examples of hydrophobic molecules include alkanes, oils and fats.

Hydrophilic: A hydrophilic (or lipophobic) group is electrically polarized and capable of H-bonding, enabling it to dissolve more readily in water than in oil or other "non-polar" solvents.

Inhibiting or treating a disease: Inhibiting the full development of a disease, disorder or condition, for example, in a subject who is at risk for a disease such as atherosclerosis and cardiovascular disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated/purified: An "isolated" or "purified" biological component (such as a nucleic acid, peptide or protein) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell. Preferably, a preparation is purified such that the biological component represents at least 50%, such as at least 70%, at least 90%, at least 95%, or greater of the total biological component content of the preparation.

Label: A detectable compound or composition that is conjugated directly or indirectly to another molecule to facilitate detection of that molecule. Specific, non-limiting examples of labels include fluorescent tags, calorimetric labels, dyes, beads, enzymatic linkages, radiodense materials, and radioactive isotopes.

Linker: A molecule that joins two other molecules, either covalently, or through ionic, van der Waals or hydrogen bonds.

Lipid: A class of water-insoluble, or partially water insoluble, oily or greasy organic substances, that are extractable from cells and tissues by nonpolar solvents, such as chloroform or ether. Types of lipids include triglycerides (e.g., natural fats and oils composed of glycerin and fatty acid chains), glycolipids, phospholipids (e.g., phosphatidylethanolamine, phosphatidylcholine, phosphatidylserine, and phosphatidylinositol), sphingolipids (e.g., sphingomyelin, cerebrosides and gangliosides), and sterols (e.g., cholesterol).

Lipid affinity: A measurement of the relative binding affinity of an amphipathic α-helix for lipids. In some embodiments, the lipid affinity of an amphipathic α-helix is determined by one or more functional tests. Specific, non-limiting examples of functional tests include: retention time on reverse phase HPLC, surface monolayer exclusion pressure (Palgunachari et al., *Arterioscler. Thromb. Vasc. Biol.* 16:328-338, 1996), binding affinity to phospholipid vesicles (Palgunachari et al., *Arterioscler. Thromb. Vasc. Biol.* 16:328-338, 1996), and DMPC vesicle solubilization (Remaley et al., *J. Lipid Res.* 44:828-836, 2003).

Further non-limiting examples of alternative methods of calculating the lipid affinity of an amphipathic a-helix include: total hydrophobic moment, total peptide hydrophobicity, total peptide hydrophobicity per residue, hydrophobicity of amino acids on the hydrophobic face, hydrophobicity per residue of amino acids on the hydrophobic face, and calculated lipid affinity based on predicted peptide penetration into phospholipid bilayers (Palgunachari et al., *Arterioscler. Thromb. Vasc. Biol.* 16:328-338, 1996).

Non-cytotoxic: A non-cytotoxic compound is one that does not substantially affect the viability or growth characteristics of a cell at a dosage normally used to treat the cell or a subject. Furthermore, the percentage of cells releasing intracellular contents, such as LDH or hemoglobin, is low (e.g., about 10% or less) in cells treated with a non-cytotoxic compound. Lipid efflux from a cell that occurs by a non-cytotoxic compound results in the removal of lipid from a cell by a process that maintains the overall integrity of the cell membrane and does not lead to significant cell toxicity.

Non-polar: A non-polar compound is one that does not have concentrations of positive or negative electric charge. Non-polar compounds, such as, for example, oil, are not well soluble in water.

Peptide: A polymer in which the monomers are amino acid residues which are joined together through amide bonds. When the amino acids are alpha-amino acids, either the L-optical isomer or the D-optical isomer can be used. The amino acid sequences disclosed herein are shown using three letter codes for amino acids, as defined in 37 C.F.R. 1.822 and as commonly known to one of ordinary skill in the art. When the three letter designation for an amino acid, for example Ser for serine is shown in upper case, SER, the serine is a D amino acid. The terms "peptide" or "polypeptide" as used herein are intended to encompass any amino acid sequence and include modified sequences such as glycoproteins. The term "peptide" is specifically intended to cover naturally occurring peptides, as well as those which are recombinantly or synthetically produced. The term "residue" or "amino acid residue" includes reference to an amino acid that is incorporated into a peptide, polypeptide, or protein. As known to one of skill in the art, the peptides presented herein are read from the N to the C terminus i.e., from left to right. Accordingly, the N-terminal amino acid in Leu Glu Lys is Leu and the C-terminal amino acid is Lys.

Substitutions: Peptides of the present invention include peptides with substitutions for amino acids in the peptide sequence. Such substitutions may be conservative substitutions, isosteric substitutions, substitutions between isosteric groups, and non-conservative substitutions as defined herein.

Peptides of the present invention include conservatively substituted peptides, wherein these conservative substitutions occur at 1%, 3%, 5%, 7%, 10%, 15%, 20%, 25%, 30%, 40%, or 50% of the amino acid residues. Peptides of the present invention include peptides that are homologous at 50%, 60%, 70%, 80%, 90%, 95%, 97%, 98%, 99% of the entire sequence of the peptide.

Pharmaceutically acceptable carriers: The pharmaceutically acceptable carriers (vehicles) useful in this disclosure are conventional. *Remington's Pharmaceutical Sciences,* by E. W. Martin, Mack Publishing Co., Easton, Pa. 15th Edition (1975), describes compositions and formulations suitable for pharmaceutical delivery of one or more therapeutic compounds or molecules, such as one or more peptides or peptide analogs and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospholipid: A phospholipid consists of a water-soluble polar head, linked to two water-insoluble non-polar tails (by a negatively charged phosphate group). Both tails consist of a fatty acid, each about 14 to about 24 carbon groups long. When placed in an aqueous environment, phospholipids form a bilayer or micelle, where the hydrophobic tails line up against each other. This forms a membrane with hydrophilic heads on both sides. A phospholipid is a lipid that is a primary component of animal cell membranes.

Polar: A polar molecule is one in which the centers of positive and negative charge distribution do not converge. Polar molecules are characterized by a dipole moment, which measures their polarity, and are soluble in other polar compounds and virtually insoluble in nonpolar compounds.

Recombinant nucleic acid: A sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of the nucleic acid.

Therapeutically effective amount: A quantity of a specified agent sufficient to achieve a desired effect in a subject being treated with that agent. For example, this can be the amount of a peptide or peptide analog useful in preventing, ameliorating, and/or treating a dyslipidemic disorder (e.g., atherosclerosis) in a subject. Ideally, a therapeutically effective amount of an agent is an amount sufficient to prevent, ameliorate, and/or treat a dyslipidemic disorder (e.g., atherosclerosis) in a subject without causing a substantial cytotoxic effect (e.g., membrane microsolubilization) in the subject. The effective amount of an agent useful for preventing, ameliorating, and/or treating a dyslipidemic disorder (e.g., atherosclerosis) in a subject will be dependent on the subject being treated, the severity of the disorder, and the manner of administration of the therapeutic composition.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

III. Peptides of the Present Invention and Analogs Thereof

A. (A-B-C)$_n$ Peptides

In one embodiment, the peptides of the present invention are described by the following generic formula I:

$$(A\text{-}B\text{-}C)_n. \qquad \text{I.}$$

It is to be understood that A and C can be switched in location as in C-B-A. One of ordinary skill in the art will understand that A and/or C can contain one or more substitutions as described herein.

One of ordinary skill in the art will also understand that A, B, and/or C can contain one or more D-amino acids. In one embodiment, the N-terminal amino acid, the C-terminal amino acid, or both are D amino acids. The presence of these D amino acids can help protect against peptide degradation. In another embodiment, all the amino acids of the peptides of the present invention are D amino acids. This embodiment is useful for protection against degradation following oral administration of a pharmaceutical composition comprising the peptides of the present invention. Any number of amino acids (e.g., between one and all of the amino acids) in the peptides of the invention can be D amino acids.

Peptides of the invention may contain an amino-terminal acetyl group and/or a carboxy-terminal amide group.

i. Segment A

Segment A comprises a modified form of Helix 8 of ApoA-I, also referred to herein as Helix 8', which is SEQ ID NO: 2 Leu Glu Ser Ala Lys Val Ser Ala Leu Ser Ala Leu Glu Glu Ala Thr Lys Lys, or a substitution thereof, as described herein. These amino acids may also appear in reverse orientation such that Lys is at the N-terminus and Leu is at the C-terminus as in SEQ ID NO: 3 Lys Lys Thr Ala Glu Glu Leu Ala Ser Leu Ala Ser Val Lys Ala Ser Glu Leu. The modification of Helix 8 to yield Helix 8' involves substitutions at positions 4 (Phe to Ala), 8 (Phe to Ala), and 15 (Tyr to Ala). It is to be understood that the present invention encompasses other amino acid substitutions at these locations. At positions 4 and 8 of SEQ ID NO: 2, Phe may be substituted with Val, Leu, Gly, Thr, Ser or gamma-aminobutyric acid (GABA). At position 15 of SEQ ID NO: 2, Tyr may be substituted with Val, Leu, Gly, Thr, Ser, or GABA. While not wanting to be bound by the following statement, it is believed that A, the modified form of helix 8 of ApoA-I, has a lower lipid affinity than segment C, the unmodified form of helix 8 of ApoA-I. It is to be understood that one or more of the amino acids in the Segment A peptide may be D amino acids.

ii. Segment B

B comprises a linking peptide that covalently joins A and C in the peptides of the present invention. In various embodiments the connecting peptide B, can be: SEQ ID NO: 4 Lys Leu Ser Pro Leu; SEQ ID NO: 5 Leu Ser Pro Leu; SEQ ID NO: 6 Ser Pro Leu; Pro Leu; SEQ ID NO: 7 Lys Leu Ser Pro; SEQ ID NO: 8 Leu Ser Pro; Ser Pro; or a substitution thereof. These amino acids may appear in reverse orientation, for example, as in SEQ ID NO: 9 Leu Pro Ser Leu Lys; SEQ ID NO: 10 Leu Pro Ser Leu; SEQ ID NO: 11 Leu Pro Ser; Leu Pro; SEQ ID NO: 12 Pro Ser Leu Lys; SEQ ID NO: 13 Pro Ser Leu; Pro Ser; or a substitution thereof. In addition, B can comprise the amino acid Pro or consist solely of the amino acid Pro. It is to be understood that one or more of the amino acids in the B peptide may be D amino acids.

iii. Segment C

C comprises Helix 8 of ApoA-I, which is SEQ ID NO: 14 Leu Glu Ser Phe Lys Val Ser Phe Leu Ser Ala Leu Glu Glu Tyr Thr Lys Lys, or a substitution thereof. These amino acids may also appear in reverse orientation such that Lys is at the N-terminus and Leu is at the C-terminus as SEQ ID NO: 15 Lys Lys Thr Tyr Glu Glu Leu Ala Ser Leu Phe Ser Val Lys Phe Ser Glu Leu. It is to be understood that A and C may be switched in location as in C-B-A. It is to be understood that one or more of the amino acids in the C peptide may be D amino acids.

iv. Specific Examples of (A-B-C)$_n$Peptides

Below is a non-limiting subset of examples of peptides represented by the basic formula (A-B-C)$_n$, in which A is Helix 8' and C is Helix 8. One of ordinary skill in the art will understand that the (A-B-C)$_n$ peptides of the invention include any of the B sequences set forth herein. One of ordinary skill in the art will understand that A and/or C can contain one or more substitutions, for example but not limited to, isosteric substitutions, substitutions between isosteric amino acid groups, conservative substitutions, and nonconservative substitutions, as described herein. A person of ordinary skill in the art will also understand that A, B, and/or C can contain one or more D-amino acids. Peptides of the invention may contain an amino-terminal acetyl group and/or a carboxy-terminal amide group.

a. Embodiments Wherein A is Helix 8' and C is Helix 8: Variations in the B Group with A and C Intact as A-B-C

SEQ ID NO: 22

```
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys;
```

SEQ ID NO: 23

```
Leu Glu Ser Ala Lys Val Ser Ala Leu Ser Ala Leu
Glu Glu Ala Thr Lys Lys Leu Ser Pro Leu Leu Leu
Glu Ser Phe Lys Val Ser Phe Leu Ser Ala Leu Glu
Glu Tyr Thr Lys Lys;
```

SEQ ID NO: 24

```
Leu Glu Ser Ala Lys Val Ser Ala Leu Ser Ala Leu
Glu Glu Ala Thr Lys Lys Ser Pro Leu Leu Leu Glu
Ser Phe Lys Val Ser Phe Leu Ser Ala Leu Glu Glu
Tyr Thr Lys Lys;
```

SEQ ID NO: 25

```
Leu Glu Ser Ala Lys Val Ser Ala Leu Ser Ala Leu
Glu Glu Ala Thr Lys Lys Pro Leu Leu Leu Glu Ser
Phe Lys Val Ser Phe Leu Ser Ala Leu Glu Glu Tyr
Thr Lys Lys;
```

-continued

SEQ ID NO: 26
Leu Glu Ser Ala Lys Val Ser Ala Leu Ser Ala Leu Glu Glu Ala Thr Lys Lys Lys Leu Ser ProLeu Leu Glu Ser Phe Lys Val Ser Phe Leu Ser Ala Leu Glu Glu Tyr Thr Lys Lys;

SEQ ID NO: 27
Leu Glu Ser Ala Lys Val Ser Ala Leu Ser Ala Leu Glu Glu Ala Thr Lys Lys Leu Ser Pro Leu Leu Glu Ser Phe Lys Val Ser Phe Leu Ser Ala Leu Glu Glu Tyr Thr Lys Lys;

SEQ ID NO: 28
Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys;

SEQ ID NO: 29
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys;

SEQ ID NO: 30
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys;

SEQ ID NO: 31
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys;

SEQ ID NO: 32
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys;

SEQ ID NO: 33
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys;

SEQ ID NO: 34
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys;

SEQ ID NO: 35
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys;

SEQ ID NO: 36
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys.

b. Embodiments Wherein A is Helix 8' and C is Helix 8: Variations in the B Group with A and C Intact but in a Different Orientation as C-B-A SEQ ID NO: 37
Leu Leu Glu Ser Phe Lys Val Ser Phe Leu Ser Ala Leu Glu Glu Tyr Thr Lys Lys Lys Leu Ser Pro Leu Leu Glu Ser Ala Lys Val Ser Ala Leu Ser Ala Leu Glu Glu Ala Thr Lys Lys;

-continued

SEQ ID NO: 38
Leu Leu Glu Ser Phe Lys Val Ser Phe Leu Ser Ala Leu Glu Glu Tyr Thr Lys Lys Leu Ser Pro Leu Leu Glu Ser Ala Lys Val Ser Ala Leu Ser Ala Leu Glu Glu Ala Thr Lys Lys;

SEQ ID NO: 39
Leu Leu Glu Ser Phe Lys Val Ser Phe Leu Ser Ala Leu Glu Glu Tyr Thr Lys Lys Ser Pro Leu Leu Glu Ser Ala Lys Val Ser Ala Leu Ser Ala Leu Glu Glu Ala Thr Lys Lys;

SEQ ID NO: 40
Leu Leu Glu Ser Phe Lys Val Ser Phe Leu Ser Ala Leu Glu Glu Tyr Thr Lys Lys Pro Leu Leu Glu Ser Ala Lys Val Ser Ala Leu Ser Ala Leu Glu Glu Ala Thr Lys Lys;

SEQ ID NO: 41
Leu Leu Glu Ser Phe Lys Val Ser Phe Leu Ser Ala Leu Glu Glu Tyr Thr Lys Lys Lys Leu Ser Pro Leu Glu Ser Ala Lys Val Ser Ala Leu Ser Ala Leu Glu Glu Ala Thr Lys Lys;

SEQ ID NO: 42
Leu Leu Glu Ser Phe Lys Val Ser Phe Leu Ser Ala Leu Glu Glu Tyr Thr Lys Lys Leu Ser Pro Leu Glu Ser Ala Lys Val Ser Ala Leu Ser Ala Leu Glu Glu Ala Thr Lys Lys;

SEQ ID NO: 43
Leu Leu Glu Ser Phe Lys Val Ser Phe Leu Ser Ala Leu Glu Glu Tyr Thr Lys Lys Ser Pro Leu Glu Ser Ala Lys Val Ser Ala Leu Ser Ala Leu Glu Glu Ala Thr Lys Lys;

SEQ ID NO: 44
Leu Leu Glu Ser Phe Lys Val Ser Phe Leu Ser Ala Leu Glu Glu Tyr Thr Lys Lys Leu Pro Ser Leu LysLeu Glu Ser Ala Lys Val Ser Ala Leu Ser Ala Leu Glu Glu Ala Thr Lys Lys;

SEQ ID NO: 45
Leu Leu Glu Ser Phe Lys Val Ser Phe Leu Ser Ala Leu Glu Glu Tyr Thr Lys Lys Leu Pro Ser Leu Leu Glu Ser Ala Lys Val Ser Ala Leu Ser Ala Leu Glu Glu Ala Thr Lys Lys;

SEQ ID NO: 46
Leu Leu Glu Ser Phe Lys Val Ser Phe Leu Ser Ala Leu Glu Glu Tyr Thr Lys Lys Leu Pro Ser Leu Glu Ser Ala Lys Val Ser Ala Leu Ser Ala Leu Glu Glu Ala Thr Lys Lys;

SEQ ID NO: 47
Leu Leu Glu Ser Phe Lys Val Ser Phe Leu Ser Ala Leu Glu Glu Tyr Thr Lys Lys Leu Pro Leu Glu Ser Ala Lys Val Ser Ala Leu Ser Ala Leu Glu Glu Ala Thr Lys Lys;

SEQ ID NO: 48
Leu Leu Glu Ser Phe Lys Val Ser Phe Leu Ser Ala Leu Glu Glu Tyr Thr Lys Lys Pro Ser Leu Lys Leu Glu Ser Ala Lys Val Ser Ala Leu Ser Ala Leu Glu Glu Ala Thr Lys Lys;

SEQ ID NO: 49
Leu Leu Glu Ser Phe Lys Val Ser Phe Leu Ser Ala Leu Glu Glu Tyr Thr Lys Lys Pro Ser Leu Leu Glu Ser Ala Lys Val Ser Ala Leu Ser Ala Leu Glu Glu Ala Thr Lys Lys;

SEQ ID NO: 50
Leu Leu Glu Ser Phe Lys Val Ser Phe Leu Ser Ala Leu Glu Glu Tyr Thr Lys Lys Pro Ser Leu Glu Ser Ala Lys Val Ser Ala Leu Ser Ala Leu Glu Glu Ala Thr Lys Lys;

-continued

SEQ ID NO: 51

Leu Leu Glu Ser Phe Lys Val Ser Phe Leu Ser Ala
Leu Glu Glu Tyr Thr Lys Lys Pro Leu Glu Ser Ala
Lys Val Ser Ala Leu Ser Ala Leu Glu Glu Ala Thr
Lys Lys.

c. Variations in the B Group with A and C Intact as A-B-C with the Amino Acids in A and C in Reverse Orientation SEQ ID NO: 52
Lys Lys Thr Ala Glu Glu Leu Ala Ser Leu Ala Ser
Val Lys Ala Ser Glu Leu Lys Leu Ser Pro Leu Lys
Lys Thr Tyr Glu Glu Leu Ala Ser Leu Phe Ser Val
Lys Phe Ser Glu Leu;

SEQ ID NO: 53
Lys Lys Thr Ala Glu Glu Leu Ala Ser Leu Ala Ser
Val Lys Ala Ser Glu Leu Leu Ser Pro Leu Lys Lys
Thr Tyr Glu Glu Leu Ala Ser Leu Phe Ser Val Lys
Phe Ser Glu Leu;

SEQ ID NO: 54
Lys Lys Thr Ala Glu Glu Leu Ala Ser Leu Ala Ser
Val Lys Ala Ser Glu Leu Ser Pro Leu Lys Lys Thr
Tyr Glu Glu Leu Ala Ser Leu Phe Ser Val Lys Phe
Ser Glu Leu;

SEQ ID NO: 55
Lys Lys Thr Ala Glu Glu Leu Ala Ser Leu Ala Ser
Val Lys Ala Ser Glu Leu Pro Leu Lys Lys Thr Tyr
Glu Glu Leu Ala Ser Leu Phe Ser Val Lys Phe Ser
Glu Leu;

SEQ ID NO: 56
Lys Lys Thr Ala Glu Glu Leu Ala Ser Leu Ala Ser
Val Lys Ala Ser Glu Leu Lys Leu Ser Pro Lys Lys
Thr Tyr Glu Glu Leu Ala Ser Leu Phe Ser Val Lys
Phe Ser Glu Leu;

SEQ ID NO: 57
Lys Lys Thr Ala Glu Glu Leu Ala Ser Leu Ala Ser
Val Lys Ala Ser Glu Leu Leu Ser Pro Lys Lys Thr
Tyr Glu Glu Leu Ala Ser Leu Phe Ser Val Lys Phe
Ser Glu Leu;

SEQ ID NO: 58
Lys Lys Thr Ala Glu Glu Leu Ala Ser Leu Ala Ser
Val Lys Ala Ser Glu Leu Ser Pro Lys Lys Thr Tyr
Glu Glu Leu Ala Ser Leu Phe Ser Val Lys Phe Ser
Glu Leu;

SEQ ID NO: 59
Lys Lys Thr Ala Glu Glu Leu Ala Ser Leu Ala Ser
Val Lys Ala Ser Glu Leu Leu Pro Ser Leu Lys Lys
Lys Thr Tyr Glu Glu Leu Ala Ser Leu Phe Ser Val
Lys Phe Ser Glu Leu;

SEQ ID NO: 60
Lys Lys Thr Ala Glu Glu Leu Ala Ser Leu Ala Ser
Val Lys Ala Ser Glu Leu Leu Pro Ser Leu Lys Lys
Thr Tyr Glu Glu Leu Ala Ser Leu Phe Ser Val Lys
Phe Ser Glu Leu;

SEQ ID NO: 61
Lys Lys Thr Ala Glu Glu Leu Ala Ser Leu Ala Ser
Val Lys Ala Ser Glu Leu Leu Pro Ser Lys Lys Thr
Tyr Glu Glu Leu Ala Ser Leu Phe Ser Val Lys Phe
Ser Glu Leu;

SEQ ID NO: 62
Lys Lys Thr Ala Glu Glu Leu Ala Ser Leu Ala Ser
Val Lys Ala Ser Glu Leu Leu Pro Lys Lys Thr Tyr
Glu Glu Leu Ala Ser Leu Phe Ser Val Lys Phe Ser
Glu Leu;

-continued

SEQ ID NO: 63
Lys Lys Thr Ala Glu Glu Leu Ala Ser Leu Ala Ser
Val Lys Ala Ser Glu Leu Pro Ser Leu Lys Lys Lys
Thr Tyr Glu Glu Leu Ala Ser Leu Phe Ser Val Lys
Phe Ser Glu Leu;

SEQ ID NO: 64
Lys Lys Thr Ala Glu Glu Leu Ala Ser Leu Ala Ser
Val Lys Ala Ser Glu Leu Pro Ser Leu Lys Lys Thr
Tyr Glu Glu Leu Ala Ser Leu Phe Ser Val Lys Phe
Ser Glu Leu;

SEQ ID NO: 65
Lys Lys Thr Ala Glu Glu Leu Ala Ser Leu Ala Ser
Val Lys Ala Ser Glu Leu Pro Ser Lys Lys Thr Tyr
Glu Glu Leu Ala Ser Leu Phe Ser Val Lys Phe Ser
Glu Leu;

SEQ ID NO: 66
Lys Lys Thr Ala Glu Glu Leu Ala Ser Leu Ala Ser
Val Lys Ala Ser Glu Leu Pro Lys Lys Thr Tyr Glu
Glu Leu Ala Ser Leu Phe Ser Val Lys Phe Ser Glu
Leu.

d. Variations in the B Group with A and C Intact as C-B-A with the Amino Acids in C and A in Reverse Orientation SEQ ID NO: 67
Lys Lys Thr Tyr Glu Glu Leu Ala Ser Leu Phe Ser
Val Lys Phe Ser Glu Leu Lys Leu Ser Pro Leu Lys
Lys Thr Ala Glu Glu Leu Ala Ser Leu Ala Ser Val
Lys Ala Ser Glu Leu;

SEQ ID NO: 68
Lys Lys Thr Tyr Glu Glu Leu Ala Ser Leu Phe Ser
Val Lys Phe Ser Glu Leu Leu Ser Pro Leu Lys Lys
Thr Ala Glu Glu Leu Ala Ser Leu Ala Ser Val Lys
Ala Ser Glu Leu;

SEQ ID NO: 69
Lys Lys Thr Tyr Glu Glu Leu Ala Ser Leu Phe Ser
Val Lys Phe Ser Glu Leu Ser Pro Leu Lys Lys Thr
Ala Glu Glu Leu Ala Ser Leu Ala Ser Val Lys Ala
Ser Glu Leu;

SEQ ID NO: 70
Lys Lys Thr Tyr Glu Glu Leu Ala Ser Leu Phe Ser
Val Lys Phe Ser Glu Leu Pro Leu Lys Lys Thr Ala
Glu Glu Leu Ala Ser Leu Ala Ser Val Lys Ala Ser
Glu Leu;

SEQ ID NO: 71
Lys Lys Thr Tyr Glu Glu Leu Ala Ser Leu Phe Ser
Val Lys Phe Ser Glu Leu Lys Leu Ser Pro Lys Lys
Thr Ala Glu Glu Leu Ala Ser Leu Ala Ser Val Lys
Ala Ser Glu Leu;

SEQ ID NO: 72
Lys Lys Thr Tyr Glu Glu Leu Ala Ser Leu Phe Ser
Val Lys Phe Ser Glu Leu Leu Ser Pro Lys Lys Thr
Ala Glu Glu Leu Ala Ser Leu Ala Ser Val Lys Ala
Ser Glu Leu;

SEQ ID NO: 73
Lys Lys Thr Tyr Glu Glu Leu Ala Ser Leu Phe Ser
Val Lys Phe Ser Glu Leu Ser Pro Lys Lys Thr Ala
Glu Glu Leu Ala Ser Leu Ala Ser Val Lys Ala Ser
Glu Leu;

SEQ ID NO: 74
Lys Lys Thr Tyr Glu Glu Leu Ala Ser Leu Phe Ser
Val Lys Phe Ser Glu Leu Leu Pro Ser Leu Lys Lys
Lys Thr Ala Glu Glu Leu Ala Ser Leu Ala Ser Val
Lys Ala Ser Glu Leu;

-continued

SEQ ID NO: 75
Lys Lys Thr Tyr Glu Glu Leu Ala Ser Leu Phe Ser Val Lys Phe Ser Glu Leu Leu Pro Ser Leu Lys Lys Thr Ala Glu Glu Leu Ala Ser Leu Ala Ser Val Lys Ala Ser Glu Leu;

SEQ ID NO: 76
Lys Lys Thr Tyr Glu Glu Leu Ala Ser Leu Phe Ser Val Lys Phe Ser Glu Leu Leu Pro Ser Lys Lys Thr Ala Glu Glu Leu Ala Ser Leu Ala Ser Val Lys Ala Ser Glu Leu;

SEQ ID NO: 77
Lys Lys Thr Tyr Glu Glu Leu Ala Ser Leu Phe Ser Val Lys Phe Ser Glu Leu Leu Pro Lys Lys Thr Ala Glu Glu Leu Ala Ser Leu Ala Ser Val Lys Ala Ser Glu Leu;

SEQ ID NO: 78
Lys Lys Thr Tyr Glu Glu Leu Ala Ser Leu Phe Ser Val Lys Phe Ser Glu Leu Pro Ser Leu Lys Lys Lys Thr Ala Glu Glu Leu Ala Ser Leu Ala Ser Val Lys Ala Ser Glu Leu;

SEQ ID NO: 79
Lys Lys Thr Tyr Glu Glu Leu Ala Ser Leu Phe Ser Val Lys Phe Ser Glu Leu Pro Ser Leu Lys Lys Thr Ala Glu Glu Leu Ala Ser Leu Ala Ser Val Lys Ala Ser Glu Leu;

SEQ ID NO: 80
Lys Lys Thr Tyr Glu Glu Leu Ala Ser Leu Phe Ser Val Lys Phe Ser Glu Leu Pro Ser Lys Lys Thr Ala Glu Glu Leu Ala Ser Leu Ala Ser Val Lys Ala Ser Glu Leu;

SEQ ID NO: 81
Lys Lys Thr Tyr Glu Glu Leu Ala Ser Leu Phe Ser Val Lys Phe Ser Glu Leu Pro Lys Lys Thr Ala Glu Glu Leu Ala Ser Leu Ala Ser Val Lys Ala Ser Glu Leu.

e. Variations in the B Group with A and C Intact as A-B-C with the Amino Acids in A in Reverse Orientation SEQ ID NO: 82
Lys Lys Thr Ala Glu Glu Leu Ala Ser Leu Ala Ser Val Lys Ala Ser Glu Leu Lys Leu Ser Pro Leu Leu Glu Ser Phe Lys Val Ser Phe Leu Ser Ala Leu Glu Glu Tyr Thr Lys Lys;

SEQ ID NO: 83
Lys Lys Thr Ala Glu Glu Leu Ala Ser Leu Ala Ser Val Lys Ala Ser Glu Leu Leu Ser Pro Leu;

SEQ ID NO: 84
Lys Lys Thr Ala Glu Glu Leu Ala Ser Leu Ala Ser Val Lys Ala Ser Glu Leu Ser Pro Leu Leu Glu Ser Phe Lys Val Ser Phe Leu Ser Ala Leu Glu Glu Tyr Thr Lys Lys;

SEQ ID NO: 85
Lys Lys Thr Ala Glu Glu Leu Ala Ser Leu Ala Ser Val Lys Ala Ser Glu Leu Pro Leu;

SEQ ID NO: 86
Lys Lys Thr Ala Glu Glu Leu Ala Ser Leu Ala Ser Val Lys Ala Ser Glu Leu Lys Leu Ser Pro Leu Glu Ser Phe Lys Val Ser Phe Leu Ser Ala Leu Glu Glu Tyr Thr Lys Lys;

SEQ ID NO: 87
Lys Lys Thr Ala Glu Glu Leu Ala Ser Leu Ala Ser Val Lys Ala Ser Glu Leu Leu Ser Pro Leu Glu Ser Phe Lys Val Ser Phe Leu Ser Ala Leu Glu Glu Tyr Thr Lys Lys;

-continued

SEQ ID NO: 88
Lys Lys Thr Ala Glu Glu Leu Ala Ser Leu Ala Ser Val Lys Ala Ser Glu Leu Ser Pro Leu Glu Ser Phe Lys Val Ser Phe Leu Ser Ala Leu Glu Glu Tyr Thr Lys Lys;

SEQ ID NO: 89
Lys Lys Thr Ala Glu Glu Leu Ala Ser Leu Ala Ser Val Lys Ala Ser Glu Leu Leu Pro Ser Leu Lys Leu Glu Ser Phe Lys Val Ser Phe Leu Ser Ala Leu Glu Glu Tyr Thr Lys Lys;

SEQ ID NO: 90
Lys Lys Thr Ala Glu Glu Leu Ala Ser Leu Ala Ser Val Lys Ala Ser Glu Leu Leu Pro Ser Leu Leu Glu Ser Phe Lys Val Ser Phe Leu Ser Ala Leu Glu Glu Tyr Thr Lys Lys;

SEQ ID NO: 91
Lys Lys Thr Ala Glu Glu Leu Ala Ser Leu Ala Ser Val Lys Ala Ser Glu Leu Leu Pro Ser Leu Glu Ser Phe Lys Val Ser Phe Leu Ser Ala Leu Glu Glu Tyr Thr Lys Lys;

SEQ ID NO: 92
Lys Lys Thr Ala Glu Glu Leu Ala Ser Leu Ala Ser Val Lys Ala Ser Glu Leu Leu Pro Leu Glu Ser Phe Lys Val Ser Phe Leu Ser Ala Leu Glu Glu Tyr Thr Lys Lys;

SEQ ID NO: 93
Lys Lys Thr Ala Glu Glu Leu Ala Ser Leu Ala Ser Val Lys Ala Ser Glu Leu Pro Ser Leu Lys Leu Glu Ser Phe Lys Val Ser Phe Leu Ser Ala Leu Glu Glu Tyr Thr Lys Lys;

SEQ ID NO: 94
Lys Lys Thr Ala Glu Glu Leu Ala Ser Leu Ala Ser Val Lys Ala Ser Glu Leu Pro Ser Leu Leu Glu Ser Phe Lys Val Ser Phe Leu Ser Ala Leu Glu Glu Tyr Thr Lys Lys;

SEQ ID NO: 95
Lys Lys Thr Ala Glu Glu Leu Ala Ser Leu Ala Ser Val Lys Ala Ser Glu Leu Pro Ser Leu Glu Ser Phe Lys Val Ser Phe Leu Ser Ala Leu Glu Glu Tyr Thr Lys Lys;

SEQ ID NO: 96
Lys Lys Thr Ala Glu Glu Leu Ala Ser Leu Ala Ser Val Lys Ala Ser Glu Leu Pro Leu Glu Ser Phe Lys Val Ser Phe Leu Ser Ala Leu Glu Glu Tyr Thr Lys Lys.

f. Variations in the B Group with A and C Intact as A-B-C with the Amino Acids in C in Reverse Orientation SEQ ID NO: 97
Leu Glu Ser Ala Lys Val Ser Ala Leu Ser Ala Leu Glu Glu Ala Thr Lys Lys Lys Leu Ser Pro Leu Lys Lys Thr Tyr Glu Glu Leu Ala Ser Leu Phe Ser Val Lys Phe Ser Glu Leu;

SEQ ID NO: 98
Leu Glu Ser Ala Lys Val Ser Ala Leu Ser Ala Leu Glu Glu Ala Thr Lys Lys Leu Ser Pro Leu Lys Lys Thr Tyr Glu Glu Leu Ala Ser Leu Phe Ser Val Lys Phe Ser Glu Leu;

SEQ ID NO: 99
Leu Glu Ser Ala Lys Val Ser Ala Leu Ser Ala Leu Glu Glu Ala Thr Lys Lys Ser Pro Leu Lys Lys Thr Tyr Glu Glu Leu Ala Ser Leu Phe Ser Val Lys Phe Ser Glu Leu;

-continued

SEQ ID NO: 100

Leu Glu Ser Ala Lys Val Ser Ala Leu Ser Ala Leu Glu Glu Ala Thr Lys Lys Pro Leu Lys Lys Thr Tyr Glu Glu Leu Ala Ser Leu Phe Ser Val Lys Phe Ser Glu Leu;

SEQ ID NO: 101

Leu Glu Ser Ala Lys Val Ser Ala Leu Ser Ala Leu Glu Glu Ala Thr Lys Lys Lys Leu Ser Pro Lys Lys Thr Tyr Glu Glu Leu Ala Ser Leu Phe Ser Val Lys Phe Ser Glu Leu;

SEQ ID NO: 102

Leu Glu Ser Ala Lys Val Ser Ala Leu Ser Ala Leu Glu Glu Ala Thr Lys Lys Leu Ser Pro Lys Lys Thr Tyr Glu Glu Leu Ala Ser Leu Phe Ser Val Lys Phe Ser Glu Leu;

SEQ ID NO: 103

Leu Glu Ser Ala Lys Val Ser Ala Leu Ser Ala Leu Glu Glu Ala Thr Lys Lys Ser Pro Lys Lys Thr Tyr Glu Glu Leu Ala Ser Leu Phe Ser Val Lys Phe Ser Glu Leu;

SEQ ID NO: 104

Leu Glu Ser Ala Lys Val Ser Ala Leu Ser Ala Leu Glu Glu Ala Thr Lys Lys Leu Pro Ser Leu Lys Lys Lys Thr Tyr Glu Glu Leu Ala Ser Leu Phe Ser Val Lys Phe Ser Glu Leu;

SEQ ID NO: 105

Leu Glu Ser Ala Lys Val Ser Ala Leu Ser Ala Leu Glu Glu Ala Thr Lys Lys Leu Pro Ser Leu Lys Lys Thr Tyr Glu Glu Leu Ala Ser Leu Phe Ser Val Lys Phe Ser Glu Leu;

SEQ ID NO: 106

Leu Glu Ser Ala Lys Val Ser Ala Leu Ser Ala Leu Glu Glu Ala Thr Lys Lys Leu Pro Ser Lys Lys Thr Tyr Glu Glu Leu Ala Ser Leu Phe Ser Val Lys Phe Ser Glu Leu;

SEQ ID NO: 107

Leu Glu Ser Ala Lys Val Ser Ala Leu Ser Ala Leu Glu Glu Ala Thr Lys Lys Leu Pro Lys Lys Thr Tyr Glu Glu Leu Ala Ser Leu Phe Ser Val Lys Phe Ser Glu Leu;

SEQ ID NO: 108

Leu Glu Ser Ala Lys Val Ser Ala Leu Ser Ala Leu Glu Glu Ala Thr Lys Lys Pro Ser Leu Lys Lys Lys Thr Tyr Glu Glu Leu Ala Ser Leu Phe Ser Val Lys Phe Ser Glu Leu;

SEQ ID NO: 109

Leu Glu Ser Ala Lys Val Ser Ala Leu Ser Ala Leu Glu Glu Ala Thr Lys Lys Pro Ser Leu Lys Lys Thr Tyr Glu Glu Leu Ala Ser Leu Phe Ser Val Lys Phe Ser Glu Leu;

SEQ ID NO: 110

Leu Glu Ser Ala Lys Val Ser Ala Leu Ser Ala Leu Glu Glu Ala Thr Lys Lys Pro Ser Lys Lys Thr Tyr Glu Glu Leu Ala Ser Leu Phe Ser Val Lys Phe Ser Glu Leu;

SEQ ID NO: 111

Leu Glu Ser Ala Lys Val Ser Ala Leu Ser Ala Leu Glu Glu Ala Thr Lys Lys Pro Lys Lys Thr Tyr Glu Glu Leu Ala Ser Leu Phe Ser Val Lys Phe Ser Glu Leu.

g. Variations in the B Group with A and C Intact as C-B-A with the Amino Acids in A in Reverse Orientation

SEQ ID NO: 112

Leu Glu Ser Phe Lys Val Ser Phe Leu Ser Ala Leu Glu Glu Tyr Thr Lys Lys Lys Leu Ser Pro Leu Lys Lys Thr Ala Glu Glu Leu Ala Ser Leu Ala Ser Val Lys Ala Ser Glu Leu;

SEQ ID NO: 113

Leu Glu Ser Phe Lys Val Ser Phe Leu Ser Ala Leu Glu Glu Tyr Thr Lys Lys Leu Ser Pro Leu Lys Lys Thr Ala Glu Glu Leu Ala Ser Leu Ala Ser Val Lys Ala Ser Glu Leu;

SEQ ID NO: 114

Leu Glu Ser Phe Lys Val Ser Phe Leu Ser Ala Leu Glu Glu Tyr Thr Lys Lys Ser Pro Leu Lys Lys Thr Ala Glu Glu Leu Ala Ser Leu Ala Ser Val Lys Ala Ser Glu Leu;

SEQ ID NO: 115

Leu Glu Ser Phe Lys Val Ser Phe Leu Ser Ala Leu Glu Glu Tyr Thr Lys Lys Pro Leu Lys Lys Thr Ala Glu Glu Leu Ala Ser Leu Ala Ser Val Lys Ala Ser Glu Leu;

SEQ ID NO: 116

Leu Glu Ser Phe Lys Val Ser Phe Leu Ser Ala Leu Glu Glu Tyr Thr Lys Lys Lys Leu Ser Pro Lys Lys Thr Ala Glu Glu Leu Ala Ser Leu Ala Ser Val Lys Ala Ser Glu Leu;

SEQ ID NO: 117

Leu Glu Ser Phe Lys Val Ser Phe Leu Ser Ala Leu Glu Glu Tyr Thr Lys Lys Leu Ser Pro Lys Lys Thr Ala Glu Glu Leu Ala Ser Leu Ala Ser Val Lys Ala Ser Glu Leu;

SEQ ID NO: 118

Leu Glu Ser Phe Lys Val Ser Phe Leu Ser Ala Leu Glu Glu Tyr Thr Lys Lys Ser Pro Lys Lys Thr Ala Glu Glu Leu Ala Ser Leu Ala Ser Val Lys Ala Ser Glu Leu;

SEQ ID NO: 119

Leu Glu Ser Phe Lys Val Ser Phe Leu Ser Ala Leu Glu Glu Tyr Thr Lys Lys Leu Pro Ser Leu Lys Lys Lys Thr Ala Glu Glu Leu Ala Ser Leu Ala Ser Val Lys Ala Ser Glu Leu;

SEQ ID NO: 120

Leu Glu Ser Phe Lys Val Ser Phe Leu Ser Ala Leu Glu Glu Tyr Thr Lys Lys Leu Pro Ser Leu Lys Lys Thr Ala Glu Glu Leu Ala Ser Leu Ala Ser Val Lys Ala Ser Glu Leu;

SEQ ID NO: 121

Leu Glu Ser Phe Lys Val Ser Phe Leu Ser Ala Leu Glu Glu Tyr Thr Lys Lys Leu Pro Ser Lys Lys Thr Ala Glu Glu Leu Ala Ser Leu Ala Ser Val Lys Ala Ser Glu Leu;

SEQ ID NO: 122

Leu Glu Ser Phe Lys Val Ser Phe Leu Ser Ala Leu Glu Glu Tyr Thr Lys Lys Leu Pro Lys Lys Thr Ala Glu Glu Leu Ala Ser Leu Ala Ser Val Lys Ala Ser Glu Leu;

SEQ ID NO: 123

Leu Glu Ser Phe Lys Val Ser Phe Leu Ser Ala Leu Glu Glu Tyr Thr Lys Lys Pro Ser Leu Lys Lys Lys Thr Ala Glu Glu Leu Ala Ser Leu Ala Ser Val Lys Ala Ser Glu Leu;

SEQ ID NO: 124

Leu Glu Ser Phe Lys Val Ser Phe Leu Ser Ala Leu Glu Glu Tyr Thr Lys Lys Pro Ser Leu Lys Lys Thr Ala Glu Glu Leu Ala Ser Leu Ala Ser Val Lys Ala Ser Glu Leu;

-continued

SEQ ID NO: 125
Leu Glu Ser Phe Lys Val Ser Phe Leu Ser Ala Leu Glu Glu Tyr Thr Lys Lys Pro Ser Lys Lys Thr Ala Glu Glu Leu Ala Ser Leu Ala Ser Val Lys Ala Ser Glu Leu;

SEQ ID NO: 126
Leu Glu Ser Phe Lys Val Ser Phe Leu Ser Ala Leu Glu Glu Tyr Thr Lys Lys Pro Lys Lys Thr Ala Glu Glu Leu Ala Ser Leu Ala Ser Val Lys Ala Ser Glu Leu.

h. Variations in the B Group with A and C Intact as C-B-A with the Amino Acids in C in Reverse Orientation SEQ ID NO: 127
Lys Lys Thr Tyr Glu Glu Leu Ala Ser Leu Phe Ser Val Lys Phe Ser Glu Leu Lys Leu Ser Pro Leu Leu Glu Ser Ala Lys Val Ser Ala Leu Ser Ala Leu Glu Glu Ala Thr Lys Lys;

SEQ ID NO: 128
Lys Lys Thr Tyr Glu Glu Leu Ala Ser Leu Phe Ser Val Lys Phe Ser Glu Leu Leu Ser Pro Leu;

SEQ ID NO: 129
Lys Lys Thr Tyr Glu Glu Leu Ala Ser Leu Phe Ser Val Lys Phe Ser Glu Leu Ser Pro Leu Leu Glu Ser Ala Lys Val Ser Ala Leu Ser Ala Leu Glu Glu Ala Thr Lys Lys;

SEQ ID NO: 130
Lys Lys Thr Tyr Glu Glu Leu Ala Ser Leu Phe Ser Val Lys Phe Ser Glu Leu Pro Leu Leu Glu Ser Ala Lys Val Ser Ala Leu Ser Ala Leu Glu Glu Ala Thr Lys Lys;

SEQ ID NO: 131
Lys Lys Thr Tyr Glu Glu Leu Ala Ser Leu Phe Ser Val Lys Phe Ser Glu Leu Lys Leu Ser Pro Leu Glu Ser Ala Lys Val Ser Ala Leu Ser Ala Leu Glu Glu Ala Thr Lys Lys;

SEQ ID NO: 132
Lys Lys Thr Tyr Glu Glu Leu Ala Ser Leu Phe Ser Val Lys Phe Ser Glu Leu Leu Ser Pro Leu Glu Ser Ala Lys Val Ser Ala Leu Ser Ala Leu Glu Glu Ala Thr Lys Lys;

SEQ ID NO: 133
Lys Lys Thr Tyr Glu Glu Leu Ala Ser Leu Phe Ser Val Lys Phe Ser Glu Leu Ser Pro Leu Glu Ser Ala Lys Val Ser Ala Leu Ser Ala Leu Glu Glu Ala Thr Lys Lys;

SEQ ID NO: 134
Lys Lys Thr Tyr Glu Glu Leu Ala Ser Leu Phe Ser Val Lys Phe Ser Glu Leu Leu Pro Ser Leu Lys Leu Glu Ser Ala Lys Val Ser Ala Leu Ser Ala Leu Glu Glu Ala Thr Lys Lys;

SEQ ID NO: 135
Lys Lys Thr Tyr Glu Glu Leu Ala Ser Leu Phe Ser Val Lys Phe Ser Glu Leu Leu Pro Ser Leu Leu Glu Ser Ala Lys Val Ser Ala Leu Ser Ala Leu Glu Glu Ala Thr Lys Lys;

SEQ ID NO: 136
Lys Lys Thr Tyr Glu Glu Leu Ala Ser Leu Phe Ser Val Lys Phe Ser Glu Leu Leu Pro Ser Leu Glu Ser Ala Lys Val Ser Ala Leu Ser Ala Leu Glu Glu Ala Thr Lys Lys;

SEQ ID NO: 137
Lys Lys Thr Tyr Glu Glu Leu Ala Ser Leu Phe Ser Val Lys Phe Ser Glu Leu Leu Pro Leu Glu Ser Ala Lys Val Ser Ala Leu Ser Ala Leu Glu Glu Ala Thr Lys Lys;

-continued

SEQ ID NO: 138
Lys Lys Thr Tyr Glu Glu Leu Ala Ser Leu Phe Ser Val Lys Phe Ser Glu Leu Pro Ser Leu Lys Leu Glu Ser Ala Lys Val Ser Ala Leu Ser Ala Leu Glu Glu Ala Thr Lys Lys;

SEQ ID NO: 139
Lys Lys Thr Tyr Glu Glu Leu Ala Ser Leu Phe Ser Val Lys Phe Ser Glu Leu Pro Ser Leu Leu Glu Ser Ala Lys Val Ser Ala Leu Ser Ala Leu Glu Glu Ala Thr Lys Lys;

SEQ ID NO: 140
Lys Lys Thr Tyr Glu Glu Leu Ala Ser Leu Phe Ser Val Lys Phe Ser Glu Leu Pro Ser Leu Glu Ser Ala Lys Val Ser Ala Leu Ser Ala Leu Glu Glu Ala Thr Lys Lys;

SEQ ID NO: 141
Lys Lys Thr Tyr Glu Glu Leu Ala Ser Leu Phe Ser Val Lys Phe Ser Glu Leu Pro Leu Glu Ser Ala Lys Val Ser Ala Leu Ser Ala Leu Glu Glu Ala Thr Lys Lys.

B. G-(A-B-C)$_n$-H Peptides

In a further embodiment, peptides of the present invention are described by the following subgeneric formula II, in which one or more additional elements, indicated as variables G and H, are added to formula I to make subgeneric formula II $$G\text{-}(A\text{-}B\text{-}C)_n\text{-}H. \qquad \text{II}$$

(A-B-C)$_n$ are as described in formula I above. G is absent or present and is a peptide as defined hereinbelow. H is absent or present and is a peptide as defined hereinbelow. Thus, within G-(A-B-C)$_n$-H, both G and H may be present or only one of G and H may be present. The peptide segments may also be arranged in reverse orientations, such as H-(A-B-C)$_n$-G, H-(C-B-A)$_n$-G, or G-(C-B-A)$_n$-H).

One of ordinary skill in the art will understand that A and/or C can contain one or more substitutions as described herein. A person of ordinary skill in the art will also understand that A, B, C, G, and/or H may contain one or more D-amino acids. In some embodiments, one or more of the amino acids of the peptides of the present invention are D amino acids. In one embodiment, the N-terminal amino acid, the C-terminal amino acid, or both are D amino acids. The presence of these D amino acids can help protect against peptide degradation. In another embodiment, all the amino acids of the peptides of the present invention are D amino acids. This embodiment is useful for protection against degradation following oral administration of a pharmaceutical composition comprising the peptides of the present invention. Any number of amino acids (e.g., between one and all of the amino acids) in the peptides of the invention can be D amino acids.

Peptides of the invention may contain an amino-terminal acetyl group and/or a carboxy-terminal amide group.

i. Segment G

G is absent or present and is a peptide as defined in herein. In one embodiment, G is SEQ ID NO: 6 Ser Pro Leu; Pro Leu; Leu; Ser Pro; Ser; Pro; or a substitution thereof. These amino acids can also appear in reverse orientation: SEQ ID NO: 11 Leu Pro Ser; Pro Ser; Leu Pro; or a conservative substitution thereof. It is to be understood that one or more of the amino acids in the G peptide may be D amino acids.

ii. Segment H

H is absent or present and is a peptide as defined in the present specification. In one embodiment, H is SEQ ID NO: 16 Leu Asn Thr Gln; SEQ ID NO: 17 Asn Thr Gln; Thr Gln;

Gln; SEQ ID NO: 18 Leu Asn Thr; Leu Asn; Leu; or a substitution thereof. These amino acids can also appear in reverse orientation: SEQ ID NO: 19 Gln Thr Asn Leu; SEQ ID NO: 20 Thr Asn Leu; Asn Leu; SEQ ID NO: 21 Gln Thr Asn; Gln Thr; or a substitution thereof. It is to be understood that one or more of the amino acids in the H peptide may be D amino acids.

iii. Specific Examples of G-(A-B-C)$_n$-H Peptides

Below is a non-limiting subset of examples of peptides represented by the basic formula G-(A-B-C)$_n$-H, in which A is Helix 8' and C is Helix 8. One of ordinary skill in the art will understand that the G-(A-B-C)$_n$H peptides of the invention include any of the B, G, and H sequences set forth herein. One of ordinary skill in the art will understand that A and/or C can contain one or more substitutions as described herein. A person of ordinary skill in the art will also understand that A, B, C, G, and/or H may contain one or more D-amino acids. Peptides of the invention may contain an amino-terminal acetyl group and/or a carboxy-terminal amide group.

a. G-(A-B-C)$_n$-H with Successive Deletions of G in Both Orientations from N— and C-Termini (A, B, C, and H are Intact)

SEQ ID NO: 142
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr Gln;

SEQ ID NO: 143
Pro Leu Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr Gln;

SEQ ID NO: 144
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn Thr Gln;

SEQ ID NO: 145
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys Leu Asn Thr Gln;

SEQ ID NO: 146
Ser Pro Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr Gln;

SEQ ID NO: 147
Ser Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn Thr Gln;

SEQ ID NO: 148
Pro Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn Thr Gln;

SEQ ID NO: 149
Leu Pro Ser Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr Gln;

SEQ ID NO: 150
Pro Ser Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr Gln;

-continued

SEQ ID NO: 151
Leu Pro Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr Gln.

b. G-(A-B-C)$_n$-H with Successive Deletions of H in Both Orientations from N— and C-Termini (G, A, B, and C are Intact)

SEQ ID NO: 152
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Asn Thr Gln;

SEQ ID NO: 153
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Thr Gln;

SEQ ID NO: 154
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Gln;

SEQ ID NO: 155
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys;

SEQ ID NO: 156
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr;

SEQ ID NO: 157
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn;

SEQ ID NO: 158
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu;

SEQ ID NO: 159
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Gln Thr Asn Leu;

SEQ ID NO: 160
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Thr Asn Leu;

SEQ ID NO: 161
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Asn Leu;

SEQ ID NO: 162
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Gln Thr Asn;

-continued

SEQ ID NO: 163
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Gln Thr.

c. G-(A-B-C)$_n$-H with Successive Deletions of G and H (A, B, and C are Intact)

SEQ ID NO: 164
Pro Leu Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr;

SEQ ID NO: 165
Pro Leu Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn;

SEQ ID NO: 166
Pro Leu Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu;

SEQ ID NO: 167
Pro Leu Leu Glu Ser Ala Lys Val Ser Ala Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys;

SEQ ID NO: 168
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn Thr;

SEQ ID NO: 169
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn;

SEQ ID NO: 170
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn

SEQ ID NO: 171
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu;

SEQ ID NO: 172
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys;

SEQ ID NO: 173
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys Leu Asn Thr;

SEQ ID NO: 174
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys Leu Asn;

-continued

SEQ ID NO: 175
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys Leu;

d. G-(A-B-C)$_n$-H with Successive Deletions in the B Group with G, A, C, and H Intact as in G-A-B-C-H SEQ ID NO: 176
Ser Pro Leu Leu Glu Ser Ala Lys Val Ser Ala Leu
Ser Ala Leu Glu Glu Ala Thr Lys Lys Leu Ser Pro
Leu Leu Leu Glu Ser Phe Lys Val Ser Phe Leu Ser
Ala Leu Glu Glu Tyr Thr Lys Lys Leu Asn Thr Gln;

SEQ ID NO: 177
Ser Pro Leu Leu Glu Ser Ala Lys Val Ser Ala Leu
Ser Ala Leu Glu Glu Ala Thr Lys Lys Ser Pro Leu
Leu Leu Glu Ser Phe Lys Val Ser Phe Leu Ser Ala
Leu Glu Glu Tyr Thr Lys Lys Leu Asn Thr Gln;

SEQ ID NO: 178
Ser Pro Leu Leu Glu Ser Ala Lys Val Ser Ala Leu
Ser Ala Leu Glu Glu Ala Thr Lys Lys Pro Leu Leu
Leu Glu Ser Phe Lys Val Ser Phe Leu Ser Ala Leu
Glu Glu Tyr Thr Lys Lys;

SEQ ID NO: 179
Ser Pro Leu Leu Glu Ser Ala Lys Val Ser Ala Leu
Ser Ala Leu Glu Glu Ala Thr Lys Lys Lys Leu Ser
ProLeu Leu Glu Ser Phe Lys Val Ser Phe Leu Ser Ala
Leu Glu Glu Tyr Thr Lys Lys Leu Asn Thr Gln;

SEQ ID NO: 180
Ser Pro Leu Leu Glu Ser Ala Lys Val Ser Ala Leu
Ser Ala Leu Glu Glu Ala Thr Lys Lys Leu Ser Pro
Leu Leu Glu Ser Phe Lys Val Ser Phe Leu Ser Ala
Leu Glu Glu Tyr Thr Lys Lys Leu Asn Thr Gln;

SEQ ID NO: 181
Ser Pro Leu Leu Glu Ser Ala Lys Val Ser Ala Leu
Ser Ala Leu Glu Glu Ala Thr Lys Lys Ser Pro Leu
Leu Glu Ser Phe Lys Val Ser Phe Leu Ser Ala Leu
Glu Glu Tyr Thr Lys Lys;

SEQ ID NO: 182
Ser Pro Leu Leu Glu Ser Ala Lys Val Ser Ala Leu
Ser Ala Leu Glu Glu Ala Thr Lys Lys Leu Pro Ser
Leu Lys Leu Leu Glu Ser Phe Lys Val Ser Phe Leu
Ser Ala Leu Glu Glu Tyr Thr Lys Lys Leu Asn Thr
Gln;

SEQ ID NO: 183
Ser Pro Leu Leu Glu Ser Ala Lys Val Ser Ala Leu
Ser Ala Leu Glu Glu Ala Thr Lys Lys Leu Pro Ser
Leu Leu Leu Glu Ser Phe Lys Val Ser Phe Leu Ser
Ala Leu Glu Glu Tyr Thr Lys Lys Leu Asn Thr Gln;

SEQ ID NO: 184
Ser Pro Leu Leu Glu Ser Ala Lys Val Ser Ala Leu
Ser Ala Leu Glu Glu Ala Thr Lys Lys Leu Pro Ser
Leu Leu Glu Ser Phe Lys Val Ser Phe Leu Ser Ala
Leu Glu Glu Tyr Thr Lys Lys Leu Asn Thr Gln;

SEQ ID NO: 185
Ser Pro Leu Leu Glu Ser Ala Lys Val Ser Ala Leu
Ser Ala Leu Glu Glu Ala Thr Lys Lys Leu Pro Leu
Leu Glu Ser Phe Lys Val Ser Phe Leu Ser Ala Leu
Glu Glu Tyr Thr Lys Lys;

SEQ ID NO: 186
Ser Pro Leu Leu Glu Ser Ala Lys Val Ser Ala Leu
Ser Ala Leu Glu Glu Ala Thr Lys Lys Pro Ser Leu
Lys Leu Leu Glu Ser Phe Lys Val Ser Phe Leu Ser
Ala Leu Glu Glu Tyr Thr Lys Lys Leu Asn Thr Gln;

-continued

SEQ ID NO: 187
Ser Pro Leu Leu Glu Ser Ala Lys Val Ser Ala Leu
Ser Ala Leu Glu Glu Ala Thr Lys Lys Pro Ser Leu
Leu Leu Glu Ser Phe Lys Val Ser Phe Leu Ser Ala
Leu Glu Glu Tyr Thr Lys Lys Leu Asn Thr Gln;

SEQ ID NO: 188
Ser Pro Leu Leu Glu Ser Ala Lys Val Ser Ala Leu
Ser Ala Leu Glu Glu Ala Thr Lys Lys Pro Ser Leu
Leu Glu Ser Phe Lys Val Ser Phe Leu Ser Ala Leu
Glu Glu Tyr Thr Lys Lys Leu Asn Thr Gln;

SEQ ID NO: 189
Ser Pro Leu Leu Glu Ser Ala Lys Val Ser Ala Leu
Ser Ala Leu Glu Glu Ala Thr Lys Lys Pro Leu Leu
Glu Ser Phe Lys Val Ser Phe Leu Ser Ala Leu Glu
Glu Tyr Thr Lys Lys Leu Asn Thr Gln.

e. G-(A-B-C)$_n$-H with Successive N— and/or C-Terminal Deletions in the B Group with Successive Deletions of G SEQ ID NO: 190
Pro Leu Leu Glu Ser Ala Lys Val Ser Ala Leu Ser
Ala Leu Glu Glu Ala Thr Lys Lys Lys Leu Ser Pro
Leu Leu Glu Ser Phe Lys Val Ser Phe Leu Ser Ala
Leu Glu Glu Tyr Thr Lys Lys Leu Asn Thr Gln;

SEQ ID NO: 191
Leu Leu Glu Ser Ala Lys Val Ser Ala Leu Ser Ala
Leu Glu Glu Ala Thr Lys Lys Lys Leu Ser Pro Leu
Leu Glu Ser Phe Lys Val Ser Phe Leu Ser Ala Leu
Glu Glu Tyr Thr Lys Lys Leu Asn Thr Gln;

SEQ ID NO: 192
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys Leu Asn Thr Gln;

SEQ ID NO: 193
Pro Leu Leu Glu Ser Ala Lys Val Ser Ala Leu Ser
Ala Leu Glu Glu Ala Thr Lys Lys Leu Ser Pro Leu
Leu Leu Glu Ser Phe Lys Val Ser Phe Leu Ser Ala
Leu Glu Glu Tyr Thr Lys Lys Leu Asn Thr Gln;

SEQ ID NO: 194
Leu Leu Glu Ser Ala Lys Val Ser Ala Leu Ser Ala
Leu Glu Glu Ala Thr Lys Lys Leu Ser Pro Leu Leu
Leu Glu Ser Phe Lys Val Ser Phe Leu Ser Ala Leu
Glu Glu Tyr Thr Lys Lys Leu Asn Thr Gln;

SEQ ID NO: 195
Leu Glu Ser Ala Lys Val Ser Ala Leu Ser Ala Leu
Glu Glu Ala Thr Lys Lys Leu Ser Pro Leu Leu Leu
Glu Ser Phe Lys Val Ser Phe Leu Ser Ala Leu Glu
Glu Tyr Thr Lys Lys Leu Asn Thr Gln;

SEQ ID NO: 196
Pro Leu Leu Glu Ser Ala Lys Val Ser Ala Leu Ser
Ala Leu Glu Glu Ala Thr Lys Lys Ser Pro Leu Leu
Leu Glu Ser Phe Lys Val Ser Phe Leu Ser Ala Leu
Glu Glu Tyr Thr Lys Lys Leu Asn Thr Gln;

SEQ ID NO: 197
Leu Leu Glu Ser Ala Lys Val Ser Ala Leu Ser Ala
Leu Glu Glu Ala Thr Lys Lys Ser Pro Leu Leu Leu
Glu Ser Phe Lys Val Ser Phe Leu Ser Ala Leu Glu
Glu Tyr Thr Lys Lys Leu Asn Thr Gln;

SEQ ID NO: 198
Leu Glu Ser Ala Lys Val Ser Ala Leu Ser Ala Leu
Glu Glu Ala Thr Lys Lys Ser Pro Leu Leu Leu Glu
Ser Phe Lys Val Ser Phe Leu Ser Ala Leu Glu Glu
Tyr Thr Lys Lys Leu Asn Thr Gln;

-continued

SEQ ID NO: 199
Pro Leu Leu Glu Ser Ala Lys Val Ser Ala Leu Ser
Ala Leu Glu Glu Ala Thr Lys Lys Pro Leu Leu Leu
Glu Ser Phe Lys Val Ser Phe Leu Ser Ala Leu Glu
Glu Tyr Thr Lys Lys Leu Asn Thr Gln;

SEQ ID NO: 200
Leu Leu Glu Ser Ala Lys Val Ser Ala Leu Ser Ala
Leu Glu Glu Ala Thr Lys Lys Pro Leu Leu Leu Glu
Ser Phe Lys Val Ser Phe Leu Ser Ala Leu Glu Glu
Tyr Thr Lys Lys Leu Asn Thr Gln;

SEQ ID NO: 201
Leu Glu Ser Ala Lys Val Ser Ala Leu Ser Ala Leu
Glu Glu Ala Thr Lys Lys Pro Leu Leu Leu Glu Ser
Phe Lys Val Ser Phe Leu Ser Ala Leu Glu Glu Tyr
Thr Lys Lys Leu Asn Thr Gln;

SEQ ID NO: 202
Pro Leu Leu Glu Ser Ala Lys Val Ser Ala Leu Ser
Ala Leu Glu Glu Ala Thr Lys Lys Lys Leu Ser ProLeu
Leu Glu Ser Phe Lys Val Ser Phe Leu Ser Ala Leu
Glu Glu Tyr Thr Lys Lys Leu Asn Thr Gln;

SEQ ID NO: 203
Leu Leu Glu Ser Ala Lys Val Ser Ala Leu Ser Ala
Leu Glu Glu Ala Thr Lys Lys Lys Leu Ser ProLeu Leu
Glu Ser Phe Lys Val Ser Phe Leu Ser Ala Leu Glu
Glu Tyr Thr Lys Lys Leu Asn Thr Gln;

SEQ ID NO: 204
Leu Glu Ser Ala Lys Val Ser Ala Leu Ser Ala Leu
Glu Glu Ala Thr Lys Lys Lys Leu Ser ProLeu Leu Glu
Ser Phe Lys Val Ser Phe Leu Ser Ala Leu Glu Glu
Tyr Thr Lys Lys Leu Asn Thr Gln;

SEQ ID NO: 205
Pro Leu Leu Glu Ser Ala Lys Val Ser Ala Leu Ser
Ala Leu Glu Glu Ala Thr Lys Lys Leu Ser Pro Leu
Leu Glu Ser Phe Lys Val Ser Phe Leu Ser Ala Leu
Glu Glu Tyr Thr Lys Lys Leu Asn Thr Gln;

SEQ ID NO: 206
Leu Leu Glu Ser Ala Lys Val Ser Ala Leu Ser Ala
Leu Glu Glu Ala Thr Lys Lys Leu Ser Pro Leu Leu
Glu Ser Phe Lys Val Ser Phe Leu Ser Ala Leu Glu
Glu Tyr Thr Lys Lys Leu Asn Thr Gln;

SEQ ID NO: 207
Leu Glu Ser Ala Lys Val Ser Ala Leu Ser Ala Leu
Glu Glu Ala Thr Lys Lys Leu Ser Pro Leu Leu Glu
Ser Phe Lys Val Ser Phe Leu Ser Ala Leu Glu Glu
Tyr Thr Lys Lys Leu Asn Thr Gln;

SEQ ID NO: 208
Pro Leu Leu Glu Ser Ala Lys Val Ser Ala Leu Ser
Ala Leu Glu Glu Ala Thr Lys Lys Ser Pro Leu Leu
Glu Ser Phe Lys Val Ser Phe Leu Ser Ala Leu Glu
Glu Tyr Thr Lys Lys Leu Asn Thr Gln;

SEQ ID NO: 209
Leu Leu Glu Ser Ala Lys Val Ser Ala Leu Ser Ala
Leu Glu Glu Ala Thr Lys Lys Ser Pro Leu Leu Glu
Ser Phe Lys Val Ser Phe Leu Ser Ala Leu Glu Glu
Tyr Thr Lys Lys Leu Asn Thr Gln;

SEQ ID NO: 210
Leu Glu Ser Ala Lys Val Ser Ala Leu Ser Ala Leu
Glu Glu Ala Thr Lys Lys Ser Pro Leu Leu Glu Ser
Phe Lys Val Ser Phe Leu Ser Ala Leu Glu Glu Tyr
Thr Lys Lys Leu Asn Thr Gln;

SEQ ID NO: 211
Pro Leu Leu Glu Ser Ala Lys Val Ser Ala Leu Ser
Ala Leu Glu Glu Ala Thr Lys Lys Leu Pro Ser Leu
Lys Leu Leu Glu Ser Phe Lys Val Ser Phe Leu Ser
Ala Leu Glu Glu Tyr Thr Lys Lys Leu Asn Thr Gln;

-continued

SEQ ID NO: 212
Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn Thr Gln;

SEQ ID NO: 213
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn Thr Gln;

SEQ ID NO: 214
Pro Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 215
Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 216
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 217
Pro Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr Gln;

SEQ ID NO: 218
Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr Gln;

SEQ ID NO: 219
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr Gln;

SEQ ID NO: 220
Pro Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr Gln;

SEQ ID NO: 221
Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr Gln;

SEQ ID NO: 222
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr Gln;

SEQ ID NO: 223
Pro Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr Gln;

SEQ ID NO: 224
Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr Gln;

-continued

SEQ ID NO: 225
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr Gln;

SEQ ID NO: 226
Pro Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 227
Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 228
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr Gln;

SEQ ID NO: 229
Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr Gln;

SEQ ID NO: 230
Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr Gln;

SEQ ID NO: 231
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr Gln;

SEQ ID NO: 232
Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr Gln;

SEQ ID NO: 233
Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr Gln;

SEQ ID NO: 234
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr Gln.

f. G-(A-B-C)$_n$-H with Successive N— and/or C-Terminal Deletions in the B Group with Successive Deletions of H SEQ ID NO: 235
Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr;

SEQ ID NO: 236
Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn;

-continued

SEQ ID NO: 237
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu;

SEQ ID NO: 238
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys;

SEQ ID NO: 239
Ser Pro Leu Leu Glu Ser Ala Lys Val Ser Ala Leu
Ser Ala Leu Glu Glu Ala Thr Lys Lys Leu Ser Pro
Leu Leu Leu Glu Ser Phe Lys Val Ser Phe Leu Ser
Ala Leu Glu Glu Tyr Thr Lys Lys Leu Asn Thr;

SEQ ID NO: 240
Ser Pro Leu Leu Glu Ser Ala Lys Val Ser Ala Leu
Ser Ala Leu Glu Glu Ala Thr Lys Lys Leu Ser Pro
Leu Leu Leu Glu Ser Phe Lys Val Ser Phe Leu Ser
Ala Leu Glu Glu Tyr Thr Lys Lys Leu Asn;

SEQ ID NO: 241
Ser Pro Leu Leu Glu Ser Ala Lys Val Ser Ala Leu
Ser Ala Leu Glu Glu Ala Thr Lys Lys Leu Ser Pro
Leu Leu Leu Glu Ser Phe Lys Val Ser Phe Leu Ser
Ala Leu Glu Glu Tyr Thr Lys Lys Leu;

SEQ ID NO: 242
Ser Pro Leu Leu Glu Ser Ala Lys Val Ser Ala Leu
Ser Ala Leu Glu Glu Ala Thr Lys Lys Leu Ser Pro
Leu Leu Leu Glu Ser Phe Lys Val Ser Phe Leu Ser
Ala Leu Glu Glu Tyr Thr Lys Lys;

SEQ ID NO: 243
Ser Pro Leu Leu Glu Ser Ala Lys Val Ser Ala Leu
Ser Ala Leu Glu Glu Ala Thr Lys Lys Ser Pro Leu
Leu Leu Glu Ser Phe Lys Val Ser Phe Leu Ser Ala
Leu Glu Glu Tyr Thr Lys Lys Leu Asn Thr;

SEQ ID NO: 244
Ser Pro Leu Leu Glu Ser Ala Lys Val Ser Ala Leu
Ser Ala Leu Glu Glu Ala Thr Lys Lys Ser Pro Leu
Leu Leu Glu Ser Phe Lys Val Ser Phe Leu Ser Ala
Leu Glu Glu Tyr Thr Lys Lys Leu Asn;

SEQ ID NO: 245
Ser Pro Leu Leu Glu Ser Ala Lys Val Ser Ala Leu
Ser Ala Leu Glu Glu Ala Thr Lys Lys Ser Pro Leu
Leu Leu Glu Ser Phe Lys Val Ser Phe Leu Ser Ala
Leu Glu Glu Tyr Thr Lys Lys Leu;

SEQ ID NO: 246
Ser Pro Leu Leu Glu Ser Ala Lys Val Ser Ala Leu
Ser Ala Leu Glu Glu Ala Thr Lys Lys Ser Pro Leu
Leu Leu Glu Ser Phe Lys Val Ser Phe Leu Ser Ala
Leu Glu Glu Tyr Thr Lys Lys;

SEQ ID NO: 247
Ser Pro Leu Leu Glu Ser Ala Lys Val Ser Ala Leu
Ser Ala Leu Glu Glu Ala Thr Lys Lys Pro Leu Leu
Leu Glu Ser Phe Lys Val Ser Phe Leu Ser Ala Leu
Glu Glu Tyr Thr Lys Lys Leu Asn Thr;

SEQ ID NO: 248
Ser Pro Leu Leu Glu Ser Ala Lys Val Ser Ala Leu
Ser Ala Leu Glu Glu Ala Thr Lys Lys Pro Leu Leu
Leu Glu Ser Phe Lys Val Ser Phe Leu Ser Ala Leu
Glu Glu Tyr Thr Lys Lys Leu Asn;

SEQ ID NO: 249
Ser Pro Leu Leu Glu Ser Ala Lys Val Ser Ala Leu
Ser Ala Leu Glu Glu Ala Thr Lys Lys Pro Leu Leu
Leu Glu Ser Phe Lys Val Ser Phe Leu Ser Ala Leu
Glu Glu Tyr Thr Lys Lys Leu;

-continued

SEQ ID NO: 250
Ser Pro Leu Leu Glu Ser Ala Lys Val Ser Ala Leu
Ser Ala Leu Glu Glu Ala Thr Lys Lys Pro Leu Leu
Leu Glu Ser Phe Lys Val Ser Phe Leu Ser Ala Leu
Glu Glu Tyr Thr Lys Lys;

SEQ ID NO: 251
Ser Pro Leu Leu Glu Ser Ala Lys Val Ser Ala Leu
Ser Ala Leu Glu Glu Ala Thr Lys Lys Lys Leu Ser
ProLeu Leu Glu Ser Phe Lys Val Ser Phe Leu Ser Ala
Leu Glu Glu Tyr Thr Lys Lys Leu Asn Thr;

SEQ ID NO: 252
Ser Pro Leu Leu Glu Ser Ala Lys Val Ser Ala Leu
Ser Ala Leu Glu Glu Ala Thr Lys Lys Lys Leu Ser
ProLeu Leu Glu Ser Phe Lys Val Ser Phe Leu Ser Ala
Leu Glu Glu Tyr Thr Lys Lys Leu Asn;

SEQ ID NO: 253
Ser Pro Leu Leu Glu Ser Ala Lys Val Ser Ala Leu
Ser Ala Leu Glu Glu Ala Thr Lys Lys Lys Leu Ser
ProLeu Leu Glu Ser Phe Lys Val Ser Phe Leu Ser Ala
Leu Glu Glu Tyr Thr Lys Lys Leu;

SEQ ID NO: 254
Ser Pro Leu Leu Glu Ser Ala Lys Val Ser Ala Leu
Ser Ala Leu Glu Glu Ala Thr Lys Lys Lys Leu Ser
ProLeu Leu Glu Ser Phe Lys Val Ser Phe Leu Ser Ala
Leu Glu Glu Tyr Thr Lys Lys;

SEQ ID NO: 255
Ser Pro Leu Leu Glu Ser Ala Lys Val Ser Ala Leu
Ser Ala Leu Glu Glu Ala Thr Lys Lys Leu Ser Pro
Leu Leu Glu Ser Phe Lys Val Ser Phe Leu Ser Ala
Leu Glu Glu Tyr Thr Lys Lys Leu Asn Thr;

SEQ ID NO: 256
Ser Pro Leu Leu Glu Ser Ala Lys Val Ser Ala Leu
Ser Ala Leu Glu Glu Ala Thr Lys Lys Leu Ser Pro
Leu Leu Glu Ser Phe Lys Val Ser Phe Leu Ser Ala
Leu Glu Glu Tyr Thr Lys Lys Leu Asn;

SEQ ID NO: 257
Ser Pro Leu Leu Glu Ser Ala Lys Val Ser Ala Leu
Ser Ala Leu Glu Glu Ala Thr Lys Lys Leu Ser Pro
Leu Leu Glu Ser Phe Lys Val Ser Phe Leu Ser Ala
Leu Glu Glu Tyr Thr Lys Lys Leu;

SEQ ID NO: 258
Ser Pro Leu Leu Glu Ser Ala Lys Val Ser Ala Leu
Ser Ala Leu Glu Glu Ala Thr Lys Lys Leu Ser Pro
Leu Leu Glu Ser Phe Lys Val Ser Phe Leu Ser Ala
Leu Glu Glu Tyr Thr Lys Lys;

SEQ ID NO: 259
Ser Pro Leu Leu Glu Ser Ala Lys Val Ser Ala Leu
Ser Ala Leu Glu Glu Ala Thr Lys Lys Ser Pro Leu
Leu Glu Ser Phe Lys Val Ser Phe Leu Ser Ala Leu
Glu Glu Tyr Thr Lys Lys Leu Asn Thr;

SEQ ID NO: 260
Ser Pro Leu Leu Glu Ser Ala Lys Val Ser Ala Leu
Ser Ala Leu Glu Glu Ala Thr Lys Lys Ser Pro Leu
Leu Glu Ser Phe Lys Val Ser Phe Leu Ser Ala Leu
Glu Glu Tyr Thr Lys Lys Leu Asn;

SEQ ID NO: 261
Ser Pro Leu Leu Glu Ser Ala Lys Val Ser Ala Leu
Ser Ala Leu Glu Glu Ala Thr Lys Lys Ser Pro Leu
Leu Glu Ser Phe Lys Val Ser Phe Leu Ser Ala Leu
Glu Glu Tyr Thr Lys Lys Leu;

SEQ ID NO: 262
Ser Pro Leu Leu Glu Ser Ala Lys Val Ser Ala Leu
Ser Ala Leu Glu Glu Ala Thr Lys Lys Ser Pro Leu
Leu Glu Ser Phe Lys Val Ser Phe Leu Ser Ala Leu
Glu Glu Tyr Thr Lys Lys;

-continued

SEQ ID NO: 263
Ser Pro Leu Leu Glu Ser Ala Lys Val Ser Ala Leu
Ser Ala Leu Glu Glu Ala Thr Lys Lys Leu Pro Ser
Leu Lys Leu Leu Glu Ser Phe Lys Val Ser Phe Leu
Ser Ala Leu Glu Glu Tyr Thr Lys Lys Leu Asn Thr;

SEQ ID NO: 264
Ser Pro Leu Leu Glu Ser Ala Lys Val Ser Ala Leu
Ser Ala Leu Glu Glu Ala Thr Lys Lys Leu Pro Ser
Leu Lys Leu Leu Glu Ser Phe Lys Val Ser Phe Leu
Ser Ala Leu Glu Glu Tyr Thr Lys Lys Leu Asn;

SEQ ID NO: 265
Ser Pro Leu Leu Glu Ser Ala Lys Val Ser Ala Leu
Ser Ala Leu Glu Glu Ala Thr Lys Lys Leu Pro Ser
Leu Lys Leu Leu Glu Ser Phe Lys Val Ser Phe Leu
Ser Ala Leu Glu Glu Tyr Thr Lys Lys Leu;

SEQ ID NO: 266
Ser Pro Leu Leu Glu Ser Ala Lys Val Ser Ala Leu
Ser Ala Leu Glu Glu Ala Thr Lys Lys Leu Pro Ser
Leu Lys Leu Leu Glu Ser Phe Lys Val Ser Phe Leu
Ser Ala Leu Glu Glu Tyr Thr Lys Lys;

SEQ ID NO: 267
Ser Pro Leu Leu Glu Ser Ala Lys Val Ser Ala Leu
Ser Ala Leu Glu Glu Ala Thr Lys Lys Leu Pro Ser
Leu Leu Leu Glu Ser Phe Lys Val Ser Phe Leu Ser
Ala Leu Glu Glu Tyr Thr Lys Lys Leu Asn Thr;

SEQ ID NO: 268
Ser Pro Leu Leu Glu Ser Ala Lys Val Ser Ala Leu
Ser Ala Leu Glu Glu Ala Thr Lys Lys Leu Pro Ser
Leu Leu Leu Glu Ser Phe Lys Val Ser Phe Leu Ser
Ala Leu Glu Glu Tyr Thr Lys Lys Leu Asn;

SEQ ID NO: 269
Ser Pro Leu Leu Glu Ser Ala Lys Val Ser Ala Leu
Ser Ala Leu Glu Glu Ala Thr Lys Lys Leu Pro Ser
Leu Leu Leu Glu Ser Phe Lys Val Ser Phe Leu Ser
Ala Leu Glu Glu Tyr Thr Lys Lys Leu;

SEQ ID NO: 270
Ser Pro Leu Leu Glu Ser Ala Lys Val Ser Ala Leu
Ser Ala Leu Glu Glu Ala Thr Lys Lys Leu Pro Ser
Leu Leu Leu Glu Ser Phe Lys Val Ser Phe Leu Ser
Ala Leu Glu Glu Tyr Thr Lys Lys;

SEQ ID NO: 271
Ser Pro Leu Leu Glu Ser Ala Lys Val Ser Ala Leu
Ser Ala Leu Glu Glu Ala Thr Lys Lys Leu Pro Ser
Leu Leu Glu Ser Phe Lys Val Ser Phe Leu Ser Ala
Leu Glu Glu Tyr Thr Lys Lys Leu Asn Thr;

SEQ ID NO: 272
Ser Pro Leu Leu Glu Ser Ala Lys Val Ser Ala Leu
Ser Ala Leu Glu Glu Ala Thr Lys Lys Leu Pro Ser
Leu Leu Glu Ser Phe Lys Val Ser Phe Leu Ser Ala
Leu Glu Glu Tyr Thr Lys Lys Leu Asn;

SEQ ID NO: 273
Ser Pro Leu Leu Glu Ser Ala Lys Val Ser Ala Leu
Ser Ala Leu Glu Glu Ala Thr Lys Lys Leu Pro Ser
Leu Leu Glu Ser Phe Lys Val Ser Phe Leu Ser Ala
Leu Glu Glu Tyr Thr Lys Lys Leu;

SEQ ID NO: 274
Ser Pro Leu Leu Glu Ser Ala Lys Val Ser Ala Leu
Ser Ala Leu Glu Glu Ala Thr Lys Lys Leu Pro Ser
Leu Leu Glu Ser Phe Lys Val Ser Phe Leu Ser Ala
Leu Glu Glu Tyr Thr Lys Lys;

SEQ ID NO: 275
Ser Pro Leu Leu Glu Ser Ala Lys Val Ser Ala Leu
Ser Ala Leu Glu Glu Ala Thr Lys Lys Leu Pro Leu
Leu Glu Ser Phe Lys Val Ser Phe Leu Ser Ala Leu
Glu Glu Tyr Thr Lys Lys Leu Asn Thr;

-continued

SEQ ID NO: 276
Ser Pro Leu Leu Glu Ser Ala Lys Val Ser Ala Leu
Ser Ala Leu Glu Glu Ala Thr Lys Lys Leu Pro Leu
Leu Glu Ser Phe Lys Val Ser Phe Leu Ser Ala Leu
Glu Glu Tyr Thr Lys Lys Leu Asn;

SEQ ID NO: 277
Ser Pro Leu Leu Glu Ser Ala Lys Val Ser Ala Leu
Ser Ala Leu Glu Glu Ala Thr Lys Lys Leu Pro Leu
Leu Glu Ser Phe Lys Val Ser Phe Leu Ser Ala Leu
Glu Glu Tyr Thr Lys Lys Leu;

SEQ ID NO: 278
Ser Pro Leu Leu Glu Ser Ala Lys Val Ser Ala Leu
Ser Ala Leu Glu Glu Ala Thr Lys Lys Leu Pro Leu
Leu Glu Ser Phe Lys Val Ser Phe Leu Ser Ala Leu
Glu Glu Tyr Thr Lys Lys;

SEQ ID NO: 279
Ser Pro Leu Leu Glu Ser Ala Lys Val Ser Ala Leu
Ser Ala Leu Glu Glu Ala Thr Lys Lys Pro Ser Leu
Lys Leu Leu Glu Ser Phe Lys Val Ser Phe Leu Ser
Ala Leu Glu Glu Tyr Thr Lys Lys Leu Asn Thr;

SEQ ID NO: 280
Ser Pro Leu Leu Glu Ser Ala Lys Val Ser Ala Leu
Ser Ala Leu Glu Glu Ala Thr Lys Lys Pro Ser Leu
Lys Leu Leu Glu Ser Phe Lys Val Ser Phe Leu Ser
Ala Leu Glu Glu Tyr Thr Lys Lys Leu Asn;

SEQ ID NO: 281
Ser Pro Leu Leu Glu Ser Ala Lys Val Ser Ala Leu
Ser Ala Leu Glu Glu Ala Thr Lys Lys Pro Ser Leu
Lys Leu Leu Glu Ser Phe Lys Val Ser Phe Leu Ser
Ala Leu Glu Glu Tyr Thr Lys Lys Leu;

SEQ ID NO: 282
Ser Pro Leu Leu Glu Ser Ala Lys Val Ser Ala Leu
Ser Ala Leu Glu Glu Ala Thr Lys Lys Pro Ser Leu
Lys Leu Leu Glu Ser Phe Lys Val Ser Phe Leu Ser
Ala Leu Glu Glu Tyr Thr Lys Lys;

SEQ ID NO: 283
Ser Pro Leu Leu Glu Ser Ala Lys Val Ser Ala Leu
Ser Ala Leu Glu Glu Ala Thr Lys Lys Pro Ser Leu
Leu Leu Glu Ser Phe Lys Val Ser Phe Leu Ser Ala
Leu Glu Glu Tyr Thr Lys Lys Leu Asn Thr;

SEQ ID NO: 284
Ser Pro Leu Leu Glu Ser Ala Lys Val Ser Ala Leu
Ser Ala Leu Glu Glu Ala Thr Lys Lys Pro Ser Leu
Leu Leu Glu Ser Phe Lys Val Ser Phe Leu Ser Ala
Leu Glu Glu Tyr Thr Lys Lys Leu Asn;

SEQ ID NO: 285
Ser Pro Leu Leu Glu Ser Ala Lys Val Ser Ala Leu
Ser Ala Leu Glu Glu Ala Thr Lys Lys Pro Ser Leu
Leu Leu Glu Ser Phe Lys Val Ser Phe Leu Ser Ala
Leu Glu Glu Tyr Thr Lys Lys Leu;

SEQ ID NO: 286
Ser Pro Leu Leu Glu Ser Ala Lys Val Ser Ala Leu
Ser Ala Leu Glu Glu Ala Thr Lys Lys Pro Ser Leu
Leu Leu Glu Ser Phe Lys Val Ser Phe Leu Ser Ala
Leu Glu Glu Tyr Thr Lys Lys;

SEQ ID NO: 287
Ser Pro Leu Leu Glu Ser Ala Lys Val Ser Ala Leu
Ser Ala Leu Glu Glu Ala Thr Lys Lys Pro Ser Leu
Leu Glu Ser Phe Lys Val Ser Phe Leu Ser Ala Leu
Glu Glu Tyr Thr Lys Lys Leu Asn Thr;

SEQ ID NO: 288
Ser Pro Leu Leu Glu Ser Ala Lys Val Ser Ala Leu
Ser Ala Leu Glu Glu Ala Thr Lys Lys Pro Ser Leu
Leu Glu Ser Phe Lys Val Ser Phe Leu Ser Ala Leu
Glu Glu Tyr Thr Lys Lys Leu Asn;

-continued

SEQ ID NO: 289
Ser Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu;

SEQ ID NO: 290
Ser Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys;

SEQ ID NO: 291
Ser Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr;

SEQ ID NO: 292
Ser Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn;

SEQ ID NO: 293
Ser Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu;

SEQ ID NO: 294
Ser Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys.

g. G-(A-B-C)$_n$-H with Successive N— and/or C-Terminal Deletions in the B Group with Successive Deletions of G and H SEQ ID NO: 295
Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr;

SEQ ID NO: 296
Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr;

SEQ ID NO: 297
Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr;

SEQ ID NO: 298
Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn;

SEQ ID NO: 299
Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn;

SEQ ID NO: 300
Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn;

-continued

SEQ ID NO: 301
Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu;

SEQ ID NO: 302
Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu;

SEQ ID NO: 303
Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu;

SEQ ID NO: 304
Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys;

SEQ ID NO: 305
Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys;

SEQ ID NO: 306
Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys;

SEQ ID NO: 307
Pro Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn Thr;

SEQ ID NO: 308
Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn Thr;

SEQ ID NO: 309
Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn Thr;

SEQ ID NO: 310
Pro Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn;

SEQ ID NO: 311
Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn;

SEQ ID NO: 312
Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu Asn;

SEQ ID NO: 313
Pro Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu;

-continued

SEQ ID NO: 314
Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu;

SEQ ID NO: 315
Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys Leu;

SEQ ID NO: 316
Pro Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys;

SEQ ID NO: 317
Leu Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys;

SEQ ID NO: 318
Leu Glu Ser Ala Lys Val Ser Ala Leu Ser Ala Leu Glu Glu Ala Thr Lys Lys Leu Ser Pro Leu Leu Leu Glu Ser Phe Lys Val Ser Phe Leu Ser Ala Leu Glu Glu Tyr Thr Lys Lys;

SEQ ID NO: 319
Pro Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn Thr;

SEQ ID NO: 320
Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn Thr;

SEQ ID NO: 321
Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn Thr;

SEQ ID NO: 322
Pro Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn;

SEQ ID NO: 323
Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn;

SEQ ID NO: 324
Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu Asn;

SEQ ID NO: 325
Pro Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu;

SEQ ID NO: 326
Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu;

-continued

SEQ ID NO: 327
Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys Leu;

SEQ ID NO: 328
Pro Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys;

SEQ ID NO: 329
Leu Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys;

SEQ ID NO: 330
Leu Glu Ser Ala Lys Val Ser Ala Leu Ser Ala Leu Glu Glu Ala Thr Lys Lys Ser Pro Leu Leu Leu Glu Ser Phe Lys Val Ser Phe Leu Ser Ala Leu Glu Glu Tyr Thr Lys Lys;

SEQ ID NO: 331
Pro Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn Thr;

SEQ ID NO: 332
Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn Thr;

SEQ ID NO: 333
Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn Thr;

SEQ ID NO: 334
Pro Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn;

SEQ ID NO: 335
Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn;

SEQ ID NO: 336
Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu Asn;

SEQ ID NO: 337
Pro Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu;

SEQ ID NO: 338
Leu Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu;

SEQ ID NO: 339
Leu Glu Ser Ala Lys Val Ser Ala Leu Ser Ala Leu Glu Glu Ala Thr Lys Lys Pro Leu Leu Leu Glu Ser Phe Lys Val Ser Phe Leu Ser Ala Leu Glu Glu Tyr Thr Lys Lys Leu;

```
                                    SEQ ID NO: 340
Pro Leu Leu Glu Ser Ala Lys Val Ser Ala Leu Ser
Ala Leu Glu Glu Ala Thr Lys Lys Pro Leu Leu Leu
Glu Ser Phe Lys Val Ser Phe Leu Ser Ala Leu Glu
Glu Tyr Thr Lys Lys;

                                    SEQ ID NO: 341
Leu Leu Glu Ser Ala Lys Val Ser Ala Leu Ser Ala
Leu Glu Glu Ala Thr Lys Lys Pro Leu Leu Leu Glu
Ser Phe Lys Val Ser Phe Leu Ser Ala Leu Glu Glu
Tyr Thr Lys Lys;

                                    SEQ ID NO: 342
Leu Glu Ser Ala Lys Val Ser Ala Leu Ser Ala Leu
Glu Glu Ala Thr Lys Lys Pro Leu Leu Leu Glu Ser
Phe Lys Val Ser Phe Leu Ser Ala Leu Glu Glu Tyr
Thr Lys Lys;

                                    SEQ ID NO: 343
Pro Leu Leu Glu Ser Ala Lys Val Ser Ala Leu Ser
Ala Leu Glu Glu Ala Thr Lys Lys Lys Leu Ser ProLeu
Leu Glu Ser Phe Lys Val Ser Phe Leu Ser Ala Leu
Glu Glu Tyr Thr Lys Lys Leu Asn Thr;

                                    SEQ ID NO: 344
Leu Leu Glu Ser Ala Lys Val Ser Ala Leu Ser Ala
Leu Glu Glu Ala Thr Lys Lys Lys Leu Ser ProLeu Leu
Glu Ser Phe Lys Val Ser Phe Leu Ser Ala Leu Glu
Glu Tyr Thr Lys Lys Leu Asn Thr;

                                    SEQ ID NO: 345
Leu Glu Ser Ala Lys Val Ser Ala Leu Ser Ala Leu
Glu Glu Ala Thr Lys Lys Lys Leu Ser ProLeu Leu Glu
Ser Phe Lys Val Ser Phe Leu Ser Ala Leu Glu Glu
Tyr Thr Lys Lys Leu Asn Thr;

                                    SEQ ID NO: 346
Pro Leu Leu Glu Ser Ala Lys Val Ser Ala Leu Ser
Ala Leu Glu Glu Ala Thr Lys Lys Lys Leu Ser ProLeu
Leu Glu Ser Phe Lys Val Ser Phe Leu Ser Ala Leu
Glu Glu Tyr Thr Lys Lys Leu Asn;

                                    SEQ ID NO: 347
Leu Leu Glu Ser Ala Lys Val Ser Ala Leu Ser Ala
Leu Glu Glu Ala Thr Lys Lys Lys Leu Ser ProLeu Leu
Glu Ser Phe Lys Val Ser Phe Leu Ser Ala Leu Glu
Glu Tyr Thr Lys Lys Leu Asn;

                                    SEQ ID NO: 348
Leu Glu Ser Ala Lys Val Ser Ala Leu Ser Ala Leu
Glu Glu Ala Thr Lys Lys Lys Leu Ser ProLeu Leu Glu
Ser Phe Lys Val Ser Phe Leu Ser Ala Leu Glu Glu
Tyr Thr Lys Lys Leu Asn;

                                    SEQ ID NO: 349
Pro Leu Leu Glu Ser Ala Lys Val Ser Ala Leu Ser
Ala Leu Glu Glu Ala Thr Lys Lys Lys Leu Ser ProLeu
Leu Glu Ser Phe Lys Val Ser Phe Leu Ser Ala Leu
Glu Glu Tyr Thr Lys Lys Leu;

                                    SEQ ID NO: 350
Leu Leu Glu Ser Ala Lys Val Ser Ala Leu Ser Ala
Leu Glu Glu Ala Thr Lys Lys Lys Leu Ser ProLeu Leu
Glu Ser Phe Lys Val Ser Phe Leu Ser Ala Leu Glu
Glu Tyr Thr Lys Lys Leu;

                                    SEQ ID NO: 351
Leu Glu Ser Ala Lys Val Ser Ala Leu Ser Ala Leu
Glu Glu Ala Thr Lys Lys Lys Leu Ser ProLeu Leu Glu
Ser Phe Lys Val Ser Phe Leu Ser Ala Leu Glu Glu
Tyr Thr Lys Lys Leu;

                                    SEQ ID NO: 352
Pro Leu Leu Glu Ser Ala Lys Val Ser Ala Leu Ser
Ala Leu Glu Glu Ala Thr Lys Lys Lys Leu Ser ProLeu
Leu Glu Ser Phe Lys Val Ser Phe Leu Ser Ala Leu
Glu Glu Tyr Thr Lys Lys;

                                    SEQ ID NO: 353
Leu Leu Glu Ser Ala Lys Val Ser Ala Leu Ser Ala
Leu Glu Glu Ala Thr Lys Lys Lys Leu Ser ProLeu Leu
Glu Ser Phe Lys Val Ser Phe Leu Ser Ala Leu Glu
Glu Tyr Thr Lys Lys;

                                    SEQ ID NO: 354
Leu Glu Ser Ala Lys Val Ser Ala Leu Ser Ala Leu
Glu Glu Ala Thr Lys Lys Lys Leu Ser ProLeu Leu Glu
Ser Phe Lys Val Ser Phe Leu Ser Ala Leu Glu Glu
Tyr Thr Lys Lys;

                                    SEQ ID NO: 355
Pro Leu Leu Glu Ser Ala Lys Val Ser Ala Leu Ser
Ala Leu Glu Glu Ala Thr Lys Lys Leu Ser Pro Leu
Leu Glu Ser Phe Lys Val Ser Phe Leu Ser Ala Leu
Glu Glu Tyr Thr Lys Lys Leu Asn Thr;

                                    SEQ ID NO: 356
Leu Leu Glu Ser Ala Lys Val Ser Ala Leu Ser Ala
Leu Glu Glu Ala Thr Lys Lys Leu Ser Pro Leu Leu
Glu Ser Phe Lys Val Ser Phe Leu Ser Ala Leu Glu
Glu Tyr Thr Lys Lys Leu Asn Thr;

                                    SEQ ID NO: 357
Leu Glu Ser Ala Lys Val Ser Ala Leu Ser Ala Leu
Glu Glu Ala Thr Lys Lys Leu Ser Pro Leu Leu Glu
Ser Phe Lys Val Ser Phe Leu Ser Ala Leu Glu Glu
Tyr Thr Lys Lys Leu Asn Thr;

                                    SEQ ID NO: 358
Pro Leu Leu Glu Ser Ala Lys Val Ser Ala Leu Ser
Ala Leu Glu Glu Ala Thr Lys Lys Leu Ser Pro Leu
Leu Glu Ser Phe Lys Val Ser Phe Leu Ser Ala Leu
Glu Glu Tyr Thr Lys Lys Leu Asn;

                                    SEQ ID NO: 359
Leu Leu Glu Ser Ala Lys Val Ser Ala Leu Ser Ala
Leu Glu Glu Ala Thr Lys Lys Leu Ser Pro Leu Leu
Glu Ser Phe Lys Val Ser Phe Leu Ser Ala Leu Glu
Glu Tyr Thr Lys Lys Leu Asn;

                                    SEQ ID NO: 360
Leu Glu Ser Ala Lys Val Ser Ala Leu Ser Ala Leu
Glu Glu Ala Thr Lys Lys Leu Ser Pro Leu Leu Glu
Ser Phe Lys Val Ser Phe Leu Ser Ala Leu Glu Glu
Tyr Thr Lys Lys Leu Asn;

                                    SEQ ID NO: 361
Pro Leu Leu Glu Ser Ala Lys Val Ser Ala Leu Ser
Ala Leu Glu Glu Ala Thr Lys Lys Leu Ser Pro Leu
Leu Glu Ser Phe Lys Val Ser Phe Leu Ser Ala Leu
Glu Glu Tyr Thr Lys Lys Leu;

                                    SEQ ID NO: 362
Leu Leu Glu Ser Ala Lys Val Ser Ala Leu Ser Ala
Leu Glu Glu Ala Thr Lys Lys Leu Ser Pro Leu Leu
Glu Ser Phe Lys Val Ser Phe Leu Ser Ala Leu Glu
Glu Tyr Thr Lys Lys Leu;

                                    SEQ ID NO: 363
Leu Glu Ser Ala Lys Val Ser Ala Leu Ser Ala Leu
Glu Glu Ala Thr Lys Lys Leu Ser Pro Leu Leu Glu
Ser Phe Lys Val Ser Phe Leu Ser Ala Leu Glu Glu
Tyr Thr Lys Lys Leu;

                                    SEQ ID NO: 364
Pro Leu Leu Glu Ser Ala Lys Val Ser Ala Leu Ser
Ala Leu Glu Glu Ala Thr Lys Lys Leu Ser Pro Leu
Leu Glu Ser Phe Lys Val Ser Phe Leu Ser Ala Leu
Glu Glu Tyr Thr Lys Lys;

                                    SEQ ID NO: 365
Leu Leu Glu Ser Ala Lys Val Ser Ala Leu Ser Ala
Leu Glu Glu Ala Thr Lys Lys Leu Ser Pro Leu Leu
Glu Ser Phe Lys Val Ser Phe Leu Ser Ala Leu Glu
Glu Tyr Thr Lys Lys;
```

-continued

SEQ ID NO: 366
Leu Glu Ser Ala Lys Val Ser Ala Leu Ser Ala Leu Glu Glu Ala Thr Lys Lys Leu Ser Pro Leu Leu Glu Ser Phe Lys Val Ser Phe Leu Ser Ala Leu Glu Glu Tyr Thr Lys Lys;

SEQ ID NO: 367
Pro Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn Thr;

SEQ ID NO: 368
Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn Thr;

SEQ ID NO: 369
Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn Thr;

SEQ ID NO: 370
Pro Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn;

SEQ ID NO: 371
Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn;

SEQ ID NO: 372
Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu Asn;

SEQ ID NO: 373
Pro Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu;

SEQ ID NO: 374
Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu;

SEQ ID NO: 375
Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys Leu;

SEQ ID NO: 376
Pro Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys;

SEQ ID NO: 377
Leu Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys;

SEQ ID NO: 378
Leu Glu Ser Ala Lys Val Ser Ala Leu Ser Ala Leu Glu Glu Ala Thr Lys Lys Ser Pro Leu Leu Glu Ser Phe Lys Val Ser Phe Leu Ser Ala Leu Glu Glu Tyr Thr Lys Lys;

-continued

SEQ ID NO: 379
Pro Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 380
Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 381
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 382
Pro Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn;

SEQ ID NO: 383
Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn;

SEQ ID NO: 384
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu Asn;

SEQ ID NO: 385
Pro Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu;

SEQ ID NO: 386
Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu;

SEQ ID NO: 387
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys Leu;

SEQ ID NO: 388
Pro Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys;

SEQ ID NO: 389
Leu Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys;

SEQ ID NO: 390
Leu Glu Ser Ala Lys Val Ser Ala Leu Ser Ala Leu Glu Glu Ala Thr Lys Lys Leu Pro Ser Leu Lys Leu Leu Glu Ser Phe Lys Val Ser Phe Leu Ser Ala Leu Glu Glu Tyr Thr Lys Lys;

SEQ ID NO: 391
Pro Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr;

-continued

SEQ ID NO: 392
Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr;

SEQ ID NO: 393
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn Thr;

SEQ ID NO: 394
Pro Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn;

SEQ ID NO: 395
Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn;

SEQ ID NO: 396
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu Asn;

SEQ ID NO: 397
Pro Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu;

SEQ ID NO: 398
Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu;

SEQ ID NO: 399
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys Leu;

SEQ ID NO: 400
Pro Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys;

SEQ ID NO: 401
Leu Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys;

SEQ ID NO: 402
Leu Glu Ser Ala Lys Val Ser Ala Leu Ser Ala Leu Glu Glu Ala Thr Lys Lys Leu Pro Ser Leu Leu Leu Glu Ser Phe Lys Val Ser Phe Leu Ser Ala Leu Glu Glu Tyr Thr Lys Lys;

SEQ ID NO: 403
Pro Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr;

SEQ ID NO: 404
Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr;

-continued

SEQ ID NO: 405
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn Thr;

SEQ ID NO: 406
Pro Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn;

SEQ ID NO: 407
Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn;

SEQ ID NO: 408
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu Asn;

SEQ ID NO: 409
Pro Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu;

SEQ ID NO: 410
Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu;

SEQ ID NO: 411
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys Leu;

SEQ ID NO: 412
Pro Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys;

SEQ ID NO: 413
Leu Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys;

SEQ ID NO: 414
Leu Glu Ser Ala Lys Val Ser Ala Leu Ser Ala Leu Glu Glu Ala Thr Lys Lys Leu Pro Ser Leu Leu Glu Ser Phe Lys Val Ser Phe Leu Ser Ala Leu Glu Glu Tyr Thr Lys Lys;

SEQ ID NO: 415
Pro Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr;

SEQ ID NO: 416
Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr;

SEQ ID NO: 417
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn Thr;

-continued

SEQ ID NO: 418
Pro Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn;

SEQ ID NO: 419
Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn;

SEQ ID NO: 420
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu Asn;

SEQ ID NO: 421
Pro Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu;

SEQ ID NO: 422
Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu;

SEQ ID NO: 423
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys Leu;

SEQ ID NO: 424
Pro Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys;

SEQ ID NO: 425
Leu Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys;

SEQ ID NO: 426
Leu Glu Ser Ala Lys Val Ser Ala Leu Ser Ala Leu Glu Glu Ala Thr Lys Lys Leu Pro Leu Leu Glu Ser Phe Lys Val Ser Phe Leu Ser Ala Leu Glu Glu Tyr Thr Lys Lys;

SEQ ID NO: 427
Pro Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 428
Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 429
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn Thr;

SEQ ID NO: 430
Pro Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn;

-continued

SEQ ID NO: 431
Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn;

SEQ ID NO: 432
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu Asn;

SEQ ID NO: 433
Pro Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu;

SEQ ID NO: 434
Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu;

SEQ ID NO: 435
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys Leu;

SEQ ID NO: 436
Pro Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys;

SEQ ID NO: 437
Leu Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys;

SEQ ID NO: 438
Leu Glu Ser Ala Lys Val Ser Ala Leu Ser Ala Leu Glu Glu Ala Thr Lys Lys Pro Ser Leu Lys Leu Leu Glu Ser Phe Lys Val Ser Phe Leu Ser Ala Leu Glu Glu Tyr Thr Lys Lys;

SEQ ID NO: 439
Pro Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr;

SEQ ID NO: 440
Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr;

SEQ ID NO: 441
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn Thr;

SEQ ID NO: 442
Pro Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn;

SEQ ID NO: 443
Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn;

-continued

SEQ ID NO: 444
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu Asn;

SEQ ID NO: 445
Pro Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu;

SEQ ID NO: 446
Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu;

SEQ ID NO: 447
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys Leu;

SEQ ID NO: 448
Pro Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys;

SEQ ID NO: 449
Leu Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys;

SEQ ID NO: 450
Leu Glu Ser Ala Lys Val Ser Ala Leu Ser Ala Leu Glu Glu Ala Thr Lys Lys Pro Ser Leu Leu Leu Glu Ser Phe Lys Val Ser Phe Leu Ser Ala Leu Glu Glu Tyr Thr Lys Lys;

SEQ ID NO: 451
Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr;

SEQ ID NO: 452
Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr;

SEQ ID NO: 453
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn Thr;

SEQ ID NO: 454
Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn;

SEQ ID NO: 455
Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn;

SEQ ID NO: 456
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu Asn;

-continued

SEQ ID NO: 457
Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu;

SEQ ID NO: 458
Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu;

SEQ ID NO: 459
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys Leu;

SEQ ID NO: 460
Pro Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys;

SEQ ID NO: 461
Leu Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys;

SEQ ID NO: 462
Leu Glu Ser Ala Lys Val Ser Ala Leu Ser Ala Leu Glu Glu Ala Thr Lys Lys Pro Ser Leu Leu Glu Ser Phe Lys Val Ser Phe Leu Ser Ala Leu Glu Glu Tyr Thr Lys Lys;

SEQ ID NO: 463
Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr;

SEQ ID NO: 464
Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr;

SEQ ID NO: 465
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn Thr;

SEQ ID NO: 466
Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn;

SEQ ID NO: 467
Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn;

SEQ ID NO: 468
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu Asn;

SEQ ID NO: 469
Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu;

-continued

SEQ ID NO: 470
Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu;

SEQ ID NO: 471
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys Leu;

SEQ ID NO: 472
Pro Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys.

SEQ ID NO: 473
Leu Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys.

SEQ ID NO: 474
Leu Glu Ser Ala Lys Val Ser Ala Leu Ser Ala Leu Glu Glu Ala Thr Lys Lys Pro Leu Leu Glu Ser Phe Lys Val Ser Phe Leu Ser Ala Leu Glu Glu Tyr Thr Lys Lys.

h. Examples of G-(A-B-C)$_n$-H with A and/or C in Reverse Orientation

SEQ ID NO: 475
Ser Pro Leu Lys Lys Thr Ala Glu Glu Leu Ala Ser Leu Ala Ser Val Lys Ala Ser Glu Leu Lys Leu Ser Pro Leu Leu Glu Ser Phe Lys Val Ser Phe Leu Ser Ala Leu Glu Glu Tyr Thr Lys Lys Leu Asn Thr Gln;

SEQ ID NO: 476
Lys Lys Thr Ala Glu Glu Leu Ala Ser Leu Ala Ser Val Lys Ala Ser Glu Leu Lys Leu Ser Pro Leu Leu Glu Ser Phe Lys Val Ser Phe Leu Ser Ala Leu Glu Glu Tyr Thr Lys Lys Leu Asn Thr Gln;

SEQ ID NO: 477
Ser Pro Leu Lys Lys Thr Ala Glu Glu Leu Ala Ser Leu Ala Ser Val Lys Ala Ser Glu Leu Lys Leu Ser Pro Leu Leu Glu Ser Phe Lys Val Ser Phe Leu Ser Ala Leu Glu Glu Tyr Thr Lys Lys;

SEQ ID NO: 478
Ser Pro Leu Lys Lys Thr Ala Glu Glu Leu Ala Ser Leu Ala Ser Val Lys Ala Ser Glu Leu Lys Leu Ser Pro Leu Lys Lys Thr Tyr Glu Glu Leu Ala Ser Leu Phe Ser Val Lys Phe Ser Glu Leu Leu Asn Thr Gln;

SEQ ID NO: 479
Lys Lys Thr Ala Glu Glu Leu Ala Ser Leu Ala Ser Val Lys Ala Ser Glu Leu Lys Leu Ser Pro Leu Lys Lys Thr Tyr Glu Glu Leu Ala Ser Leu Phe Ser Val Lys Phe Ser Glu Leu Leu Asn Thr Gln;

SEQ ID NO: 480
Ser Pro Leu Lys Lys Thr Ala Glu Glu Leu Ala Ser Leu Ala Ser Val Lys Ala Ser Glu Leu Lys Leu Ser Pro Leu Lys Lys Thr Tyr Glu Glu Leu Ala Ser Leu Phe Ser Val Lys Phe Ser Glu Leu;

SEQ ID NO: 481
Ser Pro Leu Leu Glu Ser Ala Lys Val Ser Ala Leu Ser Ala Leu Glu Glu Ala Thr Lys Lys Lys Leu Ser Pro Leu Lys Lys Thr Tyr Glu Glu Leu Ala Ser Leu Phe Ser Val Lys Phe Ser Glu Leu Leu Asn Thr Gln;

-continued

SEQ ID NO: 482
Leu Glu Ser Ala Lys Val Ser Ala Leu Ser Ala Leu Glu Glu Ala Thr Lys Lys Lys Leu Ser Pro Leu Lys Lys Thr Tyr Glu Glu Leu Ala Ser Leu Phe Ser Val Lys Phe Ser Glu Leu Leu Asn Thr Gln;

SEQ ID NO: 483
Ser Pro Leu Leu Glu Ser Ala Lys Val Ser Ala Leu Ser Ala Leu Glu Glu Ala Thr Lys Lys Lys Leu Ser Pro Leu Lys Lys Thr Tyr Glu Glu Leu Ala Ser Leu Phe Ser Val Lys Phe Ser Glu Leu;

SEQ ID NO: 484
Ser Pro Leu Leu Glu Ser Ala Lys Val Ser Ala Leu Ser Ala Leu Glu Glu Ala Thr Lys Lys Pro Leu Glu Ser Phe Lys Val Ser Phe Leu Ser Ala Leu Glu Glu Tyr Thr Lys Lys Leu Asn Thr Gln;

SEQ ID NO: 485
Leu Glu Ser Ala Lys Val Ser Ala Leu Ser Ala Leu Glu Glu Ala Thr Lys Lys Pro Leu Glu Ser Phe Lys Val Ser Phe Leu Ser Ala Leu Glu Glu Tyr Thr Lys Lys Leu Asn Thr Gln;

SEQ ID NO: 486
Ser Pro Leu Leu Glu Ser Ala Lys Val Ser Ala Leu Ser Ala Leu Glu Glu Ala Thr Lys Lys Pro Leu Glu Ser Phe Lys Val Ser Phe Leu Ser Ala Leu Glu Glu Tyr Thr Lys Lys;

SEQ ID NO: 487
Ser Pro Leu Lys Lys Thr Ala Glu Glu Leu Ala Ser Leu Ala Ser Val Lys Ala Ser Glu Leu Pro Leu Glu Ser Phe Lys Val Ser Phe Leu Ser Ala Leu Glu Glu Tyr Thr Lys Lys Leu Asn Thr Gln;

SEQ ID NO: 488
Lys Lys Thr Ala Glu Glu Leu Ala Ser Leu Ala Ser Val Lys Ala Ser Glu Leu Pro Leu Glu Ser Phe Lys Val Ser Phe Leu Ser Ala Leu Glu Glu Tyr Thr Lys Lys Leu Asn Thr Gln;

SEQ ID NO: 489
Ser Pro Leu Lys Lys Thr Ala Glu Glu Leu Ala Ser Leu Ala Ser Val Lys Ala Ser Glu Leu Pro Leu Glu Ser Phe Lys Val Ser Phe Leu Ser Ala Leu Glu Glu Tyr Thr Lys Lys;

SEQ ID NO: 490
Ser Pro Leu Lys Lys Thr Ala Glu Glu Leu Ala Ser Leu Ala Ser Val Lys Ala Ser Glu Leu Pro Lys Lys Thr Tyr Glu Glu Leu Ala Ser Leu Phe Ser Val Lys Phe Ser Glu Leu Leu Asn Thr Gln;

SEQ ID NO: 491
Lys Lys Thr Ala Glu Glu Leu Ala Ser Leu Ala Ser Val Lys Ala Ser Glu Leu Pro Lys Lys Thr Tyr Glu Glu Leu Ala Ser Leu Phe Ser Val Lys Phe Ser Glu Leu Leu Asn Thr Gln;

SEQ ID NO: 492
Ser Pro Leu Lys Lys Thr Ala Glu Glu Leu Ala Ser Leu Ala Ser Val Lys Ala Ser Glu Leu Pro Lys Lys Thr Tyr Glu Glu Leu Ala Ser Leu Phe Ser Val Lys Phe Ser Glu Leu;

SEQ ID NO: 493
Ser Pro Leu Leu Glu Ser Ala Lys Val Ser Ala Leu Ser Ala Leu Glu Glu Ala Thr Lys Lys Pro Lys Lys Thr Tyr Glu Glu Leu Ala Ser Leu Phe Ser Val Lys Phe Ser Glu Leu Leu Asn Thr Gln;

SEQ ID NO: 494
Leu Glu Ser Ala Lys Val Ser Ala Leu Ser Ala Leu Glu Glu Ala Thr Lys Lys Pro Lys Lys Thr Tyr Glu Glu Leu Ala Ser Leu Phe Ser Val Lys Phe Ser Glu Leu Leu Asn Thr Gln;
and, -continued

SEQ ID NO: 495

```
Ser Pro Leu Leu Glu Ser Ala Lys Val Ser Ala Leu
Ser Ala Leu Glu Glu Ala Thr Lys Lys Pro Lys Lys
Thr Tyr Glu Glu Leu Ala Ser Leu Phe Ser Val Lys
Phe Ser Glu Leu.
```

C. Amino Acid Substitutions within A and/or C of Peptides $(A-B-C)_n$ and $G-(A-B-C)_n-H$ The present invention includes peptides (specifically, $(A-B-C)_n$ and $G-(A-B-C)_n-H$ peptides) containing isosteric amino acid substitutions at specific amino acid positions within the peptides. By "isosteric substitution" is meant that an amino acid at a particular position within a peptide of the invention can be substituted with another amino acid belonging to the same isosteric group as described hereinbelow. Amino acids within a given isosteric group, as set forth hereinbelow, are amino acids having similar size, shape, polar/nonpolar properties, charge, and/or steric properties. The invention provides peptides wherein substitution of an amino acid with an amino acid belonging to the same isosteric group allows the substituted peptide to retain at least about 20% of the biological activity of the unsubstituted peptide, e.g., at least about: 25%, 30%, 40%, 50%, 60%, 70%, 80%, 90%, 100%, 110%, 125%, 150%, 175%, 200%, 250%, 300%, or more, of the biological activity of the unsubstituted peptide. By "biological activity" of the peptide is meant the ability of the peptide to promote lipid efflux and and/or have an anti-inflammatory effect, as described hereinbelow.

The invention also provides peptides having an amino acid substituted with an amino acid belonging to a different isosteric group from the original amino acid, such that the substitution allows the peptide to retain at least about 20% of the biological activity (e.g., lipid efflux and/or anti-inflammatory properties) of the unsubstituted peptide, e.g., at least about: 25%, 30%, 40%, 50%, 60%, 70%, 80%, 90%, 100%, 110%, 125%, 150%, 175%, 200%, 250%, 300%, or more, of the biological activity of the unsubstituted peptide.

Peptides with an amino acid substitution that retain at least about 20% or more of the biological activity of an unsubstituted peptide will be readily recognized by the skilled artisan using well-known approaches, e.g., the lipid efflux and/or other biological assays of the invention.

Isosteric amino acid groupings of the present invention are as follows:

a) Isosteric Group 1: Lys, His, and Arg;

b) Isosteric Group 2: Asp and Glu;

c) Isosteric Group 3: Ser, Thr, Leu, Ile, Gly, Ala, Val, and GABA;

d) Isosteric Group 4: Phe and Tyr; and e) Isosteric Group 5: Pro.

Tables 1 and 2 below show the numbering that is used herein to refer to amino acid positions within Helix 8' of A and Helix 8 of C for which isosteric substitutions can be made as described herein. Both Tables employ the conventional single-letter amino acid code to refer to the amino acids of each helix. This single-letter code is well-known in the art (see, e.g., Alberts et al., *Molecular Biology of the Cell,* 2nd Ed., Garland Publishing, Inc., N.Y., 1989, and similar references). Amino acids at positions 4, 8, and 15 are in bold and are underlined to highlight the amino acid sequence differences between Helix 8' and Helix 8.

TABLE 1

| Numbering of Amino Acid Positions in Helix 8' (Segment A) | | | | | | | | | | | | | | | | | | |
|---|---|---|---|---|---|---|---|---|---|---|---|---|---|---|---|---|---|---|
| | Amino Acid | | | | | | | | | | | | | | | | | |
| | L | E | S | **A** | K | V | S | **A** | L | S | A | L | E | E | **A** | T | K | K |
| Position in Helix 8' (Segment A) | 1 | 2 | 3 | 4 | 5 | 6 | 7 | 8 | 9 | 10 | 11 | 12 | 13 | 14 | 15 | 16 | 17 | 18 |

TABLE 2

| Numbering of Amino Acid Positions in Helix 8 (Segment C) | | | | | | | | | | | | | | | | | | |
|---|---|---|---|---|---|---|---|---|---|---|---|---|---|---|---|---|---|---|
| | Amino Acid | | | | | | | | | | | | | | | | | |
| | L | E | S | **F** | K | V | S | **F** | L | S | A | L | E | E | **Y** | T | K | K |
| Position in Helix 8 (Segment C) | 1 | 2 | 3 | 4 | 5 | 6 | 7 | 8 | 9 | 10 | 11 | 12 | 13 | 14 | 15 | 16 | 17 | 18 |

Isosteric substitutions can be made singly or in multiples, and in any combination. In just one non-limiting example, within Helix 8' (Segment A) and/or Helix 8 (Segment C) there may be only one amino acid in Isosteric Group 3 that is substituted. Alternatively, there may be two, three, four, five, six, etc., up to substitutions at all amino acid positions assigned to Isosteric Group 3. One of ordinary skill in the art will understand that the peptides of the invention can contain one or more isosteric amino acid substitutions in either of A and C or in both A and C. As described below, within the peptides of the invention, an amino acid can be substituted with a different amino acid belonging to the same isosteric group or with an amino acid belonging to a different isosteric group.

For each isosteric grouping described below, any number of amino acid positions may be substituted, i.e., one position, more than one position, or all positions in either one or both helices (i.e., Helix 8' and/or Helix 8) within a given isosteric group can be substituted. Moreover, when more than one amino acid position within an isosteric group is substituted, the substitutions need not be the same within one helix or between the two helices. In one non-limiting example, in a peptide having three isosteric substitutions at positions belonging to Isosteric Group 3 (e.g., but not limited to, Ser at positions 3 and 7 of Helix 8' (Segment A) and Leu at position 1 of Helix 8 (Segment C)), one position could be substituted with a Val, another position could be substituted with a Thr, and yet another position could be substituted with a Leu. Moreover, peptides of the invention can simultaneously contain substitutions at amino acid positions assigned to different isosteric groups (i.e., within Helix 8', amino acid positions 1 and 2, which are Leu (Isosteric Group 3) and Glu (Isosteric Group 2), respectively, can both carry amino acid substitutions within the same peptide). The substitutions can be mixed or matched within isosteric groups using the guidance set forth hereinbelow. The foregoing applies to any and all isosteric substitutions described herein. The isosteric substitutions disclosed herein for A and C can be mixed and matched with any deletion or conservative substitution described herein for B, G, and/or H).

i. Substitutions Within Helix 8' (Segment A)

For amino acid positions 1 through 18 in Helix 8' (Segment A), the following amino acid substitutions can be made.

Amino acid positions 5, 17, and 18 within Helix 8' (Segment A) are assigned herein to Isosteric Group 1; thus any one or more of these positions can be substituted with Lys, His, or Arg. In addition, any one or more of these amino acid positions assigned to Isosteric Group 1 can be substituted with an amino acid from Isosteric Group 2 (Asp or Glu), Isosteric Group 3 (Ser, Thr, Leu, Ile, Gly, Ala, Val, or GABA), or Isosteric Group 4 (Phe or Tyr).

Amino acid positions 2, 13, and 14 within Helix 8' (Segment A) are assigned herein to Isosteric Group 2; thus any one or more of these positions can be substituted with Asp or Glu. In addition, any one or more of these amino acid positions assigned to Isosteric Group 2 can also be substituted with amino acids from Isosteric Group 1 (Lys, His, or Arg), Isosteric Group 3 (Ser, Thr, Leu, Ile, Gly, Ala, Val, or GABA), or Isosteric Group 4 (Phe or Tyr).

Amino acid positions 1, 3, 4, 6, 7, 8, 9, 10, 11, 12, 15, and 16 within Helix 8' (Segment A) are assigned herein to Isosteric Group 3; thus any one or more of these positions can be substituted with Ser, Thr, Leu, Ile, Gly, Ala, Val, or GABA. In addition, any one or more of these amino acid positions assigned to Isosteric Group 3 can be substituted with amino acids from Isosteric Group 4 (Phe or Tyr). Moreover, amino acid positions belonging to Isosteric Group 3 that reside on the hydrophilic surface of Helix 8' (i.e., amino acid positions 3, 6, 7, 9, 10, and 16) can be substituted with amino acids from Isosteric Group 1 (Lys, His, or Arg) or Isosteric Group 2 (Asp or Glu).

The isosteric group for each individual amino acid position within Helix 8' (Segment A) is provided below.

Position 1: Leu (Isosteric Group 3) can be substituted with Ser, Thr, Ile, Gly, Ala, Val, GABA, or amino acids from other isosteric groups as provided above.

Position 2: Glu (Isosteric Group 2) can be substituted with Asp or amino acids from other isosteric groups as provided above.

Position 3: Ser (Isosteric Group 3) can be substituted with Thr, Leu, Ile, Gly, Ala, Val, GABA, or amino acids from other isosteric groups as provided above.

Position 4: Ala (Isosteric Group 3) can be substituted with Ser, Thr, Leu, Ile, Gly, Val, GABA, or amino acids from other isosteric groups as provided above.

Position 5: Lys (Isosteric Group 1) can be substituted with His or Arg (Isosteric Group 1).

Position 6: Val (Isosteric Group 3) can be substituted with Ser, Thr, Leu, Ile, Gly, Ala, GABA, or amino acids from other isosteric groups as provided above.

Position 7: Ser (Isosteric Group 3) can be substituted with Thr, Leu, Ile, Gly, Ala, Val, GABA, or amino acids from other isosteric groups as provided above.

Position 8: Ala (Isosteric Group 3) can be substituted with Ser, Thr, Leu, Ile, Gly, Val, GABA, or amino acids from other isosteric groups as provided above.

Position 9: Leu (Isosteric Group 3) can be substituted with Ser, Thr, Ile, Gly, Ala, Val, GABA, or amino acids from other isosteric groups as provided above.

Position 10: Ser (Isosteric Group 3) can be substituted with Thr, Leu, Ile, Gly, Ala, Val, GABA, or amino acids from other isosteric groups as provided above.

Position 11: Ala (Isosteric Group 3) can be substituted with Ser, Thr, Leu, Ile, Gly, Val, GABA, or amino acids from other isosteric groups as provided above.

Position 12: Leu (Isosteric Group 3) can be substituted with Ser, Thr, Ile, Gly, Ala, Val, GABA, or amino acids from other isosteric groups as provided above.

Position 13: Glu (Isosteric Group 1) can be substituted with Asp or amino acids from other isosteric groups as provided above.

Position 14: Glu (Isosteric Group 1) can be substituted with Asp or amino acids from other isosteric groups as provided above.

Position 15: Ala (Isosteric Group 3) can be substituted with Ser, Thr, Leu, Ile, Gly, Val, GABA, or amino acids from other isosteric groups as provided above.

Position 16: Thr (Isosteric Group 3) can be substituted with Ser, Leu, Ile, Gly, Ala, Val, GABA, or amino acids from other isosteric groups as provided above.

Position 17: Lys (Isosteric Group 1) can be substituted with His, Arg, or amino acids from other isosteric groups as provided above.

Position 18: Lys (Isosteric Group 1) can be substituted with His, Arg, or amino acids from other isosteric groups as provided above.

ii. Amino Acid Substitutions Within Segment C (Helix 8)

For amino acid positions 1 through 18 in Helix 8 of Segment C, the following amino acid substitutions can be made.

Amino acid positions 5, 17, and 18 within Helix 8 of Segment C are assigned herein to Isosteric Group 1; thus any one or more of these positions can be substituted with Lys, His, or Arg. In addition, any one or more of these amino acid positions assigned to Isosteric Group 1 can be substituted with an amino acid from Isosteric Group 2 (Asp or Glu), Isosteric Group 3 (Ser, Thr, Leu, Ile, Gly, Ala, Val, or GABA), or Isosteric Group 4 (Phe or Tyr).

Amino acid positions 2, 13, and 14 within Helix 8 Segment C) are assigned herein to Isosteric Group 2; thus any one or more of these positions can be substituted with Asp or Glu. In addition, any one or more of these amino acid positions assigned to Isosteric Group 2 can also be substituted with amino acids from Isosteric Group 1 (Lys, His, or Arg), Isosteric Group 3 (Ser, Thr, Leu, Ile, Gly, Ala, Val, or GABA), or Isosteric Group 4 (Phe or Tyr).

Amino acid positions 1, 3, 6, 7, 9, 10, 11, 12, and 16 within Helix 8 (Segment C) are assigned herein to Isosteric Group 3; thus any one or more of these positions can be substituted with Ser, Thr, Leu, Ile, Gly, Ala, or GABA. In addition, any one or more of these amino acid positions assigned to Isosteric Group 3 can be substituted with amino acids from Isosteric Group 4 (Phe or Tyr). Moreover, amino acid positions belonging to Isosteric Group 3 that reside on the hydrophilic surface of Helix 8 (i.e., amino acid positions 3, 6, 7, 9, 10, and 16) can be substituted with amino acids from Isosteric Group 1 (Lys, His, or Arg) or Isosteric Group 2 (Asp or Glu).

Amino acid positions 4, 8, and 15 within Helix 8 (Segment C) are assigned herein to Isosteric Group 4; thus any one or more of these positions can be substituted with Phe or Tyr. In addition, any one or more of these amino acid positions assigned to Isosteric Group 4 can be substituted with amino acids from Isosteric Group 3 (Ser, Thr, Leu, Ile, Gly, Ala, or GABA).

The isosteric group for each individual amino acid position within Helix 8 (Segment C) is provided below.

Position 1: Leu (Isosteric Group 3) can be substituted with Ser, Thr, Ile, Gly, Ala, Val, GABA, or amino acids from other isosteric groups as provided above.

Position 2: Glu (Isosteric Group 2) can be substituted with Asp or amino acids from other isosteric groups as provided above.

Position 3: Ser (Isosteric Group 3) can be substituted with Thr, Leu, Ile, Gly, Ala, Val, GABA, or amino acids from other isosteric groups as provided above.

Position 4: Phe (Isosteric Group 4) can be substituted with Tyr or amino acids from other isosteric groups as provided above.

Position 5: Lys (Isosteric Group 1) can be substituted with His or Arg (Isosteric Group 1).

Position 6: Val (Isosteric Group 3) can be substituted with Ser, Thr, Leu, Ile, Gly, Ala, Val, GABA, or amino acids from other isosteric groups as provided above.

Position 7: Ser (Isosteric Group 3) can be substituted with Thr, Leu, Ile, Gly, Ala, Val, GABA, or amino acids from other isosteric groups as provided above.

Position 8: Phe (Isosteric Group 4) can be substituted with Tyr or amino acids from other isosteric groups as provided above.

Position 9: Leu (Isosteric Group 3) can be substituted with Ser, Thr, Ile, Gly, Ala, Val, GABA, or amino acids from other isosteric groups as provided above.

Position 10: Ser (Isosteric Group 3) can be substituted with Thr, Leu, Ile, Gly, Ala, Val, GABA, or amino acids from other isosteric groups as provided above.

Position 11: Ala (Isosteric Group 3) can be substituted with Ser, Thr, Leu, Ile, Gly, Val, GABA, or amino acids from other isosteric groups as provided above.

Position 12: Leu (Isosteric Group 3) can be substituted with Ser, Thr, Ile, Gly, Ala, Val, GABA, or amino acids from other isosteric groups as provided above.

Position 13: Glu (Isosteric Group 1) can be substituted with Asp or amino acids from other isosteric groups as provided above.

Position 14: Glu (Isosteric Group 1) can be substituted with Asp or amino acids from other isosteric groups as provided above.

Position 15: Tyr (Isosteric Group 4) can be substituted with Phe or amino acids from other isosteric groups as provided above.

Position 16: Thr (Isosteric Group 3) can be substituted with Ser, Leu, Ile, Gly, Ala, Val, GABA, or amino acids from other isosteric groups as provided above.

Position 17: Lys (Isosteric Group 1) can be substituted with His, Arg, or amino acids from other isosteric groups as provided above.

Position 18: Lys (Isosteric Group 1) can be substituted with His, Arg, or amino acids from other isosteric groups as provided above.

iii. Specific Examples of Isosteric Substitutions in Helices 8' and 8 of A and C Below are some examples of isosteric substitutions that can be made in Helices 8' and 8 in the peptides of the invention. Isosteric substitutions can be mixed and matched without limit. For example, Helix 8' and/or 8 in a peptide of the invention can each contain multiple isosteric substitutions at any position belonging to any isosteric group.

a. Examples of Isosteric Group 1 Substitutions in Helix 8' (SEQ ID NO: 2)

```
                                          SEQ ID NO: 2
Leu Glu Ser Ala Lys Val Ser Ala Leu Ser Ala Leu
Glu Glu Ala Thr Lys Lys;

                                        SEQ ID NO: 496
Leu Glu Ser Ala His Val Ser Ala Leu Ser Ala Leu
Glu Glu Ala Thr Lys Lys;

                                        SEQ ID NO: 497
Leu Glu Ser Ala Lys Val Ser Ala Leu Ser Ala Leu
Glu Glu Ala Thr His Lys;

                                        SEQ ID NO: 498
Leu Glu Ser Ala Lys Val Ser Ala Leu Ser Ala Leu
Glu Glu Ala Thr Lys His;

                                        SEQ ID NO: 499
Leu Glu Ser Ala His Val Ser Ala Leu Ser Ala Leu
Glu Glu Ala Thr His Lys;

                                        SEQ ID NO: 500
Leu Glu Ser Ala Lys Val Ser Ala Leu Ser Ala Leu
Glu Glu Ala Thr His His;

                                        SEQ ID NO: 501
Leu Glu Ser Ala His Val Ser Ala Leu Ser Ala Leu
Glu Glu Ala Thr Lys His;

                                        SEQ ID NO: 502
Leu Glu Ser Ala His Val Ser Ala Leu Ser Ala Leu
Glu Glu Ala Thr His His;

                                        SEQ ID NO: 503
Leu Glu Ser Ala Arg Val Ser Ala Leu Ser Ala Leu
Glu Glu Ala Thr Lys Lys;

                                        SEQ ID NO: 504
Leu Glu Ser Ala Lys Val Ser Ala Leu Ser Ala Leu
Glu Glu Ala Thr Arg Lys;

                                        SEQ ID NO: 505
Leu Glu Ser Ala Lys Val Ser Ala Leu Ser Ala Leu
Glu Glu Ala Thr Lys Arg;

                                        SEQ ID NO: 506
Leu Glu Ser Ala Arg Val Ser Ala Leu Ser Ala Leu
Glu Glu Ala Thr Arg Lys;

                                        SEQ ID NO: 507
Leu Glu Ser Ala Lys Val Ser Ala Leu Ser Ala Leu
Glu Glu Ala Thr Arg Arg;

                                        SEQ ID NO: 508
Leu Glu Ser Ala Arg Val Ser Ala Leu Ser Ala Leu
Glu Glu Ala Thr Lys Arg;

                                        SEQ ID NO: 509
Leu Glu Ser Ala Arg Val Ser Ala Leu Ser Ala Leu
Glu Glu Ala Thr Arg Arg;

                                        SEQ ID NO: 510
Leu Glu Ser Ala Arg Val Ser Ala Leu Ser Ala Leu
Glu Glu Ala Thr His His;

                                        SEQ ID NO: 511
Leu Glu Ser Ala His Val Ser Ala Leu Ser Ala Leu
Glu Glu Ala Thr Arg His;

                                        SEQ ID NO: 512
Leu Glu Ser Ala His Val Ser Ala Leu Ser Ala Leu
Glu Glu Ala Thr His Arg

                                        SEQ ID NO: 513
Leu Glu Ser Ala Arg Val Ser Ala Leu Ser Ala Leu
Glu Glu Ala Thr Arg His;
```

-continued

SEQ ID NO: 514
Leu Glu Ser Ala Arg Val Ser Ala Leu Ser Ala Leu Glu Glu Ala Thr His Arg;

SEQ ID NO: 515
Leu Glu Ser Ala His Val Ser Ala Leu Ser Ala Leu Glu Glu Ala Thr Arg Arg;

SEQ ID NO: 516
Leu Glu Ser Ala Lys Val Ser Ala Leu Ser Ala Leu Glu Glu Ala Thr Arg His;

SEQ ID NO: 517
Leu Glu Ser Ala Lys Val Ser Ala Leu Ser Ala Leu Glu Glu Ala Thr His Arg;

SEQ ID NO: 518
Leu Glu Ser Ala Arg Val Ser Ala Leu Ser Ala Leu Glu Glu Ala Thr Lys His;

SEQ ID NO: 519
Leu Glu Ser Ala Arg Val Ser Ala Leu Ser Ala Leu Glu Glu Ala Thr His Lys;

SEQ ID NO: 520
Leu Glu Ser Ala His Val Ser Ala Leu Ser Ala Leu Glu Glu Ala Thr Lys Arg;

SEQ ID NO: 521
Leu Glu Ser Ala Lys Val Ser Ala Leu Ser Ala Leu Glu Glu Ala Thr Arg Lys.

b. Examples of Isosteric Group 1 Substitutions in Helix 8 (SEQ ID NO: 14)

SEQ ID NO: 14
Leu Glu Ser Phe Lys Val Ser Phe Leu Ser Ala Leu Glu Glu Tyr Thr Lys Lys;

SEQ ID NO: 522
Leu Glu Ser Phe His Val Ser Phe Leu Ser Ala Leu Glu Glu Tyr Thr Lys Lys;

SEQ ID NO: 523
Leu Glu Ser Phe Lys Val Ser Phe Leu Ser Ala Leu Glu Glu Tyr Thr His Lys;

SEQ ID NO: 524
Leu Glu Ser Phe Lys Val Ser Phe Leu Ser Ala Leu Glu Glu Tyr Thr Lys His;

SEQ ID NO: 525
Leu Glu Ser Phe His Val Ser Phe Leu Ser Ala Leu Glu Glu Tyr Thr His Lys;

SEQ ID NO: 526
Leu Glu Ser Phe Lys Val Ser Phe Leu Ser Ala Leu Glu Glu Tyr Thr His His;

SEQ ID NO: 527
Leu Glu Ser Phe His Val Ser Phe Leu Ser Ala Leu Glu Glu Tyr Thr Lys His;

SEQ ID NO: 528
Leu Glu Ser Phe His Val Ser Phe Leu Ser Ala Leu Glu Glu Tyr Thr His His;

SEQ ID NO: 529
Leu Glu Ser Phe Arg Val Ser Phe Leu Ser Ala Leu Glu Glu Tyr Thr Lys Lys;

SEQ ID NO: 530
Leu Glu Ser Phe Lys Val Ser Phe Leu Ser Ala Leu Glu Glu Tyr Thr Arg Lys;

-continued

SEQ ID NO: 531
Leu Glu Ser Phe Lys Val Ser Phe Leu Ser Ala Leu Glu Glu Tyr Thr Lys Arg;

SEQ ID NO: 532
Leu Glu Ser Phe Arg Val Ser Phe Leu Ser Ala Leu Glu Glu Tyr Thr Arg Lys;

SEQ ID NO: 533
Leu Glu Ser Phe Lys Val Ser Phe Leu Ser Ala Leu Glu Glu Tyr Thr Arg Arg;

SEQ ID NO: 534
Leu Glu Ser Phe Arg Val Ser Phe Leu Ser Ala Leu Glu Glu Tyr Thr Lys Arg;

SEQ ID NO: 535
Leu Glu Ser Phe Arg Val Ser Phe Leu Ser Ala Leu Glu Glu Tyr Thr Arg Arg;

SEQ ID NO: 536
Leu Glu Ser Phe Arg Val Ser Phe Leu Ser Ala Leu Glu Glu Tyr Thr His His;

SEQ ID NO: 537
Leu Glu Ser Phe His Val Ser Phe Leu Ser Ala Leu Glu Glu Tyr Thr Arg His;

SEQ ID NO: 538
Leu Glu Ser Phe His Val Ser Phe Leu Ser Ala Leu Glu Glu Tyr Thr His Arg;

SEQ ID NO: 539
Leu Glu Ser Phe Arg Val Ser Phe Leu Ser Ala Leu Glu Glu Tyr Thr Arg His;

SEQ ID NO: 540
Leu Glu Ser Phe Arg Val Ser Phe Leu Ser Ala Leu Glu Glu Tyr Thr His Arg;

SEQ ID NO: 541
Leu Glu Ser Phe His Val Ser Phe Leu Ser Ala Leu Glu Glu Tyr Thr Arg Arg;

SEQ ID NO: 542
Leu Glu Ser Phe Lys Val Ser Phe Leu Ser Ala Leu Glu Glu Tyr Thr Arg His;

SEQ ID NO: 543
Leu Glu Ser Phe Lys Val Ser Phe Leu Ser Ala Leu Glu Glu Tyr Thr His Arg;

SEQ ID NO: 544
Leu Glu Ser Phe Arg Val Ser PheLeu Ser Ala Leu Glu Glu Tyr Thr Lys His

SEQ ID NO: 545
Leu Glu Ser Phe Arg Val Ser Phe Leu Ser Ala Leu Glu Glu Tyr Thr His Lys;

SEQ ID NO: 546
Leu Glu Ser Phe His Val Ser Phe Leu Ser Ala Leu Glu Glu Tyr Thr Lys Arg;

SEQ ID NO: 547
Leu Glu Ser Phe Lys Val Ser Phe Leu Ser Ala Leu Glu Glu Tyr Thr Arg Lys.

c. Examples of Isosteric Group 2 Substitutions in Helix 8' (SEQ ID NO: 2)

SEQ ID NO: 2
Leu Glu Ser Ala Lys Val Ser Ala Leu Ser Ala Leu Glu Glu Ala Thr Lys Lys;

-continued

SEQ ID NO: 548
Leu Asp Ser Ala Lys Val Ser Ala Leu Ser Ala Leu
Glu Glu Ala Thr Lys Lys;

SEQ ID NO: 549
Leu Glu Ser Ala Lys Val Ser Ala Leu Ser Ala Leu
Asp Glu Ala Thr Lys Lys;

SEQ ID NO: 550
Leu Glu Ser Ala Lys Val Ser Ala Leu Ser Ala Leu
Glu Asp Ala Thr Lys Lys;

SEQ ID NO: 551
Leu Asp Ser Ala Lys Val Ser Ala Leu Ser Ala Leu
Asp Glu Ala Thr Lys Lys;

SEQ ID NO: 552
Leu Asp Ser Ala Lys Val Ser Ala Leu Ser Ala Leu
Glu Asp Ala Thr Lys Lys;

SEQ ID NO: 553
Leu Glu Ser Ala Lys Val Ser Ala Leu Ser Ala Leu
Asp Asp Ala Thr Lys Lys;

SEQ ID NO: 554
Leu Asp Ser Ala Lys Val Ser Ala Leu Ser Ala Leu
Asp Asp Ala Thr Lys Lys.

d. Examples of Isosteric Group 2 Substitutions in Helix 8 (SEQ ID NO: 14)

SEQ ID NO: 14
Leu Glu Ser Phe Lys Val Ser Phe Leu Ser Ala Leu
Glu Glu Tyr Thr Lys Lys;

SEQ ID NO: 555
Leu Asp Ser Phe Lys Val Ser Phe Leu Ser Ala Leu
Glu Glu Tyr Thr Lys Lys;

SEQ ID NO: 556
Leu Glu Ser Phe Lys Val Ser Phe Leu Ser Ala Leu
Asp Glu Tyr Thr Lys Lys;

SEQ ID NO: 557
Leu Glu Ser Phe Lys Val Ser Phe Leu Ser Ala Leu
Glu Asp Tyr Thr Lys Lys;

SEQ ID NO: 558
Leu Asp Ser Phe Lys Val Ser Phe Leu Ser Ala Leu
Asp Glu Tyr Thr Lys Lys;

SEQ ID NO: 559
Leu Asp Ser Phe Lys Val Ser Phe Leu Ser Ala Leu
Glu Asp Tyr Thr Lys Lys;

SEQ ID NO: 560
Leu Glu Ser Phe Lys Val Ser Phe Leu Ser Ala Leu
Asp Asp Tyr Thr Lys Lys;

SEQ ID NO: 561
Leu Asp Ser Phe Lys Val Ser Phe Leu Ser Ala Leu
Asp Asp Tyr Thr Lys Lys.

e. Examples of Isosteric Group 4 Substitutions in Helix 8 (SEQ ID NO: 14)

SEQ ID NO: 14
Leu Glu Ser Phe Lys Val Ser Phe Leu Ser Ala Leu
Glu Glu Tyr Thr Lys Lys;

SEQ ID NO: 562
Leu Glu Ser Phe Lys Val Ser Phe Leu Ser Ala Leu
Glu Glu Phe Thr Lys Lys;

-continued

SEQ ID NO: 563
Leu Glu Ser Phe Lys Val Ser Tyr Leu Ser Ala Leu
Glu Glu Phe Thr Lys Lys;

SEQ ID NO: 564
Leu Glu Ser Phe Lys Val Ser Tyr Leu Ser Ala Leu
Glu Glu Tyr Thr Lys Lys;

SEQ ID NO: 565
Leu Glu Ser Tyr Lys Val Ser Phe Leu Ser Ala Leu
Glu Glu Tyr Thr Lys Lys;

SEQ ID NO: 566
Leu Glu Ser Tyr Lys Val Ser Tyr Leu Ser Ala Leu
Glu Glu Phe Thr Lys Lys;

SEQ ID NO: 567
Leu Glu Ser Tyr Lys Val Ser Tyr Leu Ser Ala Leu
Glu Glu Tyr Thr Lys Lys;

SEQ ID NO: 568
Leu Glu Ser Tyr Lys Val Ser Phe Leu Ser Ala Leu
Glu Glu Phe Thr Lys Lys.

It is to be understood that the letters in the generic formulae I and II or in components thereof are defined by the text that follows each letter and do not designate an individual amino acid.

It is to be understood that in some embodiments, one or more of the amino acids of the peptides of the present invention are D amino acids. In one embodiment, the N-terminal amino acid, the C-terminal amino acid or both are D amino acids. The presence of these D amino acids can help protect against peptide degradation. In another embodiment, all the amino acids of the peptides of the present invention are D amino acids. This embodiment is useful for protection against degradation following oral administration of a pharmaceutical composition comprising the peptides of the present invention.

D. Peptides of the Present Invention Containing D Amino Acids

One of ordinary skill in the art will understand that any of the peptides of the present invention may containone or more D amino acids, for example, a D amino acid at the N-terminus, a D amino acid at the C-terminus, or a D amino acid at both the N— and C-termini. The presence of these D amino acids can help protect against peptide degradation. In some embodiments, all the amino acids of any peptide of the present invention may be D amino acids. This embodiment is useful for protection against degradation following oral administration of a pharmaceutical composition comprising the peptides of the present invention. Some examples of peptides of the present invention containing one or more D amino acids include but are not limited to those shown below. D amino acids are indicated in all-upper-case letters, e.g., “SER” or “PRO.”

i. Examples of Peptides with One or More Amino Acids Replaced by a D Amino Acid

Below are examples of two peptides (SEQ ID NO: 22 Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys and SEQ ID NO: 142 Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln) in which the N-terminal, C-terminal, N-terminal and C-terminal, or all amino acids are replaced by D amino acids. One of ordinary skill in the art will understand that any peptide of the invention can similarly be formulated to contain one or more D amino acids as exemplified below.

SEQ ID NO: 569
LEU Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys;

SEQ ID NO: 570
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys LYS;

SEQ ID NO: 571
LEU Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys LYS;

SEQ ID NO: 572
LEU GLU SER ALA LYS VAL SER ALA LEU SER ALA LEU
GLU GLU ALA THR LYS LYS LYS LEU SER PRO LEU LEU
GLU SER PHE LYS VAL SER PHE LEU SER ALA LEU GLU
GLU TYR THR LYS LYS;

SEQ ID NO: 573
SER Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr Gln;

SEQ ID NO: 574
Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr GLN;

SEQ ID NO: 575
SER Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr GLN;

SEQ ID NO: 576
SER PRO LEU LEU GLU SER ALA LYS VAL SER ALA LEU
SER ALA LEU GLU GLU ALA THR LYS LYS LYS LEU SER
PRO LEU LEU GLU SER PHE LYS VAL SER PHE LEU SER
ALA LEU GLU GLU TYR THR LYS LYS LEU ASN THR GLN.

E. N-Terminal Modification and/or C-terminal Modification of the Peptides of the Present Invention The peptides of the present invention may optionally be acetylated at the amino-terminus. The peptides of the present invention may optionally have a carboxy-terminal amide. In some embodiments, the peptides of the present invention may have both an amino-terminal acetyl group and a carboxy-terminal amide group. Methods of acetylating the amino-terminus or adding a carboxy terminal amide are well known to one of ordinary skill in the art. While it is to be understood that any of the peptides disclosed in this application may be modified at the N-terminus, at the C-terminus, or both at the N-terminus and at the C-terminus, the following sequences are presented as exemplary embodiments.

Below are examples of two peptides (SEQ ID NO: 22 Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys and SEQ ID NO: 142 Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln) in which the N-terminal is acetylated, the C-terminal is amidated, or the N-terminal is acetylated and the C-terminal is amidated. One of ordinary skill in the art will understand that any peptide of the invention can similarly be formulated to contain an amino-terminal acetyl group and/or a carboxy-terminal amide group as exemplified below.

i. Peptides Containing an Amino-Terminal Acetylation

SEQ ID NO: 577
Ac-Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys;

SEQ ID NO: 578
Ac-LEU Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys;

SEQ ID NO: 579
Ac-Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys LYS;

SEQ ID NO: 580
Ac-LEU Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys LYS;

SEQ ID NO: 581
Ac-LEU GLU SER ALA LYS VAL SER ALA LEU SER ALA LEU
GLU GLU ALA THR LYS LYS LYS LEU SER PRO LEU LEU
GLU SER PHE LYS VAL SER PHE LEU SER ALA LEU GLU
GLU TYR THR LYS LYS;

SEQ ID NO: 582
Ac-Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr Gln;

SEQ ID NO: 583
Ac-SER Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr Gln;

SEQ ID NO: 584
Ac-Ser Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr GLN;

SEQ ID NO: 585
Ac-SER Pro Leu Leu Glu Ser Ala Lys Val Ser Ala Leu
Ser Ala Leu Glu Glu Ala Thr Lys Lys Lys Leu Ser
Pro Leu Leu Glu Ser Phe Lys Val Ser Phe Leu Ser
Ala Leu Glu Glu Tyr Thr Lys Lys Leu Asn Thr GLN;

SEQ ID NO: 586
Ac-SER PRO LEU LEU GLU SER ALA LYS VAL SER ALA LEU
SER ALA LEU GLU GLU ALA THR LYS LYS LYS LEU SER
PRO LEU LEU GLU SER PHE LYS VAL SER PHE LEU SER
ALA LEU GLU GLU TYR THR LYS LYS LEU ASN THR GLN.

ii. Peptides Containing a Carboxy-Terminal Amidation

SEQ ID NO: 587
Leu Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys-$NH_2$;

SEQ ID NO: 588
LEU Glu Ser Ala Lys Val Ser Ala Leu Ser Ala Leu
Glu Glu Ala Thr Lys Lys Lys Leu Ser Pro Leu Leu
Glu Ser Phe Lys Val Ser Phe Leu Ser Ala Leu Glu
Glu Tyr Thr Lys Lys-$NH_2$;

-continued

SEQ ID NO: 589
Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys LYS-$NH_2$;

SEQ ID NO: 590
LEU Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys LYS-$NH_2$;

SEQ ID NO: 591
LEU GLU SER ALA LYS VAL SER ALA LEU SER ALA LEU GLU GLU ALA THR LYS LYS LYS LEU SER PRO LEU LEU GLU SER PHE LYS VAL SER PHE LEU SER ALA LEU GLU GLU TYR THR LYS LYS-$NH_2$;

SEQ ID NO: 592
Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$;

SEQ ID NO: 593
SER Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$;

SEQ ID NO: 594
Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr GLN-$NH_2$;

SEQ ID NO: 595
SER Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr GLN-$NH_2$;

SEQ ID NO: 596
SER PRO LEU LEU GLU SER ALA LYS VAL SER ALA LEU SER ALA LEU GLU GLU ALA THR LYS LYS LYS LEU SER PRO LEU LEU GLU SER PHE LYS VAL SER PHE LEU SER ALA LEU GLU GLU TYR THR LYS LYS LEU ASN THR GLN-$NH_2$.

iii. Peptides Containing an Amino-Terminal Acetylation and a Carboxy-Terminal Amidation SEQ ID NO: 597
Ac-Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys-$NH_2$;

SEQ ID NO: 598
Ac-LEU Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys-$NH_2$;

SEQ ID NO: 599
Ac-Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys LYS-$NH_2$;

-continued

SEQ ID NO: 600
Ac-LEU Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys LYS-$NH_2$;

SEQ ID NO: 601
Ac-LEU GLU SER ALA LYS VAL SER ALA LEU SER ALA LEU GLU GLU ALA THR LYS LYS LYS LEU SER PRO LEU LEU GLU SER PHE LYS VAL SER PHE LEU SER ALA LEU GLU GLU TYR THR LYS LYS-$NH_2$;

SEQ ID NO: 602
Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$;

SEQ ID NO: 603
Ac-SER Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$;

SEQ ID NO: 604
Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr GLN-$NH_2$;

SEQ ID NO: 605
Ac-SER Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr GLN-$NH_2$;

SEQ ID NO: 606
Ac-SER PRO LEU LEU GLU SER ALA LYS VAL SER ALA LEU SER ALA LEU GLU GLU ALA THR LYS LYS LYS LEU SER PRO LEU LEU GLU SER PHE LYS VAL SER PHE LEU SER ALA LEU GLU GLU TYR THR LYS LYS LEU ASN THR GLN-$NH_2$.

F. Modified Peptides of the Present Invention

The present invention may be used for the production of the peptides or peptide analogs of the present invention. "Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. When a D amino acid is present in the peptides of the present invention, the three letter designation for the amino acid appears in upper case instead of a capital letter. For example the amino acid serine, represented as Ser indicates an L amino acid. The D amino acid form is represented as the upper case letters SER. This is not to be confused with letters appearing as subscripts used in generic formula and defined as variables herein. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than about 5%, or typically less than about 1%) in a sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q), Histidine (H);
4) Arginine (R), Lysine (K);
5) Isoleucine (I), Leucine (L), Methionine (M), Valine (V); and
6) Phenylalanine (F), Tyrosine (Y), Tryptophan (W).

A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid. A "conservative substitution" also refers to utilizing a substituting amino acid which is identical to the amino acid being substituted except that a functional group in the side chain is protected with a suitable protecting group. Peptides of the present invention include conservatively substituted peptides, wherein these conservative substitutions occur at 1%, 3%, 5%, 7%, 10%, 15%, 20%, 25%, 30%, 40%, or 50% of the amino acid residues. Peptides of the present invention include peptides that are homologous at 50%, 60%, 70%, 80%, 90%, 95%, 97%, 98%, 99% of the entire sequence of the peptide.

Suitable protecting groups are described in Green and Wuts, "Protecting Groups in Organic Synthesis", John Wiley and Sons, Chapters 5 and 7, 1991, the teachings of which are incorporated herein by reference. Preferred protecting groups are those which facilitate transport of the peptide through membranes, for example, by reducing the hydrophilicity and increasing the lipophilicity of the peptide, and which can be cleaved, either by hydrolysis or enzymatically (Ditter et al., 1968. J. Pharm. Sci. 57:783; Ditter et al., 1968. J. Pharm. Sci. 57:828; Ditter et al., 1969. J. Pharm. Sci. 58:557; King et al., 1987. Biochemistry 26:2294; Lindberg et al., 1989. Drug Metabolism and Disposition 17:311; Tunek et al., 1988. Biochem. Pharm. 37:3867; Anderson et al., 1985 Arch. Biochem. Biophys. 239:538; and Singhal et al., 1987. FASEB J. 1:220). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters, as described below for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. A "nonconservative substitution" can be made by substituting an amino acid with another amino acid from a different group. It is to be understood that these groups are non-limiting, i.e. that there are additional modified amino acids which could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl glycine, and modified amino residues having substituted benzyl or phenyl side chains. Preferred substituents include one or more of the following: halogen, methyl, ethyl, nitro, $-NH_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl isopropyl, cyclohexyl, benzyl or substituted benzyl), glutamine, asparagine, —CO—NH— alkylated glutamine or asparagines (e.g., methyl, ethyl, n-propyl and iso-propyl) and modified amino acids having the side chain $-(CH_2)_3-COOH$, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, and modified amino acids having C1-C5 straight or branched alkyl side chains substituted with —OH or —SH, for example, $-CH_2CH_2OH$, $-CH_2CH_2CH_2OH$ or $-CH_2CH_2OHCH_3$. Preferably, Group VI includes serine, or threonine.

In another aspect, suitable substitutions for amino acid residues include "severe" substitutions or "nonconservative" substitutions. These terms are used interchangeably through the application. A "severe substitution" or "nonconservative substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cyclohexylmethyl glycine for alanine, isoleucine for glycine, a D amino acid for the corresponding L amino acid, or —NH—CH[(—$CH_2$)$_5$—COOH]—CO— for aspartic acid. Alternatively, a functional group may be added to the side chain, deleted from the side chain or exchanged with another functional group. Examples of severe substitutions of this type include adding of valine, leucine or isoleucine, exchanging the carboxylic acid in the side chain of aspartic acid or glutamic acid with an amine, or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —$(CH_2)_4COOH$ for the side chain of serine. These examples are not meant to be limiting.

In addition to the naturally occurring genetically encoded amino acids, amino acid residues in the peptides may be substituted with naturally occurring non-encoded amino acids and synthetic amino acids. Certain commonly encountered amino acids which provide useful substitutions include, but are not limited to, β-alanine and other omega-amino acids, such as 3-aminopropionic acid, 2,3-diaminopropionic acid, 4-aminobutyric acid and the like; α-aminoisobutyric acid; ϵ-aminohexanoic acid; δ-aminovaleric acid; N-methylglycine or sarcosine; ornithine; citrulline; t-butylalanine; t-butylglycine; N-methylisoleucine; phenylglycine; cyclohexylalanine; norleucine; naphthylalanine; 4-chlorophenylalanine; 2-fluorophenylalanine; 3-fluorophenylalanine; 4-fluorophenylalanine; penicillamine; 1,2,3,4-tetrahydroisoquinoline-3-carboxylic acid; β2-thienylalanine; methionine sulfoxide; homoarginine; N-acetyl lysine; 2,4-diaminobutyric acid; 2,3-diaminobutyric acid; p-aminophenylalanine; N-methyl valine; homocysteine; homophenylalanine; homoserine; hydroxyproline; homoproline; N-methylated amino acids; and peptoids (N-substituted glycines).

While in certain embodiments, the amino acids of the peptides will be substituted with L-amino acids, the substitutions are not limited to L-amino acids. Thus, also encompassed by the present disclosure are modified forms of the peptides, wherein an L-amino acid is replaced with an identical D-amino acid (e.g., L-Arg→D-Arg) or with a conservatively-substituted D-amino acid (e.g., LArg→D-Lys), and vice versa.

Additional aspects of the disclosure include analogs, variants, derivatives, and mimetics based on the amino acid sequence of the peptides disclosed herein. Typically, mimetic compounds are synthetic compounds having a three-dimensional structure (of at least part of the mimetic compound) that mimics, for example, the primary, secondary, and/or tertiary structural, and/or electrochemical characteristics of a selected peptide, structural domain, active site, or binding region (e.g., a homotypic or heterotypic binding site, a catalytic active site or domain, a receptor or ligand binding interface or domain, or a structural motif) thereof. The mimetic compound will often share a desired biological activity with a native peptide, as discussed herein (e.g., the ability to interact with lipids). Typically, at least one subject biological activity of the mimetic compound is not substantially reduced in comparison to, and is often the same as or greater than, the activity of the native peptide on which the mimetic was modeled.

A variety of techniques well known to one of skill in the art are available for constructing synthetic peptide mimetics with the same, similar, increased, or reduced biological activity as the corresponding native peptide. Often these analogs, variants, derivatives and mimetics will exhibit one or more desired activities that are distinct or improved from the corresponding native peptide, for example, improved characteristics of solubility, stability, lipid interaction, and/or susceptibility to hydrolysis or proteolysis (see, e.g., Morgan and Gainor, *Ann. Rep. Med. Chem.* 24:243-252, 1989). In addition, mimetic compounds of the disclosure can have other desired characteristics that enhance their therapeutic application, such as increased cell permeability, greater affinity and/or avidity for a binding partner, and/or prolonged biological half-life. The mimetic compounds of the disclosure can have a backbone that is partially or completely non-peptide, but with side groups identical to the side groups of the amino acid residues that occur in the peptide on which the mimetic compound is modeled. Several types of chemical bonds, for example, ester, thioester, thioamide, retroamide, reduced carbonyl, dimethylene and ketomethylene bonds, are known in the art to be generally useful substitutes for peptide bonds in the construction of protease-resistant mimetic compounds.

In one embodiment, peptides useful within the disclosure are modified to produce synthetic peptide mimetics by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5-membered ring to a 4-, 6-, or 7-membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (e.g., morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrinidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and thiazolyl groups. These heterocyclic groups can be substituted or unsubstituted. Where a group is substituted, the substituent can be alkyl, alkoxy, halogen, oxygen, or substituted or unsubstituted phenyl. Peptides, as well as peptide analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

Other peptide analogs and mimetics within the scope of the disclosure include glycosylation variants, and covalent or aggregate conjugates with other chemical moieties. Covalent derivatives can be prepared by linkage of functionalities to groups which are found in amino acid side chains or at the N— or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues (e.g., lysine or arginine). Acyl groups are selected from the group of alkyl-moieties including C3 to C18 alkyl, thereby forming alkanoyl aroyl species. Also embraced are versions of a native primary amino acid sequence which have other minor modifications, including phosphorylated amino acid residues, for example, phosphotyrosine, phosphoserine, or phosphothreonine, or other moieties, including ribosyl groups or cross-linking reagents.

In the peptides disclosed herein, the linkage between amino acid residues can be a peptide bond or amide linkage (e.g., —C—C(O)NH—). Alternatively, one or more amide linkages is optionally replaced with a linkage other than amide, for example, a substituted amide. Substituted amides generally include, but are not limited to, groups of the formula —C(O)NR—, where R is ($C_1$-$C_6$)alkyl, substituted ($C_1$-$C_6$) alkyl, ($C_1$-$C_6$)alkenyl, substituted ($C_1$-$C_6$)alkenyl, ($C_1$-$C_6$) alkynyl, substituted ($C_1$-$C_6$)alkynyl, ($C_5$-$C_{20}$)aryl, substituted ($C_5$-$C_{20}$)aryl, ($C_6$-$C_{26}$)alkaryl, substituted ($C_6$-$C_{26}$) alkaryl, 5-20 membered heteroaryl, substituted 5-20 membered heteroaryl, 6-26 membered alkheteroaryl, and substituted 6-26 membered alkheteroaryl. Additionally, one or more amide linkages can be replaced with peptidomimetic or amide mimetic moieties which do not significantly interfere with the structure or activity of the peptides. Suitable amide mimetic moieties are described, for example, in Olson et al., *J. Med. Chem.* 36:3039-3049, 1993.

The peptides of the present invention may optionally be acetylated at the N-terminus. The peptides of the present invention may optionally have a carboxy terminal amide. In some embodiments, the peptides of the present invention may have both an acetylated N-terminus and a carboxy terminal amide. Methods of acetylating the N-terminus or adding a carboxy terminal amide are well known to one of ordinary skill in the art.

IV. Overview of Several Embodiments

Isolated peptides and peptide analogs with domains that promote lipid efflux from cells are disclosed herein. The isolated peptides and peptide analogs are believed to stimulate LCAT activity. In some embodiments, the isolated peptides and peptide analogs of the present invention contain domains that promote lipid efflux and also possess anti-inflammatory activity. Domains that possess lipid efflux and anti-inflammatory activity provide additional benefit as many vascular conditions are considered by one of ordinary skill in the art to have inflammation as a component of the disease etiology.

For administration to an animal or a human, the peptides and peptide analogs of the present invention are combined with an acceptable carrier to form a pharmaceutical composition and are administered to the animal or the human.

In another embodiment, a method is provided for treating or inhibiting dyslipidemic and vascular disorders in an animal or a human. This method includes administering to the animal or the human a therapeutically effective amount of a pharmaceutical composition that includes one or more isolated peptides or peptide analogs and one or more anti-inflammatory domains. In specific, non-limiting examples, the dyslipidemic and vascular disorders include hyperlipidemia, hyperlipoproteinemia, hypercholesterolemia, hypertriglyceridemia, HDL deficiency, apoA-I deficiency, coronary artery disease, atherosclerosis, myocardial infarction, stroke, thrombotic stroke, peripheral vascular disease, restenosis, acute coronary syndrome, and reperfusion myocardial injury. In yet another specific example of the provided method, the isolated peptide includes a domain or domains (A and C) that possess both anti-inflammatory and lipid efflux activity and has an amino acid sequence as set forth herein.

Additionally, in representative peptides disclosed herein, the amino- and carboxy-terminal ends can be modified by conjugation with various functional groups. Neutralization of the terminal charge of synthetic peptide mimetics of apolipoproteins has been shown to increase their lipid affinity (Yancey et al., *Biochem.* 34:7955-7965, 1995; Venkatachalapathi et al., *Protein: Structure, Function and Genetics* 15:349-359, 1993). For example, acetylation of the amino terminal end of amphipathic peptides increases the lipid affinity of the peptide (Mishra et al., *J. Biol. Chem.* 269:7185-7191, 1994). Other possible end modifications are described, for example, in Brouillette et al., *Biochem. Biophys. Acta* 1256:103-129, 1995: Mishra et al., *J. Biol. Chem.* 269:7185-7191, 1994; and Mishra et al., *J. Biol. Chem.* 270:1602-1611, 1995.

In another embodiment, a detectable moiety can be linked to any of the peptides disclosed herein, creating a peptide-detectable moiety conjugate. The peptides or peptide analogs disclosed herein may be labeled using labels and techniques known to one of ordinary skill in the art. Some of these labels are described in the "Handbook of Fluorescent Probes and Research Products", ninth edition, Richard P. Haugland (ed) Molecular Probes, Inc. Eugene, OR), which is incorporated herein in its entirety. Detectable moieties suitable for such use include any composition detectable by spectroscopic, photochemical, biochemical, immunochemical, electrical, optical, magnetic or chemical means. The detectable moieties contemplated for the present disclosure can include, but are not limited to, an immunofluorescent moiety (e.g., fluorescein, rhodamine, Texas red, and the like), a radioactive moiety (e.g., $^{3}H$, $^{32}P$, $^{125}I$, $^{131}I$, $^{35}S$), an enzyme moiety (e.g., horseradish peroxidase, alkaline phosphatase), a colorimetric moiety (e.g., colloidal gold, biotin, colored glass or plastic, and the like). The detectable moiety can be liked to the peptide or peptide analog at either the N— and/or C-terminus. Optionally, a linker can be included between the peptide or peptide analog and the detectable moiety.

The detectable peptides of the present invention may be employed in imaging techniques to identify sites of atherosclerotic plaque and sites of cholesterol efflux. Such imaging techniques may occur in vivo using IVUS, NMR, CAT, PET or other techniques commonly known to one of ordinary skill in the art.

Means of detecting such moieties are well known to those of skill in the art. Thus, for example, radiolabels may be detected using photographic film, gamma counters or scintillation counters. Fluorescent markers may be detected using a photodetector to detect emitted illumination. Enzymatic labels are typically detected by providing the enzyme with a substrate and detecting the reaction product produced by the action of the enzyme on the substrate, and calorimetric labels are detected by simply visualizing the colored label.

The linkers contemplated by the present disclosure can be any bifunctional molecule capable of covalently linking two peptides to one another. Thus, suitable linkers are bifunctional molecules in which the functional groups are capable of being covalently attached to the N— and/or C-terminus of a peptide. Functional groups suitable for attachment to the N— or C-terminus of peptides are well known in the art, as are suitable chemistries for effecting such covalent bond formation.

The linker may be flexible, rigid or semi-rigid. Suitable linkers include, for example, amino acid residues such as Pro or Gly or peptide segments containing from about 2 to about 5, 10, 15, 20, or even more amino acids, bifunctional organic compounds such as $H_2N(CH_2)_nCOOH$ where n is an integer from 1 to 12, and the like. Examples of such linkers, as well as methods of making such linkers and peptides incorporating such linkers, are well-known in the art (see, e.g., Hunig et al., *Chem. Ber.* 100:3039-3044, 1974 and Basak et al, *Bioconjug. Chem.* 5:301-305, 1994).

Conjugation methods applicable to the present disclosure include, by way of non-limiting example, reductive amination, diazo coupling, thioether bond, disulfide-bond, amidation and thiocarbamoyl chemistries. In one embodiment, the amphipathic α-helical domains are "activated" prior to conjugation. Activation provides the necessary chemical groups for the conjugation reaction to occur. In one specific, non-limiting example, the activation step includes derivatization with adipic acid dihydrazide. In another specific, non-limiting example, the activation step includes derivatization with the N-hydroxysuccinimide ester of 3-(2-pyridyl dithio)-propionic acid. In yet another specific, non-limiting example, the activation step includes derivatization with succinimidyl 3-(bromoacetamido) propionate. Further, non-limiting examples of derivatizing agents include succinimidylformylbenzoate and succinimidyllevulinate.

V. Synthesis and Purification of the Peptides

The peptides or peptide analogs of the disclosure can be prepared using virtually any technique known to one of ordinary skill in the art for the preparation of peptides. For example, the peptides can be prepared using step-wise solution or solid phase peptide syntheses, or recombinant DNA techniques, or the equivalents thereof.

A. Chemical Synthesis

Peptides of the disclosure containing amino acids having either the D- or L-configuration can be readily synthesized by automated solid phase procedures well known in the art. Suitable syntheses can be performed by utilizing "T-boc" or "F-moc" procedures. Techniques and procedures for solid phase synthesis are described in *Solid Phase Peptide Synthesis: A Practical Approach,* by E. Atherton and R. C. Sheppard, published by IRL, Oxford University Press, 1989. Alternatively, the peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). This is particularly the case with glycine containing peptides. Other methods useful for synthesizing the peptides of the disclosure are described in Nakagawa et al., *J. Am. Chem. Soc.* 107:7087-7092, 1985.

Additional exemplary techniques known to those of ordinary skill in the art of peptide and peptide analog synthesis are taught by Bodanszky, M. and Bodanszky, A., *The Practice of Peptide Synthesis,* Springer Verlag, New York, 1994; and by Jones, J., *Amino Acid and Peptide Synthesis,* 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups.

Peptides of the disclosure having either the D- or L-configuration can also be readily purchased from commercial suppliers of synthetic peptides. Such suppliers include, for example, Advanced ChemTech (Louisville, Ky.), Applied Biosystems (Foster City, Calif.), Anaspec (San Jose, Calif.), and Cell Essentials (Boston, Mass.).

B. Recombinant Synthesis

If the peptide is composed entirely of gene-encoded amino acids, or a portion of it is so composed, the peptide or the relevant portion can also be synthesized using conventional recombinant genetic engineering techniques. For recombinant production, a polynucleotide sequence encoding the peptide is inserted into an appropriate expression vehicle, that is, a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, Ch. 17 and Ausubel et al *Short Protocols in Molecular Biology,* $4^{th}$ ed., John Wiley & Sons, Inc., 1999).

One of ordinary skill in the art will be familiar with the genetic code by which nucleic acids encode proteins, polypeptides, and peptides. Each amino acid is encoded by one or more sets of three nucleotides; each of these sets is called a codon. This triplet genetic code is degenerate in that all of the amino acids, except for methionine, are encoded by more than one codon. See, e.g., Watson et al., Molecular Biology of the Gene, $4^{th}$ ed., Vol. 1, Benjamin/Cummings Publishing Co., Menlo Park, 1987. For example, the amino acid serine can be encoded by six different codons. One of ordinary skill in the art will appreciate that the particular codons selected to encode a given protein, polypeptide, or peptide can be based upon the particular type of cell or in vitro translation system in which the protein, polypeptide, or peptide is to be produced (i.e., to optimize translation in the particular translation system selected for production of the protein, polypeptide, or peptide). Just one example of a DNA sequence that can encode a peptide of the invention, in this case SEQ ID NO: 142 Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln, is (from 5' to 3') SEQ ID NO: 607 tct cct ctt ctt gag tct gct aag gtt tct gct ctt tct gct ctt gaa gaa gct act aaa aaa aaa ctt tct cct ctt ctt gaa agt ttt aaa gtt tct ttt ctt tct gct ctt gaa gaa tat act aaa aaa tta aat act caa. One of ordinary skill will understand that in an mRNA sequence encoding this peptide, the base thymine (represented by "t" in the DNA sequence above) would be replaced with the base uracil ("u").

It is well-known by one of ordinary skill in the art that DNA is transcribed into messenger RNA (mRNA), after which the mRNA is translated into the encoded protein, polypeptide, or peptide. One of skill in the art will appreciate that, for an mRNA to be translated into a peptide or polypeptide within a cell or using an in vitro translation system, there must be a translation start site, i.e., the codon for the amino acid methionine (aug). Thus, nucleic acids encoding peptides of the present invention can be designed to encode fusion proteins with an optional internal cleavage site, after which the translated protein optionally can be cleaved using an endopeptidase to release free peptide, as will be understood by one of ordinary skill in the art. Alternatively, nucleic acids encoding peptides of the present invention can be designed to encode an amino-terminal methionine, which optionally can be cleaved off by an exopeptidase, as will be appreciated by one of ordinary skill in the art. As one of skill in the art will appreciate, the nucleic acid encoding the peptide can also contain a stop codon (e.g., taa, tag, or tga in DNA; uaa, uag, or uga in RNA) to terminate translation of the peptide.

To increase efficiency of production, the polynucleotide can be designed to encode multiple units of the peptide separated by enzymatic cleavage sites. The resulting polypeptide can be cleaved (e.g., by treatment with the appropriate enzyme) in order to recover the peptide units. This can increase the yield of peptides driven by a single promoter. In one embodiment, a polycistronic polynucleotide can be designed so that a single mRNA is transcribed which encodes multiple peptides, each coding region operatively linked to a cap-independent translation control sequence, for example, an internal ribosome entry site (IRES). When used in appropriate viral expression systems, the translation of each peptide encoded by the mRNA is directed internally in the transcript, for example, by the IRES. Thus, the polycistronic construct directs the transcription of a single, large polycistronic mRNA which, in turn, directs the translation of multiple, individual peptides. This approach eliminates the production and enzymatic processing of polyproteins and can significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage lambda, plac, ptrp, ptac (ptrp-lac hybrid promoter) and the like can be used. When cloning in insect cell systems, promoters such as the baculovirus polyhedron promoter can be used. When cloning in plant cell systems, promoters derived from the genome of plant cells (e.g., heat shock promoters, the promoter for the small subunit of RUBISCO, the promoter for the chlorophyll a/b binding protein) or from plant viruses (e.g., the 35S RNA promoter of CaMV, the coat protein promoter of TMV) can be used. When cloning in mammalian cell systems, promoters derived from the genome of mammalian cells (e.g., metallothionein promoter) or from mammalian viruses (e.g., the adenovirus late promoter, the vaccinia virus 7.5 K promoter) can be used.

C. Purification

The peptides or peptide analogs of the disclosure can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art.

For affinity chromatography purification, any antibody which specifically binds the peptide or peptide analog may be used.

The peptides of the present invention may optionally be acetylated at the N-terminus. The peptides of the present invention may optionally have a carboxy terminal amide. In some embodiments, the peptides of the present invention may have both an acetylated N-terminus and a carboxy terminal amide. Methods of acetylating the N-terminus or adding a carboxy terminal amide are well known to one of ordinary skill in the art.

D. Antibody Production

For the production of antibodies, various host animals, including but not limited to, rabbits, mice, rats, and the like, may be immunized by injection with a peptide or peptide analog. The peptide or peptide analog can be attached to a suitable carrier (e.g., bovine serum albumin (BSA)) by means of a side chain functional group or linker attached to a side chain functional group. Various adjuvants may be used to increase the immunological response, depending on the host species, including but not limited to, Freund's (complete and incomplete), mineral gels (e.g., aluminum hydroxide), surface active substances (e.g., lysolecithin, pluronic polyols, polyanions, and oil emulsions), keyhole limpet hemocyanin, dinitrophenol, and potentially useful human adjuvants such as BCG (bacilli Calmette-Guerin) and Corynebacterium parvum.

Booster injections can be given at regular intervals, and antiserum harvested when the antibody titer thereof, as determined semi-quantitatively, for example, by double immunodiffusion in agar against known concentrations of the antigen, begins to fall. See, e.g., Ouchterlony et al., *Handbook of Experimental Immunology,* Wier, D. (ed.), Chapter 19, Blackwell, 1973. A plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology,* Ch. 42, 1980).

Monoclonal antibodies to a peptide or peptide analog may be prepared using any technique which provides for the production of antibody molecules by continuous cell lines in culture, for example the classic method of Kohler & Milstein (*Nature* 256:495-97, 1975), or a derivative method thereof. Briefly, a mouse is repetitively inoculated with a few micrograms of the selected protein immunogen (e.g., a peptide or peptide analog) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as enzyme-linked immunosorbent assay (ELISA), as originally described by Engvall (*Meth. Enzymol.,* 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual,* CSHL, New York, 1999. Polyclonal antiserum containing antibodies can be prepared by immunizing suitable animals with a polypeptide comprising at least one peptide or peptide analog, which can be unmodified or modified, to enhance immunogenicity.

Antibody fragments may be used in place of whole antibodies and may be readily expressed in prokaryotic host cells. Methods of making and using immunologically effective portions of monoclonal antibodies, also referred to as "antibody fragments," are well known and include those described in Better & Horowitz, *Methods Enzymol.* 178:476-96, 1989; Glockshuber et al., *Biochemistry* 29:1362-67, 1990; and U.S. Pat. No. 5,648,237 (Expression of Functional Antibody Fragments); U.S. Pat. No. 4,946,778 (Single Polypeptide Chain Binding Molecules); and U.S. Pat. No. 5,455,030 (Immunotherapy Using Single Chain Polypeptide Binding Molecules), and references cited therein. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting (FACS), fluorescence in situ hybridization (FISH), immunomagnetic assays, ELISA, ELISPOT (Coligan et al., *Current Protocols in Immunology,* Wiley, N.Y., 1995), agglutination assays, flocculation assays, cell panning, etc., as are well known to one of skill in the art.

E. Peptide Reconstitution

The peptides of the present invention may be reconstituted in any pharmaceutically acceptable carrier before use or administration. In one embodiment, the peptides may be reconstituted with saline, a lipid or a phospholipid, or a combination thereof. Some phospholipids that may be employed include but are not limited to the following: dipalmitoylphosphatidylcholine (DPPC); dioleoylphosphatidylcholine (DOPC); 1-palmitoyl-2-oleoylphosphatidylcholine (POPC); 1-palmitoyl-2-linoleoylphosphatidylcholine (PLPC); 1-palmitoyl-2-arachidonylphosphatidylcholine (PAPC); 1-palmitoyl-2-docosahexanoylphosphatidylcholine (PDPC); and 1-palmitoyl-2-myristoylphosphatidylcholine (PMPC). See, e.g., Shah et al. (Circulation (2001), 103(25):3047-50), in which DPPC was used to reconstitute peptides. The peptides of the present invention may be complexed with lipids or phospholipids in weight ratios ranging from 1:0.5 to 1:10, or 1:1 to 1:5. Any ratio within these ranges may be employed.

The phospholipids may also be complexed with other agents, such as sphingomyelin before complexing with the peptides of the present invention. Ratios of phospholipids to sphingomyelin include ratios occurring in the ranges of 1:9 to 9:1, 1:5 to 5:1, 1.2 to 2.1 (all weight %).

The peptides of the present invention may be complexed with the combination of phospholipid:sphingomyelin in weight ratios ranging from 1:0.5 to 1:10, or 1:1 to 1:5. Any ratio within these ranges may be employed.

VI. Pharmaceutical Compositions and Uses Thereof

The peptides or peptide analogs of the disclosure can be used, alone or in combination, together with a pharmaceutically acceptable carrier, to treat any disorder in animals, especially mammals (e.g., humans), for which promoting lipid efflux and/or decreasing inflammation is beneficial. Such conditions include, but are not limited to, hyperlipidemia (e.g., hypercholesterolemia), cardiovascular disease (e.g., atherosclerosis), cerebrovascular disease, restenosis (e.g., atherosclerotic plaques), peripheral vascular disease, acute coronary syndrome, reperfusion myocardial injury, and the like. The peptides or peptide analogs of the disclosure can also be used alone or in combination during the treatment of thrombotic stroke, infarcts secondary to occlusion of a vessel and during thrombolytic treatment of occluded coronary artery disease. The peptides or peptide analogs of the disclosure can be used to treat tissue following hypoxia, ischemia and infarction due to impairment of blood supply, and also following hemorrhage following rupture or trauma of a blood vessel. Such tissue includes, without limitation, neural tissue in the central or peripheral nervous system, peripheral vascular tissue, and cardiac muscle.

It is to be understood that a mixture of peptides may include different amounts of the individual peptides. For example, in one embodiment, each peptide component of the combination may be present in a different relative percentage than each other peptide component due to differences in relative efficacy to promote lipid efflux or to provide one or more types of anti-inflammatory activity. In one exemplary embodiment, two or more of the peptides comprising the sequences shown in SEQ ID NO: 22 (Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys); SEQ ID NO: 142 (Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln); SEQ ID NO: 602 (Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$); and/or SEQ ID NO: 608 Asp Trp Leu Lys Ala Phe Tyr Asp Lys Val Ala Glu Lys Leu Lys Glu Ala Phe Pro Asp Trp Ala Lys Ala Ala Tyr Asp Lys Ala Ala Glu Lys Ala Lys Glu Ala Ala may be combined in a mixture for administration.

The peptides or peptide analogs can be used alone or in combination therapy with other lipid lowering compositions or drugs and/or other anti-inflammatory compositions or drugs used to treat the foregoing conditions. Such therapies include, but are not limited to simultaneous or sequential administration of the drugs involved. For example, in the treatment of hypercholesterolemia or atherosclerosis, the peptide or peptide analog formulations can be administered with any one or more of the cholesterol lowering therapies currently in use, for example, bile-acid resins, niacin, statins, fat uptake inhibitors, and HDL raising drugs.

In another embodiment, the peptides or peptide analogs can be used in conjunction with statins or fibrates to treat hyperlipidemia, hypercholesterolemia and/or cardiovascular disease, such as atherosclerosis. In yet another embodiment, the peptides or peptide analogs of the disclosure can be used in combination with an anti-microbial agent and/or an anti-inflammatory agent, such as aspirin. In another embodiment peptides or peptide analogs of the disclosure can be used in combination with anti-hypertensive medicines known to one of ordinary skill in the art. It is to be understood that more than one additional therapy may be combined with administration of the peptides or peptide analogs of the disclosure.

In a further embodiment, the peptides can also be expressed in vivo, by using any of the available gene therapy approaches.

In yet another embodiment, the peptides or peptide analogs can be used in conjunction with medicines used to treat patients with cerebrovascular and cardiovascular disease resulting in hypoxia, ischemia and infarction due to impairment of blood supply, and also following hemorrhage following rupture or trauma of a blood vessel. Such medicines are commonly known to one of ordinary skill in the art and include without limitation, modulators of excitatory amino acids and modulators of platelet aggregation.

A. Administration of Peptides or Peptide Analogs

In some embodiments, peptides or peptide analogs can be isolated from various sources and administered directly to the animal or human. For example, a peptide or peptide analog can be expressed in vitro, such as in an *E. coli* expression system, as is well known in the art, and isolated in amounts useful for therapeutic compositions. The peptide or peptide analogs of the present invention may also be made though peptide synthetic methods known to one of ordinary skill in the art, such as solid phase synthesis.

In exemplary applications, therapeutic compositions comprising the peptide or peptide analogs in an acceptable carrier are administered to an animal or a human suffering from a dyslipidemic or vascular disorder, such as hyperlipidemia, hyperlipoproteinemia, hypercholesterolemia, hypertriglyceridemia, HDL deficiency, apoA-I deficiency, coronary artery disease, atherosclerosis, stroke, ischemia, infarction, myocardial infarction, hemorrhage, peripheral vascular disease, restenosis, acute coronary syndrome, or reperfusion myocardial injury, in an amount sufficient to inhibit or treat the dyslipidemic or vascular disorder. Amounts effective for this use will depend upon the severity of the disorder and the general state of the subject's health. A therapeutically effective amount of the compound is that which provides either subjective relief of a symptom(s) or an objectively identifiable improvement as noted by the clinician or other qualified observer.

A peptide or peptide analog can be administered by any means known to one of skill in the art (see, e.g., Banga, "Parenteral Controlled Delivery of Therapeutic Peptides and Proteins," in *Therapeutic Peptides and Proteins,* Technomic Publishing Co., Inc., Lancaster, Pa. 1995), such as by intramuscular, subcutaneous, or intravenous injection, but even oral, nasal, or anal administration is contemplated. In one embodiment, administration is by subcutaneous or intramuscular injection. To extend the time during which the peptide or peptide analog is available to inhibit or treat a dyslipidemic or vascular disorder, the peptide or peptide analog can be provided as an implant, an oily injection, or as a particulate system. The particulate system can be a microparticle, a microcapsule, a microsphere, a nanoparticle, or similar particle (Banga, "Parenteral Controlled Delivery of Therapeutic Peptides and Proteins," in *Therapeutic Peptides and Proteins,* Technomic Publishing Co., Inc., Lancaster, Pa. 1995). The peptide or peptide analog may also be applied to a medical device for delivery to a specific location. For example, a surgical tool, catheter, stent, balloon, electrode, suture, or an artificial vessel or transplanted vessel may contain or be coated with the peptide or peptide analog.

It is to be understood that in some embodiments, one or more of the amino acids of the peptides of the present invention are D amino acids. In one embodiment, the N-terminal amino acid, the C-terminal amino acid or both are D amino acids. The presence of these D amino acids can help protect against peptide degradation. In another embodiment, all the amino acids of the peptides of the present invention are D amino acids. This embodiment is useful for protection against degradation following oral administration of a pharmaceutical composition comprising the peptides of the present invention.

In one specific, non-limiting example, a peptide is administered that includes one or more of the amino acid sequences disclosed herein.

B. Representative Methods of Administration Formulations and Dosage

The provided peptides or peptide analogs, constructs, or vectors encoding such peptides, can be combined with a pharmaceutically acceptable carrier (e.g., a phospholipid or other type of lipid) or vehicle for administration to human or animal subjects. As described previously in the application, the peptides may be reconstituted with acceptable carriers such as saline, lipid, phospholipid, lipid:sphingomyelin complexes and phospholipid: sphingomyelin complexes. In some embodiments, more than one peptide or peptide analog can be combined to form a single preparation. The peptides or peptide analogs can be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The pharmaceutical compositions provided herein, including those for use in treating dyslipidemic and vascular disorders, may be administered through different routes, such as oral, including buccal and sublingual, rectal, parenteral, aerosol, nasal, intramuscular, intraperitoneal, intravascular, subcutaneous, intradermal, and topical. They may be administered in different forms, including but not limited to solutions, emulsions and suspensions, microspheres, particles, microparticles, nanoparticles, and liposomes. In one embodiment, peptides or peptide analogs with suitable features of lipid efflux and low cytotoxicity can be precomplexed with phospholipids or other lipids into either discoidal or spherical shape particles prior to administration to subjects.

In another embodiment, it may be desirable to administer the pharmaceutical compositions locally to the area in need of treatment. This maybe achieved by, for example, and not by way of limitation, local or regional infusion or perfusion during surgery, direct perfusion into a vessel, such as an atherosclerotic vessel, topical application (e.g., wound dressing, peptide coated stent), injection, catheter, suppository, or implant (e.g., implants formed from porous, non-porous, or gelatinous materials, including membranes, such as silastic membranes or fibers), and the like. In one embodiment, administration can be by direct injection at the site (or former site) of a tissue that is to be treated, such as the heart or the peripheral vasculature. In another embodiment, the pharmaceutical compositions are delivered in a vesicle, in particular liposomes (see, e.g., Langer, *Science* 249:1527-1533, 1990; Treat et al., in *Liposomes in the Therapy of Infectious Disease and Cancer,* Lopez-Berestein and Fidler (eds.), Liss, N.Y., pp. 353-365, 1989). Combinations of administration methods may also be employed such as a systemic or local infusion of a peptide of the present invention, before, after or during placement of a stent coated with a peptide of the present invention.

In yet another embodiment, the pharmaceutical compositions can be delivered in a controlled release system. In one embodiment, a pump can be used (see, e.g., *Langer Science* 249:1527-1533, 1990; Sefton *Crit. Rev. Biomed. Eng.* 14:201-240, 1987; Buchwald et al., *Surgery* 88:507-516, 1980; Saudek et al., *N. Engl. J. Med.* 321:574-579, 1989). In another embodiment, polymeric materials can be used (see, e.g., Ranger et al., *Macromol. Sci. Rev. Macromol. Chem.* 23:61-64, 1983; Levy et al., *Science* 228:190-192, 1985; During et al., Ann. Neurol. 25:351-356, 1989; and Howard et al., *J. Neurosurg.* 71:105-112, 1989). Other controlled release systems, such as those discussed in the review by Langer (*Science* 249:1527-1533, 1990), can also be used.

The amount of the pharmaceutical compositions that will be effective depends on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. An example of such a dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the subject undergoing therapy.

The pharmaceutical compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. The volume of administration will vary depending on the route of administration. By way of example, intramuscular injections may range from about 0.1 ml to about 1.0 ml. Those of ordinary skill in the art will know appropriate volumes for different routes of administration.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

The subject matter of the present disclosure is further illustrated by the following non-limiting Examples.

EXAMPLES

Example 1

Lipid Efflux From Cells Mediated by Peptides of the Present Invention

This example demonstrates a method to test the ability of peptides of the present invention to efflux lipid from ABCA1-expressing cells.

HeLa cells stably transfected with human ABCA1 cDNA (ABCA1 cells) and HeLa cells transfected with only a hygromycin-resistant control plasmid (control cells) are produced and grown in α-modified Eagle's medium (aMEM) plus 10% fetal calf serum, as described by Remaley et al. (*Biochem. Biophys. Res. Commun.* 280:818-823, 2001). Cholesterol and phospholipid efflux is performed for 18 hours on noncholesterol-loaded cells radiolabeled with either cholesterol or choline (Remaley et al., *Arterioscler. Thromb. Vasc. Biol.* 17:1813-1821, 1997). Percentage efflux is calculated after subtracting the radioactive counts in the blank media (aMEM plus 1 mg/ml of BSA), and expressed as the percent of total radioactive counts removed from the cells during the efflux period.

Cell fixation is performed by a 10 minute treatment with 3% paraformaldehyde in phosphate buffered saline (PBS), followed by three washes with blank media. Lactate dehydrogenase (LDH) release from cells into the media is measured enzymatically (Roche Diagnostics, Indianapolis, Ind.) and expressed, after subtraction of LDH released into blank media, as the percentage of total cell LDH. Total cell LDH is determined after cell solubilization with 1% Triton X-100.

The peptides of the present invention are synthesized by a solid-phase procedure, using a Fmoc/DIC/HOBt protocol on a Biosearch 9600 peptide synthesizer (Applied Biosystems, Foster City, Calif.), or an equivalent instrument. Both L-amino acid and D-amino acid enantiomers are synthesized. All peptides are purified to greater than 98% homogeneity by reverse-phase HPLC on an Aquapore RP-300 column, or similar chromatographic procedure.

ABCA1 cells are used to assess the ability of apoA-I and synthetic peptides to efflux lipid from cells. As previously described (Hamon et al., *Nat. Cell Biol.* 2:399-406, 2000 and Remaley et al., *Biochem. Biophys. Res. Commun.* 280:818-823, 2001), control cells do not efflux significant amounts of cholesterol and phospholipid to apoA-I, but do so after transfection with ABCA1. The peptides of the present invention efflux approximately 2- to 4-fold more cholesterol and phospholipid from ABCA1 cells than from control cells. Both the peptides of the present invention and apoA-I began to show saturation for lipid efflux at approximately the same protein concentration of 10 μg/ml. The peptides of the present invention remove more cholesterol and phospholipids from control cells than apoA-I.

Example 2

Lipid Efflux Time Course

This example demonstrates the cholesterol efflux time course from ABCA1-expressing cells to apoA-I and peptides of the present invention.

Cholesterol efflux from ABCA1 cells to apoA-I is first detectable after 2 hours and increases throughout the 30 hour efflux period. In contrast, there is no significant increase above background in cholesterol efflux to apoA-I from control cells. Overall, the kinetics for cholesterol efflux to peptides of the present invention from ABCA1 cells is similar to that of apoA-I, except that cholesterol efflux is first detectable after 30 minutes. The peptides of the present invention, unlike apoA-I, also promote cholesterol efflux from control cells but at a lower rate.

Example 3

Identification of Non-Cytotoxic Peptides that Promote ABCA1-Dependent Lipid Efflux This example illustrates a method for identifying non-cytotoxic peptides that promote ABCA1-dependent lipid efflux from cells.

Peptide Design: Based on the principles and procedures described in the present application, an amino acid sequence can be designed for a peptide that promotes lipid efflux.

Peptide production: Peptides to be tested can be produced synthetically or by recombinant DNA methods, as described in the present application, and purified by reverse phase HPLC or other suitable techniques well known to one of skill in the art.

Peptide Cytotoxicity Testing: Peptides can be tested for cytotoxicity by any number of methods well known to one of skill in the art, such as the release of intracellular LDH.

Peptide ABCA1-specificity for Lipid Efflux: Peptides to be tested can be added to serum-free cell culture media in the approximate concentration range of 1-20 micrograms and incubated with a control cell line that does not express the ABCA1 transporter and the same cell line after transfection with human cDNA for the ABCA1 transporter, as described herein. Alternatively, cells, such as macrophages, that either express or do not express the ABCA1 transporter depending on their cholesterol content and/or exposure to agents that induce the ABCA1 transporter (e.g., cAMP and LXR agonists) can also be used. After a suitable period of approximately 4 to 24 hours, the conditioned media can be removed from the cells and the amount of cholesterol and or phospholipid effluxed can be quantified, as described herein. ABCA1-specific lipid efflux is calculated by subtracting the total lipid efflux of the cell line that does not express the ABCA1 transporter from the lipid efflux from the ABCA1 expressing cell line.

Example 4

Peptides of the Present Invention Reduce Atherosclerosis in Animal Models

The ability of the peptides of the present invention and associated fragments are tested in apoe knockout mice on a chow diet and LDL receptor knockout mice on a western high fat diet to determine the effect of these peptides to reduce atherosclerosis in a mouse model system. One or more of the peptides of the present invention, in a range of concentration of 2 mg/kg to 50 mg/kg, is injected intravenously (iv) or intraperitoneally (ip) 2 to 3 times per week over a period of approximately 6 weeks. In one study, peptides of SEQ ID NO: 142 and/or SEQ ID NO: 602 are tested. Aortic atherosclerosis is quantitated in the aortic arch before administration of the peptides and after the 6 week period of administration. (Wu et al., J. Biol. Chem.; 2004: 279, 22913-22925). The results demonstrate reduced atherosclerosis in the aortic arch in mice in both treatment groups.

Example 5

Administration of the Peptides of the Present Invention to Treat Atherosclerosis in Humans Individuals with acute coronary syndrome and documented atherosclerosis have a cardiac catherization with intravascular ultrasound (IVUS) to document coronary atherosclerosis of 20 to 50% obstruction in the target artery. Each individual is on stable hypolipidemic drug therapy and receives an acceptable dose of a peptide of the present invention and/or an associated fragment iv weekly for a period of 5 to 8 weeks. In one study, peptides of SEQ ID NO: 142 and/or SEQ ID NO: 602 are tested. A repeat IVUS measurement is made at the end of the treatment period to assess the effect of the peptide infusion on coronary atherosclerosis in the target vessel. Plaque is reduced in the atherosclerotic coronary artery following the peptide treatment demonstrating efficacy of the peptides of the present invention to treat atherosclerosis.

Example 6

Administration of the Peptides of the Present Invention to Prevent or Delay the Onset of Atherosclerosis in Humans Individuals with documented risk factors for atherosclerosis and having high plasma cholesterol levels have a ultrasound analysis of the coronary (IVUS), carotid (IMT) or popliteal arteries to establish a baseline measurement. A portion of these individuals are daily administered individual peptides of the present invention at a dose of 2 mg/kg to 50 mg/kg intravenously (iv) or intramuscular (im) 1 to 3 times per week over a period of approximately one to six months. In one study, peptides of SEQ ID NO: 142 and/or SEQ ID NO: 602 are tested. The other individuals receive a control peptide. A new ultrasound analysis at the end of the treatment period indicates higher levels of plaque in the vessels of individuals receiving the control peptide. This example indicates that the individual peptides of the present invention are effective in preventing or reducing atherosclerosis in individuals at risk for developing atherosclerosis and in reducing plaque accumulation in coronary, carotid or popliteal arteries.

Example 7

Administration of the Peptides of the Present Invention on Stents to Reduce Inflammation and Restenosis Individuals with acute coronary syndrome and having plaque in coronary vessels which require a stent to reduce the obstruction receive an IVUS procedure to document the coronary anatomy. A representative protocol divides these individuals into three groups. One group receives a stent coated with a peptide of the present invention. A second group receives an iv infusion of a peptide of the present invention at a dose of 2 mg/kg to 50 mg/kg, 1 to 3 times per week over a period of approximately 5 to 10 weeks. A third group receives a stent coated with a peptide of the present invention and an iv infusion of a peptide of the present invention at a dose of 2 mg/kg to 50 mg/kg, 1 to 3 times per week over a period of approximately 5 to 10 weeks. In one study, peptides of SEQ ID NO: 142 and/or SEQ ID NO: 602 are tested.

All individuals receive a second IVUS procedure at the end of 5 or 10 weeks. The results demonstrate that individuals receiving either a peptide coated stent, a peptide coated stent plus iv peptide infusion, or iv peptide infusion alone, all display reduced inflammation and restenosis when compared to their condition at the time of the first IVUS procedure.

Example 8

Blockade of ICAM-1/LFA-1-Mediated T-cell Adhesion to Caco-2 Cell Monolayers by the Peptides of the Present Invention The ability of the peptides of the present invention and associated fragments are tested to decrease inflammation by their ability to block the binding of ICAM-1 to LFA-1 using a model cell adhesion assay of T cells (Mott-3) and Caco-2 cells (Anderson et al., Bioorganic & Medicinal Chemistry Letters; 2004:14, 1399-1402). Peptide concentrations of from 0 μM to 500 μM are tested. In one experiment, peptides of SEQ ID NO: 142 and/or SEQ ID NO: 602 are tested. The results demonstrate dose dependent inhibition of ICAM-1/LFA-1 mediated T-cell adhesion to Caco-2 cell monolayers by the peptides of the present invention. While not wanting to be bound by theory, it is believed that the A and/or C domains of the peptides of the present invention are involved in this inhibitory effect.

These results indicate that the interaction of ICAM-1 and LFA-1 in the vessel wall can be blocked by the of the peptides of the present invention, and result in decreased movement of inflammatory cells, particularly T cells, from the plasma into the vessel wall. A decrease in the influx of inflammatory cells into the vessel wall decreases this inflammatory component of the atherosclerotic process and decreases the frequency of clinical vascular events (Yusuf-Makagiqansar, Inflammation: 2001; 25,203-213).

Example 9

Blockade of Neutrophils Through Inhibition of the Formyl Peptide Receptor-like-1 (FPRL1) by the Peptides of the Present Invention The anti-inflammatory properties of the peptides of the present invention and associated fragments are tested by evaluating the ability of the peptides to block the binding of neutrophils to the formyl peptide-like 1 receptor using techniques as described by Bae et al., (Bae et al Journal of Immunology; 2004: 173,607-614; Bae et al., Journal of Immunology; 2003: 171,6807-6813). The peptides of the present invention are tested in a range of 1 pM to 10 μM for their ability to inhibit the binding of radiolabelled SEQ ID NO: 609 Trp Lys Tyr Met Val MET peptide to FPRL1 expressing RBL-2H3 cells, and for their ability to block SEQ ID NO: 609 Trp Lys Tyr Met Val MET induced cellular chemotaxis in FPRL1 expressing RBL-2H3 cells. In one study, peptides of SEQ ID NO: 142 and/or SEQ ID NO: 602 are tested. The peptides of the present invention are also tested in other assays described in these two references by Bae et al.

The results demonstrate that the anti-inflammatory properties of the peptides of the present invention and associated fragments to inhibit the binding of radiolabelled SEQ ID NO: 609 Trp Lys Tyr Met Val MET peptide to FPRL1 expressing RBL-2H3 cells, inhibit SEQ ID NO: 609 Trp Lys Tyr Met Val MET induced cellular chemotaxis in FPRL1 expressing RBL-2H3 cells, and decrease superoxide generation.

While not wanting to be bound by theory, it is believed that administration of the peptides of the present invention to individuals decreases the early neutrophil influx into the vessel wall mediated by the formyl peptide-like 1 receptor in acute myocardial infarction or acute coronary syndrome resulting in a decrease in the inflammatory component of atherosclerosis, thereby reducing subsequent clinical events and post-perfusion injury.

Example 10

Use of Labelled Peptides of the Present Invention to Visualize and Locate Plaque in Atherosclerotic Vessels The peptides of the present invention are complexed with phospholipids as well as gadolinium or other suitable reagent and the recombined particle is targeted to cholesterol filled cells which have increased expression of the ABCA1 transporter in the vulnerable plaque of the coronary artery. In one experiment, peptides of SEQ ID NO: 142 and/or SEQ ID NO: 602 are tested. It is believed that the peptides of the present invention have a high affinity for the ABCA1 transporter and are anticipated to bind to only those cells with an increased intracellular level of cholesterol which induced upregulation of the ABCA1 transporter.

These studies on the peptides of the present invention and associated fragments are compared to results from studies employing ApoA-I protein/phospholipid complex to determine the specificity and selectivity of the peptides of the present invention versus ApoA-I in the localization of the label to vulnerable plaque. The use of the labeled peptides of the present invention to visualize vulnerable plaque provides a valuable tool for diagnosis and treatment of patients at risk for developing cardiovascular disease. (Frias et al., J Am Chem Soc; 2004:126, 16316-7).

Example 11

Synthesis of SEQ ID NO: 602 Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$ The peptide was synthesized manually on Fmoc-Rink Amide PEG resin via Fmoc chemistry. Protecting groups used for amino acids were: t-Butyl group for Ser, Thr, Glu and Tyr, Trt group for Asn and Gln, Boc group for Lys. Fmoc-protected amino acids were purchased from EMD Biosciences. Reagents for coupling and cleavage were purchased from Aldrich. Solvents were purchased from Fisher Scientific. The peptide chain was assembled on resin by repetitive removal of the Fmoc protecting group and coupling of protected amino acid. HBTU and HOBt were used as coupling reagent and NMM was used as base. 20% piperidine in DMF was used as de-Fmoc-reagent. After removal of last Fmoc protecting group, resin was treated with TFA/TIS/$H_2O$ (95:3:2) for cleavage and removal of the side chain protecting groups.

Crude peptide was precipitated from cold ether and collected by filtration. Purification of crude peptide was achieved via RP-HPLC using 47 mm×300 mm column from Waters. Peptide was purified using TFA Buffer. Pooled fractions were lyophilized. The peptide has been verified by MS analysis and amino acid analysis. The peptide purity was determined by analytical HPLC column (Supelco C18, 4.6×250 mm).

Example 12

Analysis of SR-B1-Mediated Efflux and ABCA1-Mediated Efflux

The methods employed in this study have been described in U.S. Pat. Nos. 7,029,863, 7,060,452, U.S. Patent Application Publication No. 2005/0191715, and in Moya et al., Arteriosclerosis & Thrombosis 1994:14:1056-1065 and Liu et al., J. Biol. Chem., 2003:278(44), 42976-42984. SR-B1 mediated cholesterol efflux was examined in FU5AH rat hepatoma cells and ABCA1 mediated cholesterol efflux was examined in J774 mouse macrophage cells as described in these references.

TABLE 3

Efflux Assay with Peptides minus blank

| Peptides* | SR-BI Mediated Efflux % Per 4 h | ABCA1 Mediated Efflux % Per 4 h | +ABCA1 Cells | −ABCA1 Cells |
|---|---|---|---|---|
| 1 | 0.15 | 18.71 | 20.338 ± 0.136 | 1.624 ± 0.126 |
| 2 | 0.16 | 13.08 | 14.283 ± 0.545 | 1.205 ± 0.211 |
| 3 | 0.16 | 12.14 | 13.447 ± 0.549 | 1.306 ± 0.261 |
| 4 | 0.10 | 11.20 | 12.420 ± 1.019 | 1.224 ± 0.121 |
| 5 | 0.25 | 14.50 | 15.718 ± 0.123 | 1.215 ± 0.288 |

Legend: 1 = SEQ ID NO: 602, 2 = SEQ ID NO: 610, 3 = SEQ ID NO: 610, 4 = SEQ ID NO: 142, 5 = SEQ ID NO: 602.

SEQ ID NO: 602 is Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$;

SEQ ID NO: 610 is Ser Pro Leu Ser Asp Glu Lcu Arg Gln Arg Lcu Ala Ala Arg Lcu Glu Ala Leu Lys Glu Asn Lys Leu Ser Pro Leu Leu Glu Ser Phe Lys Val Ser Phe Leu Ser Ala Leu Glu Glu Tyr Thr Lys Lys Leu Asn Thr Gln; and SEQ ID NO: 142 is Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln.

TABLE 4

Controls for Efflux Assay with Samples minus blank

| Controls | SR-BI Mediated Efflux % Per 4 h | ABCA1 Mediated Efflux % Per 4 h | +ABCA1 Cells | −ABCA1 Cells |
|---|---|---|---|---|
| 2% Human Serum Pool | 8.47 | 12.56 | 24.658 ± 0.130 | 12.100 ± 0.485 |
| Apo A-I @ 20 μg/ml | 0.26 | 18.97 | 20.682 ± 0.724 | 1.713 ± 0.409 |

* Efflux for all peptide samples was run at 30 μg/ml.

The results demonstrate that peptides SEQ ID NO: 610, SEQ ID NO: 142, and the N-terminally acetylated and C-terminally amidated form of SEQ ID NO: 142, which is SEQ ID NO: 602, each stimulated efflux of cholesterol from J774 macrophage cells (ABCA1 pathway) while having negligible or no effect on cholesterol efflux from the Fu5AH cells (SRB1 pathway), similar to the effect of Apo AI. These selective effects of these peptides demonstrates their efficacy to act as ApoA-I mimetics and selectively efflux cholesterol from cells.

Figure 3:
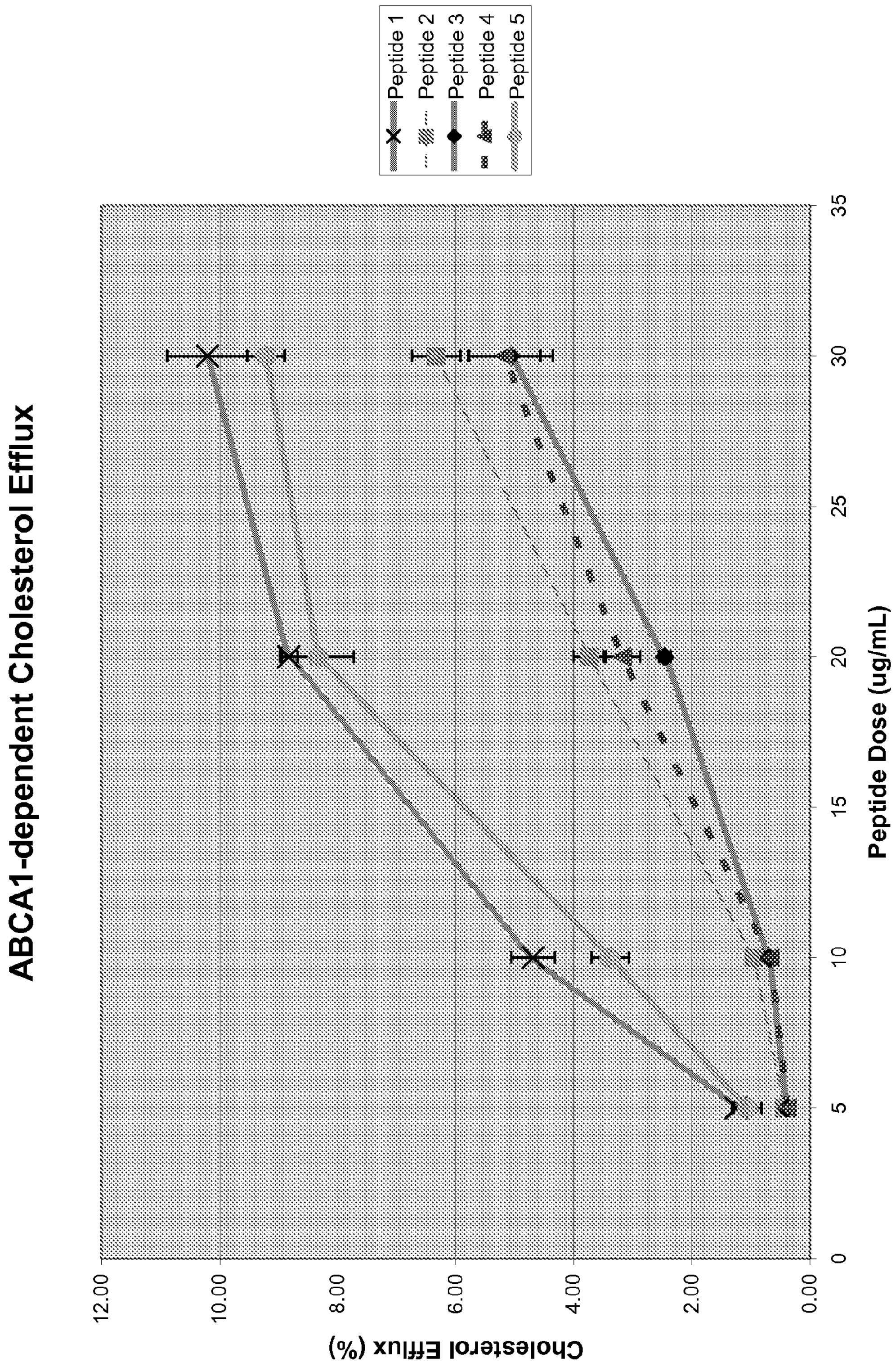
FIG. 3 is a schematic illustration of the dose dependent stimulation of cholesterol efflux from the cells containing the ABCA1 pathway (Peptide 1=SEQ ID NO: 602; Peptide 2=SEQ ID NO: 610; Peptide 3=SEQ ID NO: 610; Peptide 4=SEQ ID NO: 142; and Peptide 5=SEQ ID NO: 602).

These effects were also dose dependent as shown in FIG. 3 with increasing efflux activity demonstrated through the range of 5 ug/ml to 30 ug/ml. Based on these in vitro efflux studies, the elevation of the Apo AI mimetic peptides of the present invention, in plasma, is expected to decrease coronary and other forms of atherosclerosis in high risk patients.

Example 13

Effect of the Peptides of the Present Invention on CD11b Expression in Monocytes Methods:

Monocyte Isolation Peripheral whole blood (PWB) was drawn from healthy consenting individuals into syringes containing sodium citrate (final concentration—19.2 mM). Resting human monocytes were isolated from PWB by density centrifugation with Lymphoprep (Axis Shield). Mononuclear cells (MNCs) were collected and monocytes were further separated to purity using the Dynal negative isolation kit (Invitrogen). Monocytes were resuspended in phosphate buffered saline (PBS) and cell number was determined counting cell suspension on an automated hematology analyzer (Sysmex, KX-21N, USA).

Purification of HDL and apoA-1 Human plasma apoA-1 was isolated as previously described and the purity determined using total mass spectrometry.

Flow Cytometry 100 μL of monocytes were stimulated with either 1 μmol/L phorbol-myristate-acetate (PMA) or 1 μg/ml lipopolysaccharide (LPS) (Sigma, Australia) in the presence or absence of apoA-1 (20 μg/ml), or 20 μg/ml of the test peptide SEQ ID NO: 602 (Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$), each tested separately. The cells were incubated with the FITC conjugated antibody to either the active epitope of CD11b (eBiosciences, USA, Clone CBRM1/5) or total CD11b (Serotec, USA, Clone ICRF44) for 15 min at 37° C. Cells were then fixed with 4% para-formaldehyde. Samples were controlled for by using the appropriately matched isotype matched negative control (FITC-anti-mouse IgG) (Serotec, USA, Clone W3/25). CD11b expression was measured by flow cytometry using FACS Calibur (Becton Dickinson). Analysis was conducted using the Cell Quest Pro software.

Statistical Analysis Values are presented as the mean±SD or percentage of control±SD. FACS results were analyzed for statistical significance using one-way ANOVA followed by Bonferroni post-hoc test. Significance was accepted at $P<0.05$.

Results: As expected, ApoA1 (SEQ ID NO: 1) significantly reduced PMA-induced CD11b expression. In addition, SEQ ID NO: 602 significantly reduced PMA-induced CD11b expression (FIG. 2). This result demonstrates the anti-inflammatory properties of the peptides of the present invention. The combined effects of increasing cholesterol efflux and decreasing inflammation indicate that the peptides of the present invention effectively mimic the function of Apo AI and will decrease atherosclerosis.

Example 14

Evaluation of Peptide Utility in ApoE knockout and LDL Receptor Knockout Mice

ApoE knockout and LDL receptor knockout mice, two well established animal models for the study of atherosclerosis, are injected with either saline as control or the synthetic peptides of the present invention to ascertain if these peptides can be used to increase HDL and decrease atherosclerosis.

The mice receive 3 injections per week for either 4-6 or 8-10 weeks. After the completion of the injection, the amount of hardening of the arteries or atherosclerosis is determined in the control injected animals and peptide injected animals to determine if the injections of the synthetic peptide decreased development of atherosclerosis.

The proposed studies test if intraperitoneal infusions of the apoA-I mimetic peptides of the present invention result in decreased aortic atherosclerosis in apoe and LDL receptor knockout mice, two well established mouse models of atherosclerosis.

The mouse is ideal animal species for the proposed study since well characterized and established mouse models of atherosclerosis are readily available. In particular, apoe and LDL receptor knockout mouse models have been universally employed as animal models for atherosclerosis. Because they are available with a homogenous genetic background, these knockout mice are ideal models for analysis of atherosclerotic lesion formation which is readily impacted by genetic background variability. Additionally, lesion development in apoe and LDL-receptor knockout mice is readily modified by changes in plasma lipoproteins, including HDL, the levels of which are altered by the peptide infusion in this study.

The knockout mouse model is a well established and widely employed animal model for the study of atherosclerosis. Mice are used because of their homogenous genetic background and are ideal models for analysis of atherosclerotic lesion formation which is readily impacted by genetic background variability. Importantly, lesion development in apoe and LDL-receptor knockout mice is highly affected by changes in LDL, HDL and other plasma lipoproteins.

The peptides of the present invention are synthesized according to standard synthetic techniques using tBOC amino acids. The peptides are purified for study by high pressure liquid chromatography. Some peptides are N-acetylated and/or C-terminally amidated.

Mouse Models of Atherosclerosis

Four to six week old C57B1/6 mice, apoe knockout (JAX 2052) and LDL-receptor knockout (JAX'2207) mice, all in the C57B1/6 background, are obtained from Jackson Laboratories. During the entire study, C57B1/6 and apoe knockout mice are maintained on a regular chow diet (0.02% cholesterol, 3% fat) and LDL-receptor mice are maintained on a Western diet (TD88137; Harlan Teklad; Madison, Wis.—containing 0.20% cholesterol and 21% fat).

Infusion of Synthetic ApoA-I Mimetic Peptides

Three Different Infusion Studies are Conducted.

Aim A (Infusion Study A) to determine the functional half-life of the injection of the synthetic peptide on plasma HDL levels.

In the first study (Infusion Study A), C57B1/6 mice as well as apoe knockout and LDL receptor knockout mice are injected by the intraperitoneal (ip) route or intravenous (iv) route with synthetic peptides of the present invention mimetic (30 mg/kg) on up to four different occasions two weeks apart. To evaluate changes in the plasma lipid and lipoprotein profile associated with injection of the synthetic peptide, blood for lipid analyses is obtained before and at 2, 4, 6, 24 and 48 hours after peptide injection. At the end of the study the animals are sacrificed.

Aim B (Infusion Study B) To determine whether ip injection of the synthetic peptide 3×/wk decreases development of atherosclerosis when assayed 4-5 weeks after initiation of treatment.

Aim C (Infusion Study C) To determine whether ip injection of the synthetic peptide 3×/wk decreases development of atherosclerosis when assayed 8-10 weeks after initiation of treatment.

For infusion studies B and C, mice are injected ip with either placebo or a synthetic peptide of the present invention (30 mg/kg) three times per week for either 4 to 5 weeks (Infusion Study B) or 8 to 10 weeks (Infusion Study C). Blood for lipid and lipoprotein analyses is obtained at the beginning of the study (day 0) and every two weeks after placebo/peptide injection and at the completion of the study. At the completion of the study (4 to 5 weeks for Infusion Study B and 8 to 10 weeks for Infusion Study C), the animals are sacrificed, organs harvested for analyses of cholesterol content and for aortic atherosclerosis.

Statistical Methods Used to Analyze Data.

All statistical analyses are conducted in SAS8.2 (SAS Institute, NC). After completion of the atherosclerosis study the mean with standard deviation between the control (C57BI/6) and treated group (apoe knockout or LDL-receptor knockout) is calculated. The differences are tested by t test (PROC TTEST) and p-values less than 0.05 are considered significant. Non-parametric analysis of aortic atherosclerosis are performed by the Mann-Whitney test.

In the first infusion study (Infusion Study A), 5 C57B1/6, 5 apoE knockout and 5 LDL receptor knockout mice are injected (IP) with a synthetic peptide of the present invention and blood is obtained for lipid and lipoprotein analyses. A total of 15 mice are used for Infusion Study A.

A total of 40 mice (20 control-placebo injected and 20 study-peptide injected mice) are utilized in each of the two other infusion studies (Infusion Study B-4 to 5 weeks duration as well as Infusion Study C-8 to 10 weeks duration). Since each infusion study is conducted in two different mouse lines (i.e.: apoE-KO and LDL receptor KO), the total number of mice used for both Infusion Studies B and C is 160.

Total number of mice used for the entire protocol is 175 (five-C57B1/6, eighty five-apoe KO mice and eighty five-LDL receptor KO mice) (These animal numbers take into account an estimated 10% morbidity rate during the course of the study as well as the number of animals previously required to achieve statistical significance during analysis of the non-random distribution aortic lesion pattern that develops in mice).

For Infusion Study A, 5 four to six week old C57B1/6, apoe knockout (JAX 2052) and LDL receptor knockout (JAX 2207) control mice receive ip or iv injections of the synthetic peptide of the present invention for up to four times two weeks apart. The sequence of procedures for this study is as follows:

1) Mice are first anaesthetized by using 1-3% isoflurane by inhalation prior to each ip injection to insure appropriate and complete delivery of placebo/peptide.

2) Mice are injected with either placebo (0.2 ml saline) or apoA-I synthetic peptide (30 mg/kg in 0.2 ml saline) via either the intraperitoneal or intravenous route.

3) In order to evaluate changes in the plasma lipids and lipoproteins in the time-frame between injections, each mouse in this study group is bled from the retro-orbital sinus following administration of a topical anesthesia before and at 2, 4, 6, 24 and 48 hours after the peptide injection. No more than 300 ul blood is drawn during this 48 hour period.

4) At the end of infusion study A all mice are sacrificed by using Avertin (2.5%, 0.011 ml/gm, ip) or ketamine (80 ug/gm, ip).

For Infusion Studies B and C, 20 control and 20 study four to six weeks old apoe knockout (JAX 2052) and LDL-receptor knockout (JAX 2207) mice receive ip injections of either placebo or the synthetic peptide of the present invention three times per week for a total of either 4-5 weeks (Infusion Study B) or 8-10 weeks (Infusion Study C).

1) Mice are first anaesthetized by using 1-3% isoflurane by inhalation prior to each IP injection to insure appropriate and complete delivery of placebo/peptide.

2) Mice are injected ip with either placebo (0.2 ml saline) or apoA-I synthetic peptide (30 mg/kg in 0.2 ml saline) on Monday, Wednesday and Friday of each study week.

3) To measure plasma lipids and lipoproteins, each mouse in the two study groups is fasted for 4 hours in the morning (7 AM to 11 AM) and then bled from the retro-orbital sinus at the start and end of the infusion study as well as every two weeks after the initial infusion for a total of either 4 weeks (Infusion Study B) or 8 weeks (Infusion Study C). No more than 300 ul blood every two weeks is obtained from each mouse.

4) At the end of Infusion Study B and C all mice are sacrificed by cervical dislocation following isoflurane anesthesia and organs are harvested for analyses of cholesterol as well as aortic atherosclerosis.

Before intraperitoneal injections, brief inhaled analgesia is obtained by isoflurane utilizing the E-Z Rodent Anesthesia System in the procedure room. A topical anesthetic (proparacaine) will be applied prior to obtaining blood from the retro-orbital sinus.

The results indicate that the synthetic peptides of the present invention decrease aortic atherosclerosis compared to controls. In one test, peptide SEQ ID NO: 142 Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln or SEQ ID NO: 602 Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$ is tested and is found to decrease aortic atherosclerosis compared to controls.

Example 15

Evaluation of Peptide Utility in Rabbits

The isolated peptides of the present invention are examined for anti-inflammatory activity using an in vivo rabbit model of acute proinflammatory changes in the carotid artery. This method is explained in detail by Nicholls et al., (Circulation 2005:111, 1543-1550). Normocholesterolemic rabbits are administered the isolated peptides of the present invention iv in a dose of from 1 to 50 mg per day for 3 days, optionally contained in unilamellar vesicles of phosphatidylcholine, with only unilamellar vesicles of phosphatidylcholine with no peptide, or saline as a control. In one test, SEQ ID NOs: 142 and 602 are administered. On the second day, after administration of the peptides, a periarterial collar is introduced around the carotid artery and filled with saline. Two days later, the rabbits are humanely sacrificed and the carotid arteries are processed and analyzed for the presence of reactive oxygen species, the infiltration of neutrophils, and the expression of adhesion proteins and chemokines. The administration of the peptides of the present invention decrease the presence of reactive oxygen species, the infiltration of neutrophils, and the expression of adhesion proteins and chemokines compared to controls, thereby demonstrating anti-inflammatory activity in vivo, which can help retard the atherogenic process.

Example 16

Evaluation of Peptide Utility to Promote Reverse Cholesterol Transport In Vivo The isolated peptides of the present invention are examined for the ability to release cholesterol in mice using the method described by Zhang et al., (Circulation. 2003; 108: 661-663). Macrophages (J774 cells) are loaded with tritiated cholesterol in vitro and injected ip into mice. These mice are an administered isolated peptide of the present invention, iv, at a dose of from 1 ug to 1 mg, or saline as a control. In one test, SEQ ID NO: 142 or SEQ ID NO: 602 are administered. The peptides are administered either in saline as a vehicle or in lipid vesicles, such as vesicles of phosphatidylcholine. The mice receiving the peptides of the present invention demonstrate increased levels of tritiated cholesterol in the liver, plasma and feces, than mice receiving saline. The results demonstrate that the peptides of the present invention stimulate reverse cholesterol transport from macrophages to the liver and feces.

Example 17

An Apo A-I Mimetic Peptide (SEQ ID NO: 602) Exhibits ABCA-I Specific Efflux and Anti-Inflammatory Properties Two functions of HDL and apo A-I, efflux of cholesterol via the reverse cholesterol transport pathway with the ABCA-I transporter and anti-inflammatory properties, play a pivotal role in the reduction of atherosclerosis based on studies in mice and humans. The ability of a synthetic amphipathic peptide, SEQ ID NO: 602, to mimic these two key functions of apoA-I was evaluated.

J774 macrophages and Fu5AH hematocytes in culture were used to determine the specificity of SEQ ID NO: 602 to efflux cholesterol by the ABCA-I or SRBI pathways using the methods of de la Llera Moya, M., V., et al. "A cell culture system for screening human serum for ability to promote cellular cholesterol efflux. Relations between serum components and efflux, esterification, and transfer." *Arterioscler. Thromb.* 14: 1056-1065 (1994). Anti-inflammatory properties were evaluated by determination of inhibition of expression of activated CD11B human monocytes and suppression of cytokine-induced vascular cell adhesion molecule-1, V-CAM, expression in human coronary artery endothelial cells (HCAECs). SEQ ID NO: 602 showed significant and reproducible cholesterol efflux via the ABCA-I pathway (15.34%+2.57) comparable to apo A-I (15.99%+2.07) with no SRB-1 pathway activity. Lipid-complexed SEQ ID NO:

602 did not increase cholesterol efflux by the ABCA-I pathway compared to the uncomplexed peptide, but activity via the SRB1 pathway did increase. Inhibition of expression of CD11B on human monocytes by SEQ ID NO: 602 was statistically significant (p=<0.01) and comparable to apo A-I. Initial data showed that SEQ ID NO: 602 decreases V-CAM-1 mRNA levels in HCAECs ($p<0.05$).

In conclusion, SEQ ID NO: 602, a proprietary, synthetic, amphipathic peptide designed to mimic functions of apo A-I, demonstrated both specific ABCA-I cholesterol efflux and anti-inflammatory effects comparable to apo A-I. Therapies based upon an apo A-I mimetic peptide such as SEQ ID NO: 602 can be administered to individuals in need thereof to decrease atherosclerotic plaque formation and progression, thereby reducing morbidity and mortality in high risk patients with cardiovascular disease.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims. It will be apparent that the precise details of the constructs, compositions, and methods described herein may be varied or modified without departing from the spirit of the described invention. We claim all such modifications and variations that fall within the scope and spirit of the claims below

What is claimed is:

1. An isolated peptide comprising SEQ ID NO: 142 Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln.

2. The isolated peptide of claim 1, wherein an N-terminal amino acid is acetylated and/or a C-terminal amino acid is amidated.

3. The isolated peptide of claim 2, wherein the isolated peptide comprises

SEQ ID NO: 602

Ac-Ser Pro Leu Leu Glu Ser Ala Lys Val Ser Ala Leu Ser Ala Leu Glu Glu Ala Thr Lys Lys Lys Leu Ser Pro Leu Leu Glu Ser Phe Lys Val Ser Phe Leu Ser Ala Leu Glu Glu Tyr Thr Lys Lys Leu Asn Thr Gln-$NH_2$.

4. The isolated peptide of claim 1, wherein the isolated peptide contains at least one D-amino acid.

5. The isolated peptide of claim 1, further comprising a label.

6. A pharmaceutical composition comprising the isolated peptide of claim 1 and a pharmaceutically acceptable carrier.

* * * * *